United States Patent [19]

Wei et al.

[11] Patent Number: 5,523,400
[45] Date of Patent: Jun. 4, 1996

[54] CEPHALOSPORIN ANTIBIOTICS

[75] Inventors: Chung-Chen Wei, Cedar Knolls, N.J.; Peter Angehrn, Böckten, Switzerland

[73] Assignee: Hoffmann-La Roche Inc., Nutley, N.J.

[21] Appl. No.: 213,562

[22] Filed: Mar. 21, 1994

Related U.S. Application Data

[63] Continuation-in-part of Ser. No. 48,688, Apr. 16, 1993, abandoned.

[51] Int. Cl.$^6$ .................... C07D 501/34; A61K 31/545
[52] U.S. Cl. .................. 514/202; 514/206; 540/225; 540/222; 540/221
[58] Field of Search .................... 514/206, 202; 540/222, 221, 225

[56] References Cited

U.S. PATENT DOCUMENTS

| | | |
|---|---|---|
| 4,406,899 | 9/1983 | Aburaki et al. . |
| 4,409,214 | 10/1983 | Takaya et al. . |
| 4,496,562 | 1/1985 | Takaya et al. . |
| 5,064,649 | 11/1991 | Burton et al . |
| 5,089,491 | 2/1992 | Kamiya et al. ............ 540/222 |
| 5,171,854 | 12/1992 | Scmidt et al. . |

FOREIGN PATENT DOCUMENTS

| | | |
|---|---|---|
| 359536 | 9/1989 | European Pat. Off. . |
| 620225 | 3/1994 | European Pat. Off. . |
| 453091 | 1/1988 | Sweden . |

*Primary Examiner*—Nicholas Rizzo
*Attorney, Agent, or Firm*—George M. Gould; George W. Johnston; Alan P. Kass

[57] ABSTRACT

The present invention relates to compounds of the formula

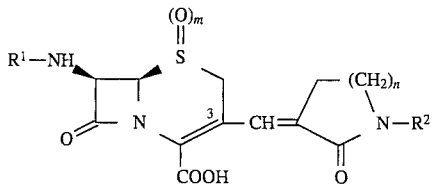

wherein
$R^1$ is an acyl group derived from a carboxylic acid, hydrogen, or an amino protecting group;
$R^2$ is hydrogen, hydroxy, lower alkyl-$Q_p$-, cycloalkyl, lower alkoxy, lower alkenyl, cycloalkenyl, lower alkynyl, aralkyl-$Q_p$-, aryl-$Q_p$-, aryloxy, aralkoxy or a heterocyclic ring, the lower alkyl, cycloalkyl, lower alkoxy, lower alkenyl, cycloalkenyl, lower alkynyl, aralkyl, aryl, aryloxy, aralkoxy and the heterocyclic ring being unsubstituted or substituted with at least one group selected from carboxy, amino, nitro, oxo, cycloalkyl, cyano, lower alkyl, lower alkoxy, hydroxy, halogen, —$CONR^4R^5$, —$N(R^5)COOR^9$, $R^5CO$—, $R^5OCO$— or $R^5COO$— where $R^4$ is hydrogen, lower alkyl, or cycloalkyl; $R^5$ is hydrogen or lower alkyl; $R^9$ is lower alkyl, lower alkenyl or a carboxylic acid protecting group;
Q is —CO— or —$SO_2$—;
m is 0 or 1;
n is 0, 1 or 2;
p is 0 or 1;
as well as readily hydrolyzable esters thereof, pharmaceutically acceptable salts of said compounds and hydrates of the compounds of formula I and of their esters and salts.

The compounds are useful as oral or parenteral antibiotics against a broad spectrum of organisms.

62 Claims, No Drawings

CEPHALOSPORIN ANTIBIOTICS

CROSS-REFERENCE TO RELATED APPLICATIONS

This application is a continuation-in-part application of Ser. No. 08/048,688, filed Apr. 16, 1993 now abandoned.

FIELD OF THE INVENTION

This invention relates to cephalosporin antibiotics and, in particular, those cephalosporin antibiotics having a lactam moiety at the 3 position of the cephalosporin, and compositions and uses thereof.

BACKGROUND

The development, success, and widespread use of cephalosporin antibiotics in recent years have led to the emergence of a number of resistant organisms. The challenge of the resistance offers opportunities for drug design in this area as well as creates the need for new β-lactam antibiotics.

Antibacterial compounds containing a cephem moiety which have a vinyl substituent or a mono-substituted vinyl group at the 3-position have been found to have broad spectrum antibacterial activity and to be orally active. Examples can be found in U.S. Pat. No. 4,409,214.

An object of the present invention is to prepare a cephem moiety having a 3-olefinic group to which is directly attached an unsubstituted or substituted heterocyclic ring to obtain superior broad spectrum antibacterials which can be administered parenterally and orally.

SUMMARY OF THE INVENTION

The present invention relates to cephalosporin derivatives of the general formula

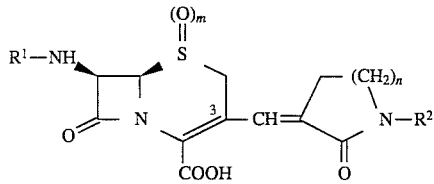

wherein
$R^1$ is an acyl group derived from a carboxylic acid, hydrogen, or an amino protecting group;
$R^2$ is hydrogen, hydroxy, lower alkyl-$Q_p$-, cycloalkyl, lower alkoxy, lower alkenyl, cycloalkenyl, lower alkynyl, aralkyl-$Q_p$-, aryl-$Q_p$-, aryloxy, aralkoxy or a heterocyclic ring, the lower alkyl, cycloalkyl, lower alkoxy, lower alkenyl, cycloalkenyl, lower alkynyl, aralkyl, aryl, aryloxy, aralkoxy and the heterocyclic ring being unsubstituted or substituted with at least one group selected from carboxy, amino, nitro, oxo, cycloalkyl, cyano, lower alkyl, lower alkoxy, hydroxy, halogen, —$CONR^4R^5$, —$N(R^5)COOR^9$, $R^5CO$—, $R^5OCO$— or $R^5COO$— where $R^4$ is hydrogen, lower alkyl, or cycloalkyl; $R^5$ is hydrogen or lower alkyl; $R^9$ is lower alkyl, lower alkenyl or a carboxylic acid protecting group;
Q is —CO— or —$SO_2$—;
m is 0 or 1;
n is 0, 1 or 2;

p is 0 or 1;
as well as readily hydrolyzable esters thereof, pharmaceutically acceptable salts of said compounds and hydrates of the compounds of formula I and of their esters and salts.

In the above compounds of formula I the substituent in position 3 can be present in the E-form:

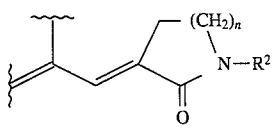

or in the Z-form:

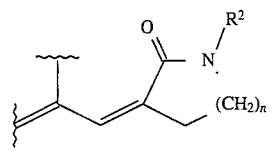

A subgroup of the compounds of the invention consists of compounds of the formula

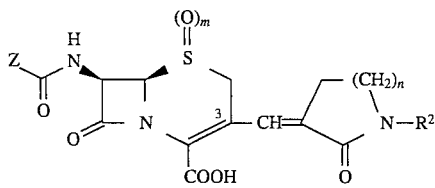

where Z is —$C(X)=CR_aR_b$[IIA], —$CH(X)NH_2$[IIB], or —$C(X)=NOR_3$ [IIC], where $R_a$ is hydrogen, lower alkyl or $CH_2CO_2R^4$, the lower alkyl being unsubstituted or substituted with at least one group selected from carboxy, amino, nitro, cyano, lower alkyl, lower alkoxy, hydroxy, halogen, —$CONR^4R^5$, —$N(R^5)COOR^9$, $R^5CO$—, $R^5OCO$—, or $R^5COO$—; $R_b$ is hydrogen or lower alkyl; X is aryl, cyclohexyl, 1,4-cyclohexadienyl, or a heterocyclic ring, the aryl, cyclohexyl, 1,4-cyclohexadienyl, and heterocyclic ring being unsubstituted or substituted with at least one group selected from carboxy, amino, nitro, cyano, lower alkyl, lower alkoxy, hydroxy, halogen, —$CONR^4R^5$, —$N(R^5)COOR^9$, $R^5CO$—, $R^5OCO$— or $R^5COO$—; $R^3$ is hydrogen, lower alkyl, cycloalkyl, aralkyl, $R^5CO$— or —$C(R^7R^8)CO_2R^{9'}$; $R^7$ and $R^8$ are each independently hydrogen or lower alkyl or $R^7$ and $R^8$ taken together form a cycloalkyl group; and $R^2$, $R^4$, $R^5$, $R^9$ and n are as defined above, $R^{9'}$ is hydrogen or $R^9$,
as well as readily hydrolyzable esters thereof, pharmaceutically acceptable salts of said compounds and hydrates of the compounds thereof and of their esters and salts.

Formulae IIA, IIB and IIC, as discussed above, have the following structures:

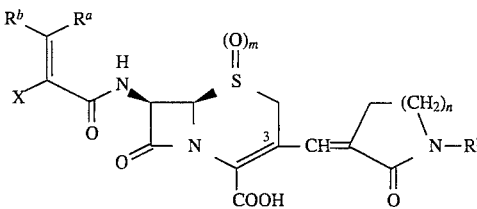

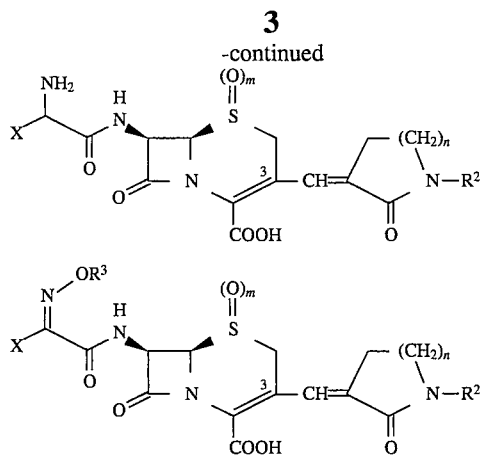

where X, $R^a$, $R^b$, $R^2$, $R^3$, m, and n are as defined above.

In formula IIC $R^3$ is preferably hydrogen.

A subgroup of the compounds of the invention consists of compounds of the formula

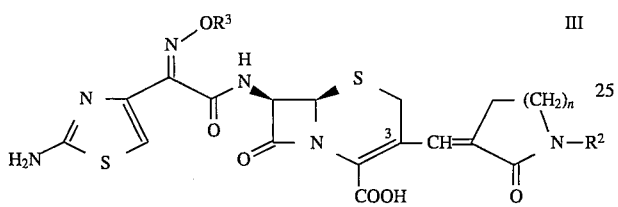

where $R^2$, $R^3$ and n are as defined above, as well as readily hydrolyzable esters thereof, pharmaceutically acceptable salts of said compounds and hydrates of the compounds thereof and of their esters and salts.

In formula III $R^3$ is preferably hydrogen, lower alkyl, cycloalkyl or $C(R^7R^8)CO_2R^9$, particularly hydrogen.

Preferred compounds of formula I and III are such where $R^2$ is hydrogen, cycloalkyl, lower alkyl which is unsubstituted or substituted with halogen, lower alkoxy or phenyl which is unsubstituted or substituted with at least one of lower alkoxy or halogen.

Further preferred compounds of formula I and III are such where $R^2$ is any of phenyl, 4-methoxyphenyl, 2,2,2-trifluoroethyl, 2-fluoroethyl, cyclopropyl, 3-pyridinyl, allyl, cyanomethyl, cyclopropylmethyl, 2-propynyl and 2-pyrazinyl.

Also preferred compounds of formulas I and III are where n is 1.

Other embodiments of the compounds of formula I are those where n is 0 or 2. Additional embodiments of the compounds of formula I also include where $R^2$ is lower alkyl-Q-, where Q is —CO— or —$SO_2$—. Other embodiments of the compounds of formula I include where $R^2$ is propargyl (2-propynyl), cyanomethyl, cyanoethyl or cyclopropylmethyl. Additional embodiments of the compounds of formula I also include where $R^2$ is 6-methoxy-pyridin-3-yl, 5-methyl-isoxazol-3-yl, 2-oxo-oxazolidin- 3-yl or 1,1-dioxo-tetrahydrothien-3-yl.

Preferred compounds of formula III include

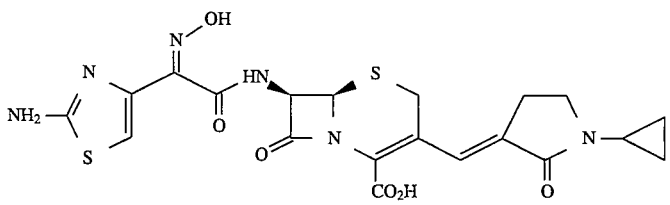

[6R-[3(E),6α,7β(Z)]]-7-[[(2-amino-4-thiazolyl)(hydroxyimino)acetyl]amino]-3-[[1-cyclopropyl-2-oxo-3-pyrrolidinylidene]methyl]-8-oxo-5-thia-1-azabicyclo[4.2.0]oct-2-ene carboxylic acid;

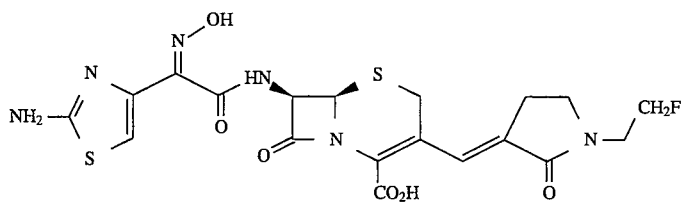

[6R-[3(E),6α,7β(Z)]]-7-[[(2-amino-4-thiazolyl)(hydroxyimino)acetyl]amino]-3-[[1-(2-fluoroethyl)-2-oxo-3-pyrrolidinylidene]-methyl]-8-oxo-5-thia-1-azabicyclo[4.2.0]oct-2-ene carboxylic acid;

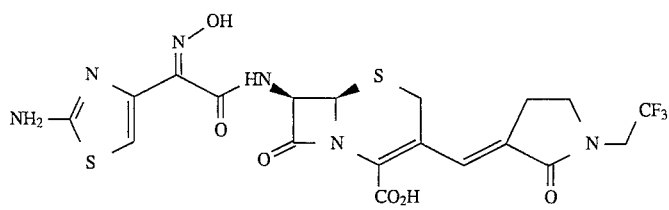

[6R-[3(E),6α,7β(Z)]]-7-[[(2-amino-4-thiazolyl)(hydroxyimino)acetyl]amino]-3-[[1-(2,2,2-trifluoroethyl)-2-oxo-3-pyrrolidinylidene]methyl]-8-oxo-5-thia-1-azabicyclo[4.2.0]oct-2-ene carboxylic acid;

nyl)-3-pyrrolidinylidene]methyl]-5-thia-1-azabicyclo[4.2.0]oct-2-ene-2-carboxylic acid;

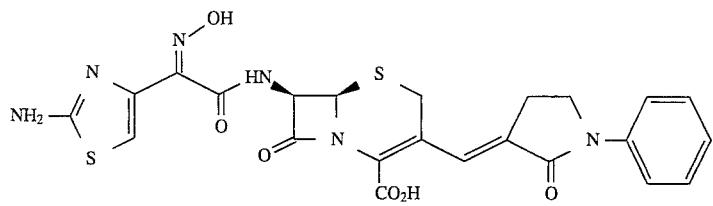

[6R-[3-(E), 6α,7β(Z)]]-7-[[(2-amino-4-thiazolyl)(hydroxyimino)acetyl]amino]-3-[[1-phenyl-2-oxo-3-pyrrolidinylidene]methyl]-8-oxo-5-thia-1-azabicyclo[4.2.0]oct-2-ene-2-carboxylic acid;

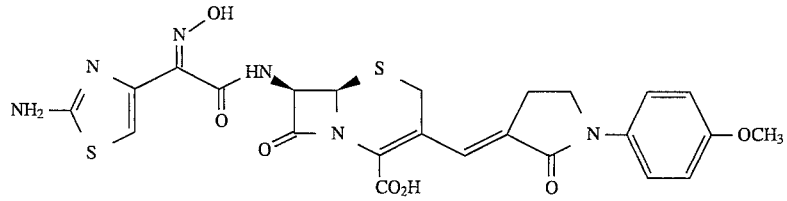

[6R-[3-(E),6α,7β(Z)]]-7-[[(2-amino-4-thiazolyl)(hydroxyimino)acetyl]amino]-3-[[1-(4-methoxyphenyl)-2-oxo-3-pyrrolidinylidene]methyl]-8-oxo-5-thia-1-azabicyclo[4.2.0]oct-2-ene-2-carboxylic acid;

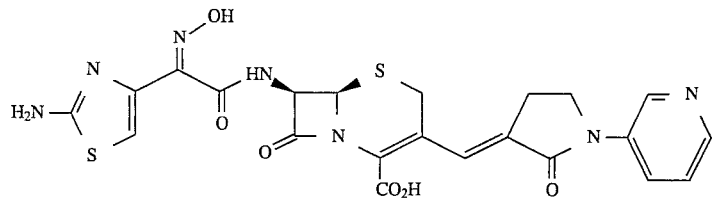

[6R-[3(E),6α,7β(Z)]]-7-[[(2-amino-4-thiazol-4-yl)(hydroxyimino)acetyl]amino]-8-oxo-3-[[2-oxo-1-(3-pyridi-

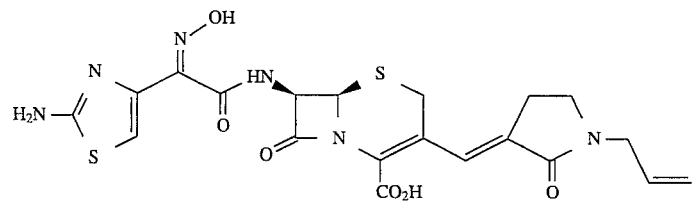

[6R-[3(E),6α,7β(Z)]]-3-[[1-allyl-2-oxo-3-pyrrolidi-
nylidene]methyl]-7-[[(2-amino- 4-thiazol-4-yl)(hydroxy-
imino)acetyl]amino]-8-oxo-5-thia-1-azabicyclo[4.2.0]oct-
2-ene-2-carboxylic acid;

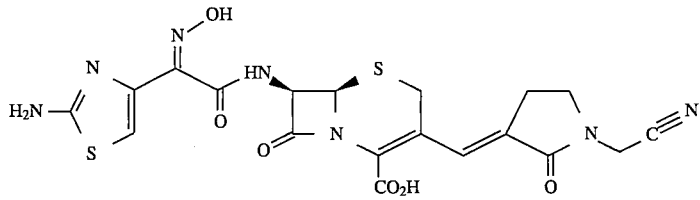

[6R-[3(E),6α,7β(Z)]]-7-[[(2-amino-4-thiazolyl)(hydroxy-
imino)acetyl]amino]-3-[[1-cyanomethyl-2-oxo-3-pyrrolidi-
nylidene]methyl]-8-oxo-5-thia- 1-azabicyclo[4.2.0]oct-2-
ene-2-carboxylic acid;

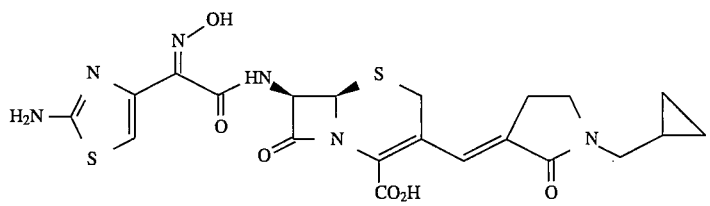

[6R-[3(E),6α,7β(Z)]]-7-[[(2-amino-4-thiazolyl)(hydroxy-
imino)acetyl]amino]-3-[[1-cyclopropylmethyl-2-oxo-3-pyr-
rolidinylidene]methyl]-8-oxo- 5-thia-1-azabicyclo[4.2.0]
oct-2-ene-2-carboxylic acid:

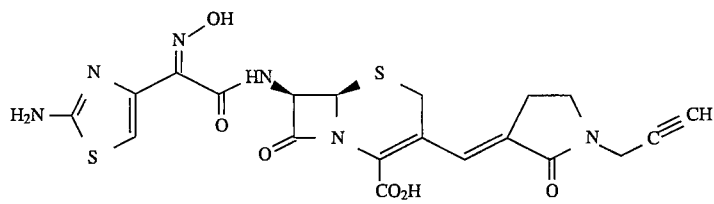

[6R-[3(E),6α,7β(Z)]]-7-[[(2-amino-4-thiazolyl)(hydroxy-
imino)acetyl]amino]-8-oxo-3-[[2-oxo-1-(2-propynyl)-3-
pyrrolidinylidene]methyl]-5-thia- 1-azabicyclo[4.2.0]-oct-
2-ene-2-carboxylic acid;

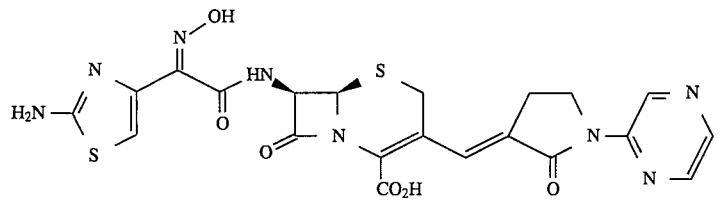

[6R-[3(E),6α,7β(Z)]]-7-[[(2-amino-4-thiazolyl)(hydroxy-
imino)acetyl]amino] -8-oxo-3-[[2-oxo-1-(2-pyrazinyl)-3-
pyrrolidinylidene]methyl]-5-thia- 1-azabicyclo[4.2.0]oct-2-
ene-2-carboxylic acid;
as well as readily hydrolyzable esters thereof, pharmaceu-
tically acceptable salts of said compounds and hydrates of
these compounds and of their esters and salts.

The invention also relates to pharmaceutical compositions
and methods of use of the above compounds.

DETAILED DESCRIPTION OF THE INVENTION

The present invention relates to cephalosporin derivatives of the general formula

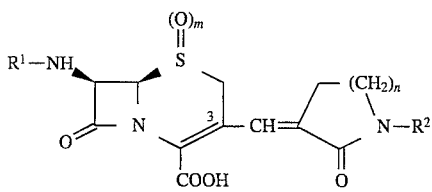

wherein $R^1$ is an acyl group derived from a carboxylic acid, hydrogen, or an amino protecting group;

$R^2$ is hydrogen, hydroxy, lower alkyl-$Q_p$-, cycloalkyl, lower alkoxy, lower alkenyl, cycloalkenyl, lower alkynyl, aralkyl-$Q_p$-, aryl-$Q_p$-, aryloxy, aralkoxy or a heterocyclic ring, the lower alkyl, cycloalkyl, lower alkoxy, lower alkenyl, cycloalkenyl, lower alkynyl, aralkyl, aryl, aryloxy, aralkoxy and the heterocyclic ring being unsubstituted or substituted with at least one group selected from carboxy, amino, nitro, oxo, cycloalkyl, cyano, lower alkyl, lower alkoxy, hydroxy, halogen, —$CONR^4R^5$, —$N(R^5)COOR^9$, $R^5CO$—, $R^5OCO$— or $R^5COO$— where $R^4$ is hydrogen, lower alkyl, or cycloalkyl; $R^5$ is hydrogen or lower alkyl; $R^9$ is hydrogen, lower alkyl, lower alkenyl or a carboxylic acid protecting group;

Q is —CO— or —$SO_2$—;

m is 0 or 1;

n is 0, 1 or 2;

p is 0 or 1;

as well as readily hydrolyzable esters thereof, pharmaceutically acceptable salts of said compounds and hydrates of the compounds of formula I and of their esters and salts.

In the above compounds of formula I the substituent in position 3 can be present in the E-form:

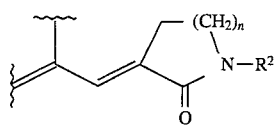

or in the Z-form:

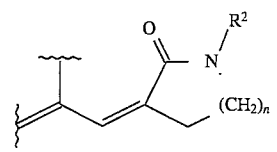

A subgroup of the compounds of the invention consists of compounds of the formula

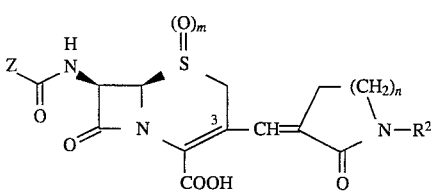

where Z is —C(X)=$CR_aR_b$[IIA], —CH(X)$NH_2$[IIB], or —C(X)=$NOR_3$ [IIC], where $R_a$ is hydrogen, lower alkyl or $CH_2CO_2R^4$, the lower alkyl being unsubstituted or substituted with at least one group selected from carboxy, amino, nitro, cyano, lower alkyl, lower alkoxy, hydroxy, halogen, —$CONR^4R^5$, —$N(R^5)COOR^9$, $R^5CO$—, $R^5OCO$—, or $R^5COO$—; $R_b$ is hydrogen or lower alkyl; X is aryl, cyclohexyl, 1,4-cyclohexadienyl, or a heterocyclic ring, the aryl, cyclohexyl, 1,4-cyclohexadienyl, and heterocyclic ring being unsubstituted or substituted with at least one group selected from carboxy, amino, nitro, cyano, lower alkyl, lower alkoxy, hydroxy, halogen, —$CONR^4R^5$, —$N(R^5)COOR^9$, $R^5CO$—, $R^5OCO$— or $R^5COO$—; $R^3$ is hydrogen, lower alkyl, cycloalkyl, aralkyl, $R^5CO$— or —$C(R^7R^8)CO_2R^{9'}$; $R^7$ and R8 are each independently hydrogen or lower alkyl or $R^7$ and $R^8$ taken together form a cycloalkyl group; and $R^2$, $R^4$, $R^5$, $R^9$ and n are as defined above, $R^{9'}$ is hydrogen or $R^9$, as well as readily hydrolyzable esters thereof, pharmaceutically acceptable salts of said compounds and hydrates of the compounds thereof and of their esters and salts.

Formulae IIA, IIB and IIC, as discussed above, have the following structures:

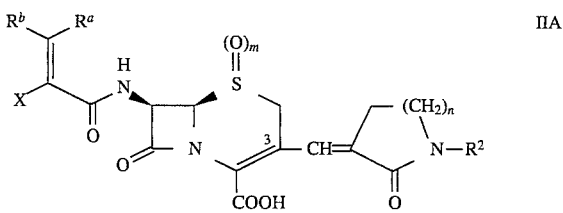

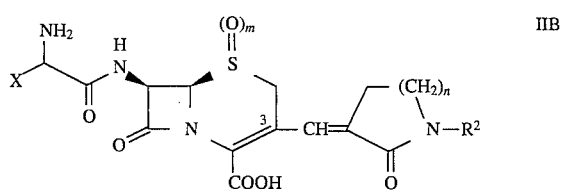

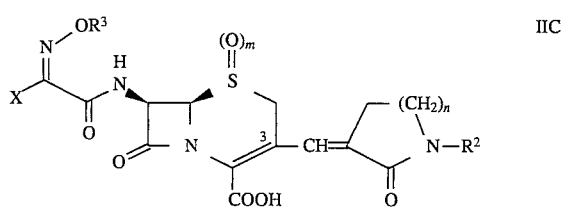

where X, $R^a$, $R^b$, $R^2$, $R^3$, m, and n are as defined above.

In formula IIC $R^3$ is preferably hydrogen.

A subgroup of the compounds of the invention consists of compounds of the formula

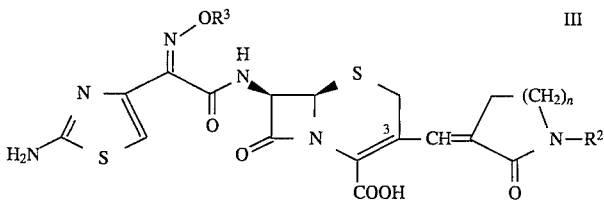

where $R^2$, $R^3$ and n are as defined above, as well as readily hydrolyzable esters thereof, pharmaceutically acceptable salts of said compounds and hydrates of the compounds thereof and of their esters and salts.

In formula III $R^3$ is preferably hydrogen, lower alkyl, cycloalkyl or $C(R^7R^8)CO_2R^9$, particularly hydrogen.

Preferred compounds of formula I and III are such where $R^2$ is hydrogen, cycloalkyl, lower alkyl which is unsubstituted or substituted with halogen, lower alkoxy or phenyl which is unsubstituted or substituted with at least one of lower alkoxy or halogen.

Further preferred compounds of formula I and III are such where $R^2$ is any of phenyl, 4-methoxyphenyl, 2,2,2-trifluoroethyl, 2-fluoroethyl, cyclopropyl, 3-pyridinyl, allyl, cyanomethyl, cyclopropylmethyl, 2-propynyl and 2-pyrazinyl.

Also preferred compounds of formulas I and III are where n is 1.

Other embodiments of the compounds of formula I are those where n is 0 or 2. Additional embodiments of the compounds of formula I also include where $R^2$ is lower alkyl-Q-, where Q is —CO— or —SO$_2$—. Other embodiments of the compounds of formula I include where $R^2$ is propargyl (2-propynyl), cyanomethyl, cyanoethyl or cyclopropylmethyl. Additional embodiments of the compounds of formula I also include where $R^2$ is 6-methoxy-pyridin-3-yl, 5-methyl-isoxazol-3-yl, 2-oxo-oxazolidin- 3-yl or 1,1-dioxo-tetrahydrothien-3-yl.

Preferred compounds of formula III include

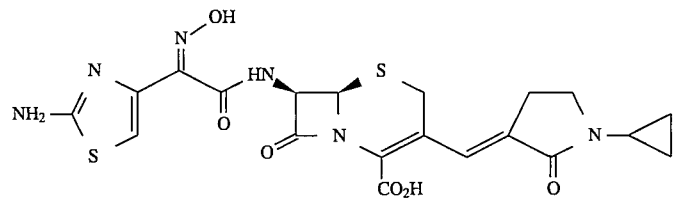

[6R-[3(E),6α,7β(Z)]]-7-[[(2-amino-4-thiazolyl)(hydroxyimino)acetyl]amino]-3-[[1-cyclopropyl-2-oxo-3-pyrrolidinylidene] methyl]-8-oxo-5-thia-1-azabicyclo[4.2.0]oct-2-ene carboxylic acid;

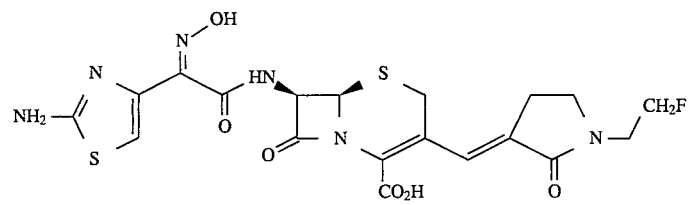

[6R-[3(E), 6α,7β(Z)]]-7-[[(2-amino-4-thiazolyl)(hydroxyimino)acetyl]amino]-3-[[1-(2-fluoroethyl)-2-oxo-3-pyrrolidinylidene] -methyl]-8-oxo-5-thia-1-azabicyclo[4.2.0]oct-2-ene carboxylic acid;

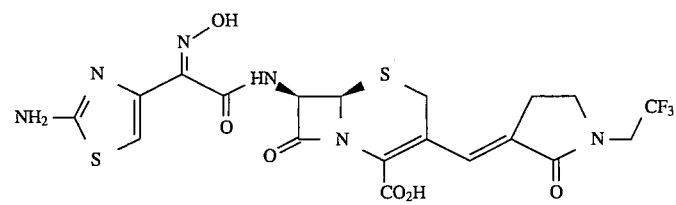

[6R-[3(E),6α,7β(Z)]]-7-[[(2-amino-4-thiazolyl)(hydroxyimino)acetyl]amino]-3-[[1-(2,2,2-trifluoroethyl)-2-oxo-3-pyrrolidinylidene]methyl]-8-oxo-5-thia-1-azabicyclo[4.2.0]oct-2-ene carboxylic acid;

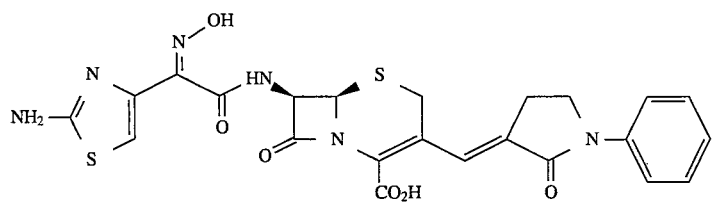

[6R-[3-(E),6α,7β(Z)]]-7-[[(2-amino-4-thiazolyl)(hydroxyimino)acetyl]amino]-3-[[1-phenyl-2-oxo-3-pyrrolidinylidene]methyl]-8-oxo-5-thia-1-azabicyclo[4.2.0]oct-2-ene-2-carboxylic acid;

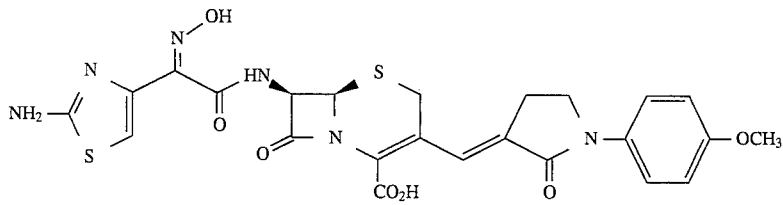

[6R-[3-(E),6α,7β(Z)]]-7-[[(2-amino-4-thiazolyl)(hydroxyimino)acetyl]amino]-3-[[1-(4-methoxyphenyl)-2-oxo-3-pyrrolidinylidene]methyl]-8-oxo-5-thia-1-azabicyclo[4.2.0]oct-2-ene- 2-carboxylic acid;

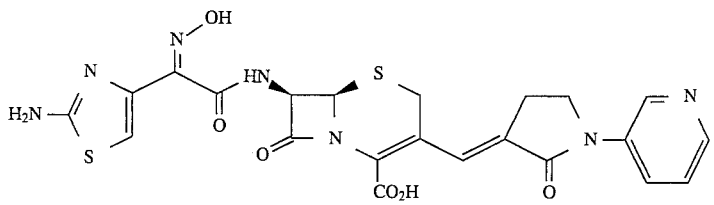

[6R -[3(E), 6α,7β(Z)]]-7-[[(2-amino-4-thiazol-4-yl)(hydroxyimino)acetyl]-amino]-8-oxo-3-[[2-oxo-1-(3-pyridinyl)-3-pyrrolidinylidene]methyl]-5-thia- 1-azabicyclo[4.2.0]oct-2-ene-2-carboxylic acid;

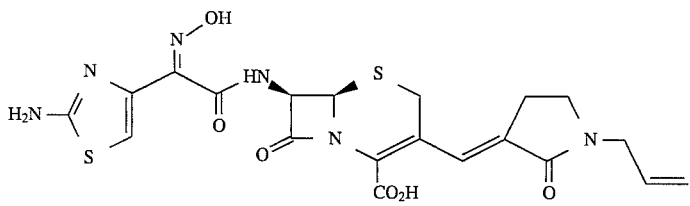

[6R-[3(E),6α,7β(Z)]]-3-[[1-allyl-2-oxo-3-pyrrolidinylidene]methyl]-7-[[(2-amino- 4-thiazol-4-yl)(hydroxyimino)acetyl]amino]-8-oxo-5-thia-1-azabicyclo[4.2.0]oct-2-ene-2-carboxylic acid;

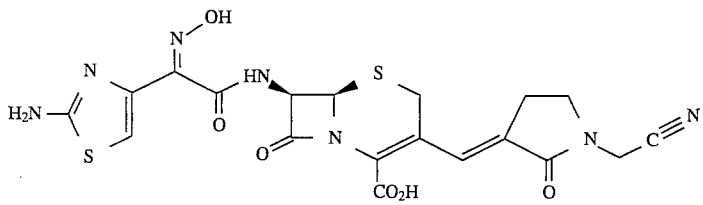

[6R-[3(E),6α,7β(Z)]]-7-[[(2-amino-4-thiazolyl)(hydroxyimino)acetyl]amino]-3-[[1-cyanomethyl-2-oxo-3-pyrrolidinylidene]methyl]-8-oxo-5-thia-1-azabicyclo[4.2.0]oct-2-ene-2-carboxylic acid;

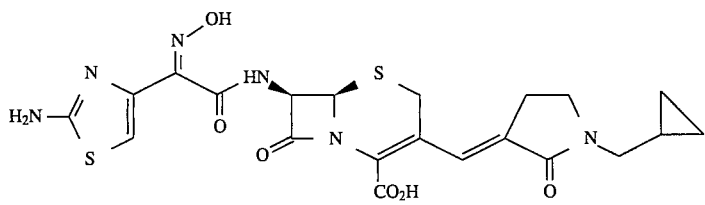

[6R-[3(E),6α,7β(Z)]]-7-[[(2-amino-4-thiazolyl)(hydroxy-imino)acetyl]amino]-3-[[1-cyclopropylmethyl-2-oxo-3-pyrrolidinylidene]methyl]-8-oxo- 5-thia-1-azabicyclo[4.2.0oct-2-ene-2-carboxylic acid;

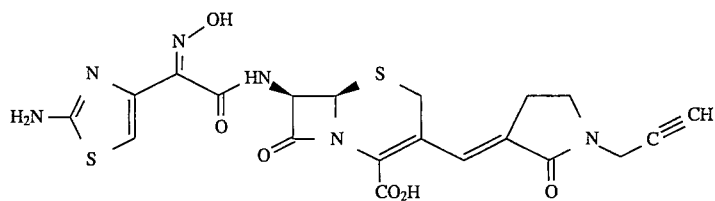

[6R-[3(E), 6α,7β(Z)]]-7-[[(2- amino-4-thiazolyl)(hydroxy-imino)acetyl]amino]-8-oxo-3-[[2-oxo-1-(2-propynyl)-3-pyrrolidinylidene]methyl]-5-thia- 1-azabicyclo[4.2.0]-oct-2-ene-2-carboxylic acid;

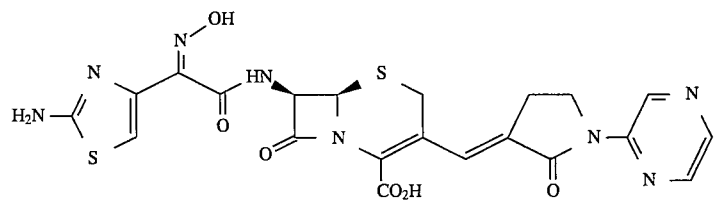

[6R-[3(E),6α,7β(Z)]]-7-[[(2-amino-4-thiazolyl)(hydroxy-imino)acetyl]amino] -8-oxo-3-[[2-oxo-1-(2-pyrazinyl)-3-pyrrolidinylidene]methyl]-5-thia- 1-azabicyclo[4.2.0]oct-2-ene-2-carboxylic acid;
as well as readily hydrolyzable esters thereof, pharmaceutically acceptable salts of said compounds and hydrates of these compounds and of their esters and salts.

The invention also relates to pharmaceutical compositions and methods of use of the above compounds.

As used herein, the terms "alkyl" and "lower alkyl" refer to both straight and branched chain saturated hydrocarbon groups having 1 to 8, and preferably 1 to 4, respectively, carbon atoms, for example, methyl, ethyl, n-propyl, isopropyl, tertiary butyl and the like.

As used herein, the term "lower alkoxy" refers to a straight or branched chain hydrocarbonoxy group wherein the "alkyl" portion is a lower alkyl group as defined above. Examples include methoxy, ethoxy, n-propoxy and the like.

The term "halogen" or "halo" used herein refers to all four forms, that is chlorine or chloro; bromine or bromo; iodine or iodo; and fluorine or fluoro, unless specified otherwise.

The term "acyl group derived from a carboxylic acid" used in conjunction with $R^1$ herein refers to all organic radicals derived from an organic carboxylic acid by removal of the hydroxyl group. Although the group $R^1$ may be any one of many acyl radicals, certain acyl groups are preferred, as described below.

Exemplary acyl groups are those groups which can be used to acylate β-lactam antibiotics, including 6-aminopenicillanic acid and derivatives and 7-aminocephalosphoranic acid and derivatives; see, for example, Cephalosporins and Penicillins, edited by Flynn, Academic Press (1972), Belgian patent 866,038, published Oct. 17, 1978, Belgian patent 867,994, published Dec. 11, 1978 and U.S. Pat. No. 3,971,778, issued Jul. 27, 1976. The portions of these references describing various acyl groups are incorporated herein by reference. The following list of acyl groups is presented to further exemplify the term "acyl", without intending to limit that term to only those groups set forth:

(a) Aliphatic acyl groups having the formula

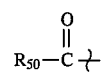

wherein $R_{50}$ is hydrogen, alkyl, cycloalkyl; alkoxy; alkenyl; cycloalkenyl; cyclohexadienyl; or alkyl or alkenyl substituted with one or more halogen, cyano, nitro, amino, mercapto, alkylthio, or cyanomethylthio groups.

(b) Aromatic acyl groups having the formula

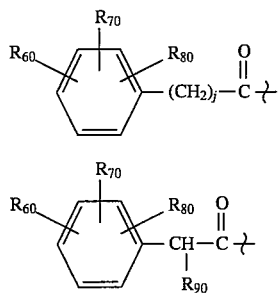

-continued

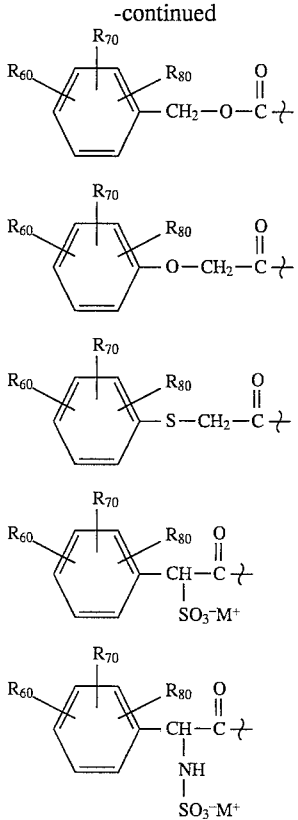

wherein j is 0, 1, 2 or 3; $R_{60}$, $R_{70}$, and $R_{80}$ each is independently hydrogen, halogen, hydroxyl, nitro, amino, cyano, carboxy, carbamoyl, trifluoromethyl, alkyl of 1 to 4 carbon atoms, alkoxy of 1 to 4 carbon atoms or aminomethyl; $R_{90}$ is amino, acylamino, hydroxyl, a carboxyl salt, protected carboxy such as benzyloxycarbonyl, formyloxy or azido; and M is a cation.

Preferred aromatic acyl groups include those having the formula

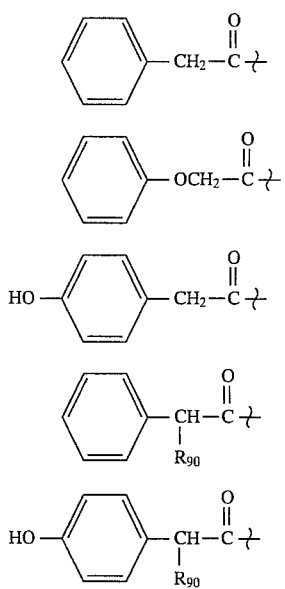

$R_{90}$ is preferably an amino group, a hydroxy group, or a carboxyl salt or sulfo salt.

Examples of other acyl groups suitable for the purposes of the present invention are hydroxysulfonyloxyphenylacetyl, sulfamoylphenylacetyl, (phenoxycarbonyl)phenylacetyl, (p-tolyloxycarbonyl)phenylacetyl, formyloxyphenylacetyl, carboxyphenyl-acetyl, formylaminophenylacetyl, benzyloxycarbonylphenylacetyl, 2-(N,N-dimethylsulfamoyl)-2-phenylacetyl, 2-amino-2-phenylacetyl etc.

(c) Heteroaromatic acyl groups having the formula

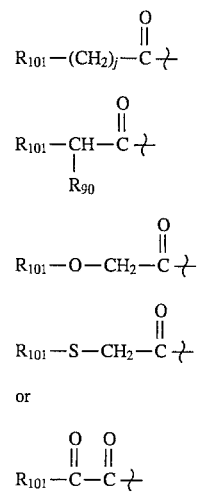

or

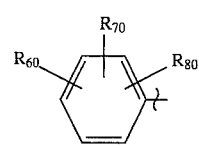

wherein j is 0, 1, 2 or 3; $R_{90}$ is as defined above; and $R_{101}$ is a heterocyclic ring or a heterocyclic ring which is fused together with a benzene ring.

Preferred heteroaromatic acyl groups included those groups of the above formulas wherein $R_{101}$ is 2-amino-4-thiazolyl, 2-amino-5-halo-4-thiazolyl, 4-aminopyridin-2-yl, 2-amino-1,3,4-thiadiazol-5-yl, 5-amino-1,2,4-thiadiazol-3-yl, 2-thienyl, 2-furanyl, 4-pyridinyl, 2,6-dichloro-4-pyridinyl, or 2-amino-4-benzothiazolyl.

(d) [[(4-Substituted-2,3-dioxo-1-piperazinyl)carbonyl]amino]acetyl groups having the formula

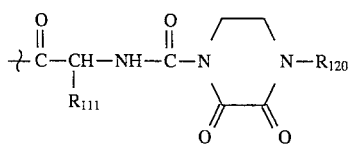

wherein $R_{111}$ is alkyl, hydroxyalkyl or an aromatic heterocyclic or carbocyclic group such as those of the formula

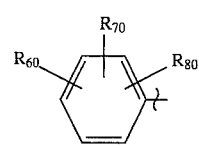

wherein $R_{60}$, $R_{70}$ and $R_{80}$ are as previously defined and heteroaromatics as included within the definition of $R_{101}$; and $R_{120}$ is alkyl, substituted alkyl (wherein the alkyl group is substituted with one or more halogen, cyano, nitro, amino or mercapto groups), e.g., 4-lower alkyl (preferably ethyl or methyl)-2,3-dioxo-1-piperazinecarbonyl-D-phenylglycyl.

(e) Oxyimino-arylacetyl groups having the formula

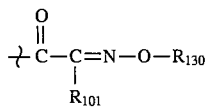

wherein $R_{101}$ is as defined above and $R_{130}$ is hydrogen, lower alkyl, lower alkanoyl or $C_3$-$C_7$ cycloalkyl, or substituted lower alkyl wherein the alkyl group is substituted with one or more halogen, cyano, nitro, amino, mercapto, lower alkylthio, aromatic group (as defined by $R_{111}$), carboxyl (including salts thereof), carbamoyl, lower alkoxycarbonyl, phenylmethoxycarbonyl, diphenylmethoxycarbonyl, hydroxyalkoxyphosphinyl, dihydroxyphosphinyl, hydroxy(phenyl-methoxy)phosphinyl, di-lower alkoxyphosphinyl substituents, carboxyl lower alkyl or carboxyl-$C_3$-$C_7$-cycloalkyl.

Examples of the

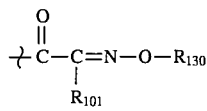

grouping are [2-[(chloroacetyl)amino]-4-thiazolyl](methoxyimino)-acetyl, (2-amino-4-thiazolyl)(1-methylethoxyimino)acetyl, (2-amino-4-thiazolyl)(methoxyimino)acetyl, (2-furyl)(methoxyimino)acetyl, (4-hydroxyphenyl)(methoxyimino)acetyl, (methoxyimino)-(phenyl)acetyl, (hydroxyimino)(phenyl)acetyl, (hydroxyimino)(2-thienyl)acetyl, [[(dichloroacetyl)oxy]imino](2-thienyl)acetyl, [5-chloro-2-[(chloroacetyl)amino]-4-thiazolyl](methoxyimino)acetyl, (2-amino-5-chloro-4-thiazolyl)(methoxyimino)acetyl, [[[1-(1,1-dimethylethoxy)carbonyl]-1-methylethoxy]imino](2-amino-4-thiazolyl)acetyl, [[[1-(1,1-dimethylethoxy)carbonyl]-1-methyl]ethoxy]imino][[2-(triphenylmethyl)amino]-4-thiazolyl]acetyl, [[2-(chloroacetyl)amino]-4-thiazolyl][[[[(4-nitrophenyl)methoxy]carbonyl]methoxy]imino]acetyl, (2-amino-4-thiazolyl)[(carboxymethoxy)imino]acetyl, (2-amino-4-thiazolyl)[1-carboxy-(1-methylethoxy)imino]acetyl, and (2-amino-4-thiazolyl)[[(amino-carbonyl)methoxy]imino]acetyl. Particularly preferred groups are (2-amino-4-thiazolyl)(hydroxyimino)acetyl, (2-amino-1,3,4-thiadiazol-5-yl)(hydroxyimino)acetyl and (5-amino-1,2,4-thiadiazol-3-yl)(hydroxyimino)acetyl.

(f) (Acylamino)acetyl groups having the formula

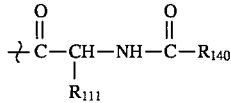

wherein $R_{111}$ is as defined above and $R_{140}$ is

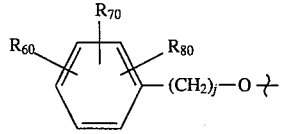

(where $R_{60}$, $R_{70}$, $R_{80}$ and j are as previously defined), hydrogen, lower alkyl, substituted lower alkyl, amino, alkylamino, dialkylamino, (cyanoalkyl)amino, hydrazino, alkyl hydrazino, aryl hydrazino and acyl hydrazino.

Preferred (acylamino)acetyl groups of the above formula include those groups wherein $R_{140}$ is amino, or acylamino. Also preferred are those groups wherein $R_{111}$ is phenyl or 2-thienyl.

(g) Substituted oxyiminoacetyl groups having the formula

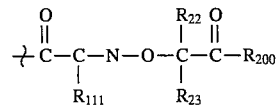

wherein $R_{111}$ is as defined above, and $R_{22}$ and $R_{23}$ are independently selected from the group consisting of hydrogen and lower alkyl, or $R_{22}$ and $R_{23}$ taken together with the carbon atom to which they are attached form a $C_3$-$C_7$ carbocyclic ring, for example, cyclopropyl, cyclobutyl or cyclopentyl, and $R_{200}$ is $R_{140}$ or hydroxy.

Preferred substituted oxyiminoacetyl groups of the above formula include those groups wherein $R_{200}$ is hydroxy or amino. Also preferred are those groups wherein $R_{111}$ is 2-amino-4-thiazolyl.

(h) [[[3-Substituted-2-oxo-1-imidazolindinyl]carbonyl]amino]acetyl groups having the formula

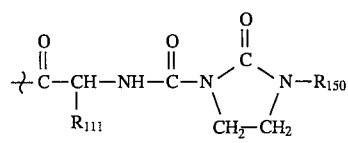

wherein $R_{111}$ is as defined above and $R_{150}$ is hydrogen, alkylsulfonyl, arylmethyleneamino (i.e., $-N=CHR_{111}$ wherein $R_{111}$
is as defined above),

(wherein $R_{160}$ is hydrogen, alkyl or halogen substituted alkyl), aromatic group (as defined by $R_{111}$ above), alkyl or substituted alkyl (wherein the alkyl group is substituted with one or more halogen, cyano, nitro, amino or mercapto groups).

Preferred [[[3-substituted-2-oxo-1-imidazolindyl]carbonyl]amino]acetyl groups of the above formula include those wherein $R_{111}$ is phenyl or 2-thienyl. Also preferred are those groups wherein $R_{150}$ is hydrogen, methylsulfonyl, phenylmethyleneamino or 2-furylmethyleneamino.

By the term "aryl" is meant a radical derived from an aromatic hydrocarbon by the elimination of one atom of hydrogen and can be substituted or unsubstituted. The aromatic hydrocarbon can be mononuclear or polynuclear. Examples of aryl of the mononuclear type include phenyl, tolyl, xylyl, mesityl, cumenyl, and the like. Examples of aryl of the polynuclear type include naphthyl, anthryl, phenanthryl, and the like. The aryl group can have at least one substituent selected from, as for example, halogen, hydroxy, cyano, carboxy, nitro, amino, lower alkyl, lower alkoxy, such as in 2,4-difluorophenyl, 4-carboxyphenyl, 4-nitrophenyl, 4-aminophenyl, 4-methoxyphenyl.

By the term "lower alkanoyl" or "alkanoyl" as utilized herein is intended a moiety of the formula

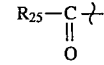

wherein $R_{25}$ is H or $C_1$ to $C_6$ lower alkanoic acid, e.g., acetyl, formyl, propionyl, butyryl and the like.

By the term "substituted phenyl" is meant phenyl mono or disubstituted by halogen, lower alkyl, amino, nitro or trifluoromethyl.

By the term "substituted alkyl" is meant a "lower alkyl" or "alkyl" moiety substituted by, for example, halogen, amino, cyano, carboxy etc.; such as in carboxymethyl, 2-fluoroacetyl, 2,2,2-trifluoroethyl.

By the term "aralkyl" is meant an alkyl group containing an aryl group. It is a hydrocarbon group having both aromatic and aliphatic structures, that is, a hydrocarbon group in which a lower alkyl hydrogen atom is substituted by a monocyclic aryl group, e.g., phenyl, tolyl, etc.

As used herein "pharmaceutically acceptable salts" or "cation" refer to those pharmaceutically acceptable salts or cations commonly used in the antibacterial field. Examples of pharmaceutically acceptable salts or cations useful in this invention include salts or cations derived from metals, the ammonium salt, quaternary ammonium salts derived from organic bases and amino acid salts. Examples of preferred metal salts or cations are those derived from the alkali metals, for example, lithium ($Li^+$), sodium ($Na^+$) and potassium ($K^+$), and from the alkaline earth metals, for example, calcium ($Ca^{++}$) and magnesium ($Mg^{++}$), although cationic forms of other metals, such as iron ($Fe^{++}$ or $Fe^{+++}$), aluminium ($Al^{+++}$), and zinc ($Zn^{++}$) are within the scope of this invention. Examples of quaternary ammonium salts derived from organic bases include tetramethylammonium ($N^+(CH_3)_4$), tetraethylammonium ($N^+(CH_2CH_3)_4$), benzyltrimethylammonium ($N^+(C_6H_5CH_2)(CH_3)_3$), phenyltriethylammonium ($N^+(C_6H_5)(CH_2CH_3)_3$), and the like, etc. Those salts derived from amines include salts with N-ethylpiperidine, procaine, dibenzylamine, N,N'-dibenzylethylenediamine, alkylamines or dialkylamines as well as salts with amino acids such as, for example, salts with arginine or lysine.

As used herein, "heterocyclic ring" refers to an unsaturated or saturated, unsubstituted or substituted 5-, 6-, or 7-membered heterocyclic ring containing at least one hetero atom selected from the group consisting of oxygen, nitrogen, or sulfur. Exemplary heterocyclic rings include, but are not limited to, for example, the following groups: pyridyl, pyrazinyl, piperidyl, piperidino, N-oxido-pyridyl, pyrimidyl, piperazinyl, pyrrolidinyl, pyridazinyl, N-oxide-pyridazinyl, pyrazolyl, triazinyl, imidazolyl, thiazolyl, 1,2,3-thiadiazolyl, 1,2,4-thiadiazolyl, 1,3,4-thiadiazolyl, 1,2,5-thiadiazolyl, 1,2,3-oxadiazolyl, 1,2,4-oxadiazolyl, 1,3,4-oxadiazolyl, 1,2,5-oxadiazolyl, 1,2,3-triazolyl, 1,2,4-triazolyl, 1H-tetrazolyl, 2H-tetrazolyl; thienyl, furyl, hexamethyleneiminyl, oxepanyl, 1H-azepinyl, thiophenyl, tetrahydrothiophenyl, 3H-1,2,3-oxathiazolyl, 1,2,3-oxadiazolyl, 1,2,5-oxadithiolyl, isoxazolyl, isothiazolyl, 4H-1,2,4-oxadiazinyl, 1,2,5-oxathiazinyl, 1,2,3,5-oxathiadiazinyl, 1,3,4-thiadiazepinyl, 1,2,5,6-oxatriazepinyl, 1,6,3,4-dioxadithiopanyl, oxazolidinyl, tetrahydrothienyl, etc., and others. Substituents for the heterocyclic ring include, for example, lower alkyls such as methyl, ethyl, propyl, etc., lower alkoxys such as methoxy, ethoxy, etc., halogens such as fluorine, chlorine, bromine, etc., halogen substituted alkyls such as trifluoromethyl, trichloroethyl, etc., amino, mercapto, hydroxyl, carbamoyl, or carboxyl group, etc., and others. A further substituent is oxo, such as in 2-oxo-oxazolidin-3-yl, 1,1-dioxo-tetrahydrothien-3-yl. Other examples of substituted heterocycles are 6-methoxy-pyridin-3-yl, and 5-methyl-isoxazol-3-yl.

By the term "cycloalkyl" is meant a 3-7 membered saturated carbocyclic moiety, e.g., cyclopropyl, cyclobutyl, cyclohexyl, etc.

As used herein, "alkenyl" and "lower alkenyl" refer to unsubstituted or substituted hydrocarbon chain radical having from 2 to 8 carbon atoms, preferably from 2 to 4 carbon atoms, and having at least one olefinic double bond, e.g. allyl, vinyl etc.

By the term "carbocyclic ring (or moiety)" is meant an unsubstituted or substituted, saturated, unsaturated or aromatic, hydrocarbon ring radical. Carbocyclic rings are monocyclic or are fused, bridged or spiro polycyclic ring systems. Monocyclic rings contain from 3 to 9 atoms, preferably 3 to 6 atoms. Polycyclic rings contain from 7 to 17 atoms, preferably from 7 to 13 atoms.

As used herein, "cycloalkenyl" refers to a carbocyclic ring radical having at least one olefinic double bond.

As used herein, "aralkyloxy" is an oxygen radical having an aralkyl substituent.

As used herein, "lower alkynyl" refers to unsubstituted or substituted hydrocarbon chain radical having from 2 to 8 carbon atoms, preferably 2 to 4 carbon atoms, and having at least one olefinic triple bond.

As used herein, "aryloxy" is an oxygen radical having an aryl substituent (i.e., -O-aryl).

As used herein, "acyloxy" is an oxygen radical having an acyl substituent (i.e., -O-acyl); for example, —O—C(=O)-alkyl.

The term "amino protecting groups" refers to protecting groups conventionally used to replace an acidic proton of an amino group. Examples of such groups are described in Green, T., Protective Groups in Organic Synthesis, Chapter 7, John Wiley and Sons, Inc. (1981), pp. 218–287, herein incorporated by reference. These examples include the carbamates of methyl, cyclopropylmethyl, 1-methyl-1-cyclopropylmethyl, diisopropylmethyl, 9-fluorenylmethyl, 9-(2-sulfo)fluorenylmethyl, 2-furanylmethyl, 2,2,2-trichloroethyl, 2-haloethyl, 2-iodoethyl, 2-trimethylsilylethyl, 2-methylthioethyl, 2-methylsulfonylethyl, 2-(p-toluenesulfonyl)ethyl, 2-phosphonioethyl, 1,1-dimethyl- 3-(N,N-dimethylcarboxamido)propyl, 1,1-diphenyl-3-(N,N-diethylamino)propyl, 1-methyl-1-(1-adamantyl)ethyl, 1-methyl-1-phenylethyl, 1-methyl-1-(3,5-dimethoxyphenyl)ethyl, 1-methyl-1-(4-biphenylyl)ethyl, 1-methyl-1-(p-phenylazophenyl)ethyl, 1,1-dimethyl- 2-haloethyl, 1,1-dimethyl-2,2,2-trichloroethyl, 1,1-diemthyl-2-cyanoethyl, isobutyl, t-butyl, t-amyl, cyclobutyl, 1-methylcyclobutyl, cyclopentyl, cyclohexyl, 1-methylcyclohexyl, 1-adamantyl, isobornyl, vinyl, allyl, cinnamyl, phenyl, 2,4, 6-tri-t-butylphenyl, m-nitrophenyl, S-phenyl, 8-quinolyl, N-hydroxypiperidinyl, 4-(1,4-dimethylpiperdinyl), 4,5-diphenyl-3-oxazolin-2-one, benzyl, 2,4,6-trimethylbenzyl, p-methoxybenzyl, 3,5-dimethoxybenzyl, p-decyloxybenzyl, p-nitro-benzyl, o-nitrobenzyl, 3,4-dimethoxy-6-nitrobenzyl, p-bromobenzyl, chlorobenzyl, 2,4-dichlorobenzyl, p-cyanobenzyl, o-(N,N-dimethylcarboxamide)benzyl, m-chloro-p-acyloxybenzyl, p-(dihydroxyboryl)benzyl, p-(phenylazo)benzyl, p-(p'-methoxyphenylazo)benzyl, 5-benzisoxazolylmethyl, 9-anthrylmethyl, diphenylmethyl, phenyl(o-nitrophenyl)methyl, di(2-pyridyl)methyl, 1-methyl-1-(4-pyridyl)ethyl, isonicotinyl, S-benzyl, N'-piperidinylcarbonyl, N'-p-touluenesulfonylaminocarbonyl, N'-phenylaminothiocarbonyl; the amides of N-formyl, N-acetyl, N-chloroacetyl, N-dichloroacetyl, N-trichloroacetyl, N-trifluoroacetyl, N-o-nitrophenylacetyl, N-o-nitrophenoxyacetyl, N-acetoacetyl, N-acetylpyridinium, N-(N'-dithiobenzyloxycarbonylamino)acetyl, N-3-phenylpropionyl, N-3-(p-hydroxyphenyl)propionyl, N-3-(o-nitrophenyl)propionyl, N-2-methyl-2-(o-nitrophenoxy-propionyl, N- 2-methyl-2-(o-phenylazophenoxy)propionyl, N-4-chlorobutyryl, N-isobutyryl, N-o-nitrocinnamoyl, N-picolinoyl, N-(N'acetylmethionyl), N-(N'benzoyl-phenylalkanyl), N-benzoyl, N-p-phenylbenzoyl, N-p-methoxybenzoyl, N-o-nitrobenzoyl, N-o-(benzoyloxymethyl)benzoyl, N-p-P-benzoyl; the cyclic imides of N-phthaloyl, N-2,3-diphenylmaleoyl, N-dithiasuccinoyl; N-allyl, N-allyloxycarbonyl, N-phenacyl, N-3-acetoxypropyl, N-(4-nitro-1-cyclohexyl-2-oxo-3-pyrrolin-3-yl), quaternary ammonium salts, N-methoxymethyl, N-2-chloroethoxymethyl, N-benzyloxymethyl, N-pivaloyloxymethyl, N-[1-(alkoxycarbonylamino)-2,2,2-trifluoro]ethyl, N-[1-trifluoromethyl-1-(p-chlorophenoxymethoxy)-2,2,2-trifluoro]ethyl, N-2-tetrahydro-pyranyl, N-2,4-dinitrophenyl, N-benzyl, N-3, 4-dimethoxybenzyl, N-o-nitrobenzyl, N-di(p-methoxyphenyl)methyl, N-triphenylmethyl, N-(p-methoxyphenyl)diphenylmethyl, N-diphenyl-4-pyridylmethyl, M-2-picolyl N'-oxide, N-5-dibenzosuberyl, N-(N',N'-dimethylaminomethylene), N,N'-isopropylidene, N-benzylidene, N-p-methoxy-benzyidene, N-p-nitrobenzylidene, N-salicylidene, N-5-chlorosalicylidene, N-diphenylmethylene, N-(5-chloro-2-hydroxyphenyl)phenyl-methylene, N-(acylvinyl), N-(5,5-dimethyl-3-oxo- 1-cyclohexenyl), N-borane, N-[phenyl-(pentacarbonylchromium or -tungsten)]carbonyl, N-copper or N-zinc chelate, N-nitro, N-nitroso, N-oxide, N-diphenylphosphinyl, N-dimethylthiophosphinyl, N-diphenylthiophosphinyl, N-diethyl phosphoryl, N-dibenzyl phosphoryl, N-diphenyl phosphoryl, N-trimethylsilyl, N-benzenesulfenyl, N-o-nitrobenzenesulfenyl, N-2,4-dinitrobenzenesulfenyl, N-2-nitro-4-methoxybenzenesulfenyl, N-triphenylmethylsulfenyl, N-benzenesulfonyl, N-p-methoxybenzenesulfonyl, N-2,4,6-trimethylbenzensulfonyl, N-toluenesulfonyl, N-benzylsulfonyl, N-p-methylbenzylsulfonyl, N-trifluoromethylsulfonyl, N-phenacylsulfonyl. Other amino protecting groups include t-butoxycarbonyl (abbreviated BOC), benzyloxycarbonyl and allyloxycarbonyl.

The term "carboxylic acid protecting group" refers to protecting groups conventionally used to replace the acidic proton of a carboxylic acid. Examples of such groups are described in Greene, T., Protective Groups in Organic Synthesis, Chapter 5, pp. 152–192 (John Wiley and Sons, Inc. 1981), incorporated herein by reference. These examples include methoxymethyl, methylthiomethyl, tetrahydropyranyl, tetrahydrofuranyl, methoxyethoxymethyl, benzyloxymethyl, phenacyl, p-bromophenacyl, α-methylphenacyl, p-methoxyphenacyl, diacylmethyl, N-phthalimidomethyl, ethyl, 2,2,2-trichloroethyl, 2-haloethyl, ω-chloroalkyl, 2-(trimethylsilyl)ethyl, 2-methylthioethyl, 2-(p-nitrophenylsulfenyl)ethyl, 2-(p-toluenesulfonyl)ethyl, 1-methyl-1-phenylethyl, t-butyl, cyclopentyl, cyclohexyl, allyl, cinnamyl, phenyl, p-methylthiophenyl, benzyl, triphenylmethyl, diphenylmethyl, bis(o-nitrophenyl)methyl, 9-anthrylmethyl, 2-(9,10-dioxo)anthrylmethyl, 5-dibenzosuberyl, 2,4,6-trimethylbenzyl, p-bromobenzyl, o-nitrobenzyl, p-nitrobenzyl, p-methoxybenzyl, piperonyl, 4-picolyl, trimethylsilyl, triethylsilyl, t-butyldimethylsilyl, i-propyl-dimethylsilyl, phenyldimethylsilyl, S-t-butyl, S-phenyl, S-2-pyridyl, N-hydroxypiperidinyl, N-hydroxysuccinimidoyl, N-hydroxyphthalimidoyl, N-hydroxybenzo-triazolyl, O-acyl oximes, 2,4-dinitrophenylsulfenyl, 2-alkyl- 1,3-oxazolines, 4-alkyl-5-oxo-1,3-oxazolidines, 5-alkyl-4-oxo-1, 3-dioxolanes, triethylstannyl, tri-n-butylstannyl; the amides or hydrazides of N,N-dimethylamino, pyrrolidinyl, piperidinyl, o-nitrophenyl, 7-nitroindolyl, 8-nitrotetra-hydroquinolyl, p-benzenesulfonamide, hydrazides, N-phenylhydrazide, N,N'-diisopropylhydrazide. Preferred are benzyhydryl, t-butyl, p-nitrobenzyl, p-methoxybenzyl and allyl.

As readily hydrolyzable esters of the compounds of formula I there are to be understood compounds of formula I, the carboxy group(s) of which (for example, the 2-carboxy group) is/are present in the form of readily hydrolyzable ester groups. Examples of such esters, which can be of the conventional type, are the lower alkanoyloxy-alkyl esters (e.g., the acetoxymethyl, pivaloyloxymethyl, 1-acetoxyethyl and 1-pivaloyloxyethyl ester), the lower alkoxycarbonyloxyalkyl esters (e.g., the methoxycarbonyloxymethyl, 1-ethoxycarbonyloxyethyl and 1-isopropoxycarbonyloxyethyl ester), the lactonyl esters (e.g., the phthalidyl and thiophthalidyl ester), the lower alkoxymethyl esters (e.g., the methoxymethyl ester) and the lower alkanoylaminomethyl esters (e.g., the acetamidomethyl ester). Other esters (e.g., the benzyl and cyanomethyl esters) can also be used. Other examples of such esters are the following: (2,2-dimethyl-1-oxopropoxy)methyl ester; 2-[(2-methylpropoxy)carbonyl]-2-pentenyl ester; 1-[[(1-methylethoxy)carbonyl]oxy] ethyl ester; 1-(acetyloxy)ethyl ester; (5-methyl-2-oxo- 1,3-dioxol-4-yl) methyl ester; 1-[[(cyclohexyloxy)carbonyl]oxy] ethyl ester; and 3,3-dimethyl-2-oxobutyl ester. It will be appreciated by those of ordinary skill in the art that the readily hydrolyzable esters of the compounds of the present invention can be formed at various points on the compound, for example, at the carboxy group in position 1 and at a carboxy group —COOR$^{9'}$.

Examples of salts of the compounds of formula I are defined under "pharmaceutically acceptable salts" above.

The compounds of formula I as well as their salts and readily hydrolyzable esters can be hydrated. The hydration can be effected in the course of the manufacturing process or can occur gradually as a result of hygroscopic properties of an initially anhydrous product.

The compounds of the present invention are useful as antibiotics having potent and broad antibacterial activity. They also possess good oral absorption properties.

The products in accordance with the invention can be used as medicaments, for example, in the form of pharmaceutical preparations for enteral (oral) administration. The products in accordance with the invention can be administered, for example, perorally, such as in the form of tablets, coated tablets, dragees, hard and soft gelatine capsules, solutions, emulsions or suspensions, or rectally, such as in the form of suppositories.

Pharmaceutical compositions containing these compounds can be prepared using conventional procedures familiar to those skilled in the art, such as by combining the ingredients into a dosage form together with suitable, non-toxic, inert, therapeutically compatible solid or liquid carrier materials and, if desired, the usual pharmaceutical adjuvants.

It is contemplated that the compounds are ultimately embodied into compositions of suitable oral or parenteral dosage forms. The compositions of this invention can contain, as optional ingredients, any of the various adjuvants which are used ordinarily in the production of pharmaceutical preparations. Thus, for example, in formulating the present compositions into the desired oral dosage forms, one may use, as optional ingredients, fillers, such as coprecipitated aluminum hydroxide-calcium carbonate, dicalcium phosphate or lactose; disintegrating agents, such as maize starch; and lubricating agents, such as talc, calcium stearate, and the like. It should be fully understood, however, that the optional ingredients herein named are given by way of example only and that the invention is not restricted to the use hereof. Other such adjuvants, which are well known in the art, can be employed in carrying out this invention.

Suitable as such carrier materials are not only inorganic, but also organic carrier materials. Thus, for tablets, coated tablets, dragees and hard gelatine capsules there can be used, for example, lactose, maize starch or derivatives thereof, talc, stearic acid or its salts. Suitable carriers for soft gelatine capsules are, for example, vegetable oils, waxes, fats and semi-solid and liquid polyols (depending on the nature of the active substance; no carriers are, however, required in the case of soft gelatine capsules). Suitable carrier materials for the preparation of solutions and syrups are, for example, water, polyols, saccharose, invert sugar and glucose. Suitable carrier materials for suppositiories are, for example, natural or hardened oils, waxes, fats and semi-liquid or liquid polyols.

As pharmaceutical adjuvants there are contemplated the usual preservatives, solubilizers, stabilizers, wetting agents, emulsifiers, sweeteners, colorants, flavorants, salts for varying the osmotic pressure, buffers, coating agents and antioxidants.

The compounds of formula I and their salts, or hydrates, can preferably be used for parenteral administration, and for this purpose are preferably made into preparations as lyophilisates or dry powders for dilution with customary agents, such as water or isotonic common salt solution.

Depending on the nature of the pharmacologically active compound the pharmaceutical preparations can contain the compound for the prevention and treatment of infectious diseases in mammals, human and non-human, a daily dosage of about 10 mg to about 4000 mg, especially about 50 mg to about 3000 mg, is usual, with those of ordinary skill in the art appreciating that the dosage will depend also upon the age, conditions of the mammals, and the kind of diseases being prevented or treated. The daily dosage can be administered in a single dose or can be divided over several doses. An average single dose of about 50 mg, 100 mg, 250 mg, 500 mg, 1000 mg, and 2000 mg can be contemplated.

Representative compounds of the present invention were tested.

In vitro activity was determined by minimum inhibitory concentration in a microorganism spectum by the agar dilution method in Mueller Hinton agar.

The following compounds were tested

A: [6R-[3(E),6α,7β(Z)]]-7-[[(2-Amino-4-thiazolyl)[(carboxymethoxy)imino]acetyl]amino]-3-[[1-(2,2,2-trifluoroethyl)-2-oxo-3-pyrrolidinylidene]methyl]-8-oxo-5-thia-1-aza-bicyclo[4.2.0]oct-2-ene- 2-carboxylic acid disodium salt

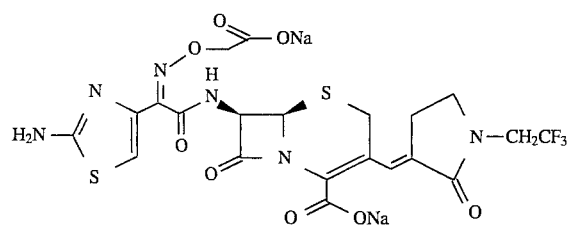

B: [6R-[3(E),6α,7β(Z)]]-7-[[(2-Amino-4-thiazolyl)[(carboxymethoxy)imino]acetyl]amino]-3-[[1-(2-fluoroethyl)-2-oxo-3-pyrrolidinylidene]methyl]-8-oxo-5-thia-1-azabicyclo[4.2.0]oct-2-ene- 2-carboxylic acid disodium salt

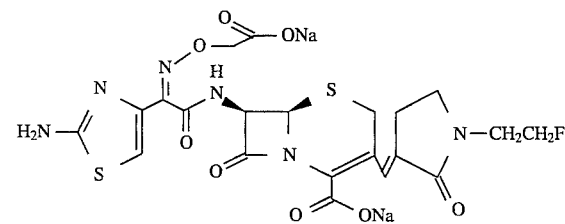

C: [6R-[3(E),6α,7β(Z)]]-7-[[(2-Amino-4-thiazolyl)[(carboxymethoxy)imino]acetyl]amino]-3-[[1-cyclopropyl-2-oxo-3-pyrrolidinylidene ]-methyl]-8-oxo-5-thia-1-azabicyclo[4.2.0]oct-2-ene- 2-carboxylic acid disodium salt

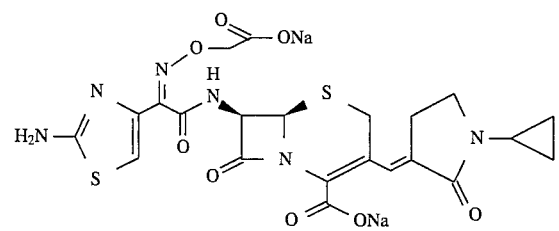

D: [6R-[3(E),6α,7β(Z)]]-7-[[(2-Amino-4-thiazolyl)(hydroxyimino)acetyl]amino]-3-[[1-cyclopropyl-2-oxo-3-pyrrolidinylidene]methyl]-8-oxo-5-thia-1-azabicyclo[4.2.0]oct-2-ene-2-carboxylic acid

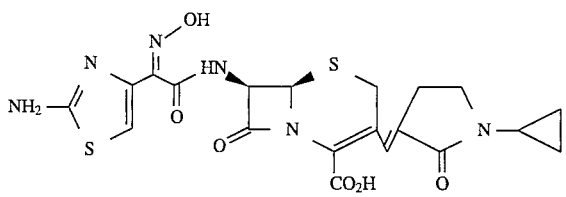

E: [6R-[3(E),6α,7β(Z)]]-7-[[(2-Amino-4-thiazolyl)(hydroxyimino)acetyl]amino]-3-[[1-(2,2,2-trifluoroethyl)-2-oxo-3-pyrrolidinylidene]methyl]-8-oxo-5-thia-1-azabicyclo[4.2.0]oct-2-ene- 2-carboxylic acid

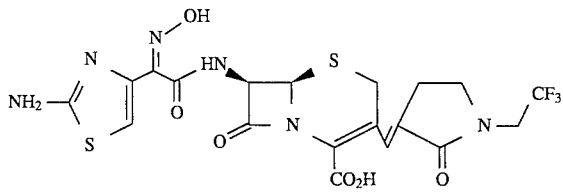

F: [6R-[3(E),6α,7β(Z)]]-7-[[(2-Amino-4-thiazolyl)(hydroxyimino)acetyl]amino]-3-[[1-(2-fluoroethyl)-2-oxo-3-pyrrolidinylidene] methyl]-8-oxo-5-thia-1-azabicyclo[4.2.0]oct-2-ene- 2-carboxylic acid

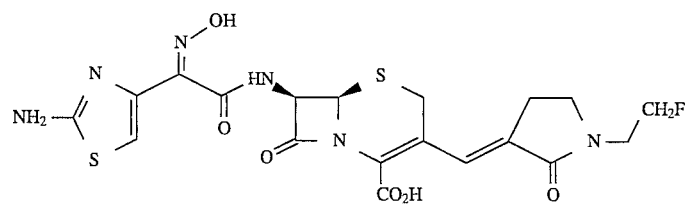

G: 6R-[3(E),6α,7β(Z)]]-7-[[(2-Amino-4-thiazolyl)(hydroxyimino)acetyl]amino]-3-[[1-methoxy-2-oxo-3-pyrrolidinylidene]-methyl]-8-oxo- 5-thia-1-azabicyclo[4.2.0]oct-2-ene-2-carboxylic acid

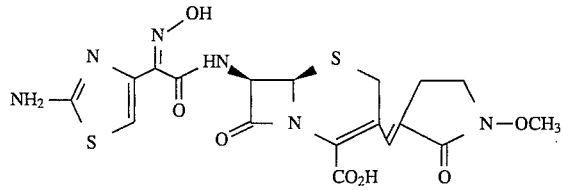

H: 6R-[3(E),6α,7β(Z)]]-7-[[(2-Amino-4-thiazolyl)(hydroxyimino)acetyl]amino]-3-[[1-phenyl-2-oxo-3-pyrrolidinylidene]-methyl]-8-oxo- 5-thia-1-azabicyclo[4.2.0]oct-2-ene-2-carboxylic acid

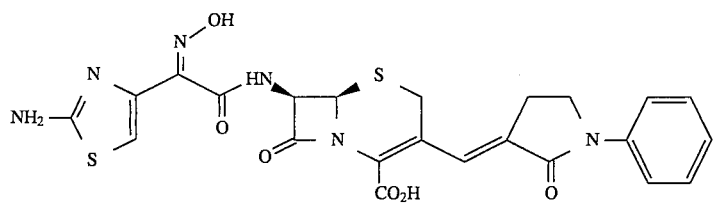

I: 6R-[3(E),6α,7β(Z)]]-7-[[(2-Amino-4-thiazolyl)(hydroxyimino)acetyl]amino]-3-[[1-(4-methoxyphenyl)-2-oxo-3-pyrrolidinyidene]methyl]-8-oxo-5-thia-1-azabicyclo[4.2.0]oct-2-ene- 2-carboxylic acid M: [6R-[3(E), 6α,7β(Z)]]-7-[[(2-Amino-4-thiazolyl)(hydroxyimino)acetyly]amino]-3-[[1-cyanomethyl-2-oxo-3-pyrrolidinylidene]methyl]-8-oxo- 5-thia-1-azabicyclo[4.2.0]oct-2-ene-2-carboxylic acid

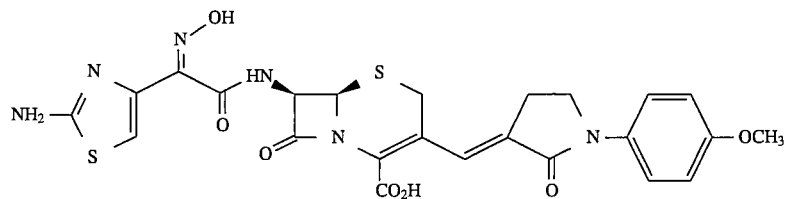

J: 6R-[3(E),6α,7β(Z)]]-7-[[(2-Amino-4-thiazolyl)(hydroxyimino)-acetyl]amino]-3-[[1-(1,1-dimethylethyl)-2-oxo-3-pyrrolidinylidene]-methyl]-8-oxo-5-thia-1-azabicyclo[4.2.0]oct-2-ene-2-carboxylic acid

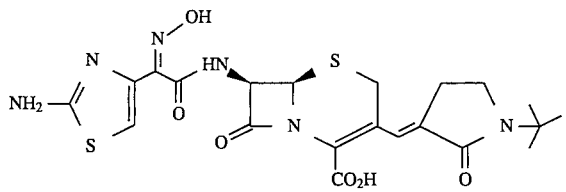

K: [6R-[3(E),6α,7β(Z)]]-7-[[(2-Amino-4-thiazolyl)(hydroxyimino)acetyl]amino]-8-oxo-3-[[2-oxo-1-(3-pyridinyl)-3-pyrrolidinylidene]methyl]-5-thia-1-azabicyclo[4.2.0]oct-2-ene-2-carboxylic acid

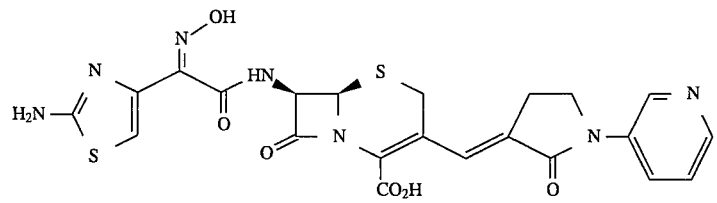

L: [6R-[3(E),6α,7β(Z)]]-3-[[1-Allyl-2-oxo-3-pyrrolidinylidene]methyl]-7-[[(2-amino-4-thiazolyl)(hydroxyimino)acetyl]amino]-8-oxo-5-thia-1-azabicyclo[4.2.0]oct-2-ene-2-carboxylic acid

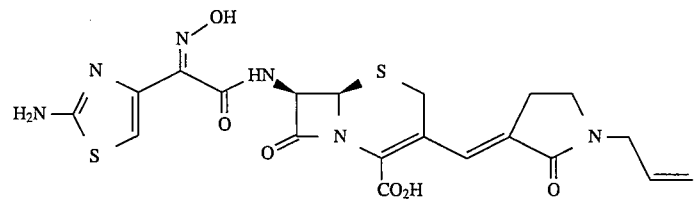

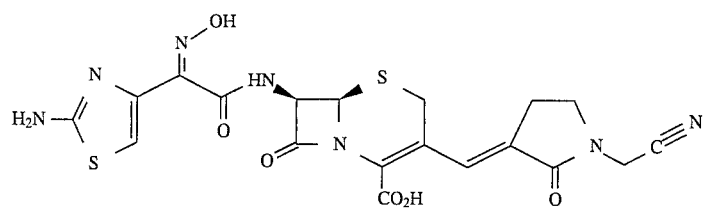

N: [6R-[3(E), 6α,7β(Z)]]-7-[[(2-Amino-4-thiazolyl)(hydroxyimino)acetyl]amino]-3-[[1-cyclopropylmethyl-2-oxo-3-pyrrolidinylidene]methyl]- 8-oxo-5-thia-1-azabicyclo[4.2.0]oct-2-ene-2-carboxylic acid

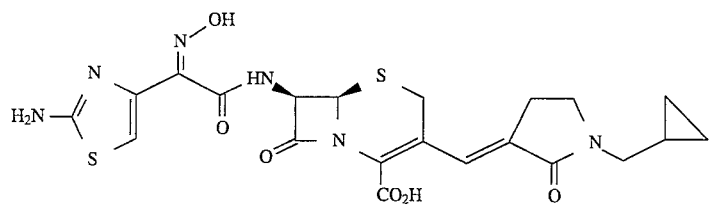

Q: 6R-[3(E), 6α,7β(Z)]]-7-[[(2-Amino-4-thiazolyl)(hydroxyimino)acetyl]amino]-8-oxo-3-[[2-oxo-1-(2-propynyl)-3-pyrrolidinylidene]methyl]-5-thia-1-azabicyclo[4.2.0]-oct-2-ene-2-carboxylic acid

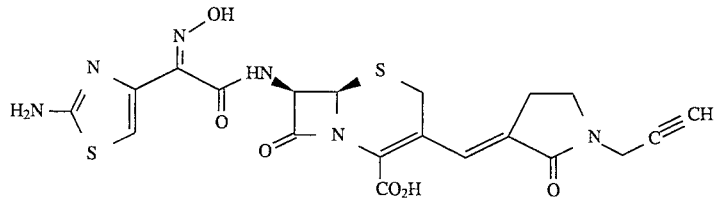

P: [6R-[3(E), 6α,7β(Z)]]-7-[[(2-Amino-4-thiazolyl)(hydroxyimino)acetyl]-amino]-8-oxo-3-[[2-oxo-1-(2-pyrazinyl)-3-pyrrolidinylidenemethyl]-5-thia-1-azabicyclo[4.2.0]oct-2-ene-2-carboxylic acid

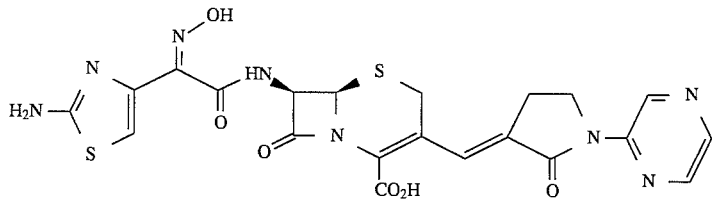

The results appear below:

| Minimum Inhibiting Concentration Values (mg/l) | | | |
|---|---|---|---|
| | A | B | C |
| E. coli ATCC 25922 | 0.0625 | 0.0313 | 0.0313 |
| E. coli TEM-1 | 0.0625 | 0.0313 | 0.0313 |
| Staph. aureus Smith | 8 | 8 | 8 |
| Staph. aureus ATCC 29213 | 16 | 16 | 16 |
| Prot. vulgaris ATCC 6380 | ≦0.0156 | ≦0.0156 | ≦0.0156 |
| Ps. aeruginosa ATCC 27853 | 8 | 4 | 4 |
| Ps. aeruginosa 5712 | 8 | 4 | 4 |
| Str. pneumoniae 6301 | 0.0625 | 0.0313 | 0.0625 |
| Str. pyrogenes 4 | 0.125 | 0.125 | 0.125 |

| Antibacterial Spectrum (MIC, µg/ml) | | | | | | | | | |
|---|---|---|---|---|---|---|---|---|---|
| | D | E | F | G | H | I | J | Cefdinir[4] | Ceftriaxone[5] |
| S. aureus 6538 | 0.5 | 0.5 | 0.5 | 0.5 | 0.5 | 0.5 | 1 | 0.5 | 4 |
| S. aureus 734 MRSA | 16 | 8 | 8 | 16 | 8 | 8 | 16 | >32 | >32 |
| S. pyogenes B15 | ≦0.06 | ≦0.06 | ≦0.06 | ≦0.06 | ≦0.06 | ≦0.06 | ≦0.06 | ≦0.06 | ≦0.06 |
| S. pneumoniae Q19 | ≦0.06 | ≦0.06 | ≦0.06 | ≦0.06 | 0.12 | ≦0.06 | 0.12 | 0.25 | ≦0.06 |
| S. agalactiae QK44 | 0.25 | 0.25 | 0.12 | 0.25 | 0.25 | 0.25 | 0.25 | 0.25 | ≦0.06 |
| S. viridans group 016 | 1 | 1 | 0.5 | 0.5 | 1 | 0.5 | 1 | 2 | 0.5 |
| E. faecalis 6 | 1 | 1 | 1 | 1 | 0.25 | 0.25 | 2 | 8 | >32 |
| L. monocytogenes BK23 | | 4 | 2 | 2 | | 2 | | 16 | >16 |
| H. influenzae 1 | 0.25 | 0.25 | 0.12 | 0.12 | 0.5 | 0.25 | 0.25 | 0.5 | <0.06 |
| M. catarrhalis RA21 | 8 | 16 | 8 | 16 | >16 | >16 | 16 | 1 | 1 |
| N. meningitidis 69480 | ≦0.06 | ≦0.06 | ≦0.06 | ≦0.06 | 0.12 | ≦0.06 | 0.12 | ≦0.06 | <0.01 |
| E. coli 25922 | ≦0.06 | 0.12 | ≦0.06 | ≦0.06 | 0.25 | 0.12 | 0.5 | 0.25 | ≦0.06 |
| K. pneumoniae 418 | ≦0.06 | 0.12 | ≦0.06 | ≦0.06 | 0.12 | 0.12 | 1 | 0.12 | ≦0.06 |
| E. cloacae 908SSi | 0.12 | 0.25 | 0.12 | 0.25 | 0.5 | 0.5 | 2 | 32 | 0.25 |
| E cloacae 908R | 8 | 16 | 16 | 32 | 16 | 32 | 8 | >32 | >32 |
| C. freundii 902 | ≦0.06 | 0.12 | 0.12 | ≦0.06 | 0.5 | 0.25 | 0.5 | 16 | 0.25 |
| C. freundii 43 | 2 | 4 | 4 | 4 | 4 | 8 | 4 | >32 | 32 |
| P. mirabilis 2117 | ≦0.06 | ≦0.06 | ≦0.06 | ≦0.06 | ≦0.06 | 0.12 | 0.12 | 0.12 | ≦0.06 |
| P. vulgaris 1028 | 1 | 1 | 2 | 2 | 2 | 2 | 0.5 | 1 | 0.12 |
| M. morganii 6H-137 | ≦0.06 | ≦0.06 | ≦0.06 | ≦0.06 | ≦0.06 | ≦0.06 | 0.25 | 8 | ≦0.06 |
| S. marcescens 69438 | 0.5 | 1 | 0.5 | 1 | 1 | 1 | 1 | 16 | 0.25 |
| P. aeruginosa 27853 | 8 | 16 | 32 | 32 | 32 | >32 | >32 | >32 | 16 |
| X. maltophilia 1AC739 | >32 | >32 | >32 | >32 | >32 | >32 | >32 | >32 | >32 |
| Acinetobacter sp. 51-156 | 16 | 16 | 16 | 8 | 32 | 32 | >32 | >32 | 32 |
| B. fragilis ATCC25285 | | 8 | | | | | | 32 | 16 |
| P. asaccharolyticus 29743 | | ≦0.12 | | | | | | ≦0.12 | 0.25 |
| C. difficile ZH1 | | 8 | | | | | | 32 | >32 |

| Antibacterial Spectrum (MIC, µg/ml) | | | | | | | | |
|---|---|---|---|---|---|---|---|---|
| | K | L | M | N | O | P | Cefdinir[4] | Ceftriaxone[5] |
| S. aureus 6538 | 1 | 1 | 1 | 0.5 | 1 | 0.5 | 0.5 | 4 |
| S. aureus 734 MRSA | 8 | 16 | 4 | 8 | 4 | 8 | >32 | >32 |
| S. pyogenes B15 | ≦0.06 | ≦0.06 | ≦0.06 | ≦0.06 | ≦0.06 | ≦0.06 | ≦0.06 | ≦0.06 |
| S. pneumoniae Q19 | 0.12 | ≦0.06 | ≦0.06 | ≦0.06 | ≦0.06 | 0.12 | 0.25 | ≦0.06 |
| S. agalactiae QK44 | 0.5 | 0.25 | 0.25 | 0.5 | 0.25 | 0.5 | 0.25 | ≦0.06 |
| S. viridans group 016 | 1 | 1 | 1 | 1 | 0.5 | 1 | 2 | 0.25 |
| E. faecalis 6 | 1 | 2 | 1 | 1 | 2 | 0.5 | 8 | >32 |
| L. monocytogenes BK23 | 8 | 4 | 4 | 4 | 2 | 4 | 16 | >16 |
| H. influenzae 1 | 0.25 | 0.5 | 0.5 | 0.25 | 0.25 | 0.5 | 0.5 | <0.06 |
| M. catarrhalis RA21 | >16 | 8 | 8 | 8 | 4 | 8 | 1 | 1 |
| N. meningitidis 69480 | ≦0.06 | ≦0.06 | ≦0.06 | 0.25 | 0.25 | 0.5 | ≦0.06 | <0.01 |
| E. coli 25922 | ≦0.12 | ≦0.06 | ≦0.06 | ≦0.06 | ≦0.06 | ≦0.06 | 0.25 | ≦0.06 |
| K. pneumoniae 418 | ≦0.12 | 0.12 | 0.12 | 0.12 | 0.12 | 0.25 | 0.12 | ≦0.06 |
| E. cloacae 908SSi | ≦0.12 | 0.25 | 1 | 1 | 1 | 0.25 | 32 | 0.25 |
| E. cloacae 908R | 4 | 16 | 16 | 8 | 16 | 8 | >32 | >32 |
| C. freundii 902 | ≦0.12 | ≦0.06 | 0.25 | 0.12 | 0.12 | 0.12 | 16 | 0.25 |
| C. freundii 43 | 2 | 4 | 8 | 4 | 4 | 2 | >32 | 32 |
| P. mirabilis 2117 | ≦0.12 | ≦0.06 | ≦0.06 | ≦0.06 | ≦0.06 | 0.12 | 0.12 | ≦0.06 |
| P. vulgaris 1028 | 4 | 2 | 8 | 0.25 | 8 | 4 | 1 | 0.12 |
| M. morganii 6H-137 | ≦0.12 | ≦0.06 | ≦0.06 | ≦0.06 | ≦0.06 | ≦0.06 | 8 | ≦0.06 |
| S. marcescens 69438 | 0.5 | 1 | 4 | 0.5 | 1 | 4 | 16 | 0.25 |
| P. aeruginosa 27853 | 16 | 16 | 8 | 16 | 8 | 8 | >32 | 16 |
| X. maltophilia 1AC739 | >32 | >32 | >32 | >32 | >32 | >32 | >32 | >32 |
| Actinetobacter sp. 51-156 | 32 | 16 | 8 | 16 | 16 | 32 | >32 | 32 |
| B. fragilis ATCC 25285 | 4 | | | | | | 32 | 16 |
| P. asaccharolyticus 29743 | ≦0.25 | | | | | | ≦0.12 | 0.25 |

-continued

| | | | | | |
|---|---|---|---|---|---|
| C. difficile ZH1 | | 16 | | 32 | >32 |

In vitro activity against selected species (μg/ml)

| | Medium | | D | E | F |
|---|---|---|---|---|---|
| S. aureus MSSA (26) | MHB[5] | $MIC_{50}$ | 1 | 1 | 0.5 |
| | | $MIC_{90}$ | 1 | 1 | 1 |
| | | Range | 0.5–1 | 0.5–1 | 0.5–1 |
| S. aureus MRSA (10) | MHA[6] | $MIC_{50}$ | 16 | 8 | 8 |
| | +NaCl | $MIC_{90}$ | 16 | 8 | 8 |
| | | Range | 16–32 | 8–16 | 8–16 |
| S. pneumoniae PEN-R (31) | IsoB[7] | $MIC_{50}$ | 0.25 | 0.25 | |
| | | $MIC_{90}$ | 0.5 | 0.5 | |
| | | Range | ≦0.12–0.5 | ≦0.12–0.5 | |
| (3) | IsoB + 20% serum | $MIC_{50}$ | 0.5 | 0.5 | 0.5 |
| | | Range | ≦0.12–0.5 | 0.25–0.5 | ≦0.12–0.5 |
| S. viridans group (19) | IsoB | $MIC_{50}$ | 2 | 2 | |
| | | $MIC_{90}$ | 2 | 2 | |
| | | Range | ≦0.12–8 | ≦0.12–4 | |
| E. faccalis (17) | IsoB | $MIC_{50}$ | 1 | 0.5 | |
| | | $MIC_{90}$ | 2 | 2 | |
| | | Range | 0.25–2 | 0.25–2 | |
| (10) | MHA | $MIC_{50}$ | 1 | 1 | 1 |
| | | $MIC_{90}$ | 2 | 2 | 2 |
| | | Range | 1–2 | 1–2 | 0.5–2 |
| E. faecium (8) | MHA | $MIC_{50}$ | 4 | 4 | 2 |
| | | Range | 1–32 | 1–16 | 1–16 |
| M. catarrhalis (24) | IsoB | $MIC_{50}$ | 4 | 4 | |
| | | $MIC_{90}$ | 16 | 16 | |
| | | Range | 1–32 | 1–16 | |

| | G | H | I | J | Cefdinir | Ceftriaxone |
|---|---|---|---|---|---|---|
| S. aureus MSSA (26) | 1 | | 0.5 | 1 | 1 | 4 |
| | 1 | | 0.5 | 2 | 2 | 16 |
| | 1–2 | | 0.5–1 | 0.5–2 | 0.5–4 | 2–16 |
| S. aureus MRSA (10) | 16 | 16 | 16 | 32 | >32 | >32 |
| | 16 | 16 | 32 | 32 | >32 | >32 |
| | 8–16 | 16–32 | 16–32 | 16–32 | 32–>32 | >32 |
| S. pneumoniae PEN-R (31) | 0.25 | | ≦0.12 | 0.25 | 2 | 0.5 |
| | 0.5 | | ≦0.12 | 0.5 | 4 | 1 |
| | ≦0.1–0.5 | | ≦0.12–0.25 | ≦0.12–0.5 | ≦0.1–8 | ≦0.1–2 |
| (3) | 0.5 | | 0.25 | 0.5 | 4 | 4 |
| | ≦0.12–0.5 | | ≦0.12–0.5 | ≦0.1–1 | ≦0.1–8 | 1–8 |
| S. viridans group (19) | 2 | | 0.5 | 2 | 8 | |
| | 2 | | 2 | 4 | 16 | |
| | ≦0.12–8 | | ≦0.12–4 | ≦0.12–8 | ≦0.12–128 | |
| E. faccalis (17) | 0.5 | | 0.5 | 2 | 8 | |
| | 2 | | 1 | 2 | 32 | |
| | 0.25–2 | | 0.25–1 | 0.5–4 | 1–64 | |
| (10) | ≦0.5 | 1 | ≦0.5 | 2 | 8 | >32 |
| | 2 | 1 | 1 | 4 | 16 | >32 |
| | ≦0.5–2 | ≦0.5–16 | ≦0.5–1 | 1–8 | 4–32 | 32–>32 |
| E. faecium (8) | 4 | | 2 | 4 | 16 | >32 |
| | 1–8 | | ≦0.1–16 | 2–32 | 8–>32 | >32 |
| M. catarrhalis (24) | 4 | | 8 | 8 | 0.25 | |
| | 16 | | 16 | 16 | 0.5 | |
| | 1–32 | | 1–64 | 2–32 | 0.25–0.5 | |

Activity against murine septicemia ($ED_{50}$ mg/kg)

| | D | E | F | G | H | I | J | Cefdinir | Ceftriaxone |
|---|---|---|---|---|---|---|---|---|---|
| S. aureus Smith | <1 sc | <1 sc | <1 sec | <1 sc | <0.5 sc | <1 sc | | <1 sc | <2 sc |
| H. coli 25922 | 3 po | 3 po | | ca. 3 po | | 4.5 po | >2 po | 1.8 po | 0.9 po |
| | ≦0.1 sc | 0.07 sc | <0.1 sc | <0.1 sc | | <0.3 sc | | <1 sc | ≦0.01 sc |

[4]Cefdinir: [6R-[6α,7β(Z)]]-7-(2-Amino-4-thiazolyl)[(hydroxyimino)]atectyl]amino]-3-ethenyl-8-oxo-5-thia-1-azabicyclo[4.2.0]oct-2-ene-2-carboxylic acid.
[5]Ceftriaxone: [6R-[6α,7β(Z)]]-7-[[(2-Amino-4-thiazolyl)(methoxyimino)acetyl]amino]-8-oxo-3-[[(1,2,5,6-tetrahydro-2-methyl-5,6-dioxo-1,2,4-triazin-3-yl)thio]methyl]-5-thia-1-azabicyclo[4.2.0]oct-2-ene-2-carboxylic acid.
[5]MHB: Mueller Hinton Broth
[6]MHA: Mueller Hinton Agar
[7]IsoB: Isosensitest Broth In Vivo Activity Septicemia was induced in outbred Swiss albino mice (Jbm MoRo [specific pathogen free]; weight 16 to 20 g, Biomedical Research Laboratories, Füllinsdorf, Switzerland). Mice were infected by intraperitoneal injection of diluted overnight cultures of the test organisms. Bacterial challenge doses were 4–10 times the number of organisms required to kill 50% of untreated animals within 48 h.

The test compounds were administered p.o. or s.c. 1 and 3 h after the bacterial challenge. To treat the infection with *Pseudomonas aeruginosa* BA an additional dose was given 5 h after challenge. Control and treatment groups at each dose were composed of five mice each. The 50% effective dose ($ED_{50}$, in milligrams per kilogram) was calculated by probit analysis as described by Finney (Finney, D. J. 1978, Statistical method in biological assay, 3rd ed. Charles Griffin & Co., Ltd., London), from the survival rates on day 4 after infection.

in which $R^h$ is hydrogen or a carboxy protecting group, $R^f$ is as $R^1$ and $R^g$ is as $R^2$ with the proviso that at least one of the following provisions is fulfilled:

(i) $R^h$ is a carboxylic acid protecting group, (ii) $R^f$ is a residue defined under $R^1$ having nitro, protected amino, protected hydroxy and/or protected carboxylic group(s), (iii) $R^g$ is a residue defined under $R^2$ having nitro, protected amino, protected hydroxy and/or protected carboxylic group(s), or a salt thereof, or (c) for making a readily hydrolyzable ester of a compound of formula I subjecting a carboxylic acid of formula I to a corresponding esterification, or (d) for the making of salts or hydrates of a compound of formula I or hydrates of said salts converting a compound of formula I into a salt or hydrate or into a hydrate of said salts.

| | Efficacy against systemic infections in mice ($ED_{50}$, mg/kg) | | | |
|---|---|---|---|---|
| Organism | A | B | C | Cefixime[1] |
| *Streptococcus pyogenes* 15 | >0.8 po[2] | 0.5 po | 0.78 po | 2.0 po |
| *Escherichia coli* 25922 | <0.1 po | <0.1 po | <0.1 po | 0.5 po |
| *Pseudomonas aeruginosa* BA | 12 sc[3] | 3.5 sc | 12 sc | — |

| | Efficacy against systemic infections in mice ($ED_{50}$ mg/kg) | | | | | | | | |
|---|---|---|---|---|---|---|---|---|---|
| | D | E | F | G | H | I | J | Cefdinir | Ceftriaxone |
| *S. aureus* Smith | <1 sc | <1 sc | <1 sec | <1 sc | <0.5 sc | <1 sc | | <1 sc | <2 sc |
| *E. coli* 25922 | 3 po ≦0.1 sc | 3 po 0.07 sc | <0.1 sc | ca. 3 po <0.1 sc | | 4.5 po <0.3 sc | >2 po | 1.8 po <1 sc | 0.9 po ≦0.01 sc |

[1]Cefixime: [6R[6α,7β(Z)]]-7-[[(2-Amino-4-thiazolyl)(carboxymethoxy)imino]acetyl]amino]-3-ethenyl]-3-ethenyl-8-oxo-5-thia-1-azabicyclo-[4.2.0]oct-2-ene-carboxylic acid
[2]orally
[3]subcutaneous The compounds of the formula I in accordance with the invention as well as their pharmaceutical acceptable salts, hydrates, or readily hydrolyzable esters can be manufactured in accordance with the invention by (a) treating a compound having the formula

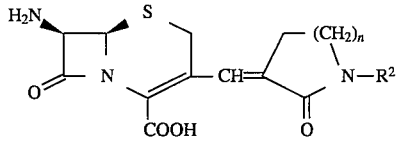

IID in which $R^2$ and n are defined above, or an ester or salt thereof, with acylating agents yielding the residue $R^1$, or (b) for making a compound of formula I in which $R^1$ and/or $R^2$ may contain free amino, hydroxy or carboxylic group(s) cleaving off the amino, hydroxy and/or carboxy protecting group(s) or reducing a nitro group to amino in a compound having the formula

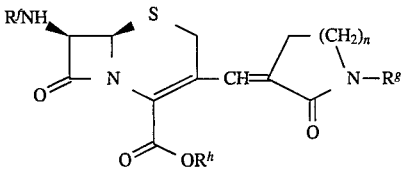

IIE

The reaction of compounds IID with acylating agents according to embodiment (a) can be carried out in a manner known per se. The carboxy group in compounds IID can be protected; for example, by esterification to form a readily cleavable ester such as a silyl ester (e.g. the trimethylsilyl ester) or benzhydryl ester. The carboxy group can also be protected in the form of one of the aforementioned readily hydrolyzable esters. Furthermore, the carboxy group can be protected by salt formation with an inorganic or tertiary organic base such as triethylamine. Amino groups present in the acyloxy agent can be protected. Possible protecting groups are, for example, protecting groups which are cleavable by acid hydrolysis (e.g. the tert.butoxycarbonyl or trityl groups) or by basic hydrolysis (e.g. the trifluoroacetyl group). Preferred protecting groups are the chloroacetyl, bromoacetyl and iodoacetyl groups, especially the chloroacetyl group. These last-mentioned protecting groups can be cleaved off by treatment with thiourea. The 7-amino group in compounds IID can be protected, for example, by a silyl protecting group such as the trimethylsilyl group.

Examples of acylating agents used in embodiment (a) are halides (e.g. chlorides, bromides, iodides, and fluorides), azides, anhydrides, especially mixed anhydrides with strong acids, reactive esters (e.g. N-hydroxysuccinimide esters) and amides (e.g. imidazolides).

In reacting a 7-amino compound of formula IID with a carboxylic acid or a reactive functional derivative thereof, for example, a free carboxylic acid can be reacted with an aforementioned ester of a compound of formula IID in the presence of a carbodiimide such as dicyclohexylcarbodiimide in an inert solvent such as ethyl acetate, acetonitrile, dioxan, chloroform, methylene chloride, benzene or dimethylformamide, and subsequently the ester group can be cleaved off. Oxazolium salts (e.g. N-ethyl-5-phenyl-isoxazolium-3'-sulphonate) can be used in place of carbodiimides in the foregoing reaction.

According to another embodiment, a salt of an acid of formula IID (e.g. a trialkylammonium salt such as the triethylammonium salt) is reacted with a reactive functional derivative of a carboxylic acid as mentioned earlier in an inert solvent (e.g. one of the aforementioned solvents).

According to a further embodiment, an acid halide, preferably the chloride, of a carboxylic acid is reacted with an amine of formula IID. The reaction is preferably carried out in the presence of an acid-binding agent, for example in the presence of aqueous alkali, preferably sodium hydroxide, or in the presence of an alkali metal carbonate such as potassium carbonate or in the presence of a lower alkylamine such as triethylamine. As the solvent there is preferably used water, optionally in admixture with an inert organic solvent such as tetrahydrofuran or dioxan. The reaction can also be carried out in an aprotic organic solvent such as dimethylformamide, dimethylacetamide, dimethylsulphoxide or hexamethylphosphoric acid triamide. When a silylated compound of formula IID is used, the reaction is carried out in an anhydrous medium.

Advantageous alternatives for acylation, where an amino group present in the acylating agent need not be protected, involves the use of a 2-benzothiazolyl thioester or a 1-hydroxybenzotriazole ester of the carboxylic acid. For instance, the 2-benzthiazolyl thioester may be reacted with the compound IID in an inert organic solvent such as a chlorinated hydrocarbon e.g. methylene chloride, in acetone, ethyl acetate or in a mixture of such solvents with water. The 1-hydroxybenzotriazole ester can be employed by reacting the carboxylic acid with 1-hydroxybenzotriazole and a carbodiimide, especially N,N'-dicyclohexylcarbodiimide or N,N'-diisopropylcarbodiimide in an inert organic solvent, preferably methylene chloride, dimethylformamide, tetrahydrofuran, acetonitrile or ethyl acetate.

The reaction of a 7-amino compond of formula IID with a carboxylic acid or a reactive derivative thereof can conveniently be carried out at a temperature between about –40° C. and +60° C., e.g. at room temperature.

Embodiment (b) of the process of the present invention involves deprotection (removal) of protected amino, hydroxy or carboxylic groups present in a compound of formula IIE and can be carried and as follows:

Removal of Amino Protecting Groups

Possible amino-protecting groups are those employed in peptide chemistry, such as an alkoxycarbonyl group, e.g., t-butoxycarbonyl, etc., a substituted alkoxycarbonyl group, e.g., trichloroethoxycarbonyl etc., an optionally substituted aralkyloxycarbonyl group, e.g., p-nitrobenzyloxycarbonyl or benzyloxycarbonyl, an aralkyl group such as trityl or benzhydryl or a halogen-alkanoyl group such as chloroacetyl, bromoacetyl, iodoacetyl or trifluoroacetyl.

Preferred protecting groups are t-butoxycarbonyl (t-BOC) and trityl.

The amino protecting groups may be cleaved off by acid hydrolysis (e.g. the t-butoxycarbonyl or trityl group), e.g. aqueous formic acid, or by basic hydrolysis (e.g. the trifluoroacetyl group). The chloroacetyl, bromoacetyl and iodoacetyl groups are cleaved off by treatment with thiourea.

Amino-protecting groups which are cleavable by acid hydrolysis are preferably removed with the aid of a lower alkanecarboxylic acid which may be halogenated. In particular, formic acid or trifluoroacetic acid is used. The reaction is carried out in the acid or in the presence of a co-solvent such as a halogenated lower alkane, e.g. methylene chloride. The acid hydrolysis is generally carried out at room temperature, although it can be carried out at a slightly higher or slightly lower temperature (e.g. a temperature in the range of about –30° C. to +40° C.). Protecting groups which are cleavable under basic conditions are generally hydrolyzed with dilute aqueous caustic alkali at 0° C. to 30° C. The chloroacetyl, bromoacetyl and iodoacetyl protecting groups can be cleaved off using thiourea in acidic, neutral or alkaline medium at about 0° C.–30° C.

Removal of Hydroxy Protecting Groups

Possible hydroxy protecting groups are such as are commonly known in the art, e.g.

for protection of hydroxyimino groups ($R^3$=hydrogen in compounds of formula III), usually trityl, lower alkanoyl, preferably acetyl, tetrahydropyranyl protecting groups are employed for protection of a hydroxy group $R^2$ usually benzyl or p-nitrobenzyl protecting groups are employed.

These protecting groups can be removed as follows:

| | |
|---|---|
| trityl | in acidic solvents like 90% formic acid at about 0 to 50° C. or triethylsilane in trifluoroacetic acid at about –20 to 25° C.; in organic solutions of hydrochloric acid at about –50 to 25° C.; |
| acetyl | with weak inorganic bases like sodium bicarbonate in ethanol/water at about 0 to 50° C.; |
| tetrahydropyranyl | with weak organic acids like p-toluenesulfonic acid in an alcohol, e.g. ethanol, at about 0° C. to the boiling point of the mixture; |
| benzyl, p-nitrobenzyl | with hydrogen or a hydrogen donor like cyclohexene or cyclohexadiene and a catalyst like Pd/C in solvents like alcohols, dichloromethane, ethyl acetate, acetic acid, DMF etc, or mixtures of these at about 0 to 50° C. |

Removal of Protecting Groups at the Carboxy Function

As ester protecting groups one may utilize an ester form which can be easily converted into a free carboxyl group under mild conditions, the ester protecting group being exemplified by, for example, t-butyl, p-nitrobenzyl, p-methoxybenzyl, benzhydryl, allyl, etc.

These protecting groups may be removed as follows:

| | |
|---|---|
| benzhydryl | trifluoroacetic acid with anisol, phenol, cresol or triethylsilane at about –40° C. to room temperature; hydrogen with Pd/C in an alcohol such as ethanol or in tetrahydrofuran; $BF_3$-etherate in acetic acid at about 0 to 50° C.; |
| t-butyl | formic acid or trifluoroacetic acid with or without anisol, phenol, cresol or triethylsilane and a solvent such as dichloromethane at about –10° C. to room temperature; |
| p-nitrobenzyl | sodium sulfide in acetone/water at about 0 to room temperature; or hydrogen with Pd/C in an alcohol such as ethanol or in tetrahydrofuran; |
| p-methoxybenzyl | formic acid at about 0 to 50° C.; or trifluoroacetic acid and anisol, phenol or triethylsilane at about –40° C. to room temperature; |
| allyl | palladium(O) catalyzed transalkylation reaction in the presence of sodium or potassium salt of 2-ethyl hexanoic acid, see | for example J. Org. Chem. 1982, 47, 587.

Embodiment (b) of the process of the present invention also involves reducing a nitro group present in $R^f$ or $R^g$ to the amino group. This reduction can be carried out in known manner, e.g. by the addition of sodium dithionate in a suitable solvent, e.g. tetrahydrofuran or water, at a temperature between about 0° C. to 100° C. Other methods involve treatment with sodium hydrogen sulfide in mixtures of alcohols with acetone or toluene at about room temperature to the boiling point of the mixture: treatment with iron filings in glacial acetic acid at 0° C. to the boiling point of the mixture; treatment with sodium borohydride in alcohols at about −40° C. to room temperature; treatment with catalysts like Pd/C and either cyclohexene or cyclohexadiene or hydrogen in water, alcohols, dichloromethane, THF, dioxane, acetic acid, DMF at about 0° to 50° C.

In order to make a readily hydrolyzable ester of the carboxylic acids of formula I in accordance with embodiment (c) of the process provided by the present invention, a carboxylic acid of formula I is preferably reacted with a corresponding halide, preferably an iodide, containing the desired ester group. The reaction can be accelerated with the aid of a base such as an alkali metal hydroxide, an alkali metal carbonate or an organic amine such as triethylamine. The esterification is preferably carried out in an inert organic solvent such as dimethylacetamide, hexamethylphosphoric acid triamide, dimethyl sulfoxide or, especially, dimethylformamide. The reaction is preferably carried out at a temperature in the range of about 0°–40° C.

Making the salts and hydrates of the compounds of formula I or the hydrates of said salts in accordance with embodiment (d) of the process provided by the present invention can be carried out in a manner known per se; for example, by reacting a carboxylic acid of formula I or a salt thereof with an equivalent amount of the desired base, conveniently in a solvent such as water or an organic solvent (e.g. ethanol, methanol, acetone and the like). Correspondingly, salt formation is brought about by the addition of an organic or inorganic salt. The temperature at which the salt formation is carried out is not critical. The salt formation is generally carried out at room temperature, but it can be carried out at a temperature slightly above or below room temperature, for example in the range of 0° C. to +50° C.

Making the hydrates usually takes place automatically in the course of the making or as a result of the hygroscopic properties of an initially anhydrous product. For the controlled making of a hydrate, a completely or partially anhydrous carboxylic acid of formula I or salt thereof can be exposed to a moist atmosphere (e.g. at about +10° C. to +40° C.).

Exemplary of the process for obtaining products in accordance with the invention are the following reaction Schemes 1 and 2 below.

Scheme 1

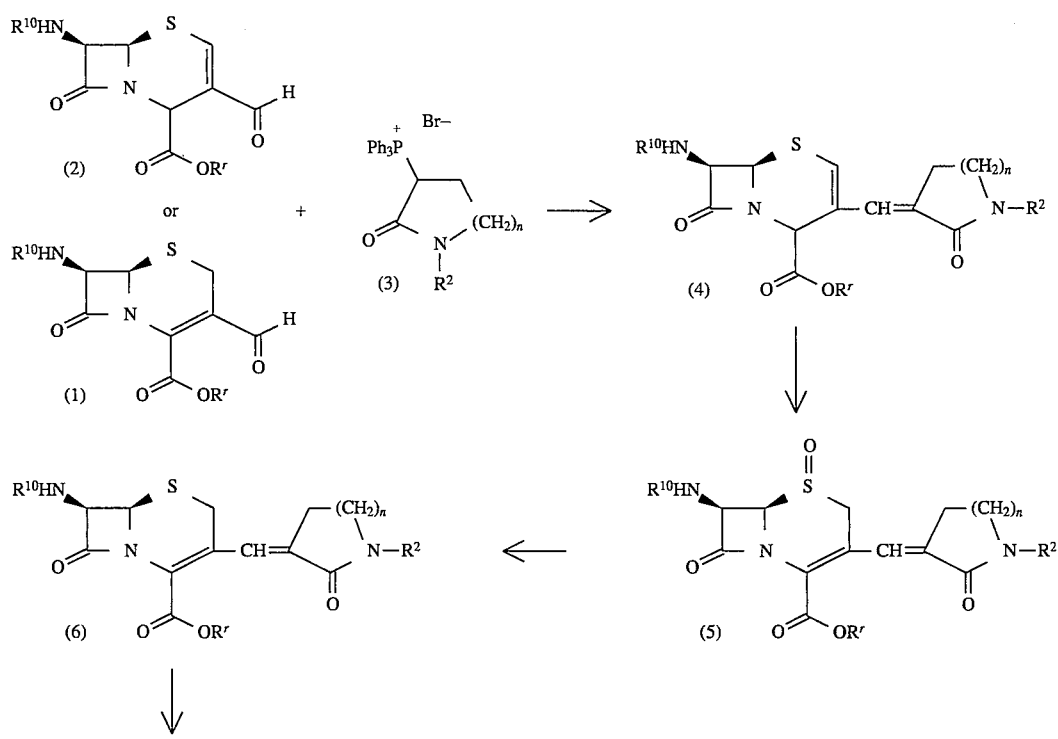

-continued
Scheme 1
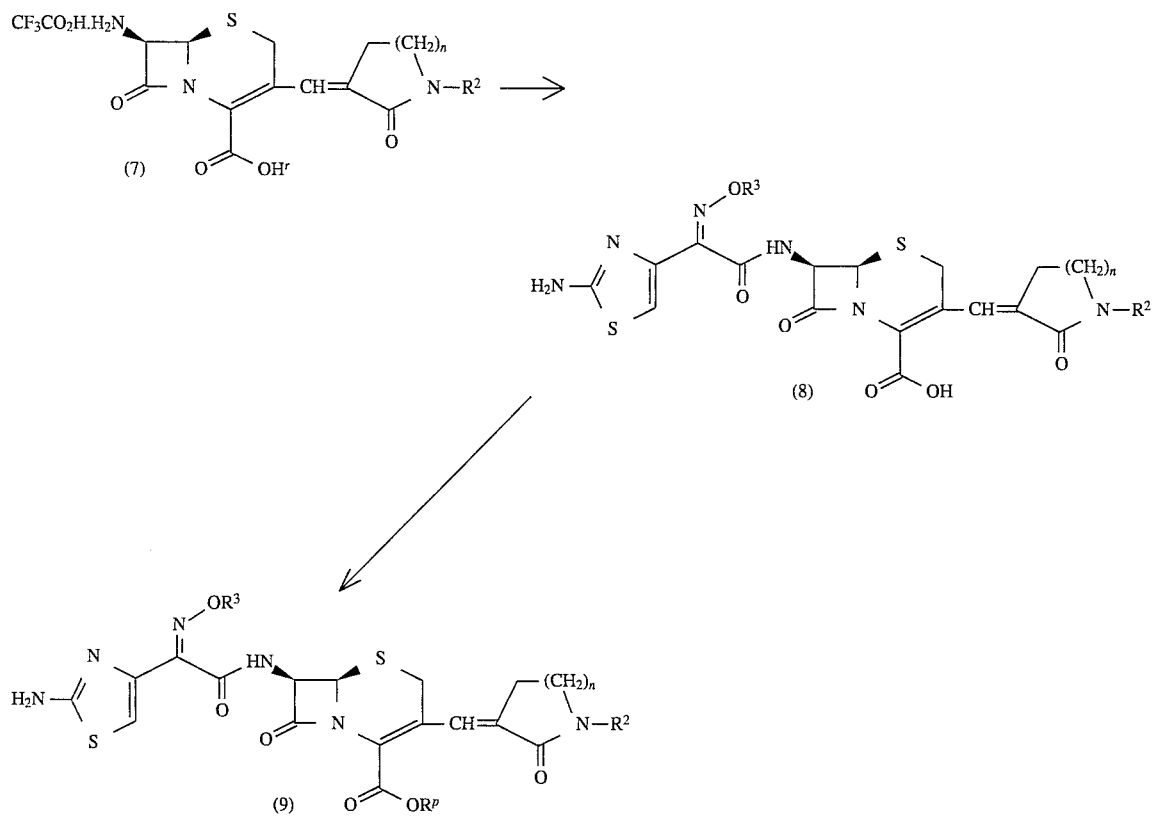
Scheme 2
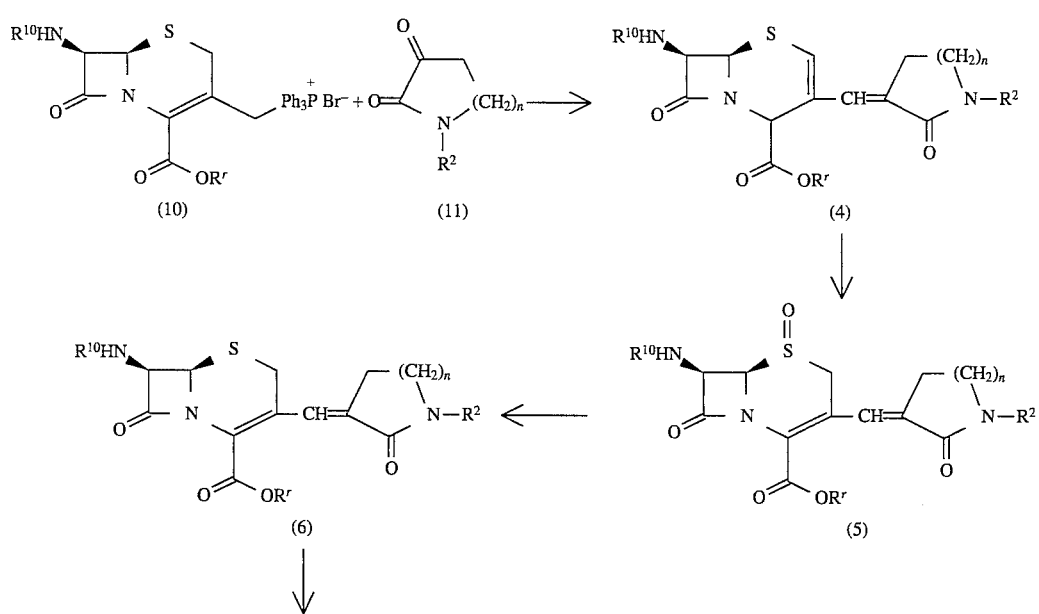

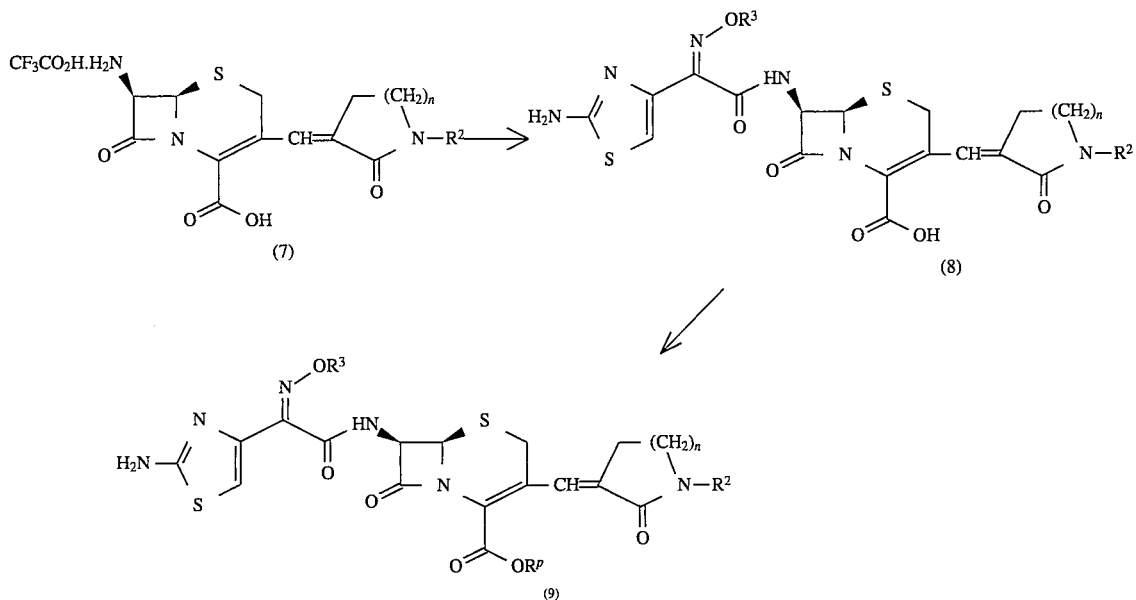

Scheme 1

1 or 2+3→4

The reaction of known 2-cephem aldehyde (1) or 3-cephem aldehyde (2) where $R^r$ is a carboxy protecting group as defined under $R^h$ above and $R^{10}$ is an amino protecting group with a Wittig reagent, exemplified by structure 3, yields the coupling product 4. The reaction is carried out in the presence of a base which is either an inorganic base (sodium or potassium hydroxide, sodium or potassium carbonate etc.), an organic base (tertiary amines), an organolithium such as butyl lithium or phenyllithium or an epoxide such as 1,2-butyleneoxide. The preferred solvents, in the case of inorganic base being used, are water and water-miscible solvent (acetone, tetrahydrofuran, or alcohols etc.); in the case of organic base being used, an inert solvent such as methylene chloride, chloroform, benzene, tetrahydrofuran; in the case of organolithium being used, benzene or tetrahydrofuran; and in the case an epoxide being used, the epoxide itself (e.g. 1,2-butyleneoxide). The temperature for the reaction ranges from −20° C. to 80° C. The preferred conditions are exemplified in the examples.

In the normal Wittig Reaction according to scheme 1, the E isomer is the predominant product. Invariably, less than 10% Z-isomer is formed, the amount depending on the reagents and conditions.

4→5

Compound 4 is converted to the sulfoxide 5 with an oxidizing agent which can be hydrogen peroxide or a peracid, preferably m-chloroperbenzoic acid. The temperature ranges from −20° C. to room temperature and any suitable solvent, preferably chlorinated hydrocarbon or benzene can be used.

5→6

The de-oxygenation of the sulfoxide 5 is carried out in the presence of phosphorus tribromide in dimethylformamide or in the mixed solvent of dimethylformamide and N-methylacetamide. The reaction temperature for the reaction is from about −40° to about 0° C.

6→7

The protecting groups $R^r$ and $R^{10}$ are removed and the reaction conditions used are depending on the nature of the protecting groups. In the case of $R^{10}$ being t-butoxycarbonyl and $R^r$ being benzhydryl, trifluoroacetic acid is employed, at temperature of about −20° C. to about room temperature (about 22° C.).

7→8

The acylation of compound 7 can be carried out with an organic acid which is activated with known reagents, preferably thionyl chloride, oxalyl chloride, dicyclohexylcarbodiimide, bis-[benzthiazolyl-(2)]disulfide, N-hydroxy benzotriazole or a 2-halo N-methylpyridinium salt. The reaction is carried out with or without the base (inorganic or organic bases) depending on the method of activation and a wide range of solvents, from water and water-miscible solvent to inert solvents such as chloroform, dimethylformamide (DMF) or dimethylsulfoxide (DMSO) can be used. The $R^3$ group, if necessary, can be further deprotected with a reaction condition suitable for the removal of the protecting group.

8→9

The 2-carboxylic function of compound 8 is converted to the prodrug esters which are readily hydrolyzable in vivo. $R^p$ can be any such esters known in the art by esterification with the corresponding alcohol of $R^p$ or by treating with the corresponding halide of $R^p$ and a base; the preferred esters are exemplified in the examples. The $R^3$ group, if necessary, can be further deprotected with a reaction condition suitable for the removal of the protecting group.

Scheme 2

10+11→4

Compound 4 can also be obtained from the Wittig salt 10 and the keto lactam 11 under the conditions similar to that of the reaction of 1 or 2+3→4.

The subsequent reactions from 4 to 9 are same as those described in the Scheme 1.

In the inverse Wittig Reaction according to Scheme 2 (which is preferably applied in the case of 4-membered rings), the ratio of Z:E isomers usually varies between 4:1 and 1:1.

Generally, the separation of Z and E isomers from each other is effected by known methods such as chromatography on silica gel in a suitable solvent or solvent mixture, such as ethyl acetate, n-hexane, methylene chloride or mixtures thereof.

The carboxy protecting group $R^r$ in Schemes 1 and 2 can, if desired, be maintained until product (8) and then be split off. The de-oxygenation of the sulfoxide (step 5→6) can be postponed until products 8 or 9 in Schemes 1 and 2, i.e. carried out as a finishing step. The Wittig reaction as per Schemes 1 and 2 can be postponed also, viz. a 3-formyl cephalosporin (1) or (2) is acylated in analogy to 6→7→8 and then subjected to Wittig reaction in analogy to Schemes 1 and 2. In such reactions the carboxy protecting group $R^r$ should be present and thus—after the Wittig reaction—be split off.

The heterocyclic reagents (3) and (11) in Schemes 1 and 2 are preferably prepared according to the following reaction schemes 3, 4 and 5. It should be noted that heterocyclic 5-and 6-rings (n=1 or 2) are preferably prepared according to Schemes 3 or 4 and further processed according to Scheme 1. On the other hand, heterocyclic 4-rings (n=0) are preferably prepared according to Scheme 5 and further processed according to Scheme 2.

Scheme 3

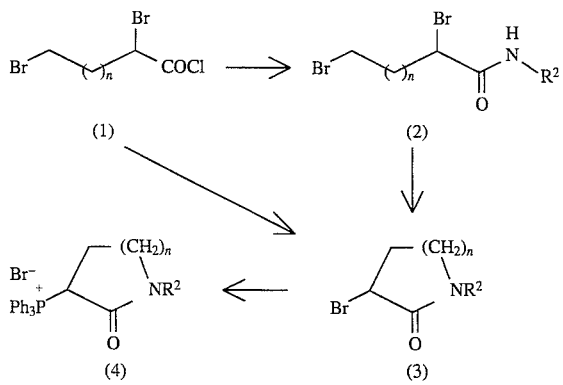

n = 1 or 2
$R^2$ = as defined above
Ph = phenyl

The processes in Scheme 3 are carried out as follows:

1 To 2

The known dibromo acid chlorides (1, n=1, 2) can be converted to the amides (2) using the appropriate amines or aminehydrohalides and inorganic bases such as sodium or potassium hydroxide, sodium or potassium carbonate etc., organic bases such as sodium methoxide or tertiary amines such as triethylamine, diisopropylethylamine etc. The reaction is carried out in biphasic solvent mixtures like water/ dichloromethane or water/chloroform etc., when inorganic bases are used. In case of organic bases or tertiary amines being used, an inert solvent such as methylene chloride, chloroform, benzene, tetrahydrofuran etc. is preferred. The reaction-temperatures range from −10° to 100° C.

2 To 3

Cyclization of the N-substituted dibromoamides (2) can be accomplished under the usual phase transfer catalytic conditions using catalysts like Dowex 2×10, tetraalkylammonium salts, tetraalkylarylammonium salts, crown ethers etc. with bases like aqueous sodium or potassium hydroxide, sodium or potassium carbonate etc.

Alternatively, strong bases like sodium hydride, lithium diisopropylamide, potassium t-butoxide can be used in solvents like tetrahydrofuran, dichloromethane, dimethoxyethane or diethylether at reaction temperatures between −78° and +80° C.

1 To 3

The direct conversion of the acid chlorides into the bromolactams is possible when the first step (1 to 2) is carried out in biphasic solvent mixtures like water/dichloromethane or water/chloroform etc. together with sodium or potassium hydroxide as base. A catalyst like Dowex 2×10, tetralkylammonium salts, tetraalkylarylammonium salts, crown ethers etc. is added when the amide (2) has formed according to TLC or HPLC analysis. The temperatures range between 0° and 50° C.

3 To 4

The triphenylphosphonium salts (4) can be prepared by treating the bromolactams with triphenylphosphine in solvents like tetrahydrofuran, toluene, benzene, ethylacetate, dichloromethane, dichloroethane, chloroform etc. at temperatures between 0° and 150° C.

Scheme 4

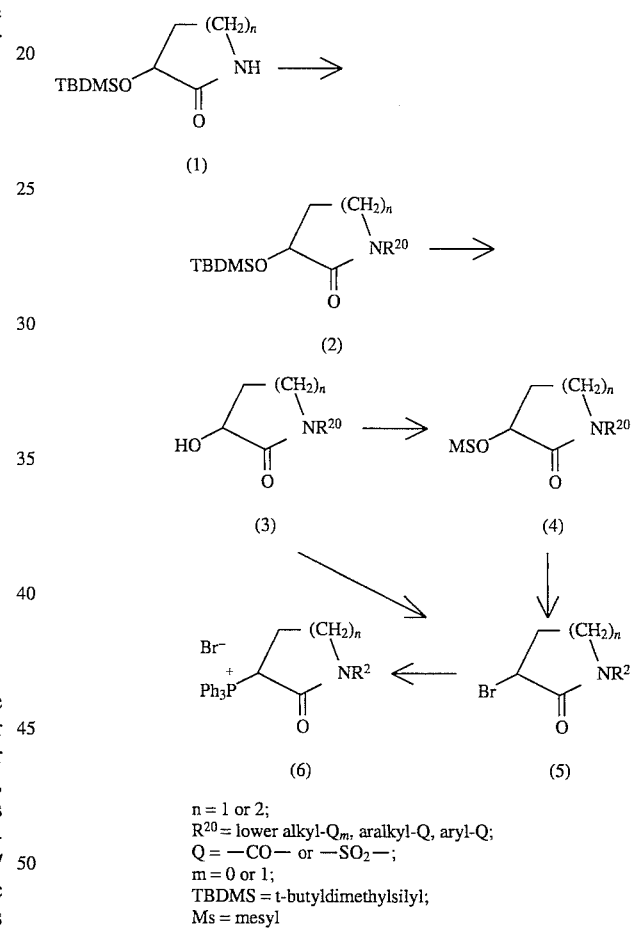

n = 1 or 2;
$R^{20}$ = lower alkyl-$Q_m$, aralkyl-Q, aryl-Q;
Q = —CO— or —$SO_2$—;
m = 0 or 1;
TBDMS = t-butyldimethylsilyl;
Ms = mesyl The processes in Scheme 4 are carried out as follows:

1 To 2

The known 3-tert-butyldimethylsilyloxy-pyrrolidin-2-one (J. Org. Chem. 55, 3684 (1990)) (1) is acylated, sulfonated or alkylated with the corresponding acid halides, sulfonyl halides or alkyl halides by using inorganic bases such as sodium or potassium hydroxide, sodium or potassium carbonate etc. or bases like sodium or potassium hydride, organolithium such as butyl lithium, phenyl lithium, lithium diisopropylamide or tertiary amines such as triethylamine, diisopropylethylamine. The reaction is carried out in a solvent such as water or a water-miscible solvent like acetone, tetrahydrofuran or an alcohol such as methanol or ethanol when inorganic bases are used. In case of hydrides, organolithium bases or tertiary amines being used, inert solvents such as methylene chloride, chloroform, benzene, tetrahydrofuran etc. are preferred. The reaction temperatures range from about −78° C. to 150° C.

2 To 3

The protecting group of (2) can be removed by standard methods known in the literature such as treatment with boron trifluoride etherate in a halogenated hydrocarbon solvent such as chloroform or methylene chloride; with tetrabutyl ammonium fluoride in an organic solvent such as tetrahydrofuran; with potassium fluoride in 18-crown-ether in an organic solvent such as methylene chloride or tetrahydrofuran; or with Dowex W-X8 in methanol, all treatments at a temperature around room temperature.

3 To 4

The hydroxy group of (3) can be converted to a mesylate by using mesylchloride in a solvent such as chloroform, dichloromethane, dichloroethane, tetrahydrofuran, dioxane and a base such as sodium hydride, triethylamine, diisopropylethylamine. The reaction temperature can range from about −80° C. to 150° C.

4 To 5

The mesylate (4) can be converted to the bromide by using tetrabutylammonium bromide or tetraalkyl-or tetraalkylarylammonium bromide in a solvent such as DMF, DMSO, tetrahydrofuran, dioxane, methylene chloride, chloroform, benzene etc. The reaction temperature can range from about −10° C. to 150° C.

3 To 5

Alternatively the alcohol (3) can be directly converted to the bromide by using dibromotriphenylphosphorane in a solvent such as DMF, DMSO, tetrahydrofuran, dioxane, methylene chloride, chloroform, benzene etc. The reaction temperature can range from about −10° C. to 150° C.

5 To 6

The triphenylphosphonium salt (6) can be prepared by treating the bromo-lactam (5) in a solvent such as tetrahydrofuran, toluene, benzene, ethyl acetate, dichloromethane, dichloroethane, chloroform, etc. with triphenylphosphine at a temperature ranging from about 0° C. to 120° C.

Scheme 5

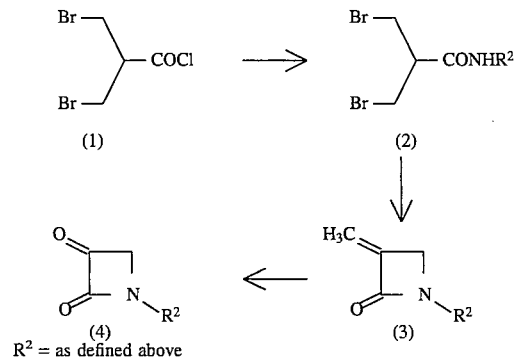

$R^2$ = as defined above

The processes in Scheme 5 are carried out as follows:

1 To 2

The amides (2) can be prepared by methods known in the literature from the known dibromo acid chloride (1) (J. Org. Chem. 20, 780 (1955)).

2 To 3

The methylene-azetidinones (3) are obtained in analogy to known methods (J. Chem. Soc. Chem. Commun., 903 (1978)) by treating 2 with a base such as sodium or potassium hydroxide, sodium or potassium carbonate etc. under usual phase transfer conditions using a tetraalkyl- or tetraalkylarylammonium salts or Dowex 2×10 as phase transfer catalyst. Solvents like tetrachloromethane, dichloromethane, dichloroethane etc. can be used at reaction temperatures ranging from −10° C. to 50° C.

3 To 4

The ketone (4) can be generated by ozonolysis in solvents like dichloromethane, ethyl acetate, methanol or mixtures of these with or without addition of pyridine, calcium carbonate etc. The reaction is carried out at temperatures between −78° C. to 0° C.

Alternatively, (4) can be prepared by using oxidizing agents like periodic acid, potassium or sodium(meta)periodate, sodium or potassium permanganate etc. with osmium tetraoxide or rutheniumtetroxide in solvents such as tetrahydrofuran, dioxane, alcohols, acetone with the addition of water. The reaction temperatures can range from 15° C. to 50° C.

The starting materials and pre-starting materials for obtaining the end products of the present invention are illustrated in the following description termed "Preparations 1–19". Subsequent thereto follow "Examples 1–29" which illustrate the manufacture of the end products of the present invention.

In the examples which follow, two different nomenclatures are employed for the end products, both of which are official, i.e. that of Chemical Abstracts Service, P. O. Box 3012, Columbus, Ohio 43210

Beilstein-Institut für Literatur der organischen Chemie, Varrentrappstrasse 40–42, Carl-Bosch-Haus, D-6000 Frankfurt (Main) 90

For easy illustration the end product of Example 21 is defined below according to both nomenclatures:

"Chemical Abstracts": [6R-[3(E),6α,7β(Z)]]-7-[[(2-Amino-4 -thiazolyl)-(hydroxyimino)acetyl]amino]-3-[(1-cyclopropyl- 2-oxo-3-pyrrolidinylidene)methyl]-8-oxo-5-thia- 1-azabicyclo[4.2.0]oct-2-ene-2-carboxylic acid "Beilstein": (6R,7R )-7-[(Z)-2-(Amino-thiazol-4-yl)-2-hydroxyimino-acetylamino] -3-[(E)-1-cyclopropyl-2-oxo-pyrrolidin-3-ylidenemethyl]-8-oxo-5-thia-1-azabicyclo[4.2.0]oct-2-ene-2-carboxylic acid

PREPARATION 1

Rac-2,4-Dibromo-N-(2,2,2-Trifluoroethyl)-Butanamide 181 g (1.3 Mol) 2,2,2-Trifluoroethylamine hydrochloride were dissolved in 165 ml of water, and 840 ml dichloromethane were added. The mixture was cooled to 0° C. and vigorously stirred. A solution of 312 g (1.18 Mol) of 2,4-dibromobutanoic acid chloride (J. Med. Chem., 1987, 30, 1995) in 165 ml dichloromethane was added within 14 min. Thereafter a solution of 109 g (2.71 Mol) NaOH in 165 ml water was added at a rate resulting in the temperature remaining between 7° and 10° C. Stirring was continued for 4 h at this temperature. Finally the phases were separated. The aqueous phase was extracted twice with 200 ml dichloromethane. The combined organic phases were washed once with 300 ml 0.5M HCl, once with 300 ml 5% sodium bicarbonate solution and once with 300 ml brine and dried over magnesium sulfate. After evaporation of the solvent a colorless solid was obtained.

Yield: 268 g (69.5%) IR (KBr): 1670, 1556 cm$^{-1}$ MS(EI): 328 (M$^+$)

According to the procedure set forth in the preceding preparation the following additional compounds were prepared:

N-Allyl-2,4-dibromo-butyramide IR (Film): 1660 MS (EI): 204 (M-Br)

(R,S)-2,4-Dibromo-N-prop-2-ynyl-butyramide NMR (DMSO-d$_6$): δ=2.39 (2H, q); 3.18 (1H, t); 3.57 (2H, m); 3.91 (2H, m); 4.52 (1H, t); 8.91 (1H, br. t).

(R,S)-2,4-Dibromo-N-cyanomethyl-butyramide IR (KBr): 2245, 1665, 1537 MS (EI): 285 (M$^+$H)$^\oplus$ (R,S)-2,4-Dibromo-N-pyridin-4-ylbutyramide (R,S)-2,5-Dibromo-pentanoyl chloride [Chem. Pharm. Bull 30, 1225 (1982)]

(R,S)-2,5-Dibromo-pentanoic acid 2,2,2-trifluoro-ethylamide IR(KBr): 1663 MS (EI): 341 (M$^+$)

(R,S)-2,5-Dibromo-pentanoic acid cyclopropylamide IR (KBr): 1652 MS (EI): 218 (M-Br)$^+$ (R,S)-2,4-Dibromo-N-pyrazin-2-yl-butyramide IR (KBr): 1698 cm$^{-1}$ MS (EI): 321 (M)

(R,S)-2,4-Dibromo-N-cyclopropylmethyl-butyramide IR (KBr): 1651 MS (EI): 298 (M+H)$^\oplus$ (R,S)-2,4-Dibromo-N-(2-cyano-ethyl)-butyramide IR (KBr): 2240, 1661, 1546 MS (EI): 299 (M+H)$^\oplus$

PREPARATION 2

(a) Rac-3-Bromo-1-(2,2,2-Trifluoroethyl)-2-Pyrrolidone 268 g (0.82 Mol) rac-2,4-dibromo-N-(2,2,2-trifluoroethyl)-butanamide were dissolved in 2 l dichloromethane and 950 ml of 50% sodium hydroxide solution and 26.8 g Dowex 2×10 were added. The mixture was stirred vigorously for 1.5 h at room temperature. Thereafter the mixture was poured on 2 l ice/water and the phases were separated. The aqueous phase was extracted twice with 1 l dichloromethane, and the combined organic phases were washed once with 1 l water, once with 1 l 10% sodium chloride solution and dried over magnesium sulfate. After evaporation of the solvent at 50° C. a colorless oil was obtained which was used in the next step without further purification.

Yield: 190.7 g (95%) IR (Film): 1717, 1267 cm$^{-1}$ MS(EI): 245 (M$^+$)

According to the procedure set forth in the preceding preparation the following additional compounds were prepared:

rac-3-Bromo-1-cyclopropyl-2-pyrrolidinone Microanalysis: calc. C 41.20, H 4.94, N 9.86, Br 39.16 found C 40.85, H 5.05, N 7.01, Br 39.77

(R,S)-1-Allyl-3-bromo-pyrrolidin-2-one IR (Film): 1649 MS (EI): 203 (M$^+$)

(R,S)-3-Bromo-1-(5-methyl-isoxazol-3-yl)-pyrrolidin-2-one IR (KBr): 1715, 1614, 1513, 1456, 1306, 1262 cm$^{-1}$ MS (EI): 244 (M-1), 165 (M-Br)

(R,S)-3-Bromo-1-pyridin-2-yl-pyrrolidin-2-one IR (KBr): 1703, 1588, 1469, 1434, 1399 cm$^1$ MS (EI): 240 (M-1), 161 (M-Br)

(R,S)-3-Bromo-1-pyridin-3-yl-pyrrolidin-2-one IR (KBr): 1699, 1578, 1483, 1430, 1399, 1304 cm$^{-1}$ MS (EI): 240 (M-1)

(R,S)-1-(3-Bromo-2-oxo-pyrrolidin-1-yl)-oxazolidin-2-one IR (KBr): 1760, 1713, 1218 cm$^{-1}$ MS (EI): 249 (M); 169 (M-Br)

(R,S)-3-Bromo-1-(5-trifluoromethyl-1,3,4-thiadiazol-2-yl)-pyrrolidin- 2-one IR (KBr): 1722, 1499, 1476, 1335, 1155, 1038 cm$^{-1}$ MS (EI): 315 (M-H); 236 (M-Br)

(R,S)-3-Bromo-1-thiazol-2-yl-pyrrolidin-2-one IR (KBr): 1705, 1505, 1462, 1384, 1326, 1263 cm$^1$ MS (EI): 246 (M-H)

(R,S)-3-Bromo-1-prop-2-ynyl-pyrrolidin-2-one NMR [DMSO-D$_6$]δ=2.20 (1H, m); 2.56 (1H, m); 3.32 (1H,t); 3.46 (2H, m); 4.08 (2H, m); 4.70 (1H, m).

Mixture of (R,S)-and (SR)-3-bromo-1-[(R,S)-1,1-dioxo-tetrahydro-thiophen- 3-yl]-pyrrolidin-2-one IR (KBr): 3435, 2949, 1687, 1432, 1297, 1126 cm$^{-1}$ MS (EI): 202 (M-Br)

(R,S)-3-Bromo-1-(6-methoxy-pyridin-3-yl)-pyrrolidin-2-one IR (KBr): 3431, 2968, 1695, 1501, 1419, 1288 cm$^{-1}$ MS (EI): 270 (M-H)

(R,S)-3-Bromo-1-pyridin-4-yl-pyrrolidin-2-one (R,S)-3-Bromo-1-(2,2,2-trifluoro-ethyl)-piperidin-2-one IR (Film): 1760 MS (EI): 259 (M$^+$)

(R,S)-3-Bromo-1-cyclopropyl-piperidin-2-one IR (Film): 1658 MS (EI): 217 (M$^+$)

(R,S)-3-Bromo-1-pyrazin-2-yl-pyrrolidin-2-one IR (KBr): 1707 cm$^{-1}$ MS (EI): 241 (M)

(R,S)-3-Bromo-1-cyclopropylmethyl-pyrrolidin-2-one IR (Film): 1700 MS (EI): 189 (M-C$_2$H$_4$)

(b) (R,S)-3-Bromo-2-oxo-pyrrolidin-1-ylacetonitrile (R,S)-2,4-Dibromo-N-cyanomethyl-butyramide (11,26 g, 39.7 mmol) was added in small portions to a suspension of sodium hydride (1.14 g, 47.5 mmol) in THF (50 ml) at 0° C. under argon. The reaction mixture was stirred for 2 h at 0° C. and for 1 h at room temperature, then poured into saturated ammonium chloride solution (250 ml). The resultant mixture was extracted with dichloromethane (2×150 ml). The combined organic layers were washed with brine (150 ml), dried over magnesium sulfate and evaporated. The residue was purified by chromatography on silica gel, using ethyl acetate:n-hexane 2:1 as eluent. Yield: 6.52 g (81%) IR (KBr): 2245, 1709 cm$^{-1}$ MS (EI): 202 (M+)

According to the procedure set forth in the preceding preparation the following additional compound was prepared:

(R,S)-3-(3-Bromo-2-oxo-pyrrolidin-1-yl)-propionitrile IR (Film): 2249, 170 MS (EI): 216 (M$^+$)

PREPARATION 3

Rac-[2-Oxo-1-(2,2,2-Trifluoroethyl)-Pyrrolidin-3-Yl]-Triphenyl-Phosphonium Bromide 189 g (0.77 Mol) rac-3-Bromo-1-(2,2,2-trifluoroethyl)-2-pyrrolidone were dissolved in 1 l toluene, and 222 g (0.85 Mol) triphenylphosphine were added. The mixture was refluxed over-night in an argon atmosphere, the product starting to precipitate. The mixture was then cooled to 5° C. and the slightly brownish crystals were filtered off. They were stirred twice in 1 l THF, filtered and dried in a vacuum at 50° C. Yield: 308 g (79%) colorless crystals $^1$H-NMR (3): δ[ppm]2.17 (m, 1 H); 3.2–3.5 (m, 3 H); 3.93 (dd, 1H); 4.24 m, 1H); 6.91 (m, 1H); 7.60–8.03 (arom., m, 15H). IR (KBr): 1690 cm$^{-1}$ MS(ISP): 428.3 (M$^+$)

| Microanalysis: C$_{24}$H$_{22}$BrF$_3$NOP | | | |
|---|---|---|---|
| | C | H | N |
| calc. | 56.71 | 4.36 | 2.76 |
| found | 56.64 | 4.37 | 2.60 |

According to the procedure set forth in the preceding preparation, the following additional compounds were prepared:

(R,S)-(1-Cyclopropyl-2-oxo-pyrrolidin-3-yl)triphenylphosphonium bromide Microanalysis: Calc C 64.39, H 5.40, N 3.00, P 6.64, Br 17.13 Found C 64.12, H 5.48, N 2.69, P 6.56, Br 17.36

(R,S)-[1-(5-Methyl-isoxazol-3-yl)-2-oxo-pyrrolidin-3-yl]-triphenyl-phosphonium bromide MS(ISP): 427.5 (M$^+$) IR (KBr): 1709, 1608, 1504, 1436, 1276, 1110 cm$^{-1}$ (R,S)-(2-Oxo-1-pyridin-2-yl-pyrrolidin-3-yl)-triphenyl-phosphonium bromide MS(ISP): 423.4 (M$^+$) IR (KBr): 1697, 1587, 1469, 1436, 1394, 1305 cm$^{-1}$ (R,S)-(2-Oxo-1-pyridin-3-yl-pyrrolidin-3-yl)-triphenyl-phosphonium bromide MS(ISP): 423.4 (M$^+$) IR (KBr): 1693, 1486, 1437, 1391, 1307, 1109 cm$^{-1}$ (R,S)-[2-Oxo-1-(2-oxo-oxazolidin-3-yl)-pyrrolidin-3-yl]-triphenyl-phosphonium bromide MS(ISP): 431.4 (M-Br) IR (KBr): 1774, 1711, 1439, 1111 cm$^{-1}$ (R,S)-[2-Oxo-1-(5-trifluoromethyl-1,3,4-thiadiazol-2-yl)-pyrrolidin- 3-yl]-triphenylphosphonium bromide MS(ISP): 498.4 (M-Br) IR (KBr): 3435, 1707, 1473, 1438, 1332 cm$^{-1}$ (R,S)-(2-Oxo-1-thiazol-2-yl-pyrrolidin-3-yl)-triphenyl-phosphonium bromide MS(ISP): 429.5 (M-Br) IR (KBr): 2781, 1694, 1504, 1460, 1437, 1324 cm$^{-1}$ (R,S)-1-(Allyl-2-oxo-pyrrolidin-3-yl)-triphenyl-phosphonium bromide MS(ISP): 466.3 (M+H)$^{\oplus}$ IR (KBr): 1685 cm$^{-1}$ (R,S)-(2-Oxo-1-prop-2-ynyl-pyrrolidin-3-yl)-triphenyl-phosphonium bromide MS(ISP): 384.3 (M$^{\oplus}$) IR (KBr): 1690 cm$^{-1}$ (R,S)-(1-Cyanomethyl-2-oxo-pyrrolidin-3-yl)-triphenyl-phosphonium bromide MS(ISP): 385.4 (M$^{\oplus}$) IR (KBr): 2240, 1695 cm$^{-1}$ Mixture of [(R,S)- and [(S,R)-1-[(R,S)-1,1-dioxo-tetrahydro-thiophen- 3-yl]-2-oxopyrrolidin-3-yl]-triphenyl-phosphonium bromide MS(ISP): 464.4 (M-Br) IR (KBr): 3431, 1684, 1437, 1300, 1114 cm$^{-1}$ (R,S)-[1-(6-Methoxy-pyridin-3-yl)-2-oxo-pyrrolidin-3-yl]-triphenyl-phosphonium bromide MS(ISP): 453.4 (M-Br) IR (KBr): 1688, 1602, 1493, 1437 cm$^{-1}$ (R,S)-(2-Oxo-1-pyridin-4-yl-pyrrolidin-3-yl)-triphenyl-phosphonium bromide (R,S)-[2-Oxo-1-(2,2,2-trifluoro-ethyl)-piperidin-3-yl]-triphenyl-phosphonium bromide MS(ISP): 442.4 (M$^+$) IR (KBr): 1747

(R,S)-(1-Cyclopropyl-2-oxo-piperidin-3-yl)-triphenyl-phosphonium bromide MS(EI): 400.2 (M$^+$) IR (KBr): 1638

(R,S)-2-Oxo-1-pyrazin-2-yl-pyrrolidin-3-yl)-triphenyl-phosphonium bromide MS(ISP): 424.5 cm$^{-1}$ IR (KBr): 1697 cm$^{-1}$ Mixture of (R)- and (S)-(1-cyclopropylmethyl-2-oxo-pyrrolidin-3-yl)-triphenyl-phosphonium bromide MS(ISP): 400.4 (M$^{\oplus}$) IR (KBr): 1679

(R,S)-[1-(2-Cyano-ethyl)-2-oxo-pyrrolidin-3-yl]-triphenyl-phosphonium bromide MS(ISP): 399.4 (M$^+$) IR (KBr): 2244, 1688, 1639 cm$^{-1}$ (R,S)-(2-Oxo-1-phenyl-piperidin-3-yl)-triphenyl-phosphonium bromide MS(ISP): 436.4 (M$^+$) IR (KBr): 1645, 1437 cm$^{-1}$

PREPARATION 4

(R,S)-3-(Tert.-Butyl-Dimethyl-Silanyloxy)-1-(4-Methyl-Phenylsulfonyl)-Pyrrolidin- 2-One 16 g (0.070 mol) of (R,S)-3-(tert.-butyl-dimethyl-silyloxy)-pyrrolidin- 2-one (J. Org. Chem. 55, 3684 [1990]) were dissolved in 150 ml of THF and cooled to −78° C. Sodium hydride (3 g, 0.077 mol) was added portionwise and the suspension was stirred for 30 min. A solution of toluene-4-sulfochloride (14.7 g, 0.077 mol) in THF was added dropwise during 30 min. and the mixture was reacted for 1 h at −78° C. and at 0° C. overnight. Then a few ml of water were cautiously added and the solution evaporated. The resulting yellow oil was taken up in 300 ml of ethyl acetate and washed twice with 150 ml of water, once with 150 ml of brine and dried over magnesium sulfate. After concentration of the organic phase, the residue was stirred in a mixture of 100 ml of n-hexane and 40 ml of diethyl ether, cooled to 0° C. and the solid material collected by filtration and dried. Yield: 17.6 g (68%) colourless crystals MS(ISP): 354 (M-CH$_3$) IR (KBr): 1742 cm$^{-1}$ According to the procedure set forth in the preceding preparation the following additional compound was prepared:

(R,S)-[3-tert.-Butyl-dimethyl-silanyloxy)-2-oxo-pyrrolidin-1-yl]-acetic acid tert.-butyl ester NMR (DMSO-d$_6$): δ 0—0 (6H, s); 0.78 (9 H, s); 1.32 (9 H, s); 1.67 (1H, m); 2.25 (1 H, m); 3.20 (2 H, m); 3.79 (2H, dd); 4.22 (1H, t).

PREPARATION 5

(R,S)-3-Hydroxy-1-(4-Methyl-Phenylsulfonyl)-Pyrrolidin-2-One 15.86 g (0.043 mol) (R,S)-3-(tert.-Butyl-dimethyl-silanyloxy)-1)4-methyl-phenylsulfonyl)-pyrrolidin- 2-one were dissolved in 250 ml chloroform and treated overnight with 16 ml of boron trifluoride etherate. The solvent was evaporated and the residue adjusted to pH 7 with saturated sodium bicarbonate solution and extracted twice with 300 ml dichloromethane. The combined organic phases were washed three times with 300 ml water, dried over magnesium sulfate and concentrated. The resulting solid material was stirred for 2 hours in diethyl ether, cooled and collected by filtration. Yield: 7.27 g (66.4%) IR(KBr): 1731 cm$^{-1}$ MS(EI): 256 (M+H)$^+$ According to the procedure set forth in the preceding preparation the following additional compound was prepared:

(R,S)-(3-Hydroxy-2-oxo-pyrrolidin-1-yl)-acetic acid tert.-butyl ester IR(KBr): 1740, 1688 cm$^{-1}$ MS(EI): 142 (M-OC$_4$H$_9$)

159 (M-C$_4$H$_8$)

PREPARATION 6

Methanesulfonic Acid (R,S)-1-(4-Methyl-Phenylsulfonyl)-2-Oxo-Pyrrolidin- 3-Yl Ester 7.2 g (28.2 mmol) (R,S)-3-Hydroxy-1-(4-methyl-phenylsulfonyl)-pyrrolidin- 2-one and 4.7 ml (33.8 mmol) triethylamine were dissolved in 100 ml dichloromethane and cooled to 0° C. 2.6 ml (33.8 mmol) methane sulfochloride were added slowly and the mixture was stirred for 30 min at 0°–5° C. and for 1 h at room temperature. Then the mixture was washed once with each of 100 ml water, dilute HCl, 5% sodium bicarbonate solution and water. The organic phase was dried over magnesium sulfate and concentrated. The residue was stirred in diethyl ether, the solid material collected by filtration and dried. Yield: 8.14 g (87%) IR(KBr): 1751 cm$^{-1}$ MS (EI) 269 (M-SO$_2$)

According to the procedure set forth in the preceding preparation the following additional compounds were prepared:

(R,S)-(3-Methylsulfonyloxy-2-oxo-pyrrolidin-1-yl)-acetic acid tert.-butyl ester IR(KBr): 1739, 1702 cm$^{-1}$ MS(EI): 220 (M-tBuO)

Methanesulfonic acid (R,S)-1-(4-methoxybenzoyl)-2-oxo-pyrrolidin- 3-yl ester NMR (DMSO-d$_6$)δ[ppm] 2.38 (m, 1H); 2.64 (m. 1H); 3.28 (s, 3H); 3.69 (m, 1H); 3.84 (s and m, 4H); 5.50 (dd, 1H); 7.0 (d, 2H); 7.62 (d, 2H).

PREPARATION 7

(R,S)-3-Bromo-1-(4-Methyl-Phenylsulfonyl)-Pyrrolidin-2-One 8.1 g (24.3 mmol) methanesulfonic acid (R,S)-1-(4-methyl-phenylsulfonyl)- 2-oxo-pyrrolidin-3-yl ester and 8.4 g (29.2 mmol) tetrabutyl-ammonium bromide were reacted in 60 ml DMF at 80° C. for 3 h. The solvent was then evaporated and the residue dissolved in 300 ml ethyl acetate. The residue was washed three times with each of 150 ml water, once with 150 ml saturated sodium bicarbonate solution and once with brine. The organic phase was dried over magnesium sulfate and concentrated and the residue purified by chromatography over silica gel (eluent: n-hexane:ethyl acetate 4:1). Yield 5.57 (72%) IR(KBr): 1738 cm$^{-1}$ MS(RI): 253 (M-SO$_2$)

According to the procedure set forth in the preceding preparation the following additional compounds were prepared:

(R,S)-3-Bromo-1-(4-methoxy-benzoyl)-pyrrolidin-2-one
NMR 8DMSO-d$_6$)δ [ppm] 2.29 (m, 1H); 2.74 (m, 1H); 3.83 (s, 3H); 3.87 (m, 2H); 4.90 (dd, 1H); 7.0 (d, 2H); 7.62 (d, 2H).

(R,S)-(3-Bromo-2-oxo-pyrrolidin-1-yl)-acetic acid tert.-butyl ester
NMR (DMSO-D$_6$): δ 1.42 (9H, s); 2.20 (1H, m); 2.61 (1H, m); 3.38 (2H, m); 3.95 (2H, dd); 4.69 (1H, m).

PREPARATION 8

(R,S)-[1-(4-Methyl-Phenylsulfonyl)-2-Oxo-Pyrrolidin-3-yl]-Triphenyl-Phosphonium Bromide 5.5 g (17.28 mmol) (R,S)-3-Bromo-1-(4-methyl-phenylsulfonyl)-pyrrolidin- 2-one were dissolved in 80 ml THF, and 5.4 g (20.74 mmol) triphenylphosphine were added. The mixture was refluxed for 72 hours. The solid material was collected by filtration and dried. Yield: 6.4 g (64%) IR(KBr): 1724 cm$^{-1}$ MS(ISN) 500.3 (M+H)$^+$ According to the procedure set forth in the preceding preparation the following additional compounds were prepared:

[1-(4-Methoxy-benzoyl)-2-oxo-pyrrolidin-3-yl]-triphenyl-phosphonium bromide
IR(KBr): 1725, 1684 cm$^{-1}$
MS: (ISP) 480 (M$^\oplus$)

(R,S)-(1-tert.-Butoxycarbonylmethyl-2-oxo-pyrrolidin-3-yl)-triphenyl-phosphonium bromide
NMR (DMSO-d$_6$)δ [ppm] 1.39 (s, 9H); 2.38 (m, 1H); 2.62 (m, 1H); 3.31 o (m. 1H); 3.55 (m, 1H); 3.89 (s, 2H); 5.72 (m, 1H); 7.7–7.9 (m, 15H).

PREPARATION 9

3-Bromo-2-Bromomethyl-N-Phenyl-Propionamide 2.45 g (10 mmol) 3-Bromo-2-bromo-methylpropionic acid [J. Org. Chem. 20, 780 (1955)] were refluxed in 2 ml thionyl chloride for 3.5 hours. Excess thionyl chloride was then removed in vacuo and the residue twice evaporated with 3 ml toluene. The residue was dissolved in 5 ml benzene and added dropwise to a solution of 2 ml (22 mmol) aniline in 25 ml benzene at 10°–20° C. After 4 hours 50 ml ethyl acetate were added to the suspension, and the mixture was extracted with each 25 ml of 0.2N HCl, water, sodiumbicarbonate solution (5%) and brine. The organic phase was dried over magnesium sulfate and evaporated in vacuo. The solid residue was recrystallized from chloroform. Yield: 1.93 g (60%) mp. 143°–144° C. Microanalysis: C$_{10}$H$_{11}$Br$_2$NO calc. C 37.42 H 3.45 N 4.36 Br 49.78 found C 37.57 H 3.56 N 4.19 Br 49.96

According to the procedure set forth in the preceding preparation the following additional compound was prepared:

3-Bromo-2-bromoethyl-N-(2,2,2-trifluoro-ethyl)-propionamide IR(KBr): 1666, 1571 cm$^{-1}$ MS(EI): 325 (M)

PREPARATION 10

Methylene-1-Phenyl-Azetidine-2-One 16.05 g (50 mmol) 3-Bromo-2-bromomethyl-N-phenyl-propionamide were dissolved in 250 ml dichloromethane and added to a solution of 30 g sodium hydroxide in 30 ml water. 1.6 g Benzyltriethylammonium chloride were added and the mixture was vigorously stirred for 7 hours. The suspension was then poured on 200 ml ethyl acetate, and the organic phases were separated, washed twice with 150 ml water and dried over magnesium sulfate. Evaporation of the solvent yielded 8.3 g of an oil which was purified by chromatography on silica gel (eluent: dichloromethane). Yield: 8.0 g (100%) M.p. 57°–58° C. Microanalysis: C$_{10}$H$_9$NO calc. C 75.45 H 5.70 N 8.80 found C 75.06 H 5.76 N 8.71

According to the procedure set forth in the preceding preparation the following additional compound was prepared:

3-Methylene-1-(2,2,2-trifluoro-ethyl)-azetidin-2-one IR(KBr): 1740 cm$^{-1}$ MS(EI): 165 (M)

PREPARATION 11

1-Phenyl-Azetidine-2,3-Dione 800 mg (5 mmol) methylene-1-phenyl-azetidine-2-one were dissolved in 50 ml of ethyl acetate and cooled to −70° C. For 15 min ozone was passed through the solution and then oxygen for 1 hour. Then 0.5 ml dimethylsulfide were added, and the solution was stirred for 1.5 hour at −70° C. The temperature was raised to 0° C., and 25 ml of water were added. After 5 min the organic phase was separated and extracted with each of 50 ml of sodium thiosulfate solution and 50 ml of ferrous sulfate solution and then dried over magnesium sulfate. The solvent was evaporated and the residue purified by chromatography over silica gel (eluent: benzene). Yield: 114 mg (14.5%) M.p. 115°–117° C. IR(KBr): 1822, 1757 cm$^{-1}$ According to the procedure set forth in the preceding preparation the following additional compound was prepared:

1-(2,2,2-Trifluoro-ethyl)-azetidine-2,3-dione IR(KBr): 1838, 1774 cm$^{-1}$ Microanalysis: C$_5$H$_4$F$_3$NO$_2$ calc. C 35.94 H 2.41 N 8.38 found C 36.18 H 2.66 N 8.17

PREPARATION 12

[6R-[3(E),6α,7β]]-7-[[(1,1-Dimethylethoxy)carbonyl] amino]3-[( 1-methoxy-2-oxo-3-pyrrolidinylidene)methyl]-8-oxo-5-thia-1-azabicyclo[4.2.0]oct-3-ene-2-carboxylic acid diphenylmethyl ester Diphenylmethyl [6R-(6α,7β)]-7-[[(1,1-dimethylethoxy)carbonyl]amino]-3-formyl-8-oxo-5-thia-1-azabicyclo[4.2.0]oct-2-ene-2-carboxylate 1.0 g (2.0 mM), rac(1-methoxy- 2-oxo-3-pyrrolidinyl)-triphenylphosphonium bromide 1.08 g (2.43 mM), 80 ml of 1,2 dichloroethane and 1.20 ml (8.67 mM) of triethylamine were combined and placed in a preheated 60° oil bath and heated for one hour. The volatile material was removed under reduced pressure, and the residue was dissolved in 50 ml of dichloromethane and washed with water (2×10 ml). The dichloromethane solution was dried (Na$_2$SO$_4$) and concentrated. The residue was purified by flash silica gel column chromatography (7:3 ethyl acetate: n-hexane) to yield 0.50 g (40% yield) of the title compound: NMR (200 MHz, CDCl$_3$)δ 1.45 (s, 9H), 2.72 (m 1H), 3.35 (m, 2H), 3.82 (s, 3H), 5.21 (d, 1H), 5.26 (s, 1H), 5.28 (m, 1H), 5.40 (m, 1H), 6.54 (s, 1H), 6.84 (s, 1H), 6.90 (t, 1H), 7.23–7.30 (m, 10H).

According to the procedure set forth in the preceding preparation the following additional compound were prepared:

[6R-[3(E),6α,7β]]-7-[[(1,1-Dimethylethoxy)carbonyl]amino]-8-oxo-3-[(2-oxo-3-pyrrolidinylidene)methyl]-5-thia-1-azabicyclo[4.2.0]oct-3-ene- 2-carboxylic acid diphenylmethyl ester NMR (200 MHz, CDCl$_3$ ) δ 1.45 (s, 9H), 2.82 (m, 2H), 3.24 (m, 2H), 5.20 (d, 2H), 5.30 (s, 1H), 5.40 (m, 1H), 5.82 (s, 1H), 6.58 (s, 1H), 6.87 (s, 2 H), 7.28 (m, 10H).

[6R-[3(E),6α,7β]]-7-[[(1,1-Dimethylethoxy)carbonyl]amino]-3-[(1-methyl- 2-oxo-3-pyrrolidinylidene)methyl]-8-oxo-5-thia-1-azabicyclo[4.2.0]oct-3-ene-2-carboxylic acid diphenylmethyl ester NMR (200 MHz, CDCl$_3$)δ 1.47 (s, 9H), 2.75 (m 2H), 2.95 (s, 3H), 3.20 (m,2H), 5.22 (d, 1H), 5.30 (s, 1H), 5.30–5.40 (m, 2H), 6.55 (s, 1H), 6.86 (s, 2H), 7.30 (m, 10H).

[6R-[3(E),6α,7β]]-7-[[(1,1-Dimethylethoxy)carbonyl]amino]-8-oxo-3-[(2-oxo-1-(phenylmethoxy)-3-pyrrolidinylidene]methyl]-5-thia-1-azabicyclo[4.2.0]oct-3-ene-2-carboxylic acid diphenylmethyl ester NMR (200 MHz, CDCl$_3$)δ 1.48 (s, 9H), 2.62 (m 2H), 2.99 (m, 2H), 5.04 (s,2H), 5.24 (d, 2H), 5.40 (m, 1H), 6.53 (s, 1H), 6.85 (s, 1H), 6.90 (t, 1H), 7.33 (m, 15H).

[6R-[3(E),6α,7β]]-7-[[(1,1-Dimethylethoxy)carbonyl]amino]-8-oxo-3-[(2-oxo-1-phenyl-3-pyrrolidinylidene)methyl]-5-thia-1 -azabicyclo[4.2.0]oct-3-ene-2-carboxylic acid diphenylmethyl ester NMR (200 MHz, CDCl$_3$)δ 1.45 (s, 9H), 2.82 (m 2H), 3.62 (m, 2H), 5.27 (d, 1H), 5.33 (s, 1H), 5.30–5.40 (m, 2H), 6.60 (s, 1H), 6.87 (s, 1H), 7.0 (t, 1H), 7.25 (m, 13H), 7.72 (d, 2H).

[6R-[3(E),6α,7β]]-7-[[(1,1-Dimethylethoxy)carbonyl]amino]3-[[1 -4-[(1,1-dimethylethoxy)carbonyl]phenyl]-2-oxo-3-pyrrolidinylidene)methyl]-8-oxo-5-thia-1-azabicyclo[4.2.0]oct-3-ene-2-carboxylic acid diphenylmethyl ester NMR (200 MHz, CDCl$_3$)δ 1.48 (s, 9H), 1.60 (s 9H), 2.82 (m, 2H), 3.60 (m,2H), 5.27 (d, 1H), 5.30 (s, 1H), 5.41 (m, 2H), 6.60 (s, 1H), 6.87 (s, 1H), 7.0 (t,1H), 7.26 (m, 10H), 7.78 (d.2H), 8.02 (d, 2H).

[6R-[3(E),6α,7β]]-3-[[1-(2,4-Difluorophenyl)2-oxo3-pyrrolidinylidene]methyl]-7-[[(1,1-dimethylethoxy)carbonyl]amino]-8-oxo- 5-thia-1-azabicyclo[4.2.0]oct-3-ene-2-carboxylic acid diphenylmethyl ester

[6R-[3(E),6α,7β]]-7-[[(1,1-Dimethylethoxy)carbonyl]amino]-3-[[1-[(4-nitrophenyl)-2-oxo-3-pyrrolidinylidene]methyl]-8-oxo-5-thia-1-azabicyclo[4.2.0]oct-3-ene-2-carboxylic acid dephenylmethyl ester NMR (200 MHz, CDCl$_3$)δ 1.46 (s, 9H), 2.89 (m 2H), 3.65 (m. 2H), 5.28 (d, 1H), 5.32 (s, 1H), 5.35–5.42 (m, 2H), 6.68 (s, 1H), 6.88 (s, 1H), 7.05 (t, 1H), 7.23 (m, 10H), 7.92 (d, 2H), 8.28 (d, 2H).

[6R-[3(E),6α,7β]]-7-[[(1,1-Dimethylethoxy)carbonyl]amino]3-[[1-(4 -methoxyphenyl)-2-oxo-3-pyrrolidinylidene]methyl]-8-oxo-5-thia-1-azabicyclo[4.2.0]oct-3-ene-2-carboxylic acid diphenylmethyl ester

[6R-[3(E),6α,7β]]-7-[[(1,1-Dimethylethoxy)carbonyl]amino]-3-[[1-[( 4-nitrophenyl)methyl]-2-oxo-3-pyrrolidinylidene]methyl]-8-oxo-5-thia- 1-azabicyclo[4.2.0]oct-3-ene-2-carboxylic acid diphenylmethyl ester NMR (200 MHz, CDCl$_3$)δ 1.47 (s, 9H), 2.70 (m 2H), 3.22 (m, 2H), 5.13 (s,2H), 5.22 (d, 1H), 5.27 (s, 1H), 5.30–5.42 (m, 2H), 6.58 (s, 1H), 6.87 (s, 1H), 6.93 (t, 1H), 7.30 (m, 10H), 7.63 (d, 2H), 8.24 (d, 2H).

[6R-[6α,7β]]-7-[[(1,1-Dimethylethoxy)carbonyl]amino]-3-[[1-phenyl- 2-oxo-3-piperidiniliden]methyl]-8-oxo-5-thia-1-azabicyclo[4.2.0]oct-3-ene- 2-carboxylic acid diphenylmethyl ester NMR (200 MHz, CDCl$_3$)δ 1.45 (s, 9H), 1.63, 1.82 (m 2H), 2.38, 2.58 (m, 2H), 3.52, 3.68 (m,2H), 5.18 (s, 1H), 5.30 (d, 1H), 5.32–5.44 (m, 2H), 6.35 (s, 1H), 6.85 (s, 1H), 7.35 (m, 16H).

[6R-[3(E),6α,7β]]-7-[[(1,1-Dimethylethoxy)carbonyl]amino]3-[[1-[(1,1-dimethylethoxy)carbonyl]1-methylethyl]-2-oxo-3-pyrrolidinylidene ]methyl]-8-oxo-5-thia-1-azabicyclo[4.2.0 1 ]oct-3-ene-2-carboxylic acid diphenylmethyl ester NMR (200 MHz, CDCl$_3$)δ 1.43 (s, 9H), 1.45 (s, 9H), 1.47 (s, 3H), 1.57 (s, 3H), 2.80 (m,2H), 3.35 (m, 2H), 5.19 (d, 1H), 5.29 (d, 2H), 5.40 (m, 1H), 6.56 (s, 1H), 6.85 (s, 2H), 7.30 (m, 10H).

(E)(6R,7R)-2-Benzylhydryloxycarbonyl-4-[3-(7-tert-butoxycarbonylamino- 8-oxo-5-thia-1-azabicyclo[4.2.0]oct-2-en-3-ylmethylene)- 2-oxo-pyrrolidin-1-yl]-1-methyl-pyridinium iodide (from the desmethyl derivative with methyl iodide in DMF at room temperature) IR(KBr): 1784, 1716, 1518 cm$^{-1}$ MS(ISP): 653.5 (M$^⊕$)

Following the procedure set forth above, there can be prepared the following compounds:

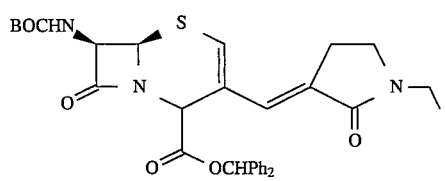

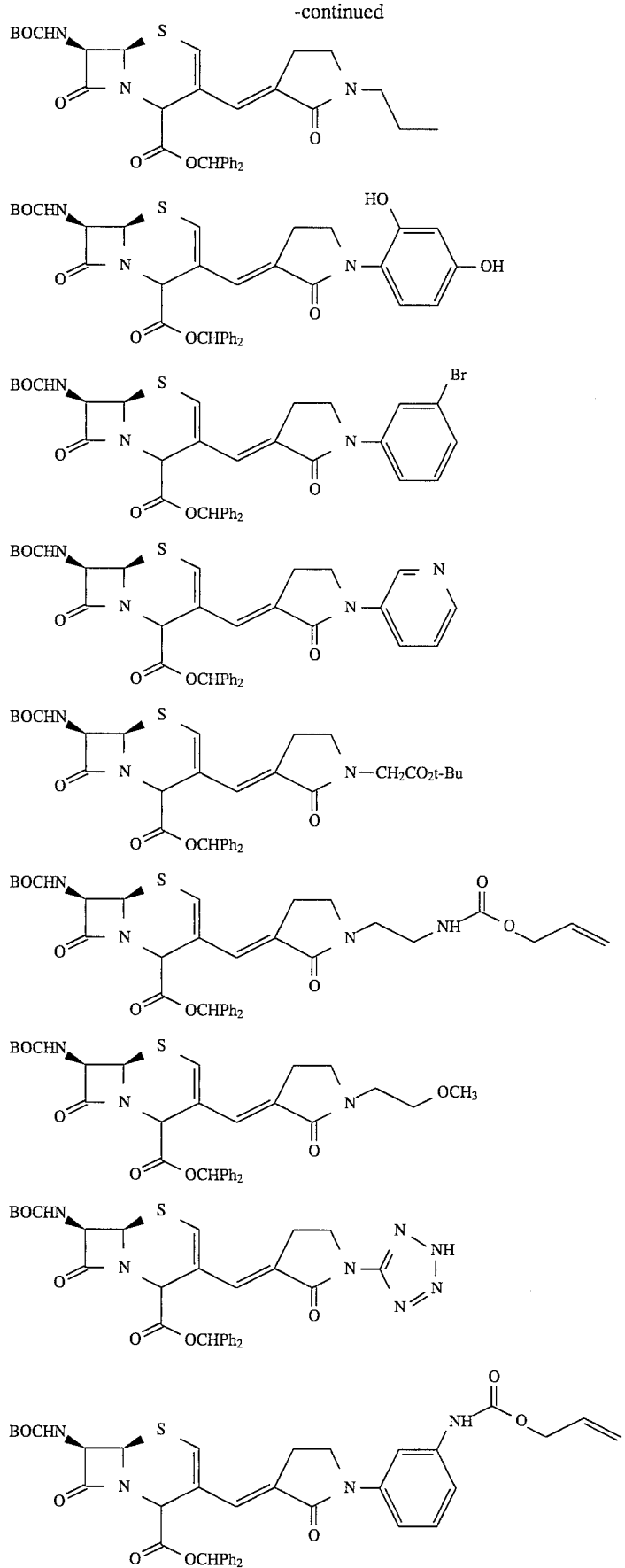

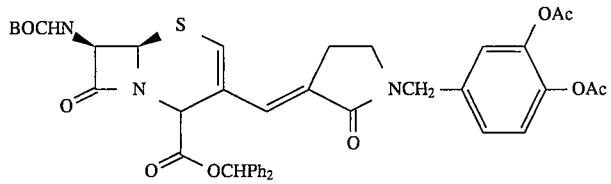

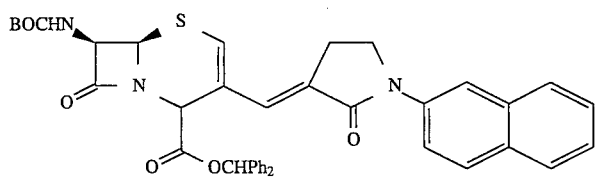

PREPARATION 13

[6R-[3(E), 6α,7β]]-7[[(1,1-Dimethylethoxy)-carbonyl]amino]-3-[[1-( 1,1-dimethylethyl)-2-oxo-3-pyrrolidinylidene]methyl]-8-oxo-5-thia-1-azabicyclo[4.2.0]oct-3-ene-2-carboxylic acid diphenylmethyl ester rac-(1-[1,1-Dimethylethyl]-2-oxo-3-pyrrolidinyl)triphenylphosphonium bromide 1.73 g (3.58 mM) and anhydrous tetrahydrofuran (7 ml) were combined and cooled in an ice bath. 1.6M n-butyl lithium in n-hexane 2.09 ml (3.34 mM) was added dropwise and stirred for 1 ½ hours at this temperature. Dropwise addition of diphenylmethyl [6R-(6α,7β)]-7-[[(1,1-dimethylethoxy)carbonyl]amino]- 3-formyl-8-oxo-5-thia-1-azabicyclo[4.2.0]-oct-3-ene-2-carboxylate 1.16 g (2.39 mM) in 5.5 ml tetrahydrofuran to this mixture at ice bath temperature was followed by stirring for 1½ hours in this bath. The reaction was poured into brine (60 ml) and ethyl acetate (200 ml) and separated. The organic portion was washed with fresh brine (60 ml) and dried ($Na_2SO_4$). The residue obtained after removal of the drying agent and solvent was purified by flash silica gel chromatography using 2:1 n-hexane:ethyl acetate as the eluting solvent. The product fractions were combined, solvent removed, and the residue triturated with 3:1 n-hexane:ethyl acetate to yield 0.99 g (70.8%) of the title material. NMR (200 MHz, $CDCl_3$) δ 1.42 (s, 9H), 1.44 (s, 9H), 2.70 (m, 2H), 3.30 (m, 2H), 5.18 (d, 1H), 5.30 (d, 1H), 5.35 (m, 1H), 6.50 (s, 1H), 6.80 (m, 2H), and 7.20–7.40 (m, 11H).

According to the procedure set forth in the preceding preparation, the following additional compounds were prepared:

[6R-[3(E),6α,7β]]-3-[(1-Cyclopropyl-2-oxo-3-pyrrolidinylidene)methyl]-7-[[(1,1-dimethylethoxy)carbonyl]amino]-8-oxo- 5-thia-1-azabicyclo[4.2.0]oct-3-ene-2-carboxylic acid diphenylmethyl ester NMR (200 MHz, $CDCl_3$) δ 0.78 (m, 4H), 1.44 (s, 9H), 1.44 (s, 9H), 2.70 (m, 3 H), 3.10 (m, 2H), 5.20 (d, 1H), 5.30 (s, 1H), 5,41 (m, 1H), 6.50 (s, 1H), 6.83 (m. 2H), and 7.25–7.35 (m, 11H).

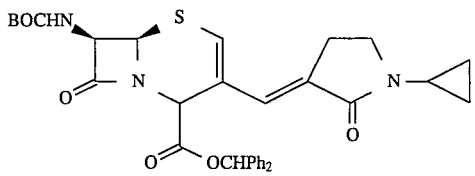

[6R-[3(E),6α,7β]]-7-[[(1,1-Dimethylethoxy)carbonyl]amino]8-oxo-3-[[2-oxo-1-(2,2,2-trifluoroethyl)-3-pyrrolidinylidene]methyl]-5-thia-1-azabicyclo[4.2.0]oct-3-ene-2-carboxylic acid diphenylmethyl ester NMR (200 MHz, $CDCl_3$) δ 1.45 (s, 9H), 2.80 (m, 2H), 3.35 (m, 2H), 3.95 (m, 2H), 5.18 (d, 1H), 5.29 (s, 1H), 5.40 (m, 1H), 6.50 (s, 1H), 6.85 (s, 2 H), 6.95 (m, 1 H) and 7.30 (m, 11H).

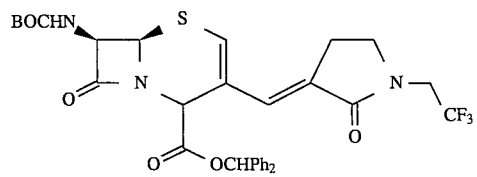

[6R-[3(E),6α,7β]]-7-[[(1,1-Dimethylethoxy)carbonyl]amino]-3-[[1-( 2-fluoroethyl)-2-oxo-3-pyrrolidinylidene]methyl-8-oxo-5-thia-1-azabicyclo[4.2.0]oct-3-ene-2-carboxylic acid diphenylmethyl ester NMR (200 MHz, $CDCl_3$) δ 1.45 (s, 9H), 2.75 (m, 2H), 3.40 (t, 2H), 3,61, 3.75 (m, 2H), 4.48, 4.70 (t, 2H), 5.20 (d, 1H), 5.31 (d, 1H), 5.40 (m, 1H), 6.56 (s, 1H), 6.88 (m, 2H) and 7.21–7.33 (m, 11H).

[6R-[3(E),6α,7β-[[(1,1-Dimethylethoxy)carbonyl]amino]3-[[1-[1-[(1,1-dimethylethoxy)carbonyl]-1-methylethyl]-2-oxo-3- pyrrolidinylidene]methyl]-8-oxo-5-thia-1-azabicyclo[4.2.0]oct-3-ene-2-carboxylic acid diphenylmethyl ester NMR (200 MHz, $CDCl_3$), δ 1.43 (s, 9H), 1.45 (s, 9H), 1.47 (s, 3H), 1.57 (s, 3H), 2.80 (m, 2H), 3.35 (m, 2H), 5.19 (d, 1H), 5.29 (d, 2H), 5.40 (m, 1H), 6.56 (s, 1H), 6.85 (s, 2H), 7.30 (m, 10H).

1:1 Mixture of (E)-(2R,6R,7R)- and -(2S,6R,7R)-7 -tert-butoxycarbonyl-amino-3-[1-(4-methoxy-phenyl)-2-oxo-pyrrolidin-3-ylidenemethyl]-5-thia-1-azabicyclo[4.2.0]oct-3-ene-2-carboxylic acid benzhydryl ester IR(KBr): 1780, 1741, 1685, 1521, $cm^{-1}$

MS(ISP): 668,5 $(M+H)^⊕$ (E)-(2R,6R,7R)-7-tert-Butoxycarbonylamino-3-[1-(6-methoxy-pyridin-3-yl)-2-oxo-pyrrolidin-3-ylidenemethyl-8-oxo-5-thia-1-azabicyclo[4.2.0]-3-ene-2-carboxylic acid benzhydryl ester IR(KBr): 1783, 1742, 1718, 1688, 1496 $cm^{-1}$

MS(ISP): 669.4 $(M+H^⊕)$

Following the procedure set forth in the above preparation, there can be prepared the following compounds:

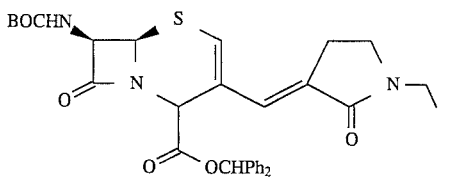

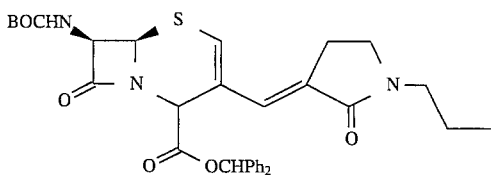

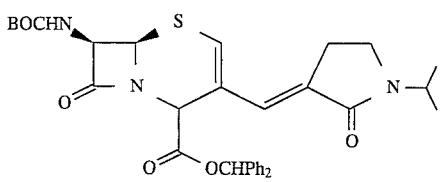

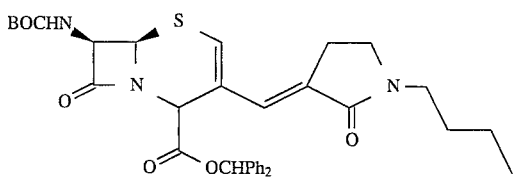

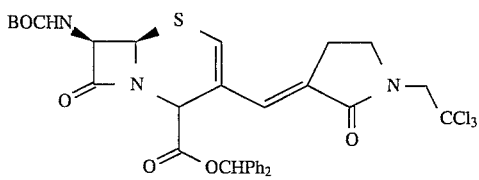

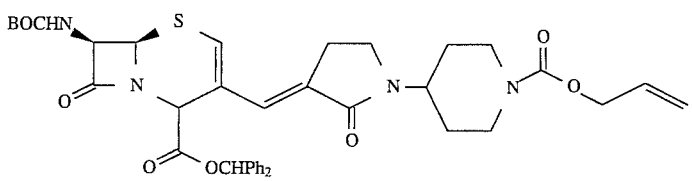

Preparation 14

[6R-[3(E),6β,7β]]-7-[[(1,1-Dimethylethoxy)carbonyl] amino]-8-oxo-3 -[[2-oxo-1-(2,2,2-trifluoroethyl)-3-pyrrolidinylidene]methyl]-5-thia-1-azabicyclo[4.2.0]oct-3-ene-2-carboxylic acid diphenylmethyl ester 1.0 g (2 mmol) diphenylmethyl-[6R-3(6α,7β)]]-7-[[(1,1 -dimethylethoxy)-carbonyl]amino]-3-formyl-8-oxo-5-thia-1-azabicyclo[4.2.0]-2-ene-2-carboxylate were suspended together with 1.23 g (2.4 mmol) rac [2-oxo-1-(2,2,2-trifluoroethyl)-3-pyrrolidinyl]triphenylphosphonium bromide in 8 ml 1,2-epoxybutane (1,2-butyleneoxide) and refluxed for 4 hours. The dark brown solution was evaporated and the residue poured on 10 ml water. The mixture was extracted with 15 ml ethyl acetate, and the organic phase was washed with 15 ml brine and dried over magnesium sulfate. The solvent was evaporated and the dark brown residue purified by chromatography over silica gel (25 g Merck, 40–63 mm, 230–400 mesh, n-hexane:ethyl acetate=95:5, 9:1, 2:1, 1:1).

Yield: 1.2 g yellowish foam (93%)

According to HPLC$^{a}$) the product is a mixture of $\Delta^3$ and $\Delta^2$ isomers: 87% oct-3-ene and 9% oct-2-ene derivative.

$^1$H-NMR (DMSO-d$_6$) δ [ppm] 1.40 (s, 9H); 2.80 (br. m, 2H), 3.40 (t, 2H), 4.20 (m, 2H), 5.11 (d, 1H), 5,29 (dd, 1H), 5.57 (s, 1H), 6.83 (s, 1H), 7.33 (m, 11H), 8.07 (d, 1H).

$^{a)}$HPLC conditions:

Lichrospher RP-18, 250 mm, 5 mm, 1240 ml acetonitrile, 4 g tetradecyl ammonium bromide, 570 ml water, 190 ml buffer pH 7 with H$_3$PO$_4$ adjusted to pH 6.7.

According to the procedure set forth in the preceding preparation the following additional compounds were prepared:

[6R-[3(E),6α,7β]]-3-[(1-Cyclopropyl-2-oxo-3-pyrrolidinylidene)methyl]7-[[(1,1-dimethylethoxy)carbonyl] amino]-8 -oxo-5-thia-1-azabicyclo[4.2.0]-3-ene-2-carboxylic acid diphenylmethyl ester Microanalysis: calc. C 65.08 H 6.09 N 6.49 S 4.96 found C 65.03 H 6.12 N 6.43 S 5.04

Mixture of (E)-(2R,6R,7R)- and -(2S,6R,7R)-7 -tert.-butoxycarbonylamino-3-(1-tert-butoxycarbonylmethyl-2-oxo-pyrrolidin-3-ylidenemethyl)-8-oxo-5-thia-1-azabicyclo[4.2.0]oct-3-ene- 2-carboxylic acid benzhydryl ester MS (ISP): 676.4 (M+H)$^{\oplus}$ IR(KBr): 1783, 1742, 1688 cm$^{-1}$ Mixture of (E)-(2R,6R,7R)- and -(2S,6R,7R)-7-tert-Butoxycarbonylamino-3-[1-(4-methoxy-benzoyl)-2-oxo-pyrrolidin-3-ylidenemethyl]-8-oxo-5-thia-1-azabicyclo[4.2.0]oct-3-ene-2-carboxylic acid benzhydryl ester MS (ISP): 696.5 (M+H)$^{\oplus}$ IR(KBr): 1782, 1721, 1666 cm$^{-1}$ (E)-(2R,6R,7R)-7-tert-Butoxycarbonylamino-3-[1-(5-methyl-isoxazol-3-yl)-2-oxo-pyrrolidin-3-ylidenemethyl-8-oxo-5-thia-1-azabicyclo[4.2.0]oct-3-ene-2-carboxylic acid benzhydryl ester MS(EI): 486 (M-Boc-NH-HC=C=O)

IR(KBr): 1784, 1741, 1706, 1609, 1505, 1456 cm$^{-1}$ (E)-(2R,6R,7R)-7-tert-Butoxycarbonylamino-8-oxo-3-(2-oxo-1-pyridin-2-yl-pyrrolidin-3-ylidenemethyl)-5-thia-1-azabicyclo[4.2.0]oct-3-ene-2-carboxylic acid benzhydryl ester MS(EI): 482 (M-Boc-NH-HC=C=O)

IR(KBr): 1785, 1738, 1693, 1587, 1460, 1387 cm$^{-1}$ (E)-(2R,6R,7R)-7-tert-Butoxycarbonylamino-8-oxo-3-(2-oxo-1-pyridin-3-yl-pyrrolidin-3-ylidenemethyl)-5-thia-1-azabicyclo[4.2.0]oct-3-ene-2-carboxylic acid benzhydryl ester

MS(EI): 538 (M-CO$_2$-CH$_2$=C(CH$_3$)$_2$).

IR(KBr): 1772, 1735, 1693, 1482 cm$^{-1}$ (E)-(2R,6R,7R)-7-tert-Butoxycarbonylamino-8-oxo-3-[2-oxo-1-oxazolidin-3-yl)-pyrrolidin-3-ylidenemethyl]-5-thia-1-azabicyclo[4.2.0]oct-3-ene-2-carboxylic acid benzhydryl ester MS(EI): 490 (M-Boc-NH-HC=C=O)

IR(KBr): 1782, 1741, 1708, 1392, 1251 cm$^{-1}$ (E)-(2R,6R,7R)-7-tert-Butoxycarbonylamino-8-oxo-3-[2-oxo-1-(trifluoromethyl-1,3,4-thiadiazol-2-yl)-pyrrolidin-3-ylidenemethyl]-5-thia-1-azabicyclo[4.2.0]oct-3-ene-2-carboxylic acid benzhydryl ester MS(EI): 557 (M-Boc-NH-CH=C=O)

IR(KBr): 1789, 1733, 1700, 1471, 1330 cm$^{-1}$ (E)-(2R,6R,7R)-7-tert-Butoxycarbonylamino-8-oxo-3-(2-oxo-1-thiazol-2-yl-pyrrolidin-3-ylidenemethyl)-5-thia-1-azabicyclo[4.2.0]oct-3-ene-2-carboxylic acid benzhydryl ester MS(ISP): 645.4 (M+H)$^{\oplus}$ IR(KBr): 1782, 1748, 1695, 1504, 1465 cm$^{-1}$ Mixture of (E)-(2R,6R,7R)- and -(2S,6R,7R)-3-(1-allyl-2-oxo-pyrrolidin-3-ylidenemethyl)-7-tert-butoxycarbonylamino-8-oxo-5-thia- 1-azabicyclo[4.2.0]oct-3-ene-2-carboxylic acid benzhydryl ester MS(ISP): 602.4 (M+H)$^{\oplus}$ IR(KBr): 1781, 1717, 1682 cm$^{-1}$ (E)-(2R,6R,7R)-7-tert-Butoxycarbonylamino-3-[1-(1,1-dioxo-tetrahydrothiophen-3-yl)-2-oxo-pyrrolidin-3-ylidenemethyl]-8-oxo-5-thia-1-azabicyclo[4.2.0]oct-3-ene-2-carboxylic acid benzhydryl ester (1:1 mixture of epimers)

MS(ISP): 680.5 (M+H)$^{\oplus}$

IR(KBr): 2935, 1782, 1719, 1684, 1319, 1272, 1161 cm$^{-1}$ (E)-(2R,6R,7R)-7-tert-Butoxycarbonylamino-8-oxo-3-(2-oxo-pyridin-4-yl-pyrrolidin-3-ylidenemethyl)-5-thia-1-azabicyclo[4.2.0]oct-3-ene-2-carboxylic acid benzhydryl ester (Z)-(2R,6R,7R)-7-tert-Butoxycarbonylamino-3-(1-cyclopropyl-2-oxo-pyrrolidin-3-ylidenemethyl)-8-oxo-5-thia-1-azabicyclo[4.2.0]oct-3-ene-2-carboxylic acid benzhydryl ester MS(ISP): 605.4 (M+H)$^{\oplus}$ IR(KBr): 1780, 1715, 1671 cm$^{-1}$ 1:1 Mixture of (E)-(2R,6R,7R)- and -(2S,6R,7R)-7-tert-butoxycarbonylamino-8-oxo-3-[2-oxo-1-(2,2,2-trifluoroethyl)-piperidin-3-ylidenemethyl]-5-thia-1-azabicyclo[4.2.0]oct-3-ene-2-carboxylic acid benzhydryl ester MS(ISP): 658.4 (M+H)$^{\oplus}$ IR(KBr): 1782, 1743, 1718, 1655 cm$^{-1}$ 1:1 Mixture of (E)-(2R,6R,7R)- and -(2S,6R,7R)-7-tert-butoxycarbonylamino-8-oxo-3-(1-phenyl-2-oxo-piperidin-3-ylidenemethyl)-5-thia-1-azabicyclo[4.2.0]oct-3-ene-2-carboxylic acid benzhydryl ester MS(ISP): 652.2 (M+H)$^{\oplus}$ IR(KBr): 1781, 1740, 1718, 1653 cm$^{-1}$ 1:1 Mixture of (E)-(2R,6R,7R)- and -(2S,6R,7R)-7-tert-butoxycarbonylamino-3-(1-cyclopropyl-2-oxo-piperidin-3-ylidenemethyl)-8-oxo-5-thia-1-azabicyclo[4.2.0]oct-3-ene-2-carboxylic acid benzhydryl ester

MS(ISP): 615 (M$^+$)

IR(KBr): 1787, 1721, 1656, 1611 cm$^{-1}$ (E)-(2R,6R,7R)-7-tert-Butoxycarbonylamino-8-oxo-3-(2-oxo-1-pyrazin-2-yl-pyrrolidin-3-ylidenemethyl)-5-thia-1-azabicyclo[4.2.0]oct-3-ene-2-carboxylic acid benzhydryl ester MS(ISP): 640.4 (M+H)$^{\oplus}$ IR(KBr): 1782, 1743, 1702, 1522 cm$^{-1}$ Mixture of (E)-(2R,6R,7R)- and -(2S,6R,7R)-3-(1-allyl-2-oxo-pyrrolidin-3-ylidenemethyl)-7-tert-butoxycarbonylamino-8-oxo-5-thia- 1-azabicyclo[4.2.0]oct-3-ene-2-carboxylic acid benzhydryl ester MS(ISP): 602.4 (M+H)$^{\oplus}$ IR(KBr): 1781, 1717, 1682, 1642 cm$^{-1}$ (E)-(2R,6R,7R)-7-tert-Butoxycarbonylamino-8-oxo-3-(2-oxo-pyridin-4-yl-pyrrolidin-3-ylidenemethyl)-5-thia-1-azabicyclo[4.2.0]oct-3-ene-2-carboxylic acid benzhydryl ester MS(ISP): 639.5 (M+H)$^{\oplus}$ IR(KBr): 1779, 1738, 1700, 1502 cm$^{-1}$ (E)-(2R,6R,7R)-7-tert-Butoxycarbonylamino-8-oxo-3-[2-oxo-1-(trifluoromethyl-1,3,4-thiadiazol-2-yl)-pyrrolidin-3-ylidenemethyl]-5-thia-1-azabicyclo[4.2.0]oct-3-ene-2-carboxylic acid benzhydryl ester

MS(ISP): 557 [M-(BOC-NH-C=C=O)]

IR(KBr): 1789, 1733, 1700, 147 1 cm$^{-1}$ (E)-(2R,6R,7R)-7-tert-Butoxycarbonylamino-3-[1-(6-methoxy-pyridin-3-yl)-2-oxo-pyrrolidin-3-ylidenemethyl)-8-oxo-5-thia-1-azabicyclo[4.2.0]oct-3-ene-2-carboxylic acid benzhydryl ester MS(ISP): 669.4 (M+H)$^{\oplus}$ IR(KBr): 1783, 1742, 1718, 1688, 1496 cm$^{-1}$ Mixture of (E)-(2R,6R,7R)- and -(2S,6R,7R)-7-tert-butoxycarbonylamino-8-oxo-3-(2-oxo-1-prop-2-ynyl-pyrrolidin-3-ylidenemethyl)-5-thia-1-azabicyclo[4.2.0]oct-3-ene-2-carboxylic acid benzhydryl ester MS(ISP): 617.5 (M+NH$_4$)$^{\oplus}$ IR(KBr): 2116, 1780, 1744, 1716, 1685 cm$^{-1}$ Mixture of (E)-(2R,6R,7R)- and -(2S,6R,7R)-7-tert-butoxycarbonylamino-3-(1-cyclopropylmethyl-2-oxo-pyrrolidin-3-ylidenemethyl)-8-oxo-5-thia-1-azabicyclo[4.2.0]oct-3-ene-2-carboxylic acid benzhydryl ester MS(ISP): 616.4 (M+H)$^{\oplus}$ IR(KBr): 1781, 1741, 1713, 1678 cm$^{-1}$ (E)-(6R,7R)-7-tert-Butoxycarbonylamino-3-[(1-cyanomethyl)-2 -oxo-pyrrolidin-3-ylidenemethyl]-8-oxo-5-thia-1-azabicyclo[4.2.0]oct-3-ene- 2-carboxylic acid benzhydryl ester MS(ISP): 601.5 (M+H)$^{\oplus}$ IR(KBr): 1781, 1743, 1695 cm$^{-1}$ Mixture of (E)-(2R,6R,7R)- and -(2S,6R,7R)-7 -tert-butoxycarbonylamino-3-[(1-cyano-ethyl)-2-oxo-pyrrolidin-3-ylidenemethyl]-8-oxo-5-thia-1-azabicyclo[4.2.0]oct-3-ene-2-carboxylic acid benzhydryl ester MS(ISP): 615.5 (M+H)$^{\oplus}$ IR(KBr): 2242, 1781, 1716, 1685 cm$^{-1}$ (E)-(2R,6R,7R)-7-tert-Butoxycarbonylamino-3-[1-(4 -methyl-phenylsulfonyl)-2-oxo-pyrrolidin-3-ylidenemethyl] -5,8-dioxo-5-thia-1-azabicyclo[4.2.0]oct-3-ene-2-carboxylic acid benzhydryl ester MS(ISP): 716.4 (M+H)$^{\oplus}$ IR(KBr): 1782, 1719 cm$^{-1}$ Preparation 15

Wittig-Reaction products: (Z)-(6R,7R)-7-tert-Butoxycarbonylamino- 8-oxo-3-(2-oxo-1-phenyl-azetidin-3-ylidenemethyl)-5-thia-1-azabicyclo[4.2.0]oct-2-ene-2-carboxylic acid benzhydryl ester, (E)-( 6R,7R)-7-tert-butoxycarbonylamino-8-oxo-3-(2-oxo-1 -phenyl-azetidin-3-ylidenemethyl)-5-thia-1-azabicyclo[4.2.0]oct-2-ene-2-carboxylic acid benzhydryl ester and Δ$^3$ isomer of (Z)-(6R,7R)-7 -tert-Butoxycarbonylamino-8-oxo-3-(2-oxo-1-phenyl-azetidin-3 -ylidenemethyl)-5-thia-1-azabicyclo[4.2.0]oct-2-ene-2-carboxylic acid benzhydryl ester 114 mg (0.708 mmol) 1-phenyl-azetidine-2,3-dione were dissolved in 15 ml 1,2-epoxybutane (1,2-butyleneoxide), 695 mg (0.80 mmol) (6R,7R )-[7-tert-butoxycarbonylamino-2-di phenylmethoxycarbonyl-8 -oxo-5-thia-1-azabicyclo[4.2.0]oct-2-en-3-ylmethyl]-triphenyl-phosphonium iodide were added, and the mixture was stirred at 60° C. for 1 hour. The dark brown solution was then evaporated and the product mixture separated by chromatography on silica gel (eluent n-hexane:ethyl acetate=4:1, 3:1, 2:1).

The first eluate yielded 140 mg (32%) yellow crystals of (Z)-(6R,7R)- 7-tert-butox ycarbonylamino-8-oxo-3-(2-oxo-1-phenyl-azetidin-3 -ylidenemethyl)-5-thia-1-azabicyclo [4.2.0]oct-2-ene-2-carboxylic acid benzhydryl ester IR(KBr): 1788, 1727 cm$^{-1}$

MS (ISP): 624.4 (M+H)$^+$

The second eluate (163 mg yellow amorphous compound mixture) was subjected to a second chromatography on silica gel (eluent CH$_2$Cl$_2$:ethyl acetate 96:4).

Yield: 82 mg (18,5%) yellow foam of (E)-(6R,7R)-7 -tert-butoxycarbonyl-amino-8-oxo-3-(2-oxo-1-phenyl-azetidin-3 -ylidenemethyl)-5-thia-1-azabicyclo[4.2.0]oct-2-ene-2-carboxylic acid benzhydryl ester were eluted first.

IR(KBr): 1790, 1727 cm$^{-1}$

MS(ISP): 624.5 (M+H)$^+$ 28 mg (6%) colourless foam (Δ$^3$ isomer of (Z)-(6R,7R)-7 -tert-butoxycarbonyl-amino-8-oxo-3-(2-oxo-1-phenyl-azetidin-3 -ylidenemethyl)-5-thia-1-azabicyclo[4.2.0]oct-2-ene-2-carboxylic acid benzhydryl ester) were subsequently eluted IR(KBr): 1782, 1740 cm$^{-1}$

MS(ISP): 624.5 (M+H)$^+$.

According to the procedure set forth in the preceding preparation the following additional compounds were prepared:

(E)-(6R,7R )-7-tert-Butoxycarbonylamino-8-oxo-3-[2-oxo-1-(2,2,2 -trifluoro-ethyl)-azetidin-3-ylidenemethyl]-5-thia-1-azabicyclo[4.2.0]oct- 2-ene-2-carboxylic acid benzhydryl ester IR(KBr): 1787, 1763, 1721 cm$^{-1}$ MS(ISP): 630.4 (M+H)$^{\oplus}$ (Z)-(6R,7R)-7-tert-Butoxycarbonylamino-8-oxo-3-[2-oxo-1-(2,2,2 -trifluoro-ethyl)-azetidin-3-ylidenemethyl]-5-thia-1-azabicyclo[4.2.0]oct- 2-ene-2-carboxylic acid benzhydryl ester IR(KBr): 1789, 1722, 1502 cm$^{-1}$ MS(ISP): 630.5 (M+H)$^{\oplus}$ Preparation 16

[6R-[3(E),6α,7β]]-3-[(1-Cyclopropyl-2-oxo-3-pyrrolidinylidene)-methyl]-7-[[(1,1-dimethylethoxy)carbonyl]amino]-8-oxo-5-thia-1 -azabicyclo[4.2.0]oct-2-ene-2-carboxylic acid diphenylmethyl ester 5-oxide A solution of [6R-[3(E),6α,7β]]-3-[(1-Cyclopropyl-2-oxo-3 -pyrrolidinylidene)-methyl]-7-[[(1,1-dimethylethoxy)carbonyl]amino]-8 -oxo-5-thia-1-azabicyclo[4.2.0]oct-3-ene-2-carboxylic acid diphenylmethyl ester 8.94 g (14.85 mM) in dichloromethane (2.0 l) was cooled to 4° C. in an ice bath. A solution of 80–90% m-chloroperoxybenzoic acid 5.13 g (25.2 mM) in dichloromethane (450 ml) was added dropwise. After one hour at 4° C., the reaction mixture was washed successively with cold solutions of 10% aqueous sodium thiosulfate, 5% aqueous sodium bicarbonate, and water. After drying over anhydrous sodium sulfate, the drying agent and solvent were removed, and the residue was purified by flash silica gel column chromatography (3:1 ethyl acetate:nhexane) to yield 8.16 g (89%) of the title compound.

NMR (200 MHz, CDCl$_3$) δ 0.75 (m, 4H), 1.46 (s, 9H), 2.30, 2.55, 2.80 (m, 3H), 3.10 (m, 2H), 3.90–4.10 (m, 2H), 4.50 (m, 1H), 5.80 (m, 2H), 7.00 (m, 1H), 6.50 (s, 1H), and 7.20–7.55 (m, 11H).

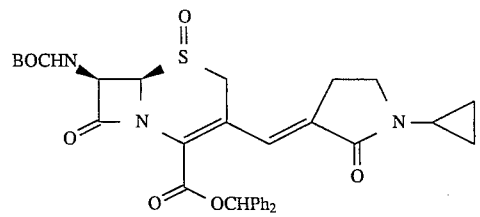

According to the procedure set forth in the preceding preparation, the following additional compounds were prepared:

[6R-[3(E),6α,7β]]-[[(1,1-dimethylethoxy)carbonyl] amino]-8-oxo-3-[(2-oxo-3-pyrrolidinylidene)methyl]-5-thia-1-azabicyclo[4.2.0]oct-2 -ene-2-carboxylic acid diphenylmethyl ester 5-oxide

[6R-[3(E),6α,7β]]-[[(1,1-dimethylethoxy)carbonyl] amino]-3-[(1 -methoxy-2-oxo-3-pyrrolidinylidene)methyl]-8-oxo-5-thia-1-azabicyclo[4.2.0]oct-2-ene-2-carboxylic acid diphenylmethyl ester 5-oxide

[6R-[3(E),6α,7β]]-7-[[(1,1-dimethylethoxy)carbonyl] amino]-3-[(1 -methyl-2-oxo-3-pyrrolidinylidene)methyl]-8- oxo-5-thia-1-azabicyclo[4.2.0]oct-2-ene-2-carboxylic acid diphenylmethyl ester 5-oxide

[6R-[3(E),6α,7β]]-7-[[(1,1-dimethylethoxy)carbonyl]amino]-8-oxo-[2 -oxo-3-[[1-(phenylmethoxy)-3-pyrrolidinylidene]methyl]-5-thia-1-azabicyclo[4.2.0]oct-2-ene-2-carboxylic acid diphenylmethyl ester 5-oxide

[6R-[3(E),6α,7β]]-7-[[(1,1-dimethylethoxy)carbonyl]amino]-8-oxo-3-[[2-oxo-1-phenyl-2-oxo-3-pyrrolidinylidene]methyl]-5-thia-1-azabicyclo[4.2.0]oct-2-ene-2-carboxylic acid diphenylmethyl ester 5-oxide

[6R-[3(E),6α,7β]]-3-[[(1-(2,4-difluorophenyl)-2-oxo-3-pyrrolidinylidene)-methyl]-7-[[(1,1-dimethylethoxy)carbonyl]amino]-8 -oxo-5-thia-1-azabicyclo[4.2.0]oct-2-ene-2-carboxylic acid diphenylmethyl ester 5-oxide

[6R-[3(E),6α,7β]]-7-[[(1,1-dimethylethoxy)carbonyl]amino]-3-[[(1 -(4-nitrophenyl)-2-oxo-3-pyrrolidinylidene]methyl]-8-oxo-5-thia-1-azabicyclo[4.2.0]oct-2-ene-2-carboxylic acid diphenylmethyl ester 5-oxide

[6R-[3(E),6α,7β]]-7-[[(1,1-dimethylethoxy)carbonyl]amino]-3-[[1-( 4-methoxyphenyl)-2-oxo-3-pyrrolidinylidene]methyl ]-8-oxo-5-thia-1-azabicyclo[4.2.0]oct-2-ene-2-carboxylic acid diphenylmethyl ester 5-oxide

[6R-[3(E),6α,7β]]-7-[[(1,1-dimethylethoxy)carbonyl]amino]-3-[[1 -[(4-nitrophenyl)methoxy[2-oxo-3-pyrrolidinylidene]methyl]-8-oxo-5 -thia-1-azabicyclo[4.2.0]oct-2-ene-2-carboxylic acid diphenylmethyl ester 5-oxide

[6R-[3(E),6α,7β]]-7-[[(1,1-dimethylethoxy)carbonyl]amino]-3-[[( 1,1-dimethylethyl)-2-oxo-3-pyrrolidinylidene]methyl]-8-oxo-5-thia-1-azabicyclo[4.2.0]oct-2-ene-2-carboxylic acid diphenylmethyl ester 5-oxide NMR (200 MHz, CDCl$_3$ δ 1.43 (3, 9H), 1.45 (s, 9H), 2.35, 2.65 (m, 2H), 3.30 (m, 2H), 3.18–4.00 (m, 2H), 4.50 (m, 1H), 5.45–5.80 (m, 2H), 7.00 (m, 1H) and 7.20–7.45 (m, 11H).

[6R-[3(E),6α,7β]]-7-[[(1,1-dimethylethoxy)carbonyl]amino]-8-oxo-3-[[2-oxo-1-(2,2,2-trifluoroethyl)-3-pyrrolidinylidene]methyl]-5-thia-1 -azabicycl[4.2.0]oct-2-ene-2-carboxylic acid diphenylmethyl ester 5-oxide NMR (200 MHz, CDCl$_3$) δ 1.46 (s, 9H), 2.45, 2.75 (m, 2H), 3.30 (m, 2H), 3.9–4.54 (m, 5H), 5.38–5.80 (m, 2H), 7.00 (m. 1H) and 7.25–7.45 (m, 11H).

[6R-[3(E),6α,7β]]-7-[[(1,1-dimethylethoxy)carbonyl]amino]-3-[[1 -(2-fluoroethyl)-2-oxo-3-pyrrolidinylidene]methyl]-8-oxo-5-thia-1-azabicyclo[4.2.0]oct-2-ene-2-carboxylic acid diphenylmethyl ester 5-oxide NMR (200 MHz, CDCl$_3$ δ 1.46 (s, 9H), 2.40, 2.70 (m, 2H), 3.20–3.8 (m, 6H), 4.10–4.45 (m, 2H), 4.70 (m, 1H), 5.40, 5.80 (m. 2H) 7.00 (m, 1H) and 7.25–7.40 (m, 11H).

[6R-[3(E),6α,7β]]-7-[[(1,1-dimethylethoxy)carbonyl]amino]-3-[[1-[4-(1,1-dimethylethoxy)carbonyl]phenyl]-2-oxo-3-pyrrolidinylidene]methyl]-8-oxo-5-thia-1-azabicyclo[4.2.0]oct-2-ene-2-carboxylic acid diphenylmethyl ester 5-oxide

[6R-[3(E),6α,7β]]-7-[[(1,1-dimethylethoxy)carbonyl]amino]-3-[[1-[1-([1,1-dimethylethoxy)carbonyl ]-1-methyl-ethyl]-2-oxo-3-pyrrolidinylidene] methyl]-8-oxo-5-thia-1-azabicyclo[4.2.0]oct-2-ene-2-carboxylic acid diphenylmethyl ester 5-oxide

[6R-[3(Z),6α,7β]]-7-[[(1,1-dimethylethoxy)carbonyl]amino]-3-[[1 -phenyl-2-oxo-3-pyrrolidinylidene]methyl]-8-oxo-5-thia-1-azabicyclo[4.2.0]oct-2-ene-2-carboxylic acid diphenylmethyl ester 5-oxide Mixture of (E)-(5R,6R,7R)- and -(5S,6R,7R)-7 -tert-butoxycarbonylamino-5,8-dioxo-3-(2-oxo-1-pyrazin-2-yl-pyrrolidin-3 -ylidenemethyl)-5-thia-1-azabicyclo[4.2.0]oct-2-ene-2-carboxylic acid benzhydryl ester IR(KBr): 1799, 1721 cm$^{-1}$

MS(ISP): 656,6 (M+H)$^⊕$

Mixture of (E)-(5R,6R,7R)- and -(5S,6R,7R)-7 -tert-butoxycarbonylamino-5,8-dioxo-3-(2-oxo-pyridin-4-yl-pyrrolidin-3 -ylidenemethyl)-5-thia-1-azabicyclo[4.2.0]oct-2-ene-2-carboxylic acid benzhydryl ester IR(KBr): 1797 1718, 1501 cm$^{-1}$

MS(ISP): 655,4 (M+H)$^⊕$,

1:1 Mixture of (E)-(5R,6R,7R)- and -(5S,6R,7R)-7 -tert-butoxycarbonyl-amino-5,8-dioxo-3-(2-oxo-3-prop-2-ynyl-pyrrolidin-3 -ylidenemethyl)-5-thia-1-azabicyclo[4.2.0]oct-2-ene-2-carboxylic acid benzhydryl ester IR(KBr): 2118, 1796, 1721 cm$^{-1}$

MS(ISP): 616,5 (M+H)$^⊕$

Mixture of (E)-(5R,6R,7R)- and -(5S,6R,7R)-7 -tert-butoxycarbonylamino-3-(1-cyclopropylmethyl-2-oxo-pyrrolidin-3 -ylidenemethyl)-5,8-dioxo-5-thia-1-azabicyclo[4.2.0]oct-2-ene-2-carboxylic acid benzhydryl ester IR(KBr): 1796, 1722, 1684 cm$^{-1}$

MS(ISP): 632.5 (M+H)$^⊕$

Mixture of (E)-(5R,6R,7R)- and -(5S,6R,7R)-7 -tert-butoxycarbonylamino-3-(1-cyanomethyl-2-oxo-pyrrolidin-3 -ylidenemethyl)-5,8-dioxo-5-thia-1-azabicyclo[4.2.0]oct-2-ene-2-carboxylic acid benzhydryl ester IR(KBr): 2240, 1796, 1719 cm$^{-1}$

MS(ISP): 634.5 (M+NH$_4$)$^⊕$

Mixture of (E)-(5R,6R,7R)- and -(5S,6R,7R)-7 -tert-butoxycarbonylamino-3-[1-(2-cyano-ethyl)-2-oxo-pyrrolidin-3 -ylidenemethyl)-5,8-dioxo-5-thia-1-azabicyclo[4.2.0]oct-2-ene-2-carboxylic acid benzhydryl ester IR(KBr): 2244, 1795, 1721, 1688 cm$^{-1}$

MS(ISP): 631.5 (M+H)$^⊕$

Mixture of (E)-(5R,6R,7R)- and -(5S,6R,7R)-7 -tert-butoxycarbonylamino-3-[1-(4-methyl-phenylsulfonyl)-2-oxo-pyrrolidin- 3-ylidenemethyl)-5,8-dioxo-5-thia-1-azabicyclo [4.2.0]oct-2-ene-2-carboxylic acid benzhydryl ester IR(KBr): 1799, 1723 cm$^{-1}$

MS(ISP): 747.5 [(M–H)$^⊕$+NH$_3$]

1:1 Mixture of (E)-(5R,6R,7R)- and -(5S,6R,7R)-7 -tert-butoxycarbonyl-amino-3-[1-(4-methoxy-phenyl)-2-oxo-pyrrolidin- 3-ylidenemethyl)-5,8-dioxo-5-thia-1-azabicyclo [4.2.0]oct-2-ene-2-carboxylic acid benzhydryl ester IR(KBr): 1796, 1722, 1687, 1512 cm$^{-1}$

MS(ISP): 684.3 (M+H)$^⊕$

Mixture of (E)-(5R,6R,7R)- and -(5S,6R,7R)-7 -tert-butoxycarbonylamino-3-(1-tert-butoxycarbonylmethyl-2 -oxo-pyrrolidin-3-ylidenemethyl)-5,8-dioxo-5-thia-1-azabicyclo[4.2.0]oct-2 -ene-2-carboxylic acid benzhydryl ester IR(KBr): 1798, 1725 cm$^{-1}$

MS(ISP): 692.5 (M+H)$^⊕$

Mixture of (E)-(5R,6R,7R)- and -(5S,6R,7R)-7 -tert-butoxycarbonylamino-3-[1-(5-methyl-isoxazol-3-yl)-2-oxopyrrolidin- 3-ylidenemethyl)-5,8-dioxo-5-thia-1-azabicyclo [4.2.0]oct-2-ene-2-carboxylic acid benzhydryl ester IR(KBr): 1796, 1718, 1609, 1506, 1456 cm$^{-1}$
MS(ISP): 676.4 (M+NH$_4$)$^⊕$; 659.4 (M+H)$^⊕$ Mixture of (E)-(5R,6R,7R)- and -(5S,6R,7R)-7 -tert-butoxycarbonyl-amino-5,8-dioxo-3-(2-oxo-1-pyridin-2-yl-pyrrolidin-3-ylidenemethyl)- 5-thia-1-azabicyclo[4.2.0]oct-2-ene-2-carboxylic acid benzhydryl ester IR(KBr): 1795, 1724, 1698, 1587, 1500, 1460 cm$^{-1}$
MS(ISP): 655.4 (M+H)$^⊕$ Mixture of (E)-(5R,6R,7R)- and -(5S,6R,7R)-7 -tert-butoxycarbonyl-amino-5,8-dioxo-3-(2-oxo-1-pyridin-3-yl-pyrrolidin-3-ylidenemethyl)- 5-thia-1-azabicyclo[4.2.0]oct-2-ene-2-carboxylic acid benzhydryl ester IR(KBr): 1797, 1721, 1485, 1368, 1306 cm$^{-1}$
MS(ISP): 655.4 (M+H)$^⊕$ Mixture of (E)-(5R,6R,7R)- and -(5S,6R,7R)-7 -tert-butoxycarbonyl-amino-5,8-dioxo-3-[2-oxo-1-(2-oxo-oxazolin-3-yl)-pyrrolidin-3 -ylidenemethyl]-5-thia-1-azabicyclo [4.2.0]oct-2-ene-2-carboxylic acid benzhydryl ester Mixture of (E)-(5R,6R,7R)- and -(5S,6R,7R)-7 -tert-butoxycarbonyl-amino-5,8-dioxo-3-(2-oxo-1-thiazol-2-yl-pyrrolidin-3-ylidenemethyl)- 5-thia-1-azabicyclo[4.2.0]oct-2-ene-2-carboxylic acid benzhydryl ester IR(KBr): 2978, 1799, 1722, 1504, 1463 cm$^{-1}$
MS(ISP): 661.4 (M+H)$^⊕$ Mixture of (E)-(5R,6R,7R)- and -(5S,6R,7R)-7 -tert-butoxycarbonyl-amino-5,8-dioxo-3-[2-oxo-1-(5-trifluoromethyl-1,3,4-thiadiazol-2 -yl)-pyrrolidin-3-ylidenemethyl]-5-thia-1-azabicyclo[4.2.0]oct-2-ene-2-carboxylic acid benzhydryl ester IR(KBr): 1800, 1718, 1475, 1331, 1159 cm$^{-1}$
MS(ISP): 730.4 (M+H)$^⊕$ Mixture of (E)-(5R,6R,7R)- and -(5S,6R,7R)-7 -tert-butoxycarbonyl-amino-3-[1-(4-methoxy-benzoyl)-2-oxo-pyrrolidin-3-ylidenemethyl]- 5,8-dioxo-5-thia-1-azabicyclo [4.2.0]oct-2-ene-2-carboxylic acid benzhydryl ester IR(KBr): 1799, 1724, 1668 cm$^{-1}$
MS(ISP): 712.4 (M+H)$^⊕$ Mixture of (E)-(5R,6R,7R)- and -(5S,6R,7R)-3-(1-allyl-2 -oxo-pyrrolidin-3-ylidenemethyl)-7-tert-butoxycarbonylamino-5,8-dioxo-5 -thia-1-azabicyclo[4.2.0]oct-2-ene-2-carboxylic acid benzhydryl ester IR(KBr): 1796, 1722, 1688 cm$^{-1}$
MS(ISP): 618.4 (M+H)$^⊕$ Mixture of (E)-(5R,6R,7R)- and -(5S,6R,7R)-7 -tert-butoxycarbonyl-amino-3-[1-(1,1-dioxo-tetrahydro-thiophen-3-yl)-2-oxo-pyrrolidin-3-ylidenemethyl ]-5,8-dioxo-5-thia-1-azabicyclo[4.2.0]oct-2-ene-2-carboxylic acid benzhydryl ester (config. in thiophene-moiety R:S=1:1).

IR(KBr): 1796, 1721, 1498, 1301 cm$^{-1}$
MS(ISP): 696.4 (M+H)$^⊕$

Mixture of (E)-(5R,6R,7R)- and -(5S,6R,7R)-7 -tert-butoxycarbonylamino-3-[1-(6-methoxy-pyridin-3-yl)-2-oxo-pyrrolidin- 3-ylidenemethyl]-5,8-dioxo-5-thia-1-azabicyclo [4.2.0]oct-2-ene-2-carboxylic acid benzhydryl ester (mixture of epimers)

IR(KBr): 1797, 1722, 1495, 1285, 1233, 1161 cm$^{-1}$
MS(ISP): 685.4 (M+H)$^⊕$

Mixture of (E)-(5R,6R,7R)- and -(5S,6R,7R)-7 -tert-butoxycarbonylamino-5,8-dioxo-3-(2-oxo-pyridin-4-yl-pyrrolidin-3 -ylidenemethyl)-5-thia-1-azabicyclo[4.2.0]oct-2-ene-2-carboxylic acid benzhydryl ester 1:1 Mixture of (Z)-(5R,6R,7R)- and -(5S,6R,7R)-7 -tert-butoxycarbonyl-amino-3-(1-cyclopropyl-2-oxo-pyrrolidin-3 -ylidenemethyl)-5,8-dioxo-5-thia-1-azabicyclo[4.2.0] oct-2-ene-2-carboxylic acid benzhydryl ester IR(KBr): 1795, 1722, 1682 cm$^{-1}$
MS(ISP): 618.4 (M+H)$^⊕$ Mixture of (E)-(5R,6R,7R)- and -(5S,6R,7R)-7 -tert-butoxycarbonylamino-5,8-dioxo-3-[2-oxo-1-(2,2,2 -trifluoroethyl)-piperidin-3-ylidenemethyl)-5-thia-1-azabicyclo [4.2.0]oct-2-ene-2-carboxylic acid benzhydryl ester IR(KBr): 1796, 1723, 1662, 1628 cm$^{-1}$
MS(ISP): 674.4 (M+H)$^⊕$ Mixture of (E)-(5R,6R,7R)- and -(5S,6R,7R)-7 -tert-butoxycarbonylamino-5,8-dioxo-3-(1-phenyl-2-oxo-piperidin-3 -ylidenemethyl)-5-thia-1-azabicyclo[4.2.0]oct-2-ene-2-carboxylic acid benzhydryl ester IR(KBr): 1797, 1723, 1720, 1657, 1048 cm$^{-1}$
MS(ISP): 668.4 (M+H)$^⊕$ 1:1 Mixture of (E)-(5R,6R,7R)- and (5S,6R,7R)-7 -tert-butoxycarbonyl-amino-3-(1-cyclopropyl-2-oxo-piperidin-3 -ylidenemethyl)-5,8-dioxo-5-thia-1-azabicyclo[4.2.0]oct-2-ene-2-carboxylic acid benzhydryl ester IR(KBr): 1796, 1722, 1654, 1610 cm$^{-1}$
MS(ISP): 649.5 (M+NH$_4$)$^⊕$ Preparation 17

[6R-[3(E),6α,7β]]-3-[(1-Cyclopropyl-2-oxo-3 -pyrrolidinylidene)-methyl]-7-[[(1,1-dimethylethoxy)carbonyl] amino]-8-oxo-5-thia-1-azabicyclo[4.2.0]oct-2-ene-2-carboxylic acid diphenylmethyl ester.

A solution of [6R-[3(E),6α,7β]]-3-[(1-Cyclopropyl-2-oxo-3 -pyrrolidinylidene)-methyl]-7-[[(1,1-dimethylethoxy)carbonyl]amino]-8 -oxo-5-thia-1-azabicyclo[4.2.0]oct-2-ene-2-carboxylic acid diphenylmethyl ester 5-oxide 8.16 g (13.2 mM), dichloromethane (92 ml), N-methyl acetamide (27 ml), and N,N-dimethyl formamide (30 ml) was cooled in a −20° C. bath and a solution of phosphorous tribromide 10.08 ml (0.106M) in dichloromethane (31 ml) was added dropwise to the stirred solution. The solution was stirred for 1 hour at this temperature and then poured into a stirred solution of ice water (400 ml) and dichloromethane (260 ml). The aqueous layer was separated and reextracted with dichloromethane (100 ml). The combined organic fraction were washed with 5% aqueous sodium bicarbonate and then water. The methylene chloride fraction was dried (Na$_2$SO$_4$) and concentrated. The residue was purified by flash silica gel column chromatography (3:1 ethyl acetate:n-hexane) to give the title compound 6.36 g (80%).

NMR (200 MHz, CDCl$_3$) δ 0.77 (m, 4H), 1.48 (s, 9H), 2.23, 2.52 (m, 2H), 2.75 (m, 1H), 2.97, 3.12 (m, 2H), 3.52 (s, 2H), 4.98 (d, 1H), 5.24 (d, 1H), 5.63 (q, 1H), 7.0 (s, 1H), and 7.12–7.48 (m, 11H).

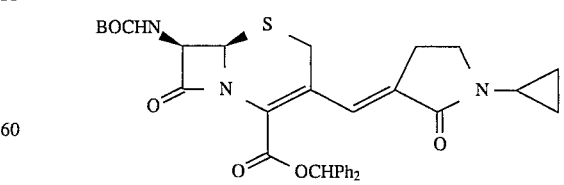

According to the procedure set forth in the preceding preparation the following compound were prepared:

[6R-[3(E),6α,7β]]-7-[[(1,1-dimethylethoxy)carbonyl] amino]-8-oxo-3-[(2-oxo-3-pyrrolidinylidene)methyl]-5- thia-1-azabicyclo[4.2.0]oct-2-ene-2-carboxylic acid diphenylmethyl ester

IR(KBr): cm⁻¹ 3350 (br.), 1782, 1718, 1525, 702.

[6R-[3(E),6α,7β]]-7-[[(1,1-dimethylethoxy)carbonyl]amino]-3-[(1-methoxy-2-oxo-3-pyrrolidinylidene)methyl]-8-oxo-5-thia-1-azabicyclo[4.2.0]oct-2-ene-2-carboxylic acid diphenylmethyl ester IR(KBr): cm¹ 3350 (br.), 2970, 1777, 1718, 1500, 702.

[6R-[3(E),6α,7β]]-7-[[(1,1-dimethylethoxy)carbonyl]amino]-3-[(1-methyl-2-oxo-3-pyrrolidinylidene)methyl]-8-oxo-5-thia-1-azabicyclo[4.2.0]oct-2-ene-2-carboxylic acid diphenylmethyl ester NMR (200 MHz, CDCl₃) δ 1.45 (s, 9H), 2.30, 2.55 (m, 2H), 2.95 (s, 3H), 3.00–3.20 (m, 2H), 3.51 (s, 2H), 4.98 (d, 1H), 5.25 (d, 1H), 5.65 (q, 1H), 7.0 (s, 1H), and 7.22–7.45 (m, 11H).

[6R-[3(E), 6α,7β]]-7-[[(1,1-dimethylethoxy)carbonyl]amino]-8-oxo-3-[[2-oxo-1-(phenylmethoxy)-3-pyrrolidinylidene]methyl]-5-thia-1-azabicyclo[4.2.0]oct-2-ene-2-carboxylic acid diphenylmethyl ester IR(KBr): cm⁻¹ 3300 (br.), 1785, 1715, 1525, 698.

[6R-[3(E),6α,7β]]-7-[[(1,1-dimethylethoxy)carbonyl]amino]-8-oxo-3-[(2-oxo-1-phenyl-3-pyrrolidinylidene)methyl]-5-thia-1-azabicyclo[4.2.0]oct-2-ene-2-carboxylic acid diphenylmethyl ester IR(KBr): cm⁻¹ 3350 (br.), 1789, 1720, 1500, 697.

[6R-[3(E),6α,7β]]-3-[[1-(2,4-Difluorophenyl)-2-oxo-3-pyrrolidinylidene]-methyl]-7-[[(1,1-dimethylethoxy)carbonyl]amino]-8-oxo-5-thia-1-azabicyclo]4.2.0]oct-2-ene-2-carboxylic acid diphenylmethyl ester IR(KBr): cm⁻¹ 3300 (br.), 1788, 1720, 1705, 698.

[6R-[3(E),6α,7β]]-7-[[(1,1-dimethylethoxy)carbonyl]amino]-3-[[1-(4-nitrophenyl)-2-oxo-3-pyrrolidinylidene]methyl]-8-oxo-5-thia-1-azabicyclo[4.2.0]oct-2-ene-2-carboxylic acid diphenylmethyl ester IR(KBr): cm⁻¹ 3350 (br.), 1783, 1720, 1672, 698.

[6R-[3(E),6α,7β]]-7-[[(1,1-dimethylethoxy)carbonyl]amino]-3-[[1-(4-methoxyphenyl)-2-oxo-3-pyrrolidinylidene]methyl]-8-oxo-5-thia-1-azabicyclo[4.2.0]oct-2-ene-2-carboxylic acid diphenylmethyl ester IR(KBr): cm⁻¹ 3350 (br.), 1785, 1722, 1685, 700.

[6R-[3(E),6α,7β]]-7-[[(1,1-dimethylethoxy)carbonyl]amino]-3-[[1-[(4-nitrophenyl)methoxy]-2-oxo-3-pyrrolidinylidene]methyl]-8-oxo-5-thia-1-azabicyclo[4.2.0]oct-2-ene-2-carboxylic acid diphenylmethyl ester IR(KBr): cm⁻¹ 3300 (br.), 1785, 1720, 1525, 700.

[6R-[3(E),6α,7β]]-7-[[(1,1-dimethylethoxy)carbonyl]amino]-3-[[1 (1,1-dimethylethyl)-2-oxo-3-pyrrolidinylidene]methyl]-8-oxo-5-thia-1-azabicyclo[4.2.0]oct-2-ene-2-carboxylic acid diphenylmethyl ester NMR (200 MHz, CDCl₃) δ 1.51(s, 9H), 1.55 (s, 9H), 2.35, 2.55 (m, 2H), 3.28 (m, 2H), 3.55 (s, 2H), 4.98 (d, 1H), 5.24 (d, 1H), 5.62 (q, 1H), 7.0 (s, 1H), and 7.17–7.50 (m, 11H).

[6R-[3(E),6α,7β-[[-7-[[(1,1-dimethylethoxy)carbonyl]amino]-8-oxo-3-[[2-oxo-1-(2,2,2-trifluoroethyl)-3-pyrrolidinylidene]methyl]-5-thia-1-azabicylo[4.2.0]oct-2-ene-2-carboxylic acid diphenylmethyl ester NMR (200 MHz, CDCl₃) δ 1.48(s, 9H), 2.40, 2.65 (m, 2H),3.20, 3.40 (m, 2H), 3.55 (s, 2H), 3.92 (m, 2H), 5.00 (d, 1H), 5.23 (d, 1H), 5.48 (q, 1H), 7.02 (s, 1H), and 7.31 (m, 11H).

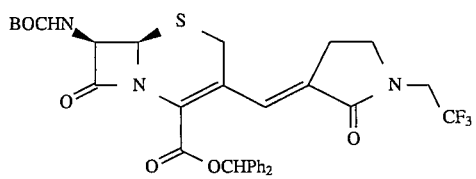

[6R-[3(E),6α,7β]]-7-[[(1,1-dimethylethoxy)carbonyl]amino]-3-[[1-(2-fluoroethyl)-2-oxo-3-pyrrolidinylidene]methyl]-8-oxo-5-thia-1-azabicyclo[4.2.0]oct-2-ene-2-carboxylic acid diphenylmethyl ester NMR (200 MHz, CDCl3) δ 1.48 (s, 9H), 2.38.2.65 (m, 2H),3.23, 3.40 (m, 2H), 3.54 (s, 2H), 3.55, 3.70 (m, 2H), 4.45, 4.68 (m, 2H), 5.00 (d, 1H), 5.25 (d, 1H), 5.65 (q, 1H), 7.0 (s, 1H), and 7.32 (m, 11H).

[6R-[3(E),6α,7β]]-7-[[(1,1-dimethylethoxy)carbonyl]amino]-3-[[1-[4-[(1,1-dimethylethoxyl)carbonyl]phenyl]-2-oxo-3-pyrrolidinylidene ]methyl]-8-oxo-5-thia-1-azabicyclo[4.2.0]oct-2-ene-2-carboxylic acid diphenylmethyl ester NMR (200 MHz, CDCl₃) δ 1.46(s, 9H), 1.59 (s, 9H), 2.35, 2.65 (m, 2H),3.40, 3.65 (m, 2H), 3.55 (s, 2H), 5.00 (d, 1H), 5.28 (d, 1H), 5.68 (q, 1H), 7.05 (s 1H), 7.10–7.45 (m, 11H), 7.78 (d, 2H), and 7.98 (d, 2H).

[6R-[3(E),6α,7β]]-7-[[(1,1-dimethylethoxy)carbonyl]amino]-3-[[1-[1-[(1,1-dimethylethoxyl)carbonyl]1-methylethyl]-2-oxo-3-pyrrolidinylidene ]methyl]-8-oxo-5-thia-1-azabicyclo[4.2.0]oct-2-ene-2-carboxylic acid diphenylmethyl ester IR(KBr) cm¹ 3300 (br.), 1787, 1727, 1688, 700.

[6R-[3(Z),6,60 ,7β]]-7-[[(1,1-dimethylethoxy)carbonyl]amino]-3-[[1-phenyl-2-oxo-3-piperidinylidene]methyl]-8-oxo-5-thia-1-azabicyclo[4.2.0]oct-2-ene-2-carboxylic acid diphenylmethyl ester IR(KBr) cm⁻¹ 3515 (br.), 1785, 1720, 1672, 695.

(E)-(6R,7R)-7-tert-Butoxycarbonylamino-8-oxo-3-(2-oxo-1-pyrazin-2-yl-pyrrolidin-3-ylidenemethyl)-5-thia-1-azabicyclo[4.2.0]oct-2-ene-2-carboxylic acid benzylhydryl ester IR(KBr): 1788, 1719, 1495 cm⁻¹

MS(ISP): 640.5 (M+H)⊕

(E)-(6R,7R)-7-tert-Butoxycarbonylamino-8-oxo-3-(2-oxo-1-prop-2-ynyl-pyrrolidin-3-ylidenemethyl)-5-thia-1-azabicyclo[4.2.0]oct-2-ene-2-carboxylic acid benzylhydryl ester IR(KBr): 2115, 1794, 1720, 1688 cm⁻¹

MS(ISP): 600.4 (M+H)⊕

(E)-(6R,7R)-7-tert-Butoxycarbonylamino-3-(1-cyclopropylmethyl-2-oxo-pyrrolidin-3-ylidenemethyl)-8-oxo-5-thia-1-azabicyclo[4.2.0]oct-2-ene-2-carboxylic acid benzylhydryl ester IR(KBr): 1785, 1721, 1684 cm⁻¹

MS(ISP): 633.6 (M+NH₄)⊕

(E)-(6R,7R)-7-tert-Butoxycarbonylamino-3-(1-cyanomethyl-2-oxo-pyrrolidin-3-ylidenemethyl)-8-oxo-5-thia-1-azabicyclo[4.2.0]oct-2-ene-2-carboxylic acid benzylhydryl ester IR(KBr): 1785, 1718, 1655 cm⁻¹

MS(ISP): 618.4 (M+NH₄)⊕

(E)-(6R,7R)-7-tert-Butoxycarbonylamino-3-[1-(2-cyanoethyl)-2-oxo-pyrrolidin-3-ylidenemethyl)-8-oxo-5-thia-1-azabicyclo[4.2.0]oct-2-ene-2-carboxylic acid benzylhydryl ester IR(KBr): 2241, 1786, 1729, 1688 cm$^{-1}$
MS(ISP): 615.5 (M+H)$^{\oplus}$ (E)-(6R,7R)-7-tert-Butoxycarbonylamino-3-[1-(6-methoxy-pyridin-3-yl)-2-oxo-pyrrolidin-3-ylidenemethyl)-8-oxo-5-thia-1-azabicyclo[4.2.0]oct-2-ene-2-carboxylic acid benzylhydryl ester IR(KBr): 1787, 1721, 1495 cm$^{-1}$
MS(ISP): 686.4 (M+NH$_4$)$^{\oplus}$; 669.4 (M+H)$^{\oplus}$ (E)-(6R,7R)-7-tert-Butoxycarbonylamino-3-(1-tert-butoxycarbonylmethyl-2-oxo-pyrrolidin-3-ylidenemethyl)-8-oxo-5-thia-1-azabicyclo[4.2.0]oct-2-ene-2-carboxylic acid benzylhydryl ester IR(KBr): 1781, 1724 cm$^{-1}$
MS(ISP): 676.5 (M+H)$^{\oplus}$ (E)-(6R,7R)-7-tert-Butoxycarbonylamino-8-oxo-3-(2-oxo-1-pyridin-2-yl-pyrrolidin-3-ylidenemethyl)-5-thia-1-azabicyclo[4.2.0]oct-2-ene-2-carboxylic acid benzylhydryl ester IR(KBr): 1787, 1719, 1587, 1469, 1386 cm$^{-1}$
MS(ISP): 639.4 (M+H)$^{\oplus}$ (E)-(6R,7R)-7-tert-Butoxycarbonylamino-8-oxo-3-(2-oxo-1pyridin-3-yl-pyrrolidin-3-ylidenemethyl)-5-thia-1-azabicyclo[4.2.0]oct-2-ene-2-carboxylic acid benzylhydryl ester IR(KBr): 1787, 1720, 1485, 1367, 1307 cm$^{-1}$
MS(ISP): 639.4 (M+H)$^{\oplus}$ (E)-(6R,7R)-7-tert-Butoxycarbonylamino-8-oxo-3-[2-oxo-1-(2-oxo-oxazolidin-3-yl)-pyrrolidin-3-ylidenemethyl]-5-thia-1-azabicyclo[4.2.0]oct-2-ene-2-carboxylic acid benzylhydryl ester IR(KBr): 1784, 1715, 1488, 1369, 1225 cm$^{-1}$
MS(ISP): 664.4 (M+NH$_4$)$^{\oplus}$; 647.4 (M+H)$^{\oplus}$ (E)-(6R,7R)-7-tert-Butoxycarbonylamino-3-[1-(5-methyl-isoxazol-3-yl)-2-oxo-pyrrolidin-3-ylidenemethyl)-8-oxo-5-thia-1-azabicyclo[4.2.0]oct-2-ene-2-carboxylic acid benzylhydryl ester IR(KBr): 1788, 1718, 1609, 1507, 1456 cm$^{-1}$
MS(ISP): 660.4 (M+NH$_4$)$^{\oplus}$; 643.4 (M+H)$^{\oplus}$ (E)-(6R,7R)-7-tert-Butoxycarbonyl amino-8-oxo-3-(2-oxo-1-thiazol-2-yl-pyrrolidin-3-ylidenemethyl)-5-thia-1-azabicyclo[4.2.0]oct-2-ene-2-carboxylic acid benzylhydryl ester IR(KBr): 1788, 1721, 1505, 1464, 1369 cm$^{-1}$
MS(ISP): 645.4 (M+H)$^{\oplus}$ (E)-(6R,7R)-7-tert-Butoxycarbonylamino-8-oxo-3-[2-oxo-1-(5-trifluoromethyl-1,3,4-thiadiazol-2-yl)-pyrrolidin-3-ylidenemethyl]-5-thia-1-azabicyclo[4.2.0]oct-2-ene-2-carboxylic acid benzylhydryl ester IR(KBr): 1790, 1720, 1475, 1330 cm$^{-1}$
MS(ISP): 731.4 (M+NH$_4$)$^{\oplus}$; 714.4 (M+H)$^{\oplus}$ (E)-(6R,7R)-7-tert-Butoxycarbonylamino-3-[1-(4-methoxy-benzoyl)-2-oxo-pyrrolidin-3-ylidenemethyl)-8-oxo-5-thia-1-azabicyclo[4.2.0]oct-2-ene-2-carboxylic acid benzylhydryl ester IR(KBr): 1788, 1723 cm$^{-1}$
MS(ISP): 696.4 (M+H)$^{\oplus}$; 713.4 (M+NH$_4$)$^{\oplus}$ (E)-(6R,7R)-3-(1-allyl-2-oxo-pyrrolidin-3-ylidenemethyl)-7-tert.-butoxy-carbonylamino-8-oxo-5-thia-1-azabicyclo[4.2.0]oct-2-ene-2-carboxylic acid benzylhydryl ester IR(KBr): 1785, 1720, 1686 cm$^{-1}$
MS(ISP): 602.5 (M+H)$^{\oplus}$;

(E)-(6R,7R)-7-tert-Butoxycarbonylamino-3-[1-(1,1-dioxo-tetrahydro-thiophen-3-yl)-2-oxo-pyrrolidin-3-ylidenemethYl]-8-oxo-5-thia-1-azabicyclo[4.2.0]oct-2-ene-2-carboxylic acid benzylhydryl ester IR(KBr): 1786, 1720, 1368, 1305, 1162 cm$^{-1}$
MS(ISP): 680.5 (M+H)$^{\oplus}$;

(E)-(6R,7R)-tert-Butoxycarbonylamino-3-[1-(4-methylphenylsulfonyl)-2-oxo-pyrrolidin-3-ylidenemethyl]-8-oxo-5-thia-1-azabicyclo[4.2.0]oct-2-ene-2-carboxylic acid benzylhydryl ester (E)-(6R,7R)-7-tert.-Butoxycarbonylamino-8-oxo-3-(2-oxo-pyridin-4-yl pyrrolidin-3-ylidenemethyl)-5-thia-1-azabicyclo[4.2.0]oct-2-ene-2-carboxylic acid benzylhydryl ester (Z)-(6R,7R)-7-tert-Butoxycarbonylamino-3-(1-cyclopropyl-2-oxo-pyrrolidin-3-ylidenemethyl)-8-oxo-5-thia-1-azabicyclo[4.2.0]oct-2-ene-2-carboxylic acid benzylhydryl ester IR(KBr): 1787, 1721, 1686 cm$^{-1}$
MS(ISP): 602.4 (M+H)$^{\oplus}$;

[6R-[3(E),(6α,7β)]]-7-[[(1,1-Dimethylethoxy)carbonyl]amino]-8-oxo-3-[(2-oxo-1-phenyl-3-piperidinylidene)methyl]-5-thia-1-azabicyclo[4.2.0]oct-2-ene-2-carboxylic acid diphenylmethyl ester IR(KBr): 1786, 1722, 1658 cm$^{-1}$
MS(ISP): 652.5 (M+H)$^{\oplus}$;

(E)-(6R,7R)-7-tert-Butoxycarbonylamino-8-oxo-3-[1-(2,2,2-trifluoroethyl)-2-oxo-piperidin-3-ylidenemethyl]-5-thia-1-azabicyclo[4.2.0]oct-2-ene-2-carboxylic acid benzylhydryl ester IR(KBr): 1791, 1715, 1689, 1658 cm$^{-1}$
MS(ISP): 658.4 (M+H)$^{\oplus}$;

(E)-(6R,7R)-7-tert-Butoxycarbonylamino-3-(1-cyclopropyl-2-oxo-piperidin-3-ylidenemethyl)-8-oxo-5-thia-1-azabicyclo[4.2.0]oct-2-ene-2-carboxylic acid benzylhydryl ester IR(KBr): 1786, 1721, 1656 cm$^{-1}$
MS(ISP): 633.5 (M+NH$_4$)$^{\oplus}$, 616.5 (M+H)$^{\oplus}$ Preparation 18

[6R-[3(E),6,α,7β]]-7-Amino-3-[(1-cyclopropyl-2-oxo-1-pyrrolidinylidene)methyl-8-oxo-5-thia-1-azabicyclo[4.2.0]oct-2-ene-2-carboxylic acid trifluoroacetic acid salt

[6R-[3(E),6α,7β]]-3-[(1-Cyclopropyl-2-oxo-1-pyrrolidinylidene)methyl]-7-[[1,1-dimethylethoxy)carbonyl]amino]-8-oxo-5-thia-1-azabicyclo[4.2.0]oct-2-ene-2-carboxylic acid diphenylmethyl ester 6.36 g (10.6 mM) in dichloromethane (254 ml) and anisole (25.4 ml) were cooled in an ice/water bath and trifluoroacetic acid (254 ml) was added dropwise. The solution was stirred for two hours at room temperature and then the volatile material was removed on a rotary evaporator at reduced pressure. The residue was treated dropwise with ethyl ether (280 ml) at 4° C., stirred for 30 minutes and filtered under nitrogen to afford the title compound 4.42 g (93%).

NMR (200 MHz, DMSO-D$_6$) δ 0.70 (s, 4H), 2.80 (m, 1H), 3.00, 3.40 (m, 4H), 3.91 (s, 2H), 5.10 (d, 1H), 5.18 (d, 1H), and 7.22 (s, 1H).

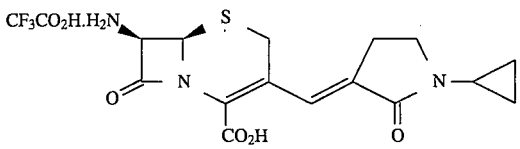
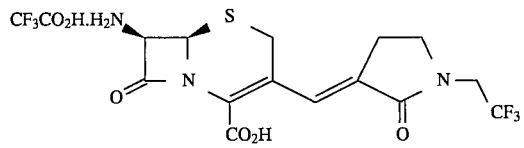

According to the procedure set forth in the preceding preparation, the following compounds were prepared:

[6R-[3(E),6α,7β]]-7-Amino-8-oxo-3-[(2-oxo-3 -pyrrolidinylidene)methyl]-5-thia-1-azabicyclo[4.2.0]oct-2-ene-2-carboxylic acid trifluoroacetic acid salt NMR (200 MHz), DMSO-$d_6$) δ 3.00, 310 (m, 2H), 3.28 (m, 4H), 3.95 (s, 2H), 5.16 (d, 1H), 5.123 (d, 1H), and 7.26 (s, 1H).

[6R-[3(E),6α,7β]]-7-Amino-3-[(1-methoxy-2-oxo-1 -pyrrolidinylidene)-methyl]-8-oxo-5-thia-1-azabicyclo [4.2.0]oct-2-ene-2-carboxylic acid trifluoroacetic acid salt NMR (200 MHz, DMSO-$d_6$/$D_2O$) δ 2.82, 2.92 (m, 2H), 3.54 (m, 4H), 3.68 (s, 2H), 4.88 (d, 1H), 5.05 (d, 1H), and 7.20 (s, 1H).

[6R-[3(E),6,α,7β]]-7-Amino-3-[(1-methyl-2-oxo-3 -pyrrolidinylidene)-methyl]-8-oxo-5-thia-1-azabicyclo[4.2.0] oct-2-ene-2-carboxylic acid trifluoroacetic acid salt NMR (200 MHz, DMSO-$d_6$) δ 2.86 (s, 3H), 2.95 3.08 (m, 2H), 3.39 (m, 2H), 3.96 (s, 2H), 5.18 (d, 1H), 5.22 (d, 1H), and 7.25 (s, 1H).

[6R-[3(E),6α,7β]]-7-Amino-8-oxo-3-[[2-oxo-1-(phenylmethoxy)-3 -pyrrolidinylidene)-methyl]-5-thia-1-azabicyclo[4.2.0]oct-2-ene-2-carboxylic acid trifluoroacetic acid salt

[6R-[3(E),6α,7β-]]-7-Amino-8-oxo-3-[[2-oxo-1-phenyl-3 -pyrrolidinylidene)-methyl]-5-thia-1-azabicyclo [4.2.0]oct-2-ene-2-carboxylic acid trifluoroacetic acid salt

[6R-[3(E),6α,7β]]-7-Amino-3-[[1-(2,4-difluorophenyl)-2-oxo-3 -pyrrolidinylidene]-methyl]-8-oxo-5-thia-1-azabicyclo[4.2.0]oct-2-ene-2-carboxylic acid trifluoroacetic acid salt

[6R-[3(E),6α,7β]]-7-Amino-3-[[1-(4-nitrophenyl)-2-oxo-3 -pyrrolidinylidene]-methyl]-8-oxo-5-thia-1-azabicyclo[4.2.0]oct-2-ene-2-carboxylic acid trifluoroacetic acid salt

[6R-[3(E),6α,7β]]-7-Amino-3-[[1-(4-methoxyphenyl)-2-oxo-3 -pyrrolidinylidene]-methyl]-8-oxo-5-thia-1-azabicyclo[4.2.0]oct-2-ene-2-carboxylic acid trifluoroacetic acid salt

[6R-[3(E),6α,7β]]-7-Amino-3-[[1-[(4-nitrophenyl)methoxy]-2-oxo-3 -pyrrolidinylidene]-methyl]-8-oxo-5-thia-1-azabicyclo[4.2.0]oct-2-ene-2-carboxylic acid trifluoroacetic acid salt

[6R-[3(E),6α,7β]]-7-Amino-3-[[1-(1,1-dimethylethyl)-2-oxo-3 -pyrrolidinylidene]-methyl]-8-oxo-5-thia-1-azabicyclo[4.2.0]oct-2-ene-2-carboxylic acid trifluoroacetic acid salt NMR (200 MHz, DMSO-$d_6$) δ 1.37 (s, 9H), 2.85–2.96 (m, 4H), 3.93 (s, 2H), 5.08 (d, 1H), 5.18 (d, 1H), and 7.22 (s, 1H).

[6R-[3(E),6α,7β]]-7-Amino-8-oxo-3-[[2-oxo-1-(2,2,2 -trifluoroethyl)-3-pyrrolidinylidene]-methyl]-5-thia-1-azabicyclo[4.2.0]oct-2-ene-2-carboxylic acid trifluoroacetic acid salt NMR (200 MHz, DMSO-$d_6$) δ 3.05 (m, 2H), 3.77 (s, 2H), 3.6–3.8 (m, 2H), 4.08 (m, 2H), 5.22 (d, 1H), 5.32 (d, 1H), and 7.75 (s, 1H).

[6R-[3(E),6α,7β]]-7-Amino-3-[[(1-(2-fluoroethyl)-2-oxo-3 -pyrrolidinylidene]-methyl]-8-oxo-5-thia-1-azabicyclo[4.2.0]oct-2-ene-2-carboxylic acid trifluoroacetic acid salt NMR (200 MHz, DMSO-$d_6$) δ 3.0–3.25 (m, 4H), 3.67 (m, 2H), 3.92 (s, 2H), 4.43 (t, 1H), 4.68 (t, 1H), 5.10 (d, 1H), 5.18 (d, 1H), and 7.26 (s, 1H).

[6R-[3(E),6α,7β]]-7-Amino-3-[[1-(4-carboxyphenyl)-2-oxo-3 -pyrrolidinylidene]-methyl]-8-oxo-5-thia-1-azabicyclo[4.2.0]oct-2-ene-2-carboxylic acid trifluoroacetic acid salt

[6R-[3(Z),6α,7β]]-7-Amino-3-[[1-phenyl-2-oxo-3-pyrrolidinylidene]-methyl]-8-oxo-5-thia-1-azabicyclo[4.2.0]oct-2-ene-2-carboxylic acid trifluoroacetic acid salt

[6R-[3(E),6α,7β]]-7-Amino-3-[[1-[1-carboxy- 1-methylethyl]-2-oxo-3-pyrrolidinylidene]-methyl]-8-oxo-5-thia-1-azabicyclo[4.2.0]oct-2-ene- 2-carboxylic acid trifluoroacetic acid salt (E)-(6R,7R)-7-Amino-3-[1-(6-methoxy-pyridin-3-yl)-2 -oxo-pyrrolidin-3-ylidenemethyl]-8-oxo-5-thia-1-azabicyclo[4.2.0]oct-2-ene- 2-carboxylic acid IR(KBr): 1782, 1685, 1618, 1570, 1496, 1407 cm$^{-1}$

MS(ISP): 403.4 (M+H)$^⊕$ (E)-(6R,7R)-7-Amino-8-oxo-3-(2-oxo-1-pyrazin-2-yl-pyrrolidin-3-ylidenemethyl]-5-thia-1-azabicyclo[4.2.0]oct-2-ene-2-carboxylic acid IR(KBr): 1787,1697, 1619 cm$^{-1}$

MS(ISP): 374.4 (M+H)$^⊕$ (E)-(6R,7R)-7-Amino-8-oxo-3-[2-oxo-1-(2,2,2 -trifluoroethyl)-azetidin-3-ylidenemethyl]-5-thia-1-azabicyclo[4.2.0] oct-2-ene-2-carboxylic acid trifluoroacetate (1:0.1)

IR(KBr): 1749 cm$^{-1}$

MS(ISP): 364.3 (M+H)$^⊕$

Microanalysis: $Cl_3H_{12}F_3N_3O_4S$ calc. C 42.27 H 3.25 N 11.19 S 8.54

Found C 42.32 H 3.40 N 10.91 S 8.48

(Z)-(6R,7R)-7-Amino-8-oxo-3-[2-oxo-1-(2,2,2 -trifluoroethyl)-azetidin-3-ylidenemethyl]-5-thia-1-azabicyclo[4.2.0] oct-2-ene-2-carboxylic acid trifluoroacetate (1:0.13)

IR(KBr): 1801, 1739 cm$^{-1}$

MS(ISP): 364.3 (M+H)$^⊕$ (E)-(6R,7R)-7-Amino-3-[1-(4-methyl-phenylsulfonyl)-2 -oxo-pyrrolidin-3-ylidenemethyl]-8-oxo-5-thia-1-azabicyclo[4.2.0]oct-2-ene- 2-carboxylic acid trifluoroacetate (1:0.2)

IR(KBr): 1790, 1721, 1624 cm$^{-1}$

MS(ISP): 465.3 (M−H+$NH_3$)$^⊖$ (E)-(6R,7R)-7-Amino-8-oxo-3-(2-oxo-1-prop-2-ynyl-pyrrolidin-3-ylidenemethyl]-5-thia-1-azabicyclo[4.2.0]oct-2-ene-2-carboxylic acid trifluoroacetate (1:0.2)

IR(KBr): 2115, 1779, 1682, 1626 cm$^{-1}$

MS(ISP): 334.3 (M+H)$^⊕$ (E)-(6R,7R)-7-Amino-3-(1-cyclopropylmethyl-2-oxo-pyrrolidin-3 -ylidenemethyl)-8-oxo-5-thia-1-azabicyclo [4.2.0]oct-2-ene-2-carboxylic acid trifluoroacetate (1:0.7)

IR(KBr): 1785, 1679, 1628 cm$^{-1}$
MS(ISP): 350.3 (M+H)$^{⊕}$ (E)-(6R,7R)-7-Amino-3-(1-cyanomethyl-2-oxo-pyrrolidin-3-ylidenemethyl)-8-oxo-5-thia-1-azabicyclo[4.2.0]oct-2-ene-2-carboxylic acid trifluoroacetate (1:0.21)

IR(KBr): 1781, 1688, 1628 cm$^{-1}$
MS(ISP): 332.2 (M+H)$^{⊖}$ (E)-(6R,7R)-7-Amino-3-[1-(2-cyano-ethyl)-2-oxo-pyrrolidin-3-ylidenemethyl]-8-oxo-5-thia-1-azabicyclo[4.2.0]oct-2-ene-2-carboxylic acid trifluoroacetate (1:1)

IR(KBr): 2245, 1784, 1720, 1675 cm$^{-1}$
MS(ISP): 349.4 (M+H)$^{⊕}$ (E)-(6R,7R)-4-[3-(7-Amino-2-carboxy-8-oxo-5-thia-1-azabicyclo[4.2.0]oct-2-en-3-ylmethylene)-2-oxo-pyrrolidin-1-yl]-1-methyl-pyridiniumiodide trifluoroacetate (1:1.15)

IR(KBr): 1779, 1704, 1670, 1519 cm$^{-1}$
MS(ISP): 387.3 (M)$^{⊕}$ (Z)-(6R,7R)-7-2-Amino-8-oxo-3-(2-oxo-1-phenyl-azetidin-3-ylidenemethyl)-5-thia-1-azabicyclo[4.2.0]oct-2-ene-2-carboxylic acid trifluoroacetate (1:0.09)

IR(KBr): 1788, 1716 cm$^{-1}$
MS(ISP): 356.2 (M–H)$^{⊕}$ (E)-(6R,7R)-7-Amino-8-oxo-3-(2-oxo-1-phenyl-azetidin-3-ylidenemethyl)-5-thia-1-azabicyclo[4.2.0]oct-2-ene-2-carboxylic acid trifluoroacetate (1:0.14)

IR(KBr): 1782, 1734 cm$^{-1}$
MS(ISP): 358.3 (M+H)$^{⊕}$ (E)-(6R,7R)-7-Amino-3-(1-carboxymethyl-2-oxo-pyrrolidin-3-ylidenemethyl)-8-oxo-5-thia-1-azabicyclo[4.2.0]oct-2-ene-2-carboxylic acid trifluoroacetate (1:0.25)

IR(KBr): 1781, 1680 cm$^{-1}$
MS(ISP): 352.2 (M–H)$^{⊕}$ (E)-(6R,7R)-7-Amino-3-[1-(5-methyl-isoxazol-3-yl)-2-oxo-pyrrolidin-3-ylidenemethyl)-8-oxo-5-thia-1-azabicyclo[4.2.0]oct-2-ene-2-carboxylic acid IR(KBr): 3434, 1793, 1705, 1607, 1507 cm$^{-1}$
MS(ISN): 392.3 (M+NH$_3$–H)$^{⊕}$ (E)-(6R,7R)-7-Amino-8-oxo-3-(2-oxo-1-pyridin-2-yl-pyrrolidin-3-ylidenemethyl)-5-thia-1-azabicyclo[4.2.0]oct-2-ene-2-carboxylic acid trifluoroacetate (1:1)

IR(KBr): 3437, 1789, 1690, 1388, 1204 cm$^{-1}$
MS(ISN): 388.3 (M+NH$_3$–H)$^{⊕}$ (E)-(6R,7R)-7-Amino-8-oxo-3-(2-oxo-1-pyridin-3-yl-pyrrolidin-3-ylidenemethyl)-5-thia-1-azabicyclo[4.2.0]oct-2-ene-2-carboxylic acid trifluoroacetate (1:2)

IR(KBr): 3422, 1783, 1679, 1557, 1393, 1201 cm$^{-1}$
MS(ISN): 388.3 (M+NH$_3$–H)$^{⊕}$ (E)-(6R,7R)-7-Amino-8-oxo-3-[2-oxo-1-(2-oxo-oxazolidin-3-yl)-pyrrolidin-3-ylidenemethyl)-5-thia-1-azabicyclo[4.2.0]oct-2-ene-2-carboxylic acid IR(KBr): 3435, 1701, 1627, 1395 cm$^{-1}$
MS(ISN): 396.3 (M+NH$_3$–H)$^{⊕}$ (E)-(6R,7R)-7-Amino-8-oxo-3-(2-oxo-1-thiazol-2-yl-pyrrolidin-3-ylidenemethyl)-5-thia-1-azabicyclo[4.2.0]oct-2-ene-2-carboxylic acid IR(KBr): 1783, 1691, 1575, 1506, 1464, 1385 cm$^{-1}$
MS(ISP): 379.3 (M+H)$^{⊕}$ (E)-(6R,7R)-3-(1-Allyl-2-oxo-pyrrolidin-3-ylidenemethyl)-7-amino-8-oxo-5-thia-1-azabicyclo[4.2.0]oct-2-ene-2-carboxylic acid trifluoroacetate (1:0.65)

IR(KBr): 1784, 1679, 1627 cm$^{-1}$
MS(ISP): 336.3 (M+H)$^{⊕}$ (E)-(6R,7R)-7-Amino-3-[1-(1,1-dioxo-tetrahydro-thiophen-3-yl)-2-oxo-pyrrolidin-3-ylidenemethyl)-8-oxo-5-thia-1-azabicyclo[4.2.0]oct-2-ene-2-carboxylic acid (1:1 mixture of epimers)

IR(KBr): 1782, 1678, 1296, 1200, 1124 cm$^{-1}$ (E)-(6R,7R)-7-Amino-3-[1-(4-methoxy-benzoyl)-2-oxo-pyrrolidin-3-ylidenemethyl]-8-oxo-5-thia-1-azabicyclo[4.2.0]oct-2-ene-2-carboxylic acid trifluoroacetate (1:0.2)

IR(KBr): 1785, 1726, 1665 cm$^{-1}$
MS(ISN): 430.4 (M+H)$^{⊕}$ (E)-(6R,7R)-7-Amino-8-oxo-3-(2-oxo-pyridin-4-yl-pyrrolidin-3-ylidenemethyl)-5-thia-1-azabicyclo[4.2.0]oct-2-ene-2-carboxylic acid trifluoroacetate (1:1.63)

(Z)-(6R,7R)-7-Amino-3-(1-cyclopropyl-2-oxo-pyrrolidin-3-ylidenemethyl)-8-oxo-5-thia-1-azabicyclo[4.2.0]oct-2-ene-2-carboxylic acid trifluoroacetate (1:0.83)

IR(KBr): 1778, 1700 cm$^{-1}$
MS(ISP): 336.3 (M+H)$^{⊕}$ (E)-(6R,7R)-7-Amino-8-oxo-3-[1-(2,2,2-trifluoro-ethyl)-2-oxo-piperidin-3-ylidenemethyl)-5-thia-1-azabicyclo[4.2.0]oct-2-ene-2-carboxylic acid trifluoroacetate (1:0.32)

IR(KBr): 1782, 1658, 1617 cm$^{-1}$
MS(ISN): 407.3 (M+NH$_3$–H)$^{⊕}$ (E)-(6R,7R)-7-Amino-3-(1-cyclopropyl-2-oxo-piperidin-3-ylidenemethyl)-8-oxo-5-thia-1-azabicyclo[4.2.0]oct-2-ene-2-carboxylic acid IR(KBr): 1784, 1677, 1598 cm$^{-1}$
MS(ISN): 365.4 [(M–H)$^{⊕}$+NH$_3$]; 348.4 (M–H)$^{⊕}$ (E)-(6R,7R)-7-Amino-8-oxo-3-(2-oxo-1-phenyl-piperidin-3-ylidenemethyl)-5-thia-1-azabicyclo[4.2.0]oct-2-ene-2-carboxylic acid trifluoroacetate (1:1)

IR(KBr): 1784, 1676 cm$^{-1}$
MS(ISN): 384.3 (M–H)$^{⊕}$

Preparation 19

Diphenylmethyl [6R-6α,7β]-7-tert-butoxycarbonylamino-3-formyl-8-oxo-5-thia-1-azabicyclo[4.2.0]oct-2-ene-2-carboxylate.

A 500 ml 3-neck flask was charges with methylene chloride (60 ml) and dimethyl sulfoxide (3.24 ml). The mixture was cooled in a –50° C. bath and trifluoroacetic anhydride (5.34 ml) was added dropwise. The mixture was stirred for 30 minutes in the –50° C. bath and then treated dropwise, over 15 minutes, with a cloudy solution of (6R-trans)-7-[[(1,1-Dimethylethoxy)-carbonyl]amino]-3-(hydroxymethyl)-8-oxo-5-thia-1-azabicyclo[4.2.0]oct-2-ene-2-carboxylic acid diphenylmethyl ester (15.0 g, 0.03M) in methylene chloride (150 ml). The reaction mixture was stirred for 30 minutes at –50° C. and then treated dropwise with triethylamine (16.9 ml). The reaction mixture darkened in colour, but remained clear.

The reaction mixture was stirred in the bath for two hours and the temperature allowed to rise ambiently. The final temperature was about –20° C. The reaction mixture was poured into 0.5N hydrochloric acid (360 ml) and ethyl acetate (1.0 l) with stirring. The organic layer was separated, washed with brine and dried over anhydrous sodium sulfate. After removal of the drying agent and solvent, the residue was purified by flash chromatography (n-hexane/ethyl acetate 2/1). The product fractions were combined and the solvent concentration was adjusted to 3/1 n-hexane/ethyl acetate. The solution was refrigerated overnight and the solid collected for 6.93 g. The flitrate was reduced to dryness and triturated with 3/1 n-hexane/ethyl acetate for 1.66 g. The combined yield of 8.59 g (57.4%) was confirmed by NMR to be the title compound.

Example 1 a) [6R-[3(E),6α,7β(Z)]]-7[[(2-Amino-4-thiazolyl-)(methoxyimino)acetyl]amino]-8-oxo-3-[(2-oxo-1-phenyl-3-pyrrolidinylidene)methyl]-5-thia-1-azabicyclo[4.2.0]oct-2-ene-2 carboxylic acid monosodium salt At room temperature, [6R-[3(E),6α,7β]]-3-[[(2-oxo-1-phenyl)-3 -pyrrolidinylidene]methyl]-7-amino-8-oxo-5-thia-1-azabicyclo[4.2.0]oct-2-ene-2-carboxylic acid trifluoroacetic acid salt 0.15 g (0.29 mM), tetrahydrofuran (8.4 mL), water (5.6 mL), and sodium bicarbonate 77 mg (0.92 mM) were combined and stirred to form a solution. 2-(2-Aminothiazol-4-yl)-(Z)-2-methoxyimino-acetic acid 2-benzothiazolyl thioester 0.15 g (0.43 mM) were added. The reaction mixture became soluble within fifteen minutes. After stirring for four hours at room temperature, the tetrahydrofuran was removed under reduced pressure, water (14 mL) and sodium bicarbonate 0.16 g (1.9 mM) were added, and the reaction mixture extracted with ethyl acetate (2×10 mL). The aqueous portion was purified on a C18 reverse phase silica gel column, eluting with water/acetonitrile. The product fractions were combined to yield the title compound 0.17 g (98%).

NMR (400MHz, DMSO-d_6) δ 3.02, 3.20 (m, 2H), 3.75 (d, 1H), 3.83 (m, 6H), 5.05 (d, 1H), 5.63 (d, 1H), 6.75 (s, 1H), 7.13 (t, 1H), 7.24 (s, 2H), 7.40 (t, 2H), 7.54 (s, 1H), 7.78 (d, 2H) and 9.61(d, 1H); IR (KBr) cm$^{-1}$ 1765, 1670, 1615, 691.

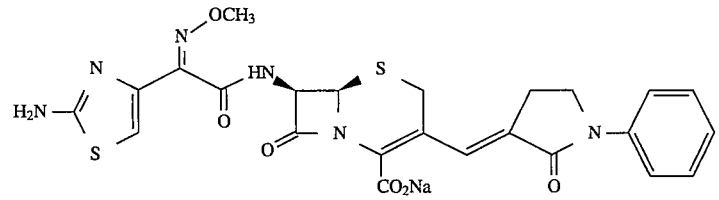

According to the procedure set forth in the preceding example, the following compounds were prepared:

[6R-[3(E),6α,7β(Z)]]-7[[(2-Amino-4-thiazolyl-)(methoxyimino)acetyl]amino]-8-oxo-3-[(2-oxo-3-pyrrolidinylidene)methyl]-5-thia-1-azabicyclo[4.2.0]oct-2-ene-2 -carboxylic acid monosodium salt NMR (200 MHz, D_2O) δ 3.05 (m, 2H), 3.48 (t, 2H), 3.84 (q, 2H), 4.0 (s, H), 5.28 (d, 1H), 5.87 (d, 1H), 7.02 (s, 2H).

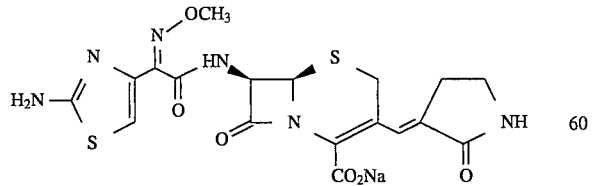

[6R-[3(E),6α,7β(Z)]]-7[[(2-Amino-4-thiazolyl-)(methoxyimino)acetyl]amino]-3-[(1-methoxy-2-oxo-3-pyrrolidinylidene)methyl ]-8-oxo-5-thia-1-azabicyclo[4.2.0]oct-2 -ene-2-carboxylic acid monosodium salt NMR (400 MHz, DMSO-d_6) δ 2.95, 3.15 (m, 2H), 3.58 (m, 2H), 3.72 (s, H), 3.88 (s, 2H), 4.09 (s, 3H) 5.08 (d, 1H), 5.83 (q, 1H), 6.67 (s, 1H), 7.12 (s, 2H), 7.25 (s, 1H).

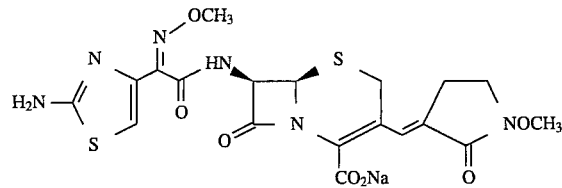

[6R-[3(E), 6α,7β(Z)]]-7[[(2-Amino-4 -thiazolyl-)(methoxyimino)acetyl]amino]-3-[(1-methyl-2-oxo-3 -pyrrolidinylidene)methyl]-8-oxo-5-thia-1-azabicyclo[4.2.0] oct-2 -ene-2-carboxylic acid monosodium salt NMR (400 MHz, D_2O) δ 2.95 (s, 3H), 2.92, 3.02 (m, 2H), 3.54 (m, 2H), 3.80, 3.82 (q, 2H), 4.01 (s, 3H), 5.71 (d, 1H), 5.85 (d, 1H), 7.0 (s, 1H), 7.04 (s, 1H); IR (KBr) cm$^{-1}$ 1765, 1668, 1615.

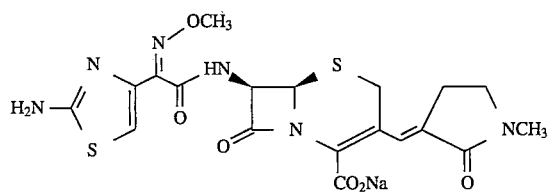

[6R-[3(E),6α,7β(Z)]]-7[[(2-Amino-4-thiazolyl-)(methoxyimino)acetyl]amino]-8-oxo-3-[[2-oxo-1 -(benzyloxy)-3-pyrrolidinylidene]methyl]-5-thia-1-azabicyclo [4.2.0]oct-2-ene-2-carboxylic acid monosodium salt NMR (400 MHz, DMSO-d_6) δ 2.5 (m, 2H), 2.83, 303 (m, 2H), 3.69 (q, 2H), 3.83 (s, 3H), 4.95 (s, 2H), 5.02 (d, 1H), 5.62 (q, 1H), 6.74 (s, 1H), 7.22(s, 3H), 7.40 (m, 5H); IR (KBr) cm$^{-1}$ 1765, 1677, 1615, 700.

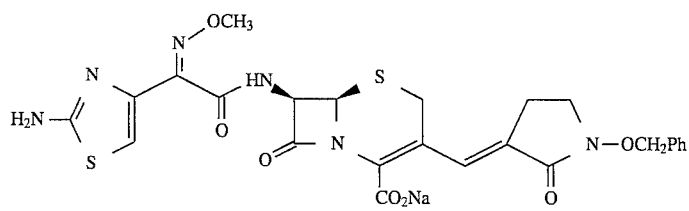

[6R-[3(E),6α,7β(Z)]]-7[[(2-Amino-4-thiazolyl-)(methoxyimino)acetyl]amino]-3-[[1-(4-carboxyphenyl)2-oxo-3-pyrrolidinylidene]methyl]-8-oxo-5-thia-1 -azabicyclo[4.2.0]oct-2-ene-2-carboxylic acid disodium salt NMR (200 MHz, D₂O) δ 3.16 (m, 2H), 3.90 (q, 2H), 4.02 (s, 3H), 4.04 (m, 2H), 5.31 (d, 1H), 5.88 (d, 1H), 7.05 (s, 1H), 7.23 (s, 1H), 7.67 (d, 2H) 7.93 (d, 2H); IR (KBr)cm⁻¹ 1765, 1670, 1602.

[6R-[3(E),6α,7β(Z)]]-7[[(2-Amino-4-thiazolyl-)(methoxyimino)acetyl]amino]-3-[[1-(4-methoxyphenyl)-2-oxo-3-pyrrolidinylidene]methyl]-8-oxo-5-thia-1-azabicyclo[4.2.0]oct- 2-ene-2-carboxylic acid monosodium salt NMR (400 MHz, D₂O) δ 3.10 (m, 2H), 3.87 (s, 5H), 3.91 (m, 2H), 4.03 (s, 3H), 5.28 (d, 1H), 5.87 (d, 1H), 7.08 (d, 2H), 7.18 (s, 1H), 7.49 (d, 2H);
IR (KBr)cm⁻¹ 3420, 1762, 1670, 1615.

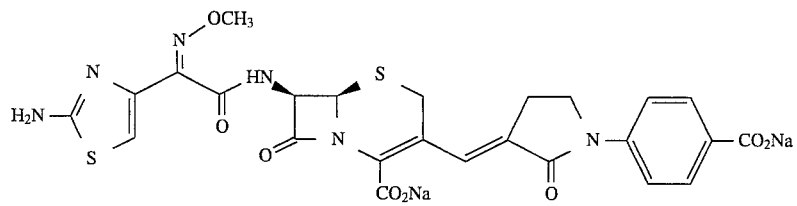

[6R-[3(E),6α,7β(Z)]]-7[[(2-Amino-4-thiazolyl-)(methoxyimino)acetyl]amino]-3-[[1-(2,4-diflurophenyl)-2-oxo-3-pyrrolidinylidene]methyl]-8-oxo-5-thia-1-azabicyclo[4.2.0]oct- 2-ene-2-carboxylic acid monosodium salt NMR (400 MHz, D₂O) δ 3.20 (m, 2H), 3.89 (m, 4H), 4.01 (s, 3H), 5.30 (d, 1H), 5.87 (d, 1H), 7.04 (s, 1H), 7.12 (m, 2H), 7.19(s, 2H), 7.45 (m, 1H); IR (KBr)cm⁻¹ 1770, 1678, 1612, 700.

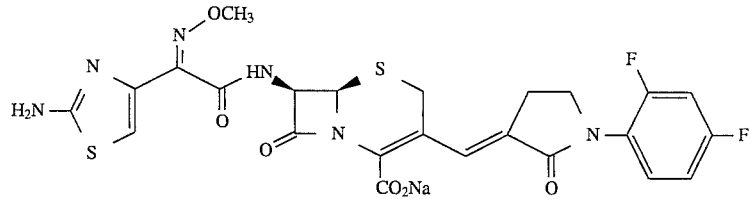

[6R-[3(E),6,60 ,7β(Z)]]-7[[(2-Amino-4-thiazolyl-)(methoxyimino)acetyl]amino]-3-[[1-[4-nitrophenyl)-2-oxo- 3-pyrrolidinylidene]methyl]-8-oxo-5-thia-1-azabicyclo[4.2.0]oct-2 -ene-2-carboxylic acid monosodium salt NMR (400 MHz, D₂O) δ 3.12 (m, 2H), 3.83 (q, 2H), 4.00 (m, 2H), 4.00 (s, 3H), 5.28 (d, 1H), 5.87 (d, 1H), 7.03 (s, 1H), 7.28 (s, 1H), 7.87 (d, 2H) and 8.29 (d, 2H); IR (KBr) cm⁻¹ 1765, 1679, 1618, 1338.

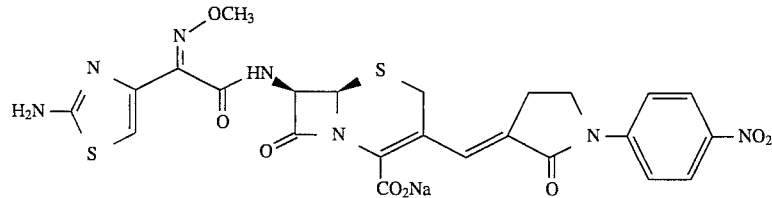

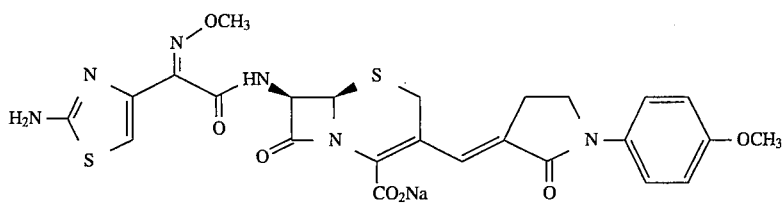

6R-[3(E),6α,7β(Z)]]-7[[(2-Amino-4-thiazolyl)(methoxy-imino)acetyl]amino]-3-[[1-[(4-nitrophenyl)methoxy]-2-oxo-3-pyrrolidinylidene]methyl]-8-oxo-5-thia-1-azabi-cyclo[4.2.0]oct-2-ene-2-carboxylic acid monosodium salt NMR (400 MHz, DMSO-d$_6$) δ 2.85 (m, 2H), 3.05 (m, 2H), 3.30–3.49 (m, H), 3.70 (q, 2H), 3.85 (s, 3H), 5.02 (d, 1H), 5.12 (S, 2H), 5.63 (q, 1H), 6.75 (s, 1H), 7.23 (s, 2H), 7.40(s, 1H), 7.76 (d, 2H), 8.26 (d, 2H), and 9.60 (d, 1H) ;IR (KBr)cm$^{-1}$ 1765, 1670, 1615, 691.

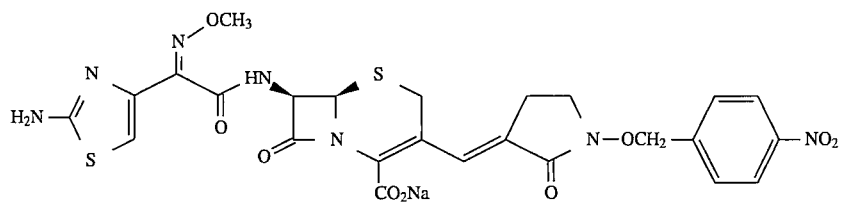

[R-[3(E),6α,7β(Z)]]-7[[(2-Amino-4-thiazolyl)(methoxy-imino)acetyl]amino]-3-[[1-(1,1-dimethylethyl)-2-oxo-3-pyrrolidinylidene]methyl]-8-oxo-5-thia-1-azabicyclo[4.2.0] oct-2-ene-2-carboxylic acid monosodium salt

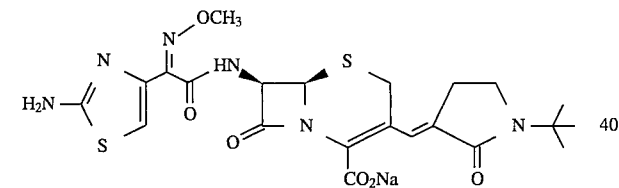

[6R-[3(E),6α,7β(Z)]]-7-[[2-Amino-4-thiazolyl-)(methoxyimino)acetyl]amino]-3-[[1-(2,2,2-trifluoroethyl)-2-oxo-3-pyrrolidinylidene]methyl]-8-oxo-5-thia-1-azabicyclo[4.2.0]-oct-2-ene-2-carboxylic acid monosodium salt

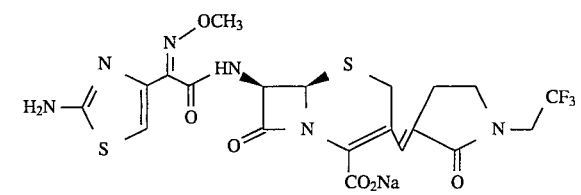

[6R-[3(E),(6α,7β(Z)]]-7-[[(2-Amino-4-thiazolyl)(cyclopentoxyimino)-acetyl]amino]-3-[[1-methoxy-2-oxo-3-pyrrolidinylene]methyl]-8-oxo-5-thia-1-azabicyclo[4.2.0]oct-2-ene-2-carboxylic acid monosodium salt NMR (400 MHz, DMSO-d$_6$) δ 1.68 (m, 8H), 2.88, 3.08 (m, 2H), 3.48, 3.50 (m, 2H), 3.67 (m, 5H), 4.65 (s, 1H), 5.03 (d, 1H), 5.64 (q, 1B), 6.69 (s, H), 7.22 (s, 2H), 7.39 (s, 1H), 9.49 (d, 1H); IR (KBr) cm$^{-1}$ 1768, 1678, 1622, 1612.

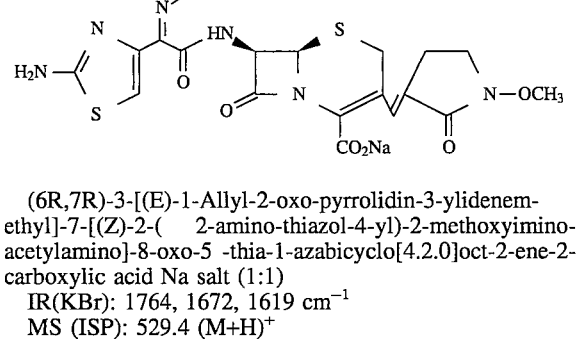

(6R,7R)-3-[(E)-1-Allyl-2-oxo-pyrrolidin-3-ylidenemethyl]-7-[(Z)-2-( 2-amino-thiazol-4-yl)-2-methoxyimino-acetylamino]-8-oxo-5 -thia-1-azabicyclo[4.2.0]oct-2-ene-2-carboxylic acid Na salt (1:1)
IR(KBr): 1764, 1672, 1619 cm$^{-1}$
MS (ISP): 529.4 (M+H)$^+$

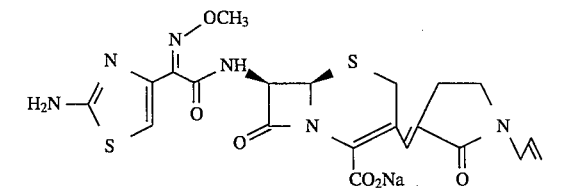

b) In a variant of the procedure of Example 1a), the following compound was prepared:
(6R,7R)-7-[(Z)-2-(2-Amino-thiazol-4-yl)-2-methoxy-imino-acetylamino]-3-[(E)-1-carboxymethyl-2-oxo-pyrrolidin-3 -ylidenmethyl]-8-oxo-5-thia-1-azabicyclo[4.2.0]oct-2-ene-2-carboxylic acid 300 mg (0.785 mmol) (E)-(6R,7R)-7-Amino-3-(1-carboxymethyl-2 -oxo-pyrrolidin-3-ylidene)-8-oxo-5-thia-1-azabicyclo[4.2.0]oct-2 -ene-2-carboxylic acid trifluoroacetate were suspended in 20 ml DMF and 302 mg (0.864 mmol) 2-(2-aminothiazol-4-yl)-(Z)-2 -methoxyimino-acetic acid 2-benzothiazolyl thioester were added. The mixture was reacted for 24 h at room temperature and then concentrated to 3 ml in vacuo. 30 ml ethyl acetate were added slowly upon which the product separated. After 30 min stirring, the solid material was filtered off and dried.

yield: 369 mg
IR(KBr): 1780, 1727, 1662 cm$^{-1}$
MS (ISN): 537.4 (M+H)$^+$ 2-oxo-piperidin- 3-ylidenemethyl]-5-thia-1-azabicyclo[4.2.0]oct-2-ene-2-carboxylic acid trifluoroacetate (1:1)
IR(KBr): 1783, 1667, 1635 cm$^{-1}$
MS(EI): 575.1 (M+H)$^+$

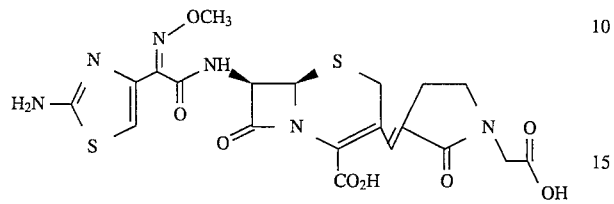

The following compounds were also prepared in the same manner:

(6R,7R)-7-[(Z)-2-(2-Amino-thiazol-4-yl)-2-methoxy-imino-acetylamino]-3-[(E)-1-(4-methoxy-benzoyl)-2-oxo-pyrrolidin-3-ylidenemethyl]-8-oxo-thia-1-azabicyclo[4.2.0]oct-2-ene-2-carboxylic acid
IR(KBr): 1783, 1727, 167 1 cm$^{-1}$
MS(ISP): 613.4 (M+H)$^+$

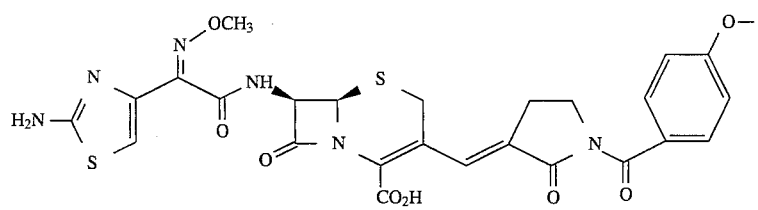

(6R,7R)-7-[(Z)-2-(2-Amino-thiazol-4-yl)-2 -methoxy-imino-acetylamino]-3-[(E)-1-cyclopropyl-2-oxo-piperidin-3-ylidenemethyl]-8-oxo-5-thia-1-azabicyclo[4.2.0]oct-2-ene-2 -carboxylic acid trifluoroacetate (1:0.5)
IR(KBr): 1777, 1677, 1615 cm$^{-1}$
MS (ISP): 533.4 (M+H)$^+$

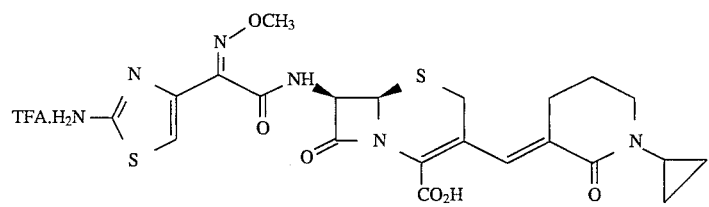

(6R,7R)-7-[(Z)-2-(2-Amino-thiazol-4-yl)-2 -methoxy-imino-acetylamino]-8-oxo-3-[(E)-1-(2,2,2-trifluoro-ethyl)-

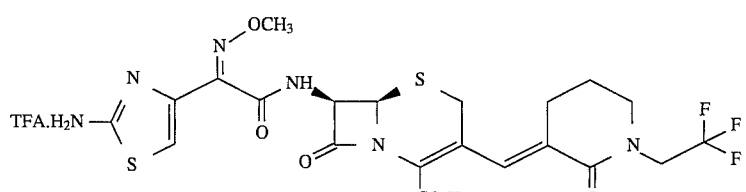

(6R,7R)-7-[(Z)-2-(2-Amino-thiazol-4-yl)-2 -methoxy-imino-acetylamino]-3-[(E)-1-cyclopropyl-2-oxo-pyrrolidin-3 -ylidenemethyl]-8-oxo-5-thia-1-azabicyclo[4.2.0]oct-2-ene-2-carboxylic acid trifluoroacetate (1:0.26)

IR(KBr): 1779, 1679, 1629, 1531 cm⁻¹
MS(ISP): 519.3 (M+H)⁺

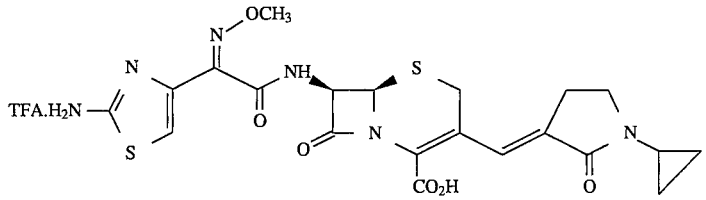

(6R,7R)-7-[(Z)-2-(2-Amino-thiazol-4-yl)-2-methoxy-imino-acetylamino]-3-[(E)-1-cyclopropylmethyl-2-oxo-pyrrolidin-3-ylidenemethyl]-8-oxo-5-thia-1-azabicyclo[4.2.0]oct-2-ene-2-carboxylic acid trifluoroacetate (1:0.25)

IR(KBr): 1781, 1675, 1630 cm⁻¹
MS(ISP): 533.3 (M+H)⁺

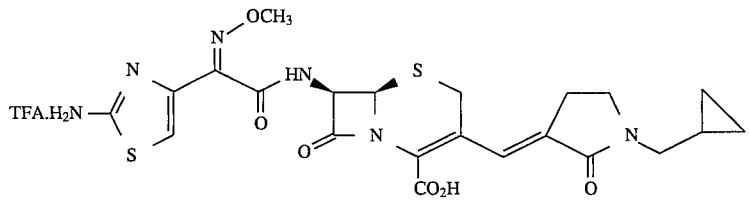

(6R,7R)-7-[(Z)-2-(2-Amino-thiazol-4-yl)-2 -methoxy-imino-acetylamino]-8-oxo-3-[(E)-2-oxo-1-prop-2-ynyl-pyrrolidin-3-ylidenemethyl ]-5-thia-1-azabicyclo[4.2.0]oct-2-ene-2-carboxylic acid IR(KBr): 2118, 1779, 1678, 1629 cm⁻¹
MS(ISP): 517.4 (M+H)⁺

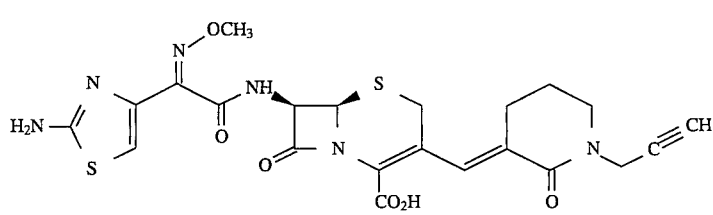

Example 2

[6R-[3(E),(6α,7β(Z)]]-3-[[1-(4 -Aminophenyl)-2-oxo-3 -pyrrolidinylidene ]-methyl]-7-[[(2-amino-4-thiazolyl)(methoxyimino)acetyl]amino]-8-oxo-5-thia-1-azabicyclo[4.2.0]oct-2 -ene-2-carboxylic acid monosodium salt To [6R-[3(E),(6α,7β(Z)]]-3-[[1-(4-Nitrophenyl)-2-oxo-3 -pyrrolidinylidene]-methyl]-7-[[(2-amino-4-thiazolyl)(methoxyimino)acetyl]amino]-8-oxo-5-thia-1-azabicyclo[4.2.0]oct-2 -ene-2-carboxylic acid monosodium salt 105 mg (0.17 mM) in tetrahydrofuran (10 mL) was added water (15 mL) and sodium bicarbonate 95 mg (0.11 mM) to form a solution. Sodium dithionate 125 mg (1.7 mM) was added to the solution portionwise as a solid. The solvent was removed after 15 minutes and the residue purified on a reverse phase C18 silica column eluting with water/acetonitrile to obtain 70.5 mg (70%) of the title compound.

NMR (400 MHz, D₂O), δ 3.12 (m, 2H), 3.93 (m, 4H), 4.03 (s, 3H), 5.30 (d, 1H), 5.87 (d, 1H), 7.05 (s, 1H), 7.18 (s, 1H), 7.25 (d, 2H), 7.50 (d, 2H);

IR (KBr)cm⁻¹ 3430, 1762, 1662, 1618.

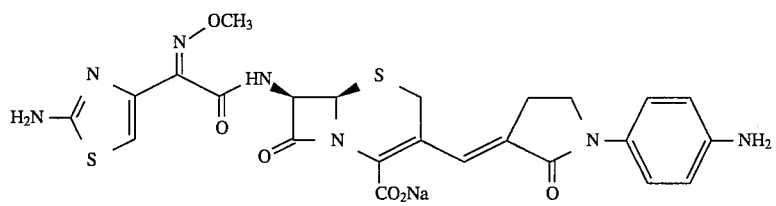

Example 3

[6R-[3(E),(6,60 ,7β(Z)]]-7-[[(2-Amino-4-thiazolyl)(methoxyimino)acetyl]-amino]-3-[(1-hydroxy-2-oxo-3-pyrrolidinylene)methyl]-8-oxo-5-thia-1-azabicyclo[4.2.0]oct-2-ene-2-carboxylic acid monosodium salt

[6R-[3(E),6α,7β(Z)]]-7-[[(2-Amino-4-thiazolyl-)(methoxyimino) acetyl]amino]-3-[[1-[(4-nitrophenyl-)methoxy]-2-oxo-3 -pyrrolidinylidene]methyl]-8-oxo-5-thia-1-azabicyclo[4.2.0]oct-2 -ene-2-carboxylic acid monosodium salt 65 mg (0.1 mM) in water (4 mL) was hydrogenated in the presence of methanol (0.5 mL), 97 mg of 10% Pd/C and hydrogen at one atmosphere for two hours. Removal of the catalyst and purification of the residue on a reverse phase C18 silica gel column using water/methanol afforded 25 mg (49%) of the title compound.

NMR (400 MHz, DMSO-$d_6$) δ 2.85, 3.05 (m,2H), 3.45 (m, 2H), 3.72 (q, 2H), 3.85 (s, 3H), 5.0 (d, 1H), 5.61 (q, 1H), 6.75 (s, 1H), 7.23 (s, 2H), 7.35 (s, 1H), 9.60 (d, 1H), 9.70 (br. s, 1H).

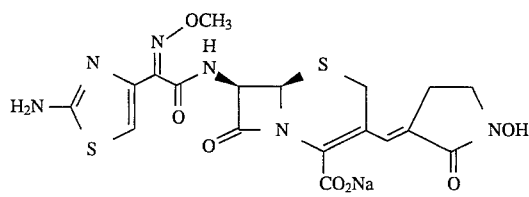

Example 4

[6R-[3(E),6α,7β(Z)]]-7-[[(2-Amino-4-thiazolyl)[[2-(1,1-dimethylethoxy)-2-oxoethoxy]imino]acetyl]amino]-3-[(1-cyclopropyl-2-oxo-3-pyrrolidinylidene)methyl]-8-oxo-5-thia-1-azabicyclo[4.2.0]oct-2-ene-2-carboxylic acid At room temperature, [6R-[3(E),6α,7β]]-7-amino-3-[(1-cyclopropyl-2-oxo-1-pyrrolidinylidene)methyl]-8-oxo-5-thia-1-azabicyclo[4.2.0]oct-2-ene-2-carboxylic acid mono(trifluoroacetate) salt 4.42 g (9.84 mM), tetrahydrofuran (170 mL), and water (170 mL) were combined. The salt became partially soluble. Sodium bicarbonate 2.39 g (28.4 mM) and 2-(2-aminothiazol-4-yl)-(Z)-2-[(t-butoxy-carbonyl)methoxyimino]-acetic acid-2-benzothiazolyl thioester 6.71 g (14.9 mM) were added. The reaction became soluble within ten minutes. After stirring for seven hours at room temperature, the tetrahydrofuran was remove under reduced pressure, water (50 mL) added, and the reaction extracted with ethyl acetate (2×100 mL). The aqueous portion was cooled in an ice water bath and acidified with 2N HCl to pH 3. The resulting white solid was filtered and washed with cold water. The solid was dried at high vacuum for 15 hours to yield the title compound 5.49 g (87%).

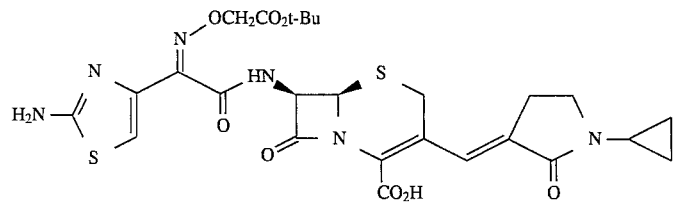

According to the procedure set forth in the preceding example, the following additional compounds were prepared:

[6R-[3(E),6α,7β(Z)]]-7-[[(2-Amino-4-thiazolyl)[[2-(1,1-dimethylethoxy)-2-oxoethoxyimino]acetyl]amino]-8-oxo-3-[(2 -oxo-pyrrolidinylidene)methyl]-5-thia-1-azabicyclo[4.2.0]oct-2-ene-2 -carboxylic acid NMR (200 MHz, D$_2$O) of the sodium salt δ 1.48 (s, 9H), 3.00 (m, 2H), 3.44 (t, 2H), 3.86 (q, 2H), 4.68 (s, 2H), 5.24 (d, 1H), 5.85 (d, 1H), 6.99 (s, 1H), 7.07 (s, 1H).

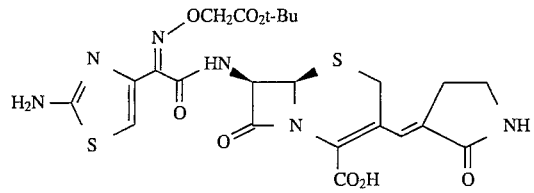

[6R-[3(E),6α,7β(Z)]]-7-[[(2-Amino-4-thiazolyl)[[2-(1,1-dimethylethoxy)-2-oxoethoxy]imino]acetyl]amino]-3-[(1-methyl-2 -oxo-3-pyrrolidinylidene)methyl]-8-oxo-5-thia-1-azabicyclo[4.2.0]oct-2-ene-2-carboxylic acid

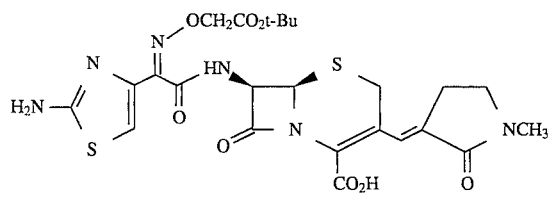

[6R-[3(E),6α,7β(Z)]]-7-[[(2-Amino-4-thiazolyl)[[2-(1,1-dimethylethoxy)-2-oxoethoxy]imino]acetyl]amino]-3-[[1-(1,1 -dimethylethyl)-2-oxo-3-pyrrolidinylidene]methyl]-8-oxo-5-thia-1-azabicyclo[4.2.0]oct-2-ene-2-carboxylic acid IR (KBr) cm$^1$ 3403 (br.), 1762, 1669, 1617

MS (LR(+)FAB) 657 (M+H)

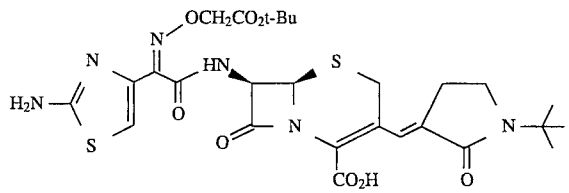

[6R-[3(E),6α,7β(Z)]]-7-[[(2-Amino-4-thiazolyl)[[2-(1,1-dimethylethoxy)-2-oxoethoxy]imino]acetyl]amino]-8-oxo-3-[[2-oxo- 1-(2,2,2-trifluroethyl)-3-pyrrolidinylidene]methyl]-5-thia-1-azabicyclo[4.2.0]oct-2-ene-2-carboxylic acid IR (KBr)cm$^{-1}$ 1780, 1685; MS (LR(+)FAB) 661 (M+H).

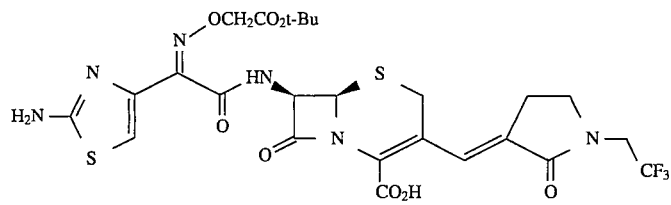

[6R-[3(E),6α,7β(Z)]]-7[[(2-Amino-4-thiazolyl)[[2-(1,1-dimethylethoxy)-2-oxoethoxy]imino]acetyl]amino]-3-[[1-(2 -fluoroethyl)-2-oxo-3-pyrrolidinylidene]methyl]-8-oxo-5-thia-1-azabicyclo[4.2.0]oct-2-ene-2-carboxylic acid IR (KBr)cm$^{-1}$ 1779, 1733, 1679

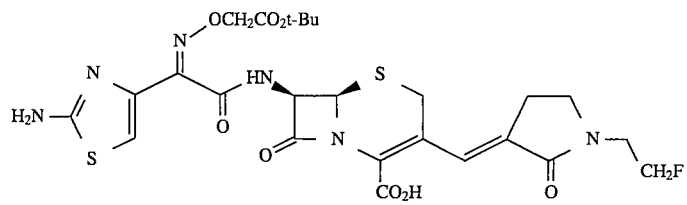

[6R-[3(E),6α,7β(Z)]]-7[[(2-Amino-4-thiazolyl)[[2-(1,1-dimethylethoxy)-2-oxoethoxy]imino]acetyl]amino]-3-[[1-(4 -carboxyphenyl)-2-oxo-3-pyrrolidinylidene]methyl]-8-oxo-5-thia-1-azabicyclo[4.2.0]oct-2-ene-2-carboxylic acid

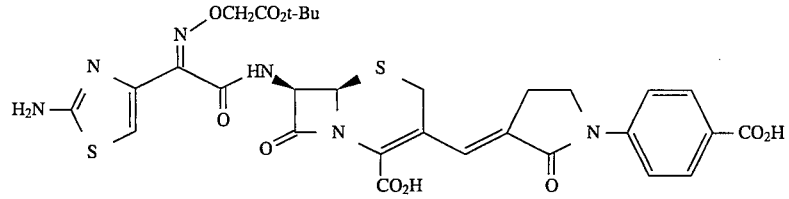

[6R-[3(E),6α,7β(Z)]]-7[[(2-Amino-4-thiazolyl)[[2-(1,1-dimethylethoxy)-2-oxoethoxy]imino]acetyl]amino]-3-[[1-(1 -carboxy-1-methylethyl)-2-oxo-3-pyrrolidinylidene]methyl]-8-oxo-5-thia-1 -azabicyclo[4.2.0]oct-2-ene-2-carboxylic acid

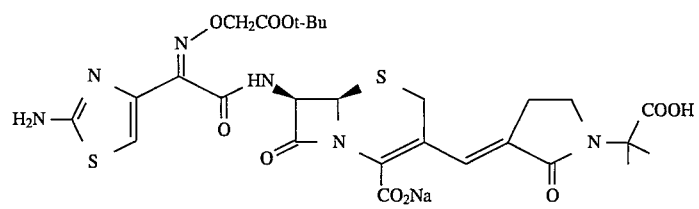

[(6R,7R)-7[(Z)-2-(2-Amino-thiazol-4-yl)-2-2 -tert-butoxycarbonyl-methoxyimino-acetylamino]-3-[(E)-1-(2,2,2-trifluoroethyl)-2 -oxo-piperidin-3-ylidenemethyl]-8-oxo-5-thia-1-azabicyclo[4.2.0]oct-2 -ene-2-carboxylic acid IR(KBr): 1784, 1728, 1660 cm$^{-1}$
MS(ISN): 673.2 (M−H)$^-$

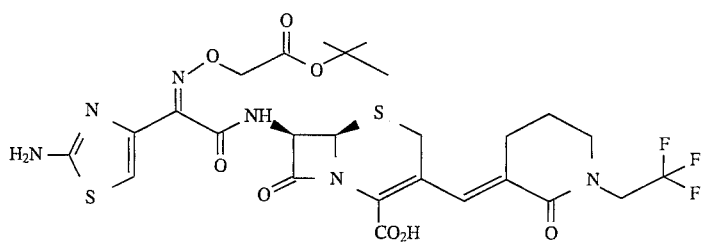

(6R,7R)-7[(Z)-2-(2-Amino-thiazol-4-yl)-2-tert-butoxycarbonyl-methoxyimino-acetylamino]-3-[(E)-1-cyclopropyl-2-oxo-piperidin-3-ylidenemethyl]-8-oxo-5-thia-1-azabicyclo[4.2.0]oct-2-ene-2-carboxylic acid trifluoroacetate (1:0.4)

IR(KBr): 1782, 1730, 1683 cm$^{-1}$
MS(ISP): 633.5 (M+H)$^{+}$

NMR (DMSO-d$_6$): δ(ppm) 1.43 (s,9H) 2.9–3.3 (brm, 2H), 3.3–3.5 (brm,2H), 3.91 (brs,1H), 4.05 (s,2H), 4.55 (s,2H), 5.21 (d,1H), 5.86 (dd,1H), 6.78 (s,1H), 7.25 (brs,3H), 9.64 (d,1H)

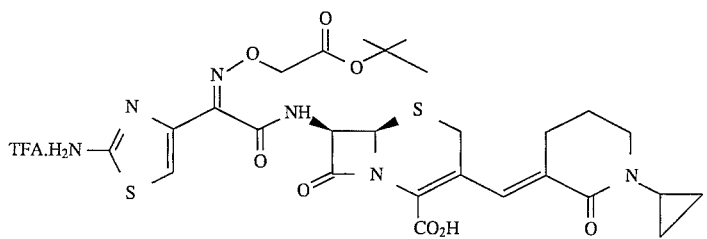

(6R,7R)-3-[(E)-1-Allyl-2-oxo-pyrrolidin-3-ylidenemethyl]-7-[(Z)-2-(2-amino-thiazol-4-yl)-2-tert-butoxycarbonylmethoxyimino]-8-oxo-5-thia-1-azabicyclo[4.2.0]oct-2-ene-2-carboxylic acid IR(KBr): 1782, 1727, 1679 cm$^{-1}$
MS(ISP): 619.4 (M+H)$^{+}$

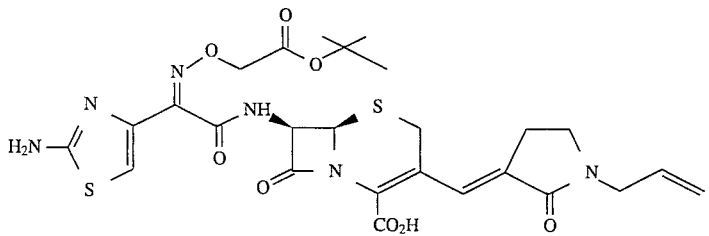

(6R,7R)-7[(Z)-2-(2-Amino-thiazol-4-yl)-2-tert.butoxycarbonyl-methoxyimino-acetylamino]-3-[(E)-1-carboxymethyl-2-oxo-pyrrolidin-3-ylidenemethyl]-8-oxo-5-thia-1-azabicyclo[4.2.0]oct-2-ene-2-carboxylic acid

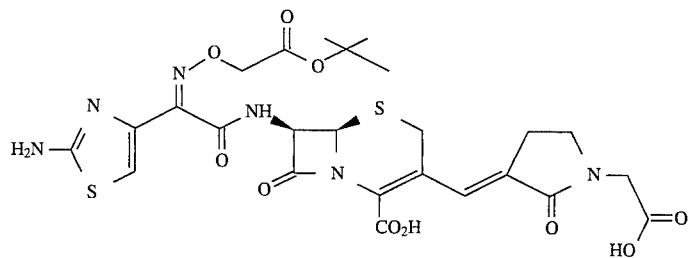

(6R,7R)-7[(Z)-2-(2-Amino-thiazol-4-yl)-2 -tert.butoxycarbonyl-methoxyimino-acetylamino]-3-[(E)-1-(4-methoxy-benzoyl)-2 -oxo-pyrrolidin-3-ylidenemethyl]-8-oxo-5-thia-1-azabicyclo[4.2.0]oct-2 -ene-2-carboxylic acid NMR (DMSO-d$_6$): δ[ppm] 1.43 (s,9H) 2.9–3.3 (brm, 2H), 3.82 (s,5H), 4.55 (s,2H), 5.21 (d,1H), 5.88 (dd,1H), 6.76 (s, 1H), 6.95 (d,2H), 7.26 (s,2H), 7.4 (s,1H), 7.64 (d,2H), 9.64 (d,1H)

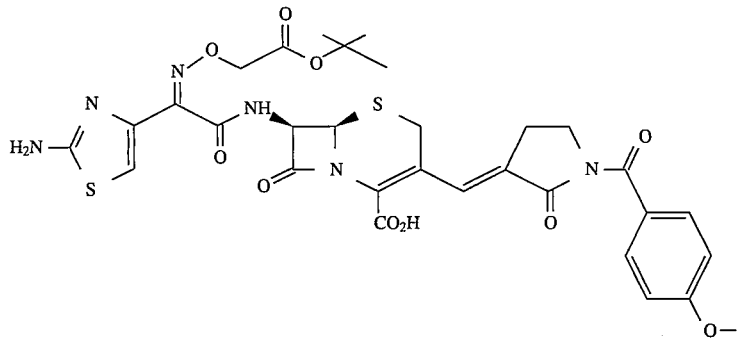

(6R,7R)-7[(Z)-2-(2-Amino-thiazol-4-yl)-2 -tert-butoxycarbonyl-methoxyimino-acetylamino]8-oxo-3-[(E)-2-oxo-1-prop-2 -ynyl-pyrrolidin-3-ylidenemethyl]-5-thia-1-azabicyclo[4.2.0]oct-2-ene-2-carboxylic acid IR(KBr): 2120, 1781, 1729, 1683, 1628 cm$^{-1}$
MS(ISP): 617.4 (M+H)$^+$

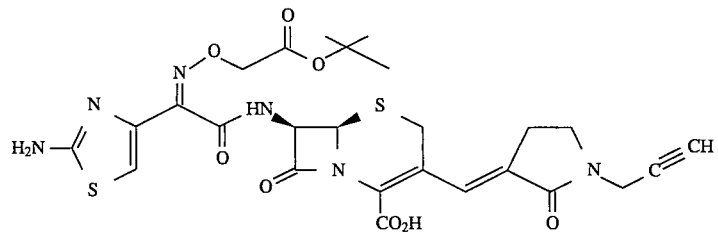

(6R,7R)-7-[(Z)-2-(2-Amino-thiazol-4-yl)-2 -tert-butoxycarbonyl-methoxyimino-acetylamino]3-[(E)-1-cyclopropylmethyl-2 -oxo-pyrrolidin-3-ylidenemethyl]-8-oxo-5-thia-1-azabicyclo[4.2.0]oct-2 -ene-2-carboxylic acid trifluoroacetate (1:0.2)

IR(KBr): 1784, 1727, 1680 cm$^{-1}$
MS(ISP): 633.3 (M+H)$^+$

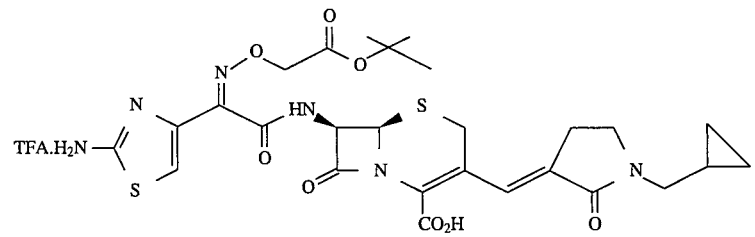

Example 5 a)
[6R-[3(E),6α,7β(Z)]]-7-[[(2-Amino-4-thiazolyl)[(carboxymethoxy)imino]acetyl]amino]-3-[(1-cyclopropyl-2 -oxo-3-pyrrolidinylidene)methyl]-8-oxo-5-thia-1 -azabicyclo[4.2.0]oct-2-ene-2-carboxylic acid disodium salt

[6R-[3(E),6α,7β(Z)]]-7[[(2-Amino-4-thiazolyl)[[2-(1,1 -dimethylethoxy)-2-oxoethoxy]imino]acetyl]amino]-3-[(1 -cyclopropyl-2-oxo-3-pyrrolidinylidene)methyl]-8-oxo-5-thia-1-azabicyclo[4.2.0]oct-2-ene-2 carboxylic acid 5.49 g (8.57 mM) in dichloromethane (220 mL) and anisole (22 mL) were cooled in an ice/water bath, and trifluoroacetic acid (220 mL) was added dropwise. The solution was stirred for one and one half hours at this temperature and then at room temperature for two and one half hours. The volatile material was removed on the rotary evaporator at water aspirator pressure. The residue was treated dropwise with ethyl ether (300 mL) at 4° C., stirred for 30 minutes, and filtered under nitrogen to obtain 5.90 g of solid. The solid was dissolved in water with the addition of sodium bicarbonate 2.16 g (25.7 mM) and purified on a C18 reverse phase column to afford the titled compound 3.93 g (75%).

NMR (400 MHz, D$_2$O) δ 0.80 (m, 4H), 2.75 (m, 1H), 2.95 (m, 2H), 3.50 (t, 2H), 3.82 (q, 2H), 4.95 (s, 2H), 5.28 (d, 1H), 5.88 (d, 1H), 7.02 (s, 1H), 7.07 (s, 1H); IR (KBr)cm$^{-1}$ 1763, 1662, 1603.

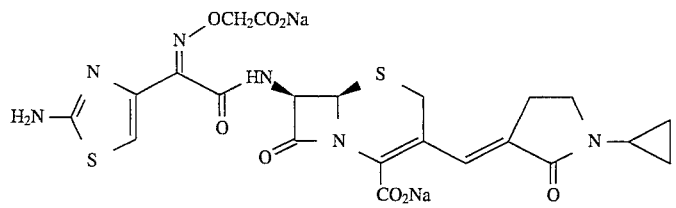

According to the procedure set forth in the preceding example, the following additional compounds were prepared:

[6R-[3(E),6α,7β(Z)]]-7-[[(2-Amino-4-thiazolyl)[(carboxymethoxy) imino]acetyl]amino]-8-oxo-3-[(2-oxo-3-pyrrolidinylidene)methyl]-5 -thia-1-azabicyclo[4.2.0]oct-2-ene-2-carboxylic acid disodium salt NMR (200 MHz, D$_2$O) δ 3.02 (m, 2H), 3.42 (t, 2H), 3.77 (s, 2H), 4.53 (s, 2H), 5.24 (d, 1H), 5.82 (d, 1H), 7.00 (s, 2H).

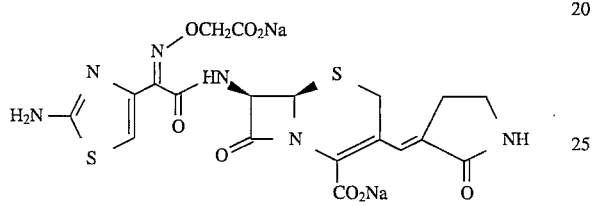

[6R-[3(E),6α,7β(Z)]]-7-[[(2-Amino-4-thiazolyl)[(carboxymethoxy) imino]acetyl]amino]-3-[[1-(1,1-dimethylethyl)-2-oxo-3-pyrrolidinylidene]methyl]-8-oxo-5-thia-1-azabicyclo[4.2.0]oct-2 -ene-2-carboxylic acid disodium salt NMR (400 MHz, D$_2$O) δ 1.42(s, 9H), 2.92 (m, 1H), 3.66 (t, 2H), 3.81 (q, 2 H), 4.58 (s, 2H), 5.26 (d, 1H), 5.88 (d, 1H), 6.98 (s, 1H), 7.07 (s, 1H);

IR (KBr)cm$^{-1}$ 1761, 1662, 1606.

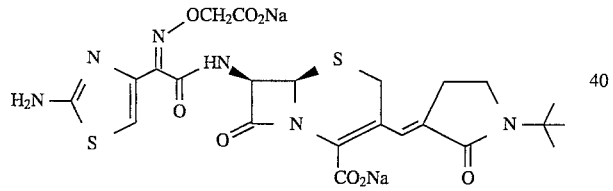

6R-[3(E),6α,7β(Z)]]-7-[[(2-Amino-4-thiazolyl[(carboxymethoxy) imino]acetyl]amino]-8-oxo-3-[[2-oxo-1-(2,2,2-trifluoroethyl)-1-pyrrolidinylidene ]methyl]-5-thia-1-azabicyclo[4.2.0]oct-2-ene-2-carboxylic acid disodium salt NMR (400 MHz, DMSO-d$_6$) δ 2.93, 3.14 (m, 2H), 3.43 (m, 2H), 3.68 (q, H), 4.12(m, 2H), 4.22 (s, 2H), 5.02 (d, 1H), 5.62 (q, 1H), 6.84 (s, 1H), 7.18 (s, 1H);7.43 (s, 2H);

IR (KBr)cm$^{-1}$ 1763, 1671, 1606.

[6R-[3(E),6α,7β(Z)]]-7-[[(2-Amino-4-thiazolyl)[(carboxymethoxy) imino]acetyl]amino]-3-[[1-(2-fluoroethyl)-2-oxo-3-pyrrolidinylidene]methyl]-8-oxo-5-thia-1-azabicyclo[4.2.0]oct-2 -ene-2-carboxylic acid disodium salt NMR (400 MHz, DMSO-d$_6$) δ 2.88, 3.08 (m, 2H), 3.37 (m, 2H), 3.63 (m, H), 4.22 (s, 2H), 4.50 (t, 1H), 4.62 (t, 1H), 5.00 (d, 1H), 5.62 (q, 1H), 6.84 (s, 1H), 7.18 (s, 1H) 7.35 (s, 2H);

IR (KBr) cm$^{-1}$ 1762, 1669, 1607.

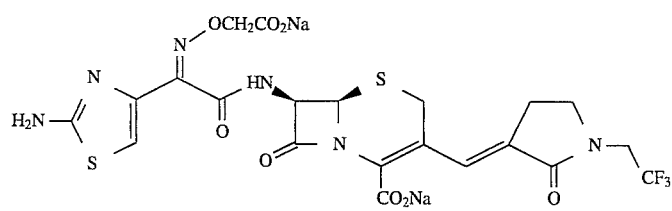

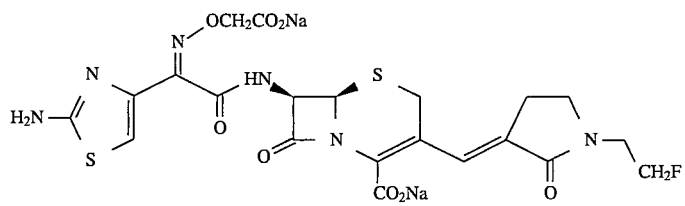

[6R-[3(E), 6,6O ,7β(Z)]]-7-[[(2-Amino-4-thiazolyl)[(carboxymethoxy) imino]acetyl]amino]-3-[(1-methyl-2-oxo-3-pyrrolidinylidene) methyl]-8-oxo-5-thia-1-azabicyclo[4.2.0]oct-2-ene-2-carboxylic acid disodium salt NMR (200 MHz, D$_2$O) δ 2.92 (s, 3H), 3.50 (t,2H), 3.78 (t,2H), 4.55 (s, H), 4.75 (q, 2H), 5.24 (d, 1H), 5.86 (d, 1H), 6.98 (t, 1H), 7.04 (s, 1H).

methylethyl)-2-oxo- 3-pyrrolidinylidene]methyl]-8-oxo-5-thia-1-azabicyclo[4.2.0]oct-2 -ene-2-carboxylic acid trisodium salt NMR (400 MHz, DMSO-d$_6$) δ 1.36, (s, 3H), 1.37 (s, 3H), 2.75, 2.95 (m, H), 3.48 (m, 2H), 3.66 (q, 2H), 4.23 (s, 2H), 4.99 (d, 1H), 5.60 (d, 1H), 6.85 (s, 1H), 7.19 (s, 1H);

IR (KBr)cm$^{-1}$ 3414, 1764, 1658, 1597.

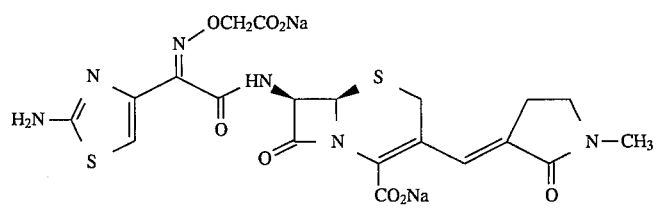

[6R-[3(E),6α,7β(Z)]]-7-[[(2-Amino-4-thiazolyl)[(carboxymethoxy) imino]acetyl]amino]-3-[[1-(4-carboxyphenyl)-2-oxo-3-pyrrolidinylidene]methyl]-8-oxo-5-thia-1-azabicyclo[4.2.0]oct-2 -ene-2-carboxylic acid trisodium salt NMR (400 MHz, D$_2$O) δ 3.10 (m, 2H), 3.84 (s, 2H), 3.95 (m, 2H), 4.55 (s, 2H), 5.25 (d, 1H), 5.85 (d, 1H), 7.0 (s, 1H), 7.21 (s, 1H) 7.61 (d, 2H), 7.90 (d, 2H).

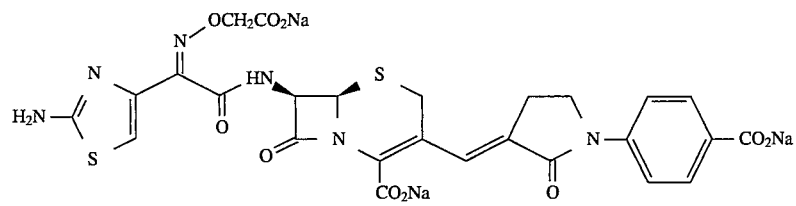

[6R-[(E),6α,7β(Z)]]-7-[[(2-Amino-4-thiazolyl)[(1-carboxy-1 -methylethoxy)imino]acetyl]amino]-3-[(1-methyl-2-oxo-3-pyrrolidinylidene)methyl]-8-oxo-5-thia-1-azabicyclo[4.2.0]oct-2 -ene-2-carboxylic acid disodium salt NMR (200 MHz, DMSO-d$_6$) δ 1.34 (s, 3H), 1.42 (s, 3H), 2.78 (s, 3H), 2.50, 2.82 (m, 2H), 2.93 (m, 2H), 3.65 (q, 2H), 4.96 (s, 2H), 5.62 (q, H), 6.70 (s, 1H), 7.10 (s, 2H);7.24 (s, 1H), 12.0 (d, 1H).

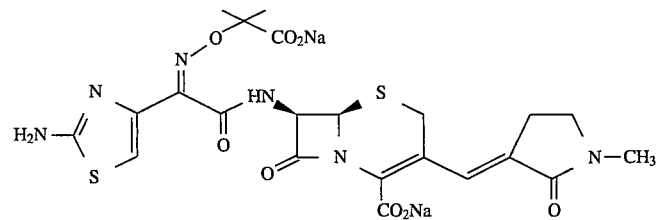

[6R-[3(E),6α,7β(Z)]]-7-[[(2-Amino-4-thiazolyl)[(carboxymethoxy) imino]acetyl]amino]-3-[[1-(1-carboxy-1-

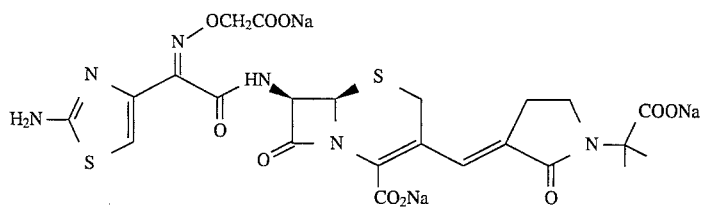

b) (6R,7R)-7-[(Z)-2-(2-Amino-thiazol-4-yl)-2 -carboxymethoxyimino-acetylamino]-3-[(E)-1-(2,2,2 -trifluoro-ethyl)-2-oxo-piperidin-3-ylidenemethyl]-8-oxo-5-thia-1-azabicyclo[4.2.0]oct-2-ene-2-carboxylic acid trifluoroacetate (1:2)

540 mg (0.8 mmol) (6R,7R)-7-[(Z)-2-(2-Amino-thiazol-4-yl)-2 -tert-butoxycarbonyl-methoxyimino-acetylamino]-3-[(E)-1-(2,2,2 -trifluoro-ethyl)-2-oxo-piperidin-3-ylidenemethyl]-8-oxo-5-thia-1-azabicyclo[4.2.0]oct-2-ene-2-carboxylic acid was added in small portions over 20 min. to 5 ml trifluoroacetic acid at 0° C. The resulting orange solution was stirred for 4 h at 0° C. and then poured on 25 ml diethylether. The solid materials was filtered off, washed with ether and n-hexane and dried.

yield: 445 mg
IR(KBr): 1780, 1725, 1664, 1638 cm$^{-1}$
MS(ISN): 617.3 (M–H)$^-$ imino-acetylamino]-8 -oxo-5-thia-1-azabicyclo[4.2.0]oct-2-ene-2-carboxylic acid Na salt (1:2)
IR(KBr):1763, 1669, 1612 cm$^{-1}$
MS(ISP): 563.3 (M–2Na+3H)$^+$

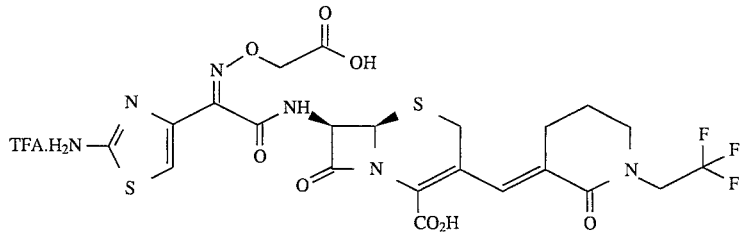

The following additional compounds were prepared in the same manner:

(6R,7R)-7-[(Z)-2-(Amino-thiazol-4-yl)-2 -carboxymethoxyimino-acetyl-amino]-3-[(E)-1-carboxymethyl-2-oxo-pyrrolidin-3-ylidenemethyl]-8-oxo-5-thia-1-azabicyclo[4.2.0]oct-2-ene-2-carboxylic acid trifluoroacetate (1:0.6)

IR(KBr): 1776, 1730, 1677, 1634 cm$^{-1}$

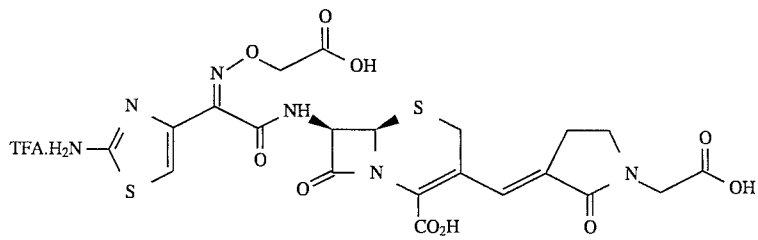

(6R,7R)-3-[(E)-1-Allyl-2-oxo-pyrrolidin-3-ylidenemethyl]-7-[(Z)-2 -(2-amino-thiazol-4-yl)2-carboxymethoxy-

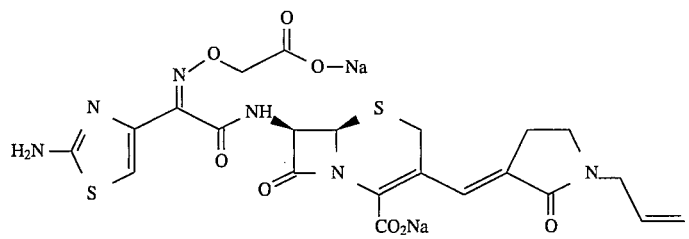

(6R,7R)-7-[(Z)-2-(2-Amino-thiazol4-yl)2 -carboxymethoxyimino-acetylamino]-3-[(E)-1-cyclopropyl-2-oxo-piperidin-3 -ylidenemethyl]-8-oxo-5-thia-1-azabicyclo[4.2.0]oct-2-ene-2-carboxylic acid trifluoroacetate (1:1)
IR(KBr). 1779, 1678, 1635 cm$^{-1}$
MS(ISP: 577.4 (M+H)$^+$

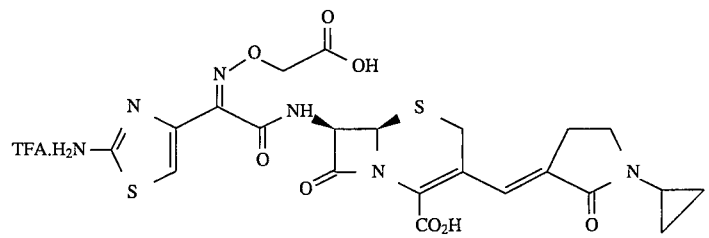

(6R,7R)-7-[(Z)-2-(2-Amino-thiazol-4-yl)2 -carboxymethoxyimino-acetylamino]-3-[(E)-1-(4-methoxybenzoyl)-2-oxo-pyrrolidin-3-ylidenemethyl]-8-oxo-5-thia-1-azabicyclo[4.2.0]oct-2-ene-2-carboxylic acid Na salt (1:2)

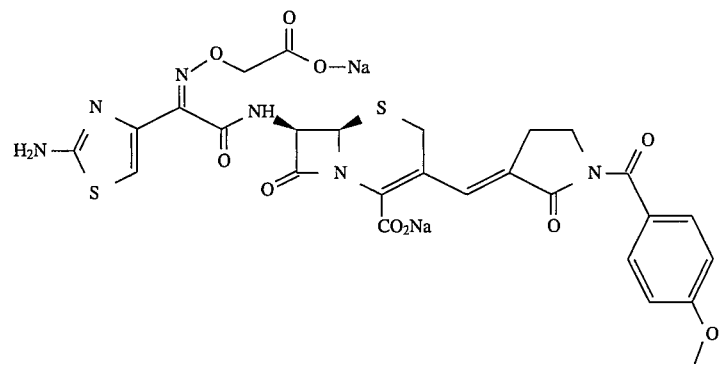

(6R,7R)-7-[(Z)-2-(2-Amino-thiazol-4-yl)2-carboxymethoxyimino-acetylamino]-8-oxo-3-[(E)-2-oxo-1-prop-2-ynyl-pyrrolidin-3-ylidenemethyl]-5-thia-1-azabicyclo[4.2.0]oct-2-ene-2-carboxylic acid trifluoroacetate (1:1)
IR(KBr): 2121, 1779, 1677, 1635 cm$^{-1}$
MS(ISP): 561.4 (M+H)$^+$

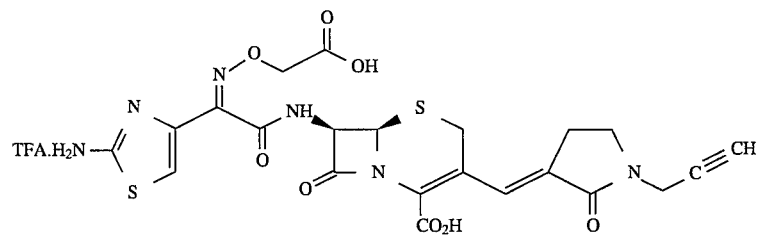

(6R,7R)-7-[(Z)-2-(2-Amino-thiazol-4-yl)2 -carboxymethoxyimino-acetyl-amino]-3-[(E)-1-cyclopropylmethyl-2-oxo-pyrrolidin-3-ylidenemethyl]-8-oxo-5-thia-1-azabicyclo[4.2.0]oct-2-ene-2-carboxylic acid trifluoroacetate (1:0.75)

IR(KBr): 1778, 1676, 1633 cm$^{-1}$
MS(ISP): 577.4 (M+H)$^+$

[[6R-[3(E), 6α,7β(Z)]]-7-[[(2-Amino-4-thiazolyl) (triphenylmethoxy)imino]acetyl]amino]-8-oxo-3-[(2-oxo-1-phenyl-3-pyrrolidinylidene)methyl]-5-thia-1-azabicyclo[4.2.0] oct-2-ene-2-carboxylic acid

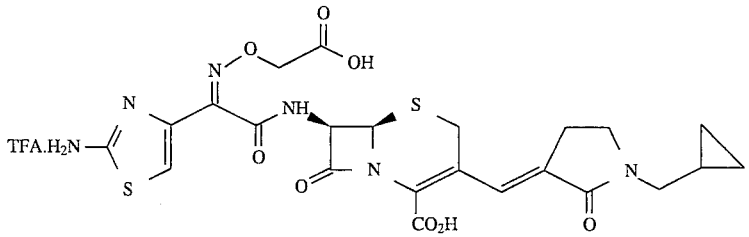

Example 6

[6R-[3(E),6α,7β(Z)]]-7-[[(2-Amino-4-thiazolyl) [(triphenylmethoxy)imino]acetyl]amino]-3-[[1-(4-methoxyphenyl)-2-oxo-3-pyrrolidinylidene]methyl]-8-oxo-5-thia-1-azabicyclo[4.2.0]oct-2-ene-2-carboxylic acid

[6R-[3(E),6α,7β(Z)]]-7-Amino-3-[[(1-[4-Methoxyphenyl)]-2-oxo-3-pyrrolidinylidene]methyl]-8-oxo-5-thia-1-azabicyclo[4.2.0]oct-2-ene-2-carboxylic acid mono(trifluoroacetate) salt 0.3 g (0.59 mM), dimethylformamide (9.5

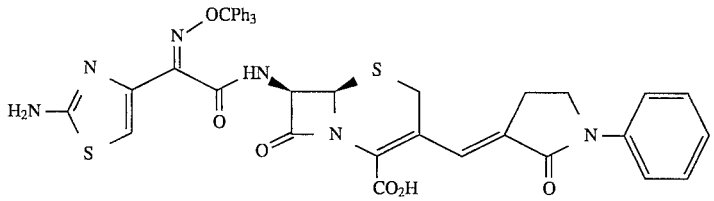

mL), and 2-(2-aminothiazol-4-yl)-(Z)-2-trityloxyiminoacetic acid 1-benzotriazole ester 0.43 g (0.7 mM) were combined and stirred at room temperature for 16 hours. The reaction mixture was poured into brine (45 mL) and ethyl acetate (90 mL) The ethyl acetate layer was washed with brine, dried over anhydrous sodium sulfate, filtered and the solvent removed. The residue was treated with ethyl ether, the solid filtered and retreated with ethyl ether to obtain the title compound 0.24 g (51%).

NMR (400 MHz, CDCl$_3$) δ 2.99 (s, 2H), 3.62 (s, 2H), 3.80 (s, 3H), 3.83 (m, 2H), 5.10 (d, 1H), 5.80 (br.s, 2H), 5.96 (q, 1H), 6.65 (s, 1H), 6.90 (d, 2H), 7.32 (m, 15H), 7.58 (s, 1H), 7.61 (d, 2H).

[6R-[3(E),6α,7β(Z)]]-7-[[(2-Amino-4-thiazolyl) (triphenylmethoxy)imino]acetyl]amino]-3-[(1-methoxy-2-oxo-3-pyrrolidinylidene)methyl]-8-oxo-5-thia-1-azabicyclo [4.2.0]oct-2-ene-2-carboxylic acid

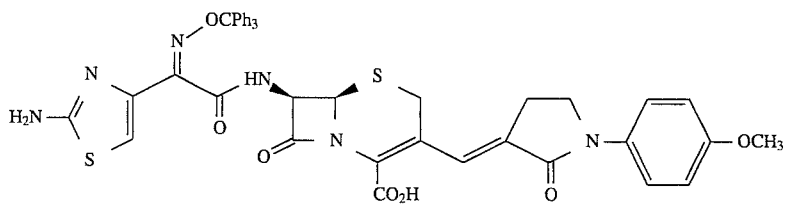

Following the procedure set forth in the preceding example the following additional compounds were prepared:

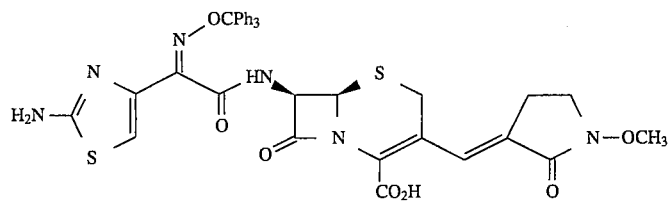

[6R-[3(E),6,60 ,7β(Z)]]-7-[[(2-Amino-4 -thiazolyl)[(triphenylmethoxy)imino]acetyl]amino]-3-[(1-methyl-2-oxo-3 -pyrrolidinylidene)methyl]-8-oxo-5-thia-1-azabicyclo[4.2.0]oct-2 -ene-2-carboxylic acid

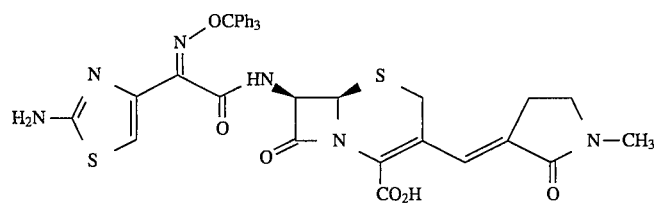

[6R-[3(E),6α,7β(Z)]]-7-[[(2-Amino-4-thiazolyl)[(triphenylmethoxy)imino]acetyl]amino]-3-[[(1-(2,2,2 -trifluoroethyl)-2-oxo-3-pyrrolidinylidene]methyl]-8-oxo-5-thia-1-azabicyclo[4.2.0]oct-2-ene-2-carboxylic acid

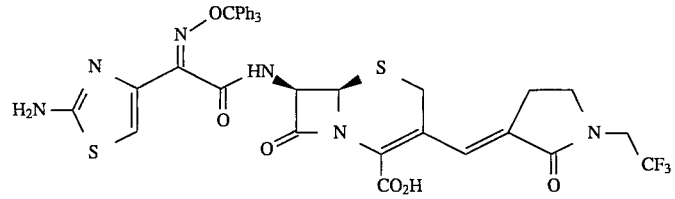

[6R-[3(E), 6α,7β(Z)]]-7-[[(2-Amino-4-thiazolyl)[(triphenylmethoxy)imino)]acetyl]amino]-3-[[(1-(1,1 -dimethylethyl)-2-oxo-3-pyrrolidinylidene]methyl]-8-oxo-5-thia-1-azabicyclo[4.2.0]oct-2-ene-2-carboxylic acid

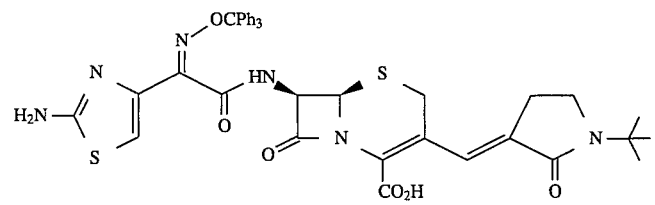

(6R,7R)-7-[(Z)-2-(2-Amino-thiazol-4-yl)-2-trityloxy-imino-acetylamino]-3[(E)-1-(5-methyl-isoxazol-3-yl)-2-oxo-pyrrolidin-3-ylidenemethyl]-8-oxo-5-thia-1-azabicyclo[4.2.0]oct-2-ene-2-carboxylic acid IR(KBr): 3430, 1786, 1699, 1609, 1505 cm$^{-1}$
MS(ISN): 803.4 (M−H+NH$_3$)$^−$; 786.4 (M−H)$^−$

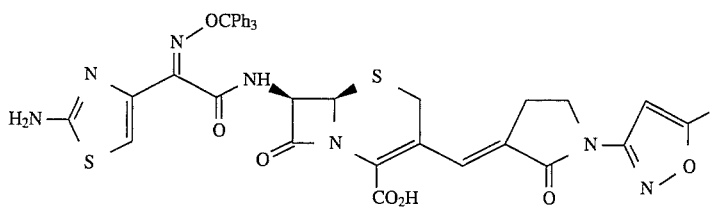

(6R,7R)-7-[(Z)-2-(2-Amino-thiazol-4-yl)-2-trityloxy-imino-acetylamino]-8-oxo-3-[(E)-2-oxo-1-pyridin-2-yl-pyrrolidin-3-ylidenemethyl]-5-thia-1-azabicyclo[4.2.0]oct-2-ene-2-carboxylic acid IR(KBr): 3492, 1781, 1687, 1620, 1587, 1468, 1385 cm$^{-1}$
MS(ISN): 782.4 (M−H)$^-$; 799.4 (M−H+NH$_3$)$^-$ IR(KBr): 1782, 1689, 1620, 1505, 1465, 1382 cm$^{-1}$
MS(ISP): 790.4 (M+H)$^+$

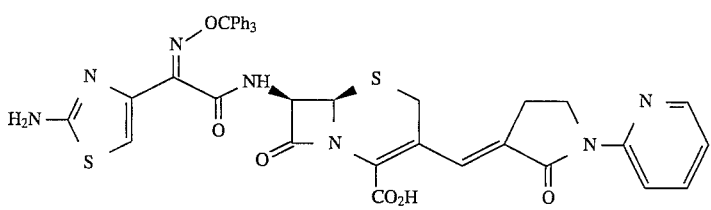

(6R,7R)-7-[(Z)-2-(2-Amino-thiazol-4-yl)-2-trityloxy-imino-acetylamino]-8-oxo-3-[(E)-2-oxo-1-pyridin-3-yl-pyrrolidin-3-ylidenemethyl]-5-thia-1-azabicyclo[4.2.0]oct-2-ene-2-carboxylic acid IR(KBr): 1781, 1686, 1619, 1577, 1532, 1485 cm$^{-1}$
MS(ISN): 782.4 (M−H$^-$, 799.4 (M−H+NH$_3$)$^-$

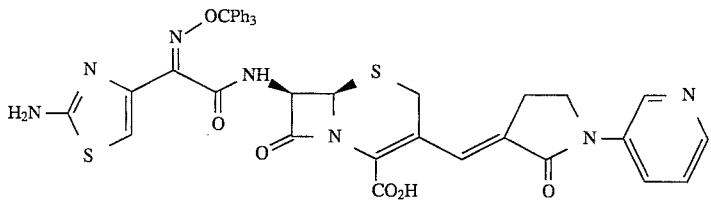

(6R,7R)-7-[(Z)-2-(2-Amino-thiazol-4-yl)-2-trityloxy-imino-acetylamino]-8-oxo-3-[(E)-[2-oxo-1-(2-oxo-oxazolidin-3-yl)-pyrrolidin-3-ylidenemethyl]-5-thia-1-azabicyclo[4.2.0]oct-2-ene-2-carboxylic acid IR(KBr): 3429, 1778, 1701, 1625 cm$^{-1}$ 15 MS(ISN): 790.4 (−H)$^-$

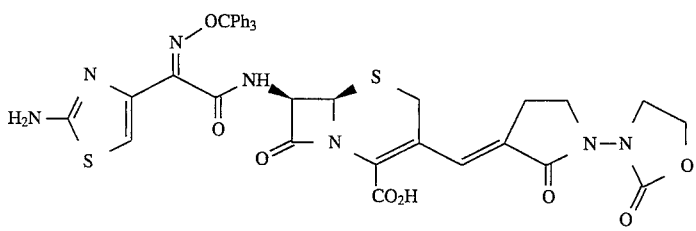

(6R,7R)-7-[(Z)-2-(2-Amino-thiazol-4-yl)-2-trityloxy-imino-acetylamino]-8-oxo-3-[(E)-2-oxo-1-thiazol-2-pyrrolidin-3-ylidenemethyl]-5-thia-1-azabicyclo[4.2.0]oct-2-ene-2-carboxylic acid

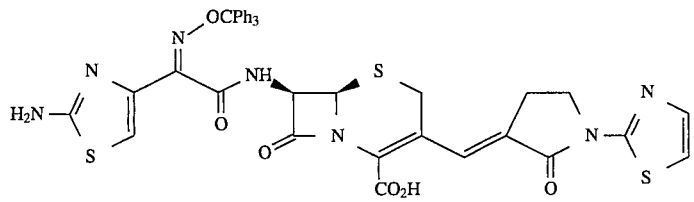

(6R,7R)-7-[(Z)-2-(2-Amino-thiazol-4-yl)-2-trityloxy-imino-acetylamino]-3-[(E)-1-carboxymethyl-2-oxo-pyrrolidin-3-ylidenemethyl]-8-oxo-5-thia-1-azabicyclo[4.2.0]oct-2-ene-2-carboxylic acid IR(KBr): 1784, 1727, 1661 cm$^{-1}$

MS(EI): 765.2 (M+H)$^+$ 787.2 (M+NO$^+$)

MS(ISP): 798.5 (M)$^+$

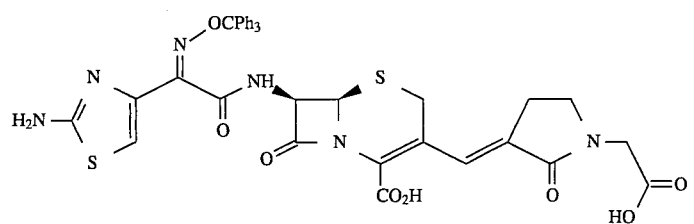

(6R,7R)-7-[(Z)-2-(2-Amino-thiazol-4-yl)-2-trityloxy-imino-acetylamino]-3-[(E)-1-allyl-2-oxo-pyrrolidin-3-ylidenemethyl]-8 -oxo-5-thia-1-azabicyclo[4.2.0]oct-2-ene-2-carboxylic acid IR(KBr):1784, 1686, 1626 cm$^{-1}$

MS(ISP): 747.5 (M+H)$^+$

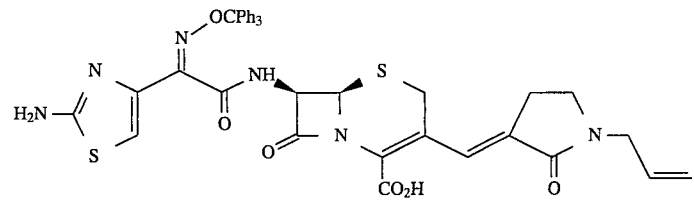

(6R,7R)-7-[(Z)-2-(2-Amino-thiazol-4-yl)-2-trityloxy-imino-acetylamino]-3-[(E)-2-oxo-pyridin-4-yl-pyrrolidin-3-ylidenemethyl]-5-thia-1-azabicyclo[4.2.0]oct-2-ene-2-carboxylic acid Na salt (1:1)

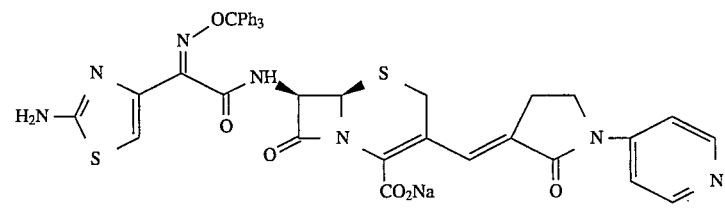

(6R,7R)-4-[(E)-3-[7-[(Z)-2-(2-Amino-thiazol-4-yl)-2-trityloxyimino-acetylamino]-2-carboxy-8-oxo-5-thia-1-azabicyclo[4.2.0]oct-2-en-3-ylidenemethyl]-2-oxo-pyrrolidin-1-yl]-1-methyl-pyridinium iodide IR(KBr): 1780, 1710, 1639, 1518 cm$^{-1}$

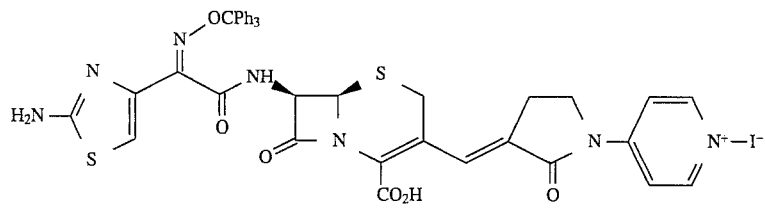

(6R,7R)-7-[(Z)-2-(2-Amino-thiazol-4-yl)-2-trityloxy-imino-acetylamino]-3-[(Z)-1-cyclopropyl-2-oxo-pyrrolidin-3-ylidenemethyl]-8-oxo-5-thia-1-azabicyclo[4.2.0]oct-2-ene-2-carboxylic acid IR(KBR): 1783, 1680 cm$^{-1}$
MS(ISP): 747.4 (M+H)$^+$

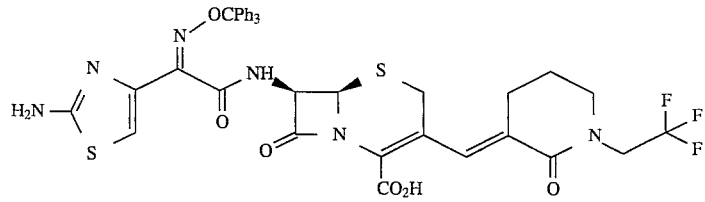

(6R,7R)-7-[(Z)-2-(2-Amino-thiazol-4-yl)-2-trityloxy-imino-acetylamino]-8-oxo-3-[(E)-1-(2,2,2-trifluoro-ethyl)-piperidin-3-ylidenemethyl]-5-thia-1-azabicyclo[4.2.0]oct-2-ene-2-carboxylic acid IR(KBr): 1785, 1758, 1695, 1620
MS(ISP): 803.5 (M+H)$^+$ (6R,7R)-7-[(Z)-2-(2-Amino-thiazol-4-yl)-2-trityloxy-imino-acetylamino]-3-[(E)-1-cyclopropyl-2-oxo-piperidin-3-ylidenemethyl]-8-oxo-5-thia-1-azabicyclo[4.2.0]oct-2-ene-2-carboxylic acid IR(KBr): 1786, 1686, 1612 cm$^{-1}$

MS(ISN): 776.4 (M−H+NH$_3$)$^−$, 759.4 (M−H)$^−$ (6R,7R)-7-[(Z)-2-(2-Amino-thiazol-4-yl)-2-trityloxy-imino-acetylamino]-3-[(E)-1-phenyl-piperidin-3-ylidenemethyl]-5-thia-1-azabicyclo[4.2.0]oct-2-ene-2-carboxylic acid IR(KBr): 1786, 1686, 1658 cm$^{-1}$
MS(ISP): 797.5 (M+H)$^+$

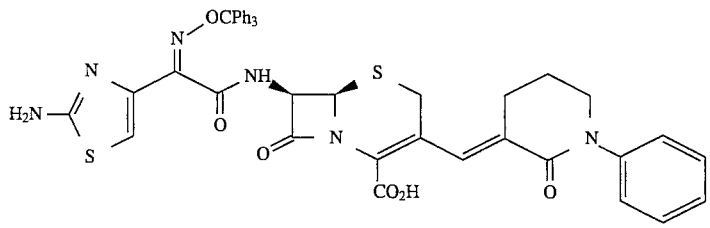

(6R,7R)-7-[(Z)-2-(2-Amino-thiazol-4-yl)-2-trityloxy-imino-acetylamino]-8-oxo-3-[(Z)-2-oxo-1-phenyl-azetidin-3-ylidenemethyl]-5-thia-1-azabicyclo[4.2.0]oct-2-ene-2-carboxylic IR(KBr): 1766, 1707, 1675, 1532 cm$^{-1}$

MS(ISP): 769.5 (M+H)+

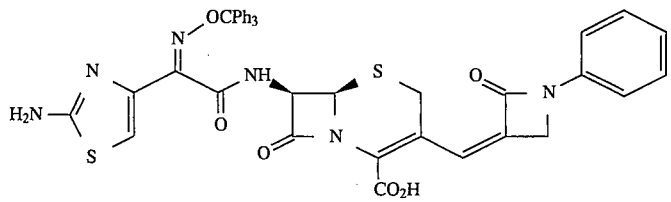

(6R,7R)-7-[(Z)-2-(2-Amino-thiazol-4-yl)-2-trityloxy-imino-acetylamino]-8-oxo-3-[(E)-2-oxo-1-phenyl-azetidin-3-ylidenemethyl]-5-thia-1-azabicyclo[4.2.0]oct-2-ene-2-carboxylic acid IR(KBr): 1788, 1742, 1686 cm⁻¹
MS(ISP): 769.5 (M+H)+

(6R,7R)-7-[(Z)-2-(2-Amino-thiazol-4-yl)-2-trityloxy-imino-acetylamino]-8-oxo-3-[(E)-2-oxo-1-(2,2,2-trifluoro-ethyl)-azetidin-3-ylidenemethyl]-5-thia-1-azabicyclo[4.2.0]oct-2-ene-2-carboxylic acid IR(KBr): 1784, 1757, 1682, 1530 cm⁻¹

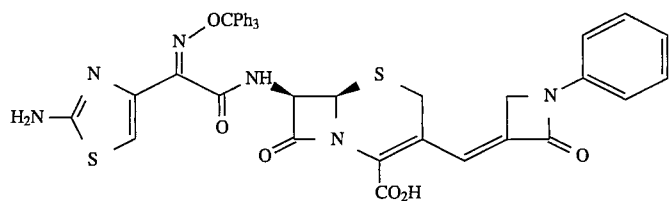

(6R,7R)-7-[(Z)-2-(2-Amino-thiazol-4-yl)-2-trityloxy-imino-acetylamino]-3-[(E)-1-(6-methoxy-pyridin-3-yl)-2-oxo-pyrrolidin-3-ylidenemethyl]-8-oxo-5-thia-1-azabicyclo[4.2.0]oct-2-ene-2-carboxylic acid triethylamine salt (1:1)

IR(KBr): 1782, 1684, 1619, 1530, 1494 cm⁻¹
MS(ISP): 814.4 (M+H)+

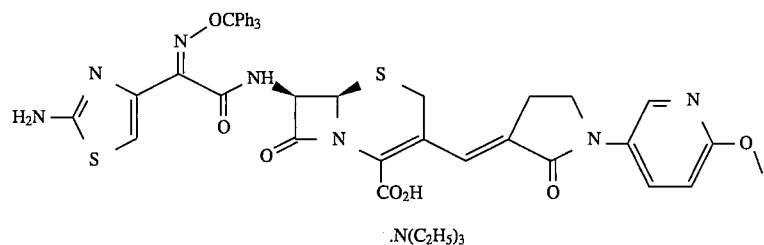

(6R,7R)-7-[(Z)-2-(2-Amino-thiazol-4-yl)-2-trityloxy-imino-acetylamino]-8-oxo-3-[(E)-2-oxo-1-pyrazin-2-yl-pyrrolidin-3-ylidenemethyl]-5-thia-1-azabicyclo[4.2.0]oct-2-ene-2-carboxylic acid IR(KBr): 1785, 1694, 1624, 1526 cm⁻¹
MS(ISP): 785.4 (M+H)+

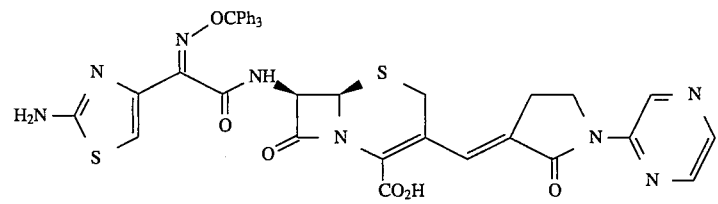

117

MS(ISP): 775.3 (M+H)⁺

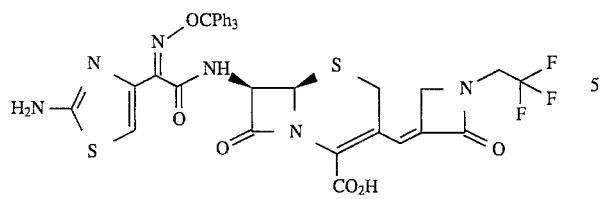

(6R,7R)-7-[(Z)-2-(2-Amino-thiazol-4-yl)-2-trityloxy-imino-acetylamino]-8-oxo-3-[(Z)-2-oxo-1-(2,2,2-trifluoro-ethyl)-azetidin-3-ylidenemethyl]-5-thia-1-azabicyclo[4.2.0]oct-2-ene-2-carboxylic acid IR(KBr): 1768, 1733 cm$^{-1}$
MS(IS): 775.3 (M+H)⁺

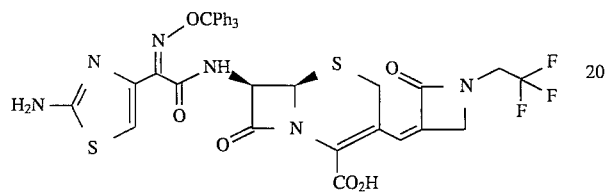

(6R,7R)-7-[(Z)-2-(2-Amino-thi azol-4-yl)-2-trityloxy-imino-acetylamino]-3-[(E)-1-(4-methyl-phenylsulfonyl)-2-oxo-pyrrolidin- 3-ylidenemethyl]-8-oxo-5-thia-1-azabi-cyclo[4.2.0]oct-2-ene-2-carboxylic acid Na salt (1:1)

IR(KBr): 1767, 1684, 1621 cm$^{-1}$
MS(ISP): 861.6 (M+Na)⁺

118

MS(ISP): 746.5 (M+H)⁺

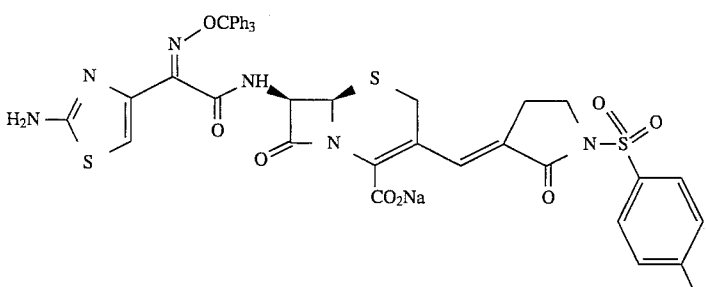

(6R,7R)-7-[(Z)-2-(2-Amino-thiazol-4-yl)-2-trityloxy-imino-acetylamino]-2-[(E)-1-cyanomethyl-2-oxo-pyrrolidin-3-ylidenemethyl] -8-oxo-5-thia-1-azabicyclo[4.2.0]oct-2-ene-2-carboxylic acid IR(KBr): 1783, 1685, 1628 cm$^{-1}$

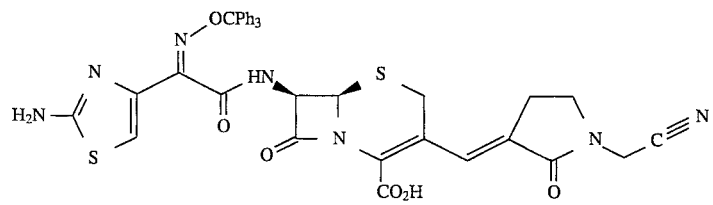

(6R,7R)-7-[(Z)-2-(2-Amino-thiazol-4-yl)-2-trityloxy-imino-acetylamino]-3-[(E)-1-(1,1-dioxo-tetrahydro-thiophen-3-yl)-2-oxo-pyrrolidin-3-ylidenemethyl]-8-oxo-5-thia-1-azabicyclo[4.2.0]oct-2-ene-2-carboxylic acid IR(KBr): 1781, 1680, 1626, 1531, 1490 cm$^{-1}$
MS(ISP): 825.4 (M+H)$^+$

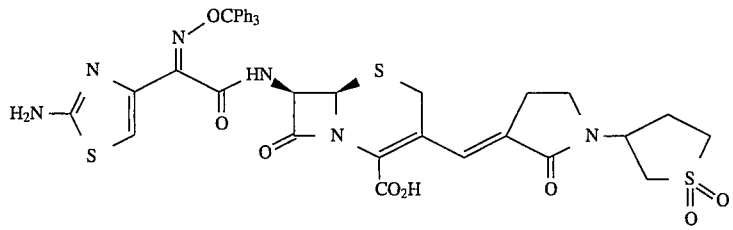

(6R,7R)-7-[(Z)-2-(2-Amino-thiazol-4-yl)-2-trityloxy-imino-acetylamino]-3-[(E)-1-cyclopropylmethyl-2-oxo-pyrrolidin-3-ylidenemethyl]-8-oxo-5-thia-1-azabicyclo[4.2.0]oct-2-ene-2-carboxylic acid IR(KBr): 1786, 1681, 1624 cm$^{-1}$
MS(ISP): 761.5 (M+H)$^+$

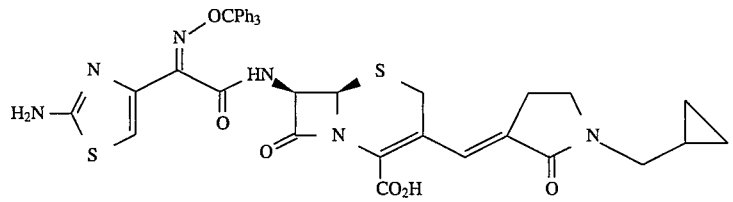

(6R,7R)-7-[(Z)-2-(2-Amino-thiazol-4-yl)-2-trityloxy-imino-acetylamino]-3-[(E)-(2-cyano-ethyl)-2-oxo-pyrrolidin-3-ylidenemethyl]-8-oxo-5-thia-1-azabicyclo[4.2.0]oct-2-ene-2-carboxylic acid Na salt (1:1)

IR(KBr): 2243, 1766, 1675, 1618 cm$^{-1}$
MS(ISP): 760.5 (M+H)$^+$

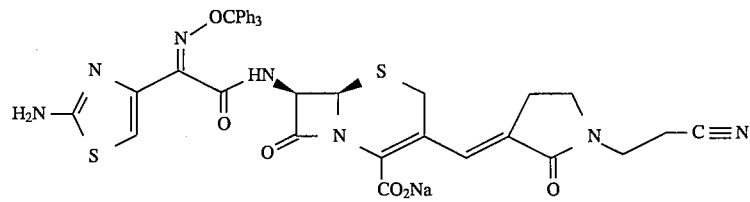

(6R,7R)-7-[(Z)-2-(2-Amino-thiazol-4-yl)-2-trityloxy-imino-acetylamino]-8-oxo-3-[(E)-2-oxo-1-prop-2-ynyl-pyrrolidin-3-ylidenemethyl]-5-thia-1-azabicyclo[4.2.0]oct-2-ene-2-carboxylic acid IR(KBr): 2118, 1783, 1681, 1626 cm$^{-1}$
MS(ISP): 745.5 (M+H)$^+$

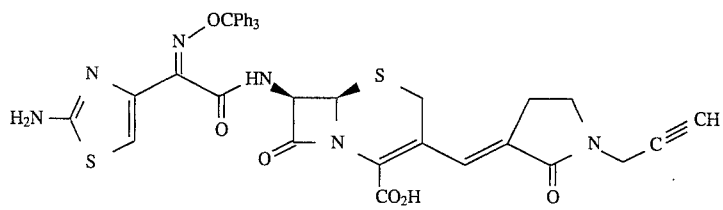

Example 7 a)

[6R-[3(E),6α,7β(Z)]]-7-[[[(Acetyloxy)imino](2-amino-4-thiazolyl)acetyl]amino]-3-[(1-methyl-2-oxo-3-pyrrolidinylidene)methyl]-8-oxo-5-thia-1-azabicyclo[4.2.0]oct-2-ene-2-carboxylic acid monosodium salt

[6R-[3(E),6α,7β(Z)]]-7-Amino-3-[(1-methyl-2-oxo-3-pyrrolidin-ylidene)methyl]-8-oxo-5-thia-1-azabicyclo[4.2.0]oct-2-ene-2 -carboxylic acid trifluoroacetic acid salt 110 mg (0.26 mM), dimethylformamide (4 mL), and water (0.15 mL) were cooled in an ice bath and triethylamine 0.06 mL was added. To the straw colored solution was added benzotriazole-1-yl-(Z)-2-(2-aminothiazole-4-yl)- 2-trityloxyiminoacetate 105 mg (0.29 mM) as a solid. The solution was stirred for five hours at ice bath temperature. A solution of sodium-2-ethyl hexanoate (80 mg) in ethyl acetate (8 mL) was added dropwise. The resulting precipitate was further triturated with ethyl acetate (12 mL) and filtered, and washed with ethyl acetate containing 5% dimethylformamide (2×8 mL) under nitrogen to obtain 143 mg of solid.

IR (KBr)cm$^{-1}$ 3400, 1762, 1665, 1615, 1400.

nylidene)methyl]-5-thia- 1-azabicyclo[4.2.0]oct-2-ene-2-carboxylic acid monosodium salt IR (KBr)cm$^{-1}$ 3350, 1762, 1672, 1615, 1390.

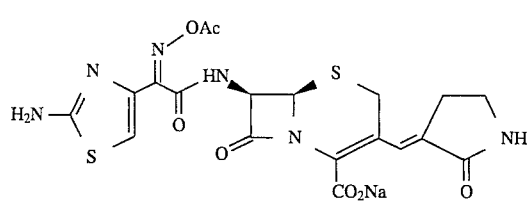

[6R-[3(E),6α,7β(Z)]]-7-[[[(Acetoxy)imino](2-Amino-4-thiazolyl)acetyl]amino]-8-oxo-3-[(2-oxo-1-phenylmethoxy-3 -pyrrolidinylidene)-methyl]-5-thia-1-azabicyclo[4.2.0]oct-2-ene-2 -carboxylic acid monosodium salt IR (KBr)cm$^{-1}$ 3400, 1762, 1675, 1615, 700.

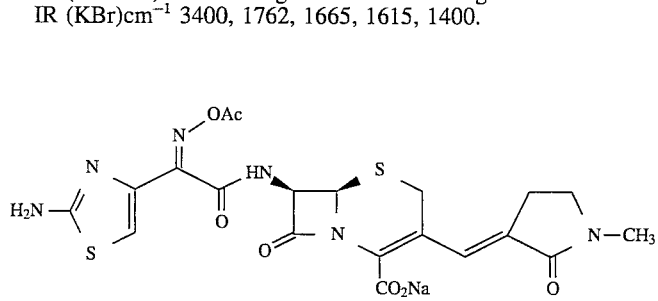

According to the procedure set forth in the preceding example the following additional compounds were prepared:

[6R-[3(E),6α,7β(Z)]]-7-[[[(Acetyloxy)imino](2-amino-4-thiazolyl)acetyl]amino]-3-[(1-methoxy-2-oxo-3-pyrrolidinylidene)methyl]-8 -oxo-5-thia-1-azabicyclo[4.2.0]oct-2-ene-2-carboxylic acid monosodium salt IR (KBr) cm$^{-1}$ 3400, 1762, 1670, 1615, 1390.

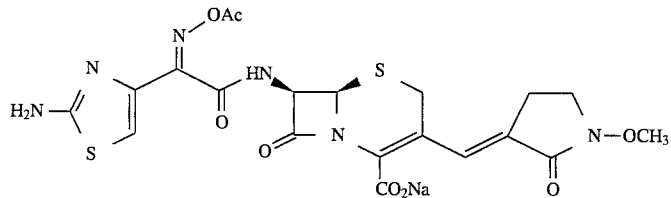

[6R-[3(E),6α,7β(Z)]]-7-[[[(Acetyloxy)imino](2-Amino-4-thiazolyl)acetyl]amino]-8-oxo-3-[(2-oxo-3-pyrrolidi-

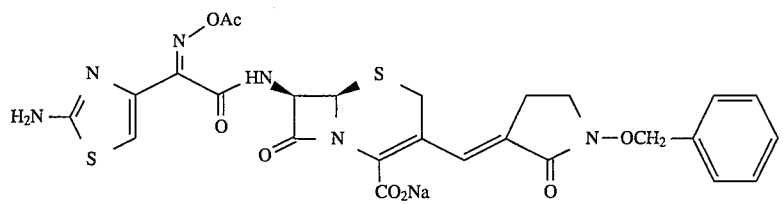

[6R-[3(E),6α,7β(Z)]]-7-[[[(Acetyloxy)imino](2-Amino-4-thiazolyl)acetyl]amino]-8-oxo-3-[(2-oxo-1-phenyl-2-oxo-3-pyrrolidinylidene)methyl ]-5-thia-1-azabicyclo[4.2.0]oct-2-ene-2-carboxylic acid mono sodium salt IR (KBr)cm$^{-1}$ 3450, 1762, 1670, 1615, 690.

(6R,7R)-7-[(Z)-2-(Amino-thiazol-4-yl)-2-acetoxyimino-acetylamino]-3-[(E)-1-cyclopropyl-2-oxo-pyrrolidin-3-ylidenemethyl]-8-oxo-5 -thia-1-azabicyclo[4.2.0]oct-2-ene-2-carboxylic acid IR(KBr): 1777, 1679 cm$^{-1}$

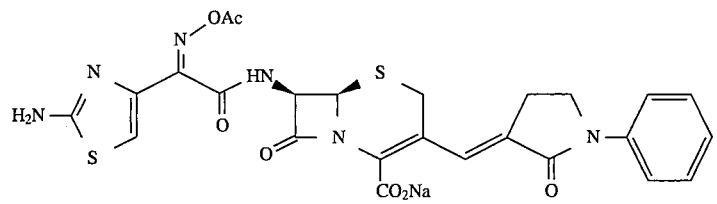

b) (6R,7R)-7-[(Z)-2-(2-Amino-thiazol-4-yl)-2-acetoxy-imino-acetylamino]-8-oxo-3-[(E)-1-(2,2,2-trifluoro-ethyl)-pyrrolidin-3-ylidenemethyl]-5-thia-1-azabicyclo [4.2.0]oct-2-ene-2-carboxylic acid 786 mg (2 mmol) (E)-(6R,7R)-7-Amino-8-oxo-3-[1-(2,2,2-trifluoroethyl -2-oxo-pyrrolidin-3-ylidenemethyl]-5-thia-1-azabicyclo[4.2.0]oct-2-ene-2-carboxylic acid trifluoroacetate (1:1) were suspended in 30 ml of DMF and stirred for 1 h, then 906 mg (2.4 mmol of 2-(2-aminothiazol-4-yl)-(Z)-2-acetoxyiminoacetic acid- 2-benzothiazolyl thioester were added. The mixture was reacted for 18 hours at room temperature and then concentrated in vacuo. To the oily residue were added 300 ml of ethyl acetate, and the organic solution was washed three times with water and dried over magnesium sulfate. Upon concentration to a volume of 20 ml a solid precipitated, which was filtered off, washed with ethyl acetate and dried. It was purified by reprecipitation from acetone/ethyl acetate. yield: 570 mg (48%)

IR(KBr): 1779, 1687, 1533 cm$^{-1}$
MS(EI): 589.0 (M+H)$^+$
Microanalysis: calc. C 42.86 H 3.25N 14.28 S 10.89
$C_{21}H_{19}F_3N_6O_7S_2$ found C 42.52 H 3.69N 13.85 S 10.68

MS(ISP): 547.4 (M+H)$^+$

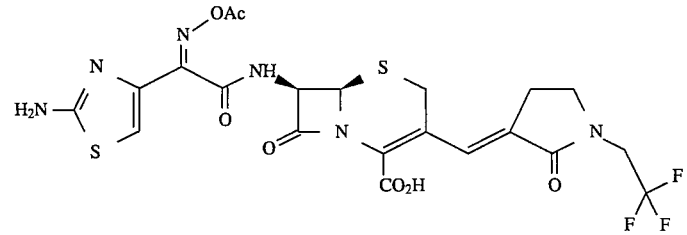

The following additional compound was prepared in the same manner:

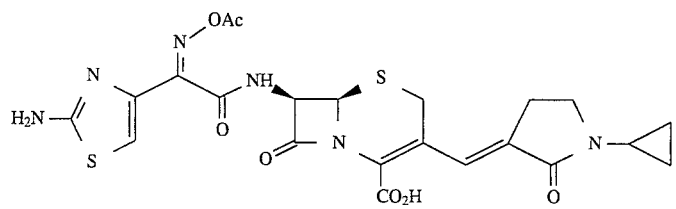

c) (6R,7R)-7-[(Z)-2-(2-Amino-thiazol-4-yl)-2-(2,2-dimethyl-propionyloxyimino-acetylamino]-3-[(E)-1-cyclopropyl-2-oxo-pyrrolidin-3-ylidenemethyl]-8-oxo-5-thia-1-azabicyclo[4.2.0]oct-2-ene-2-carboxylic acid 200 mg (0.47 mmol) [6R-[3(E),6α,7β]]-7-Amino-3-[(1-cyclopropyl-2-oxo-3-pyrrolidinylidene)methyl]-8-oxo-5-thia-1-azabicyclo[4.2.0]oct-2-ene-2-carboxylic acid monotrifluoroacetate were suspended in 7 ml of DMF and stirred for 1 hour, then 217 mg (0.52 mmol) of 2-(2-aminothiazol-4-yl)-(Z)-2-pivaloyloxyimino-acetic acid-2-benzothiazolyl thioester were added. The mixture was reacted for 22 hours at room temperature and then concentrated in vacuo. To the oily residue were added 100 ml of ethyl acetate, and the organic solution was washed with ethyl acetate and dried.

yield: 165 mg (60%)
IR(KBr): 1783, 1682 cm$^{-1}$
MS(ISP): 589.4 (M+H)$^+$

[4.2.0]oct-2-ene-2-carboxylic acid monosodium monohydrochloride salt

[6R-[3(E),6α,7β(Z)]]-7-[[(2-Amino-4-thiazolyl)(triphenylmethoxyimino]acetyl]amino]-3-[[1-(4-methoxyphenyl)-2-oxo-3-pyrrolidinylidene]methyl]-8-oxo-5-thia-1-azabicyclo[4.2.0]oct-2-ene-2-carboxylic acid 0.24 g (0.3 mM) and 90% formic acid were combined at room temperature and stirred for two hours. Ethyl acetate (8 mL) was added and the yellow solid filtered for 0.13 g. The solid was added to water (20 mL) and sodium bicarbonate 57 mg, the solution was filtered through celite, and then purified on C18 silica gel column (water/acetonitrile). The desired fractions were combined yield the title compound 74 mg (41%).

NMR (400 MHz, DMSO-d$_6$) δ 3.03, 3.21 (m, 2H), 3.75 (s, 3H), 3.86 (m, 4H), 5.15 (d, 1H), 5.28 (q, 1H), 6.67 (s, 1H), 6.96 (d, 2H), 7.14 (s, 2H), 7.24 (s, 1H), 7.70 (d, 2H), 9.50 (d, 1H), 11.31 (s, 1H);

IR (KBr) cm$^{-1}$ 1768, 1668, 1620.

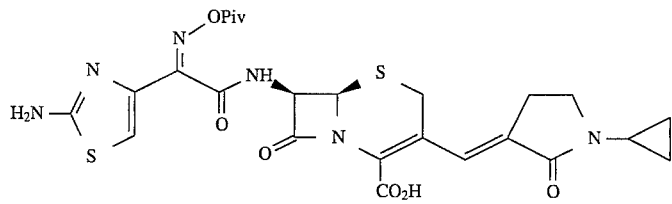

The following additional compound was prepared in the same manner:

(6R,7R)-7-[(Z)-2-(2-Amino-thiazol-4-yl)-2-(2,2-dimethyl-propionyloxyimino-acetylamino]-8-oxo-3-[(E)-2-oxo-1-(2,2,2-trifluoro-ethyl)-pyrrolidin-3-ylidenemethyl]-5-thia-1-azabicyclo[4.2.0]oct-2-ene-2-carboxylic acid IR(KBr): 1782, 1689 cm$^{-1}$
MS(ISP): 631.3 (M+H)$^+$

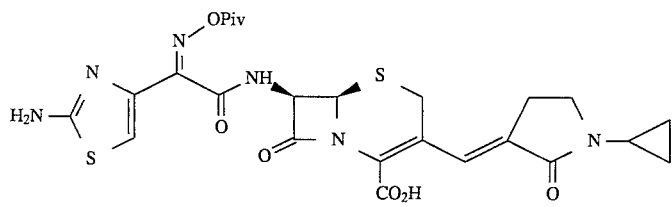

Example 8

[6R-[3(E),6α,7β(Z)]]-7-[[(2-Amino-4-thiazolyl)(hydroxyimino)acetyl]amino]-3-[[1-(4-methoxyphenyl)-2-oxo-3-pyrrolidinylidene]methyl]-8-oxo-5-thia-1-azabicyclo

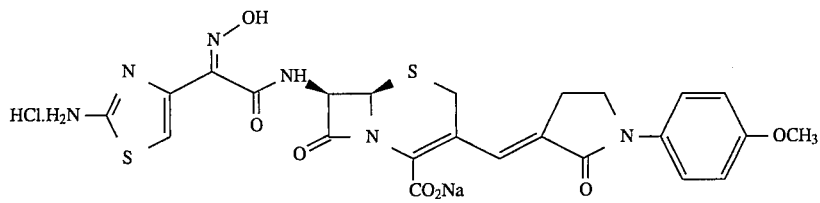

Example 9

(6R,7R)-7-[(Z)-2-(Amino-thiazol-4-yl)-2-hydroxyimino-acetylamino]-8-oxo-3-[(Z)-2-oxo-1-phenyl-azetidin-3-ylidenemethyl]-5-thia-1-azabicyclo[4.2.0]oct-2-ene-2-carboxylic acid 384 mg (0.5 mmol) (6R,7R)-7-[(Z)-2-(2-Amino-thiazol-4-yl)-2-trityloxyimino-acetylamino]-8-oxo-3-[(Z)-2-oxo-1-phenyl-azetidin- 3-ylidenemethyl]-5-thia-1-azabicyclo [4.2.0]oct-2-ene-2-carboxylic acid were stirred for 75 min in 4 ml of 90% formic acid. The suspension is concentrated in vacuo and the residue triturated with 50 ml of ethyl acetate. The solid was filtered off, dried and stirred for 1 hour with 20 ml of 90% ethanol. The product was isolated by filtration, washed with n-hexane and dried.

yield: 209 mg (80%)

IR(KBr): 1776, 1721, 1676 cm$^{-1}$

MS(ISP): 527.4 (M+H)$^+$

Microanalysis: calc. C 50.18 H 3.45N 15.96 S 12.18

$C_{22}H_{18}N_6O_6S_2$ found C 50.01 H 3.33N 15.60 S 12.12

IR(KBr): 1754, 1672, 1528 cm$^{-1}$

MS(ISP): 533.3 (M+H)$^+$

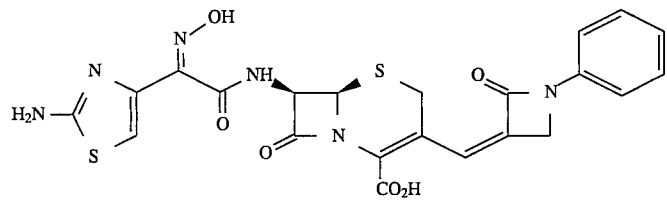

The following additional compounds were prepared in the same manner:

(6R,7R)-7-[(Z)-2-(Amino-thiazol-4-yl)-2-hydroxyimino-acetylamino]-8-oxo-3-[(E)-2-oxo-1-phenyl-azetidin-3-ylidenemethyl]-5-thia-1-azabicyclo[4.2.0]oct-2-ene-2-carboxylic acid IR(KBr): 1778, 1738, 1676, 1528 cm$^{-1}$

MS(ISP): 527.4 (M+H)$^+$

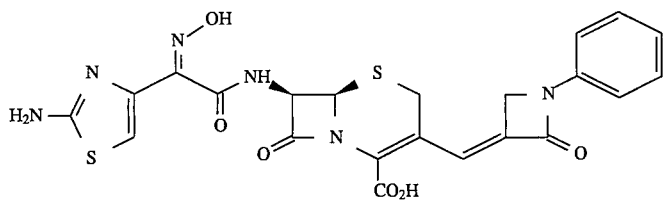

(6R,7R )-7-[(Z)-2-(2-Amino-thiazol-4-yl)-2-hydroxy-imino-acetylamino ]-8-oxo-3-[(E)-2-oxo-1-(2,2,2-trifluoro-ethyl)-azetidin- 3-ylidenemethyl]-5-thia-1-azabicyclo [4.2.0]oct-2-ene-2-carboxylic acid

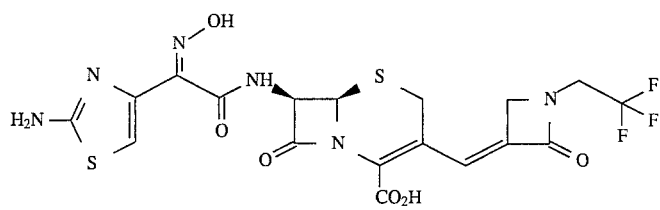

(6R,7R )-7-[(Z)-2-(2-Amino-thiazol-4-yl)-2-hydroxy-imino-acetylamino]-8-oxo-3-[(Z)-2-oxo-1-(2,2,2-trifluoro-ethyl)-azetidin-3-ylidenemethyl]-5-thia-1-azabicyclo[4.2.0]oct-2-ene-2-carboxylic acid IR(KBr): 1746, 1673 cm$^{-1}$
MS(ISP): 533.3 (M+H)$^+$

[6R-[3(E),6α,7β(Z)]]-7-[[(2-Amino-4-thiazolyl)(hydroxyimino)-acetyl]amino]-3-[(2-oxo-1-phenyl-3-pyrrolidinylidene)methyl]-8-oxo-5-thia-1-azabicyclo[4.2.0]oct-2-ene-2-carboxylic acid monohydrochloride salt

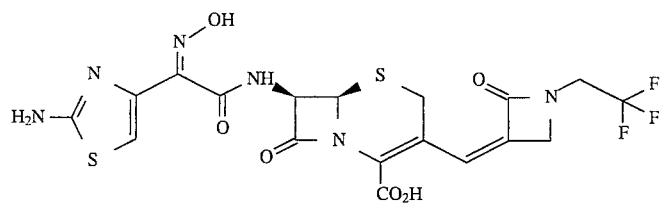

Example 10

[6R-[3(E),6α,7β(Z)1]-7-[[(2-Amino-4-thiazolyl)(hydroxyimino) amino]-3-[(1-methyl-2-oxo-3-pyrrolidinylidene)methyl]-8-oxo-5-thia-1-azabicyclo[4.2.0]oct-2-ene-2-carboxylic acid monohydrochloride salt

[6R-[3(E),6α,7β(Z)]]-7-[[[(Acetyloxy)imino](2-amino-4-thiazolyl)acetyl]amino]-3-[(1-methyl-2-oxo-3-pyrrolidinylidene)methyl]-8-oxo-5-thia-1-azabicyclo[4.2.0]oct-2-ene-2-carboxylic acid monosodium salt 116 mg (0.21 mM) was treated with methanol:water 15 mL (1:2) at room temperature with sodium bicarbonate 19 mg (0.23 mM) for two hours. The reaction was adjusted to pH 2 with 2N HCl and purified on C18 silica gel (water/acetonitrile) to obtain 58.8 mg (54%) of the title compound.

NMR (400 MHz, DMSO-d$_6$) δ 2.85 (s, 3H), 2.90, 3.10 (m, 2H), 3.35 (m, 2H), 3.88 (s, 2H), 5.17 (d, 1H), 5.83 (q, 1H), 6.68 (s, 1H), 7.12 (s, 2H), 7.20 (s, 1H), 9.51 (d, 1H), 11.32 (s, 1H);

IR (KBr) cm$^1$ 1770, 1665.

NMR (400 MHz, DMSO-d$_6$) δ 3.08, 3.22 (m, 2H), 3.92 (m, 4H), 5.22 (d, 1H), 5.87 (q, 1H), 6.67 (s, 1H), 7.15 (s, 2H), 7.18 (t, 1H), 7.40 (m, 3H), 7.80 (m, 2H), 9.54 (d, 1H), 11.34 (s, 1H);

IR (KBr) cm$^{-1}$ 1768, 1666, 1628.

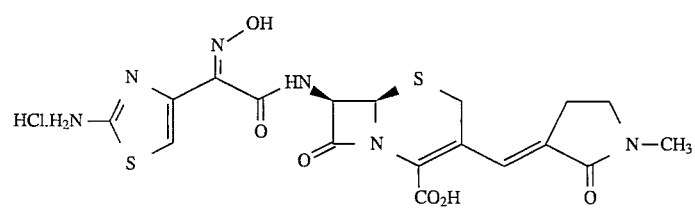

Following the procedure set forth in the preceeding example the following additional compounds were prepared:

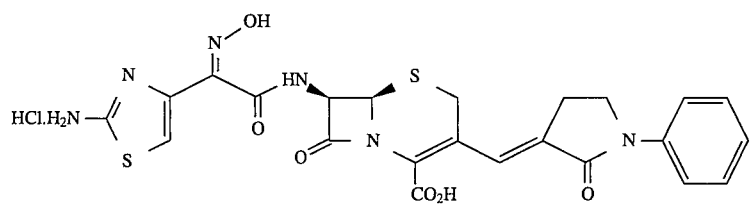

[6R-[3(E),6α,7β(Z)]]-7-[[(2-Amino-4-thiazolyl)(hydroxyimino)acetyl]amino]-3-[(1-methoxy-2-oxo-3-pyrrolidinylidene)methyl]-8-oxo-5-thia-1-azabicyclo[4.2.0]oct-2-ene-2-carboxylic acid monohydrochloride salt NMR (400 MHz, DMSO-$d_6$) δ 2.95, 3.14 (m, 2H), 3.57 (m, 2H), 3.72 (s, H), 3.86 (s, 2H), 5.18 (d, 1H), 5.83 (q, 1H), 6.66 (s, 1H), 7.13 (s, 2H), 7.25 (s, 1H), 9.51 (d, 1H), 11.32 (s, 1H);

IR (KBr) cm$^{-1}$ 1770, 1672.

NMR (400 MHz, DMSO-$d_6$) δ 3.11 (m, 2H), 3.68 (m, 2H), 3.92 (s, 2H), 4.12 (q, 2H), 5.28 (d, 1H), 5.88 (q, 1H), 6.85 (s, 1H), 7.34 (s, 1H), 8.10 (br.s, 2H), 9.80 (d, 1H), 12.3 (s, 1H).

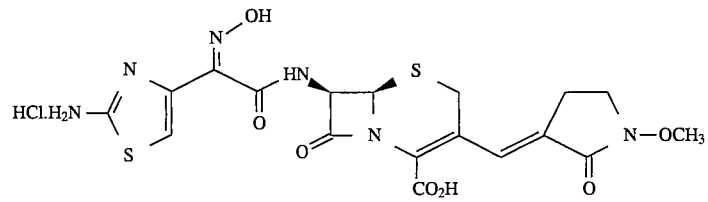

[6R-[3(E),6α,7β(Z)]]-7-[[(2-Amino-4-thiazolyl)(hydroxyimino)acetyl]amino]-3-[[1-(1,1-dimethylethyl)-2-oxo-3-pyrrolidinylidene]methyl]-8-oxo-5-thia-1-azabicyclo[4.2.0]oct-2-ene-2-carboxylic acid monohydrochloride salt NMR (400 MHz, DMSO-$d_6$) δ 1.36 (s, 9H), 2.85, 3.00 (m, 2H), 3.46 (m, 2H), 3.87 (s, 2H), 5.20 (d, 1H), 5.84 (q, 1H), 6.79 (s, 1H), 7.13 (S, 2H), 7.18 (s, 1H), 9.67 (d, 1H), 11.95 (s, 1H).

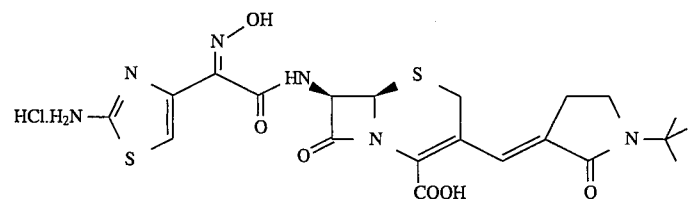

6R-[3(E),6α,7β(Z)]]-7-[[(2-Amino-4-thiazolyl)(hydroxyimino)acetyl]amino]-3-[[1-(2,2,2-trifluoroethyl)-2-oxo-3-pyrrolidinylidene]methyl]-8-oxo-5-thia-1-azabicyclo[4.2.0]oct-2-ene-2-carboxylic acid monohydrochloride salt

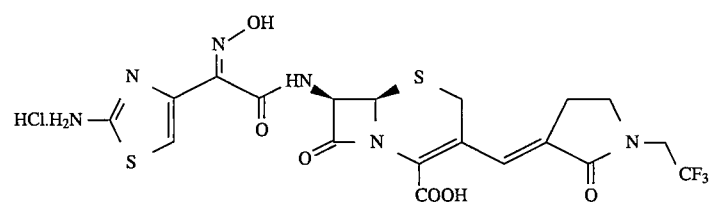

Example 11

(6R 7R)-7-[(Z)-2-(2-Amino-thiazol-4-yl)-2-hydroxy-imino-acetylamino ]-8-oxo-3-[(E)-2-oxo-1-(2,2,2-trifluoro-ethyl)-pyrrolidin-3-ylidenemethyl]-5-thia-1-azabicyclo [4.2.0]oct-2-ene-2-carboxylic acid trifluoroacetate 3.5 ml Trifluoroacetic acid was cooled to 0° C., and 430 mg (0.55 mmol) (6R,7R)-7-[(Z)-2-(2-Amino-thiazol-4-yl)-2-triphenylmethoxyimino-acetylamino]-8-oxo-3-[(E)-2-oxo-1-(2,2,2-trifluoro-ethyl)-pyrrolidin-3-ylidenemethyl]-5-thia-1-azabicyclo[4.2.0]oct-2-ene-2-carboxylic acid were added portionwise, the temperature being kept below 5° C. To the orange solution 0.2 ml (1.26 mmol) triethylsilane were added dropwise. A beige suspension was formed, which was poured after 20 min at 0° C. on 20 ml diethyl ether. This mixture was stirred for 30 min and then filtered. The solid was washed with diethyl ether and n-hexane and dried.

Yield: 304 mg beige powder (87%)

$^1$H-NMR (DMSO-$d_6$) δ [ppm] 3.10 (br. m, 2H); 3.50 (t, 2H); 3.90 (s, 2H); 4.17 (q, 2H); 5.20 (d, 1H); 5.86 (dd, 1H); 6.74 (s, 1H); 7.31 (s, 1H); 7.80 (d, 1H).

Microanalysis: $C_{19}H_{17}F_3N_6O_6S_2$, calculated with 0.83 mol trifluoroacetic acid calc. C 38.70 H 2.95 N 12.93 S 9.93 F 16.12 found C 38.45 H 2.80 N 13.11 S 10.00 F 16.27

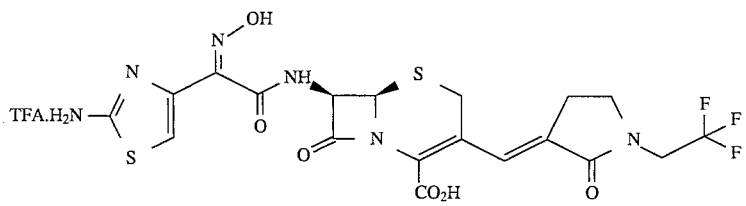

The following additional compounds were prepared in the same manner:

(6R,7R)-7-[(Z)-2-(2-Amino-thiazol-4-yl)-2-hydroxy-imino-acetylamino ]-3-[(E)-1-cyclopropyl-2-oxo-pyrrolidin-3-ylidenemethyl]-8-oxo-5-thia-1-azabicyclo[4.2.0]oct-2-ene-2-carboxylic acid trifluoroacetate (1:1)

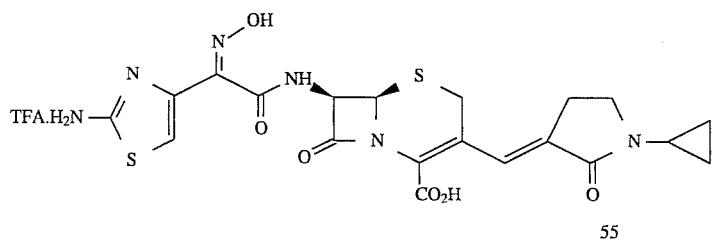

(6R,7R)-7-[(Z)-2-(2-Amino-thiazol-4-yl)-2-hydroxy-imino-acetylamino]-3-[(E)-1-(5-methyl-isoxazol-3-yl)-2-oxo-pyrrolidin-3-ylidenemethyl]-8-oxo-5-thia-1-azabicyclo [4.2.0]oct-2-ene-2-carboxylic acid MS(ISN): 561.2 $(M+NH_3-H)^\oplus$ IR(KBr): 3399, 1780, 1681, 1609, 1505 cm$^{-1}$

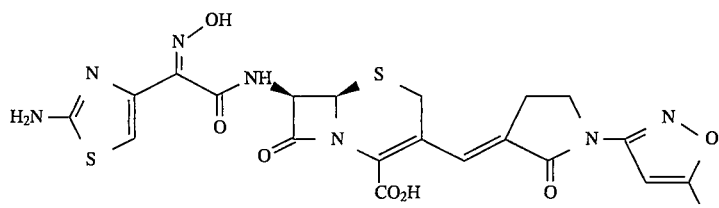

(6R,7R)-7-[(Z)-2-(2-Amino-thiazo 1-4-yl)-2-hydroxy-imino-acetylamino]-8-oxo-3-[(E)-2-oxo-1-pyridin-2-yl-pyrrolidin-3-ylidenemethyl]-5-thia-1-azabicyclo[4.2.0]oct-2-ene-2-carboxylic acid MS(ISP): 542.3 (M+H)⊕
IR(KBr): 1778, 1671, 1629, 1533, 1387 cm⁻¹

(6R,7R)-7-[(Z)-2-(2-Amino-thiazol-4-yl)-2-hydroxy-imino-acetylamino ]-8-oxo-3-[(E)-1-(2,2,2-trifluoro-ethyl)-2-oxo-piperidin- 3-ylidenemethyl]-5-thia-1-azabicyclo[4.2.0]oct-2-ene-2-carboxylic acid trifluoroacetate (1:2)

IR(KBr): 1774, 1679, 1635
MS(ISP): 561.3 (M+H)⊕

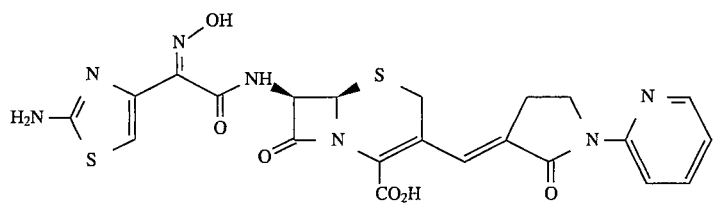

(6R,7R)-7-[(Z)-2-(2-Amino-thiazol-4-yl)-2-hydroxy-imino-acetylamino ]-8-oxo-3-[(E)-2-oxo-1-pyridin-3-yl-pyrrolidin-3-ylidenemethyl]-5-thia-1-azabicyclo[4.2.0]oct-2-ene-2-carboxylic acid MS(ISP): 542.2 (M+H)⊕
IR(KBr): 1777, 1672, 1537, 1483, 1389 cm⁻¹

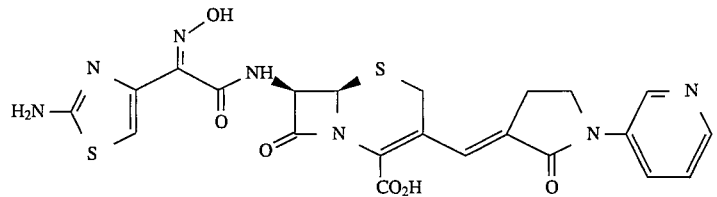

(6R 7R)-7-[(Z)-2-(2-Amino-thiazol-4-yl)-2-hydroxy-imino-acetylamino]-8-oxo-3-[(E)-1-[2-oxo-1-(2-oxo-oxazolidin-3 -yl)-pyrrolidin-3-ylidenemethyl]-5-thia-1-azabicyclo[4.2.0]oct-2-ene-2-carboxylic acid IR(KBr): 3381, 1769, 1630, 1530, 1392 cm⁻¹
MS(ISP): 550 (M+H)⊕
Elemental analysis for $C_{20}H_{18}N_7O_8S_2Na$
Calc C 43.71 H 3.49 N 17.84 S 11.67
found C 43.26 H 3.57 N 17.63 S 11.47

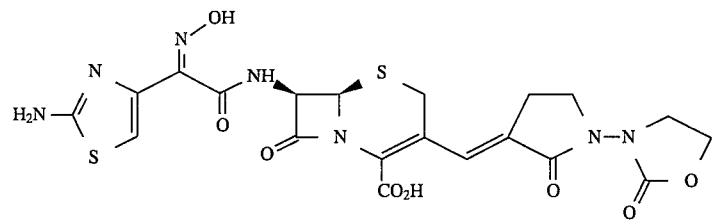

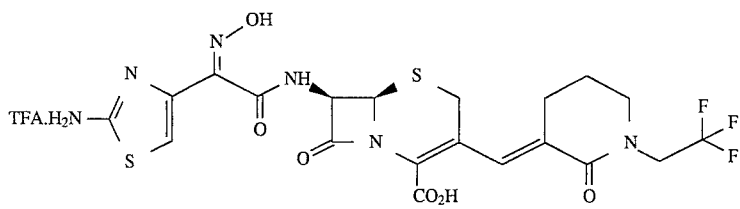

(6R,7R)-7-[(Z)-2-(2-Amino-thiazol-4-yl)-2-hydroxy-imino-acetylamino]-3-[(E)-1-carboxymethyl-2-oxo-pyrrolidin-3-ylidenemethyl]-8-oxo-5-thia-1-azabicyclo[4.2.0]oct-2-ene-2-carboxylic acid trifluoroacetate (1:0.77)

IR(KBr): 1776, 1673, 1635 cm$^{-1}$

IR(KBr): 2255, 1765, 1677, 1620
MS(ISP): 504.5 (M+H)$^{\oplus}$

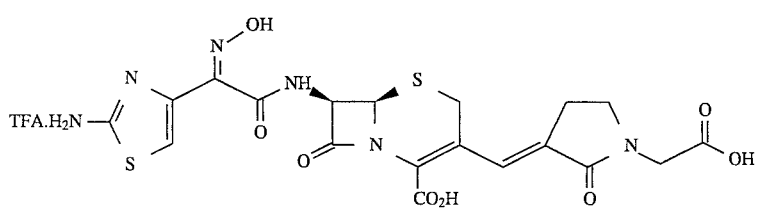

(6R,7R)-7-[(Z)-2-(2-Amino-thiazol-4-yl)-2-hydroxy-imino-acetylamino ]-3-[(E)-1-cyclopropyl-2-oxo-piperidin-3-ylidenemethyl]-8-oxo-5-thia-1-azabicyclo[4.2.0]oct-2-ene-2-carboxylic acid trifluoroacetate (1:1)

IR(KBr): 1780, 1676, 1632
MS(ISP): 519.4 (M+H)$^{\oplus}$

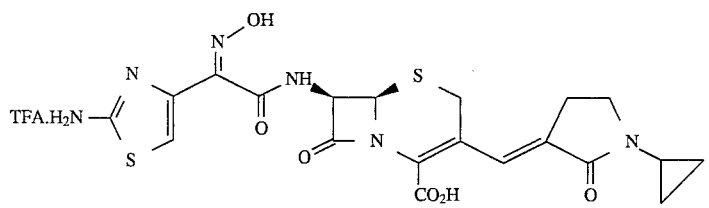

(6R,7R)-3-[(E)-1-Allyl-2-oxo-pyrrolidin-3-ylidenemethyl]-7-[(Z)-2 -(2-amino-thiazol-4-yl)-2-hydroxyimino- acetylamino]-8-oxo-5-thia- 1-azabicyclo[4.2.0]oct-2-ene-2-carboxylic acid trifluoroacetate (1:1.2)

IR(KBr): 1781, 1671, 1635 1
MS(ISP): 505.4 (M+H)$^{\oplus}$

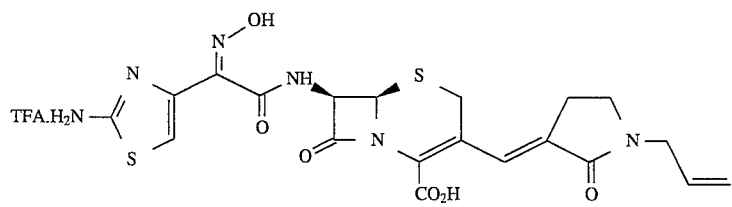

(6R,7R)-7-[(Z)-2-(2-Amino-thiazol-4-yl)-2-hydroxy-imino-acetylamino ]-3-[(E)-1-cyanomethyl-2-oxo-pyrrolidin-3-ylidenemethyl]-8-oxo-5-thia-1-azabicyclo[4.2.0]oct-2-ene-2-carboxylic acid Na salt (1:1)

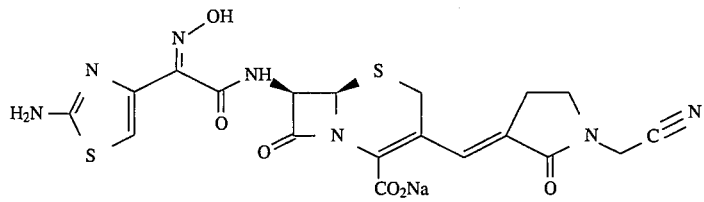

(6R,7R)-7-[(Z)-2-(2-Amino-thiazol-4-yl)-2-hydroxyiminoacetylamino]-3-[(E)-1-(4-methoxy-benzoyl)-2-oxo-pyrrolidin-3-ylidenemethyl]-8-oxo-5-thia-1-azabicyco[4.2.0]oct-2-ene-2-carboxylic acid
IR(KBr): 1782, 1729, 1669, cm⁻¹ MS(ISP): 599.4 (M+H)⊕ cyclo[4.2.0]oct-2-ene-2-carboxylic acid trifluoroacetate (1:0.2)
IR(KBr): 1778, 1679, 1629 cm⁻¹ MS(ISP): 619.3 (M+H)⊕

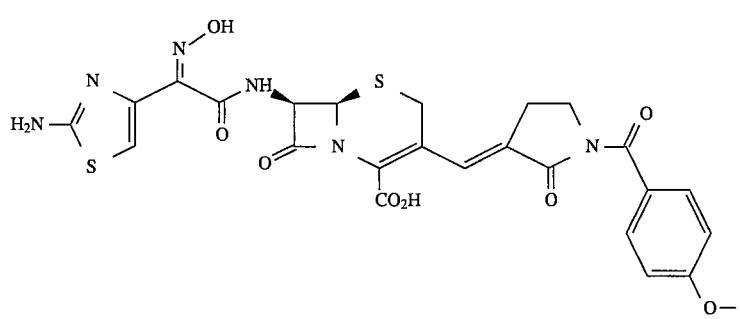

(6R,7R )-7-[(Z)-2-(2-Amino-thiazol-4-yl)-2-hydroxyiminoacetylamino]-3-[(E)-1-(6-methoxy-pyridin-3-yl )-2-oxo-pyrrolidin-3ylidenemethyl]-8-oxo-5-thia-1-azabicyclo[4.2.0]oct-2-ene-2-carboxylic acid trifluoroacetate (1:1)
IR(KBr):1781, 1677, 1496 cm⁻¹ MS(ISP): 572.3 (M+H)⊕

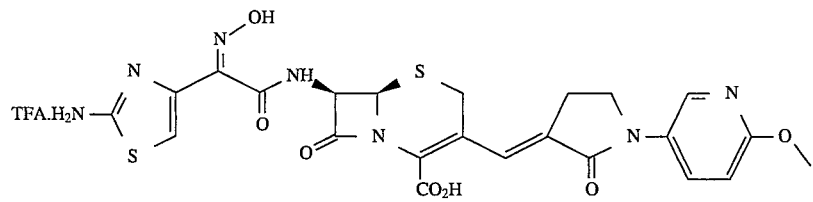

(6R,7R )-7-[(Z)-2-(2-Amino-thiazol-4-yl)-2-hydroxyiminoacetylamino]-8-oxo-3-[(E)-2-oxo-1-thiazol-2-yl-pyrrolidin-3-ylidenemethyl]-5-thia-1-azabicyclo[4.2.0]oct-2-ene-2-carboxylic acid dimethylformamide (1:1)
IR(KBr): 1781, 1670, 1505, 1465, 1386 cm⁻¹ MS(ISP): 548.3 (M+H)⊕

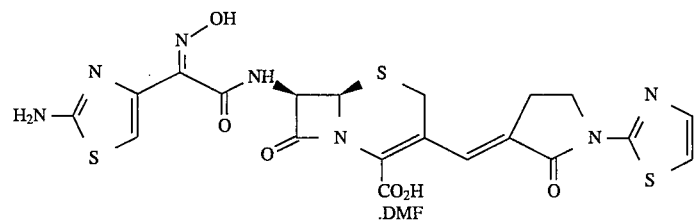

(6R, 7R )-7 -[(Z)-2-(2-Amino-thiazol-4-yl )-2-hydroxyiminoacetylamino]-3-[(E)-1-(4-methyl-phenylsulfonyl)-2-oxo-pyrrolidin- 3-ylidenemethyl]-8-oxo-5-thia-1-azabi-

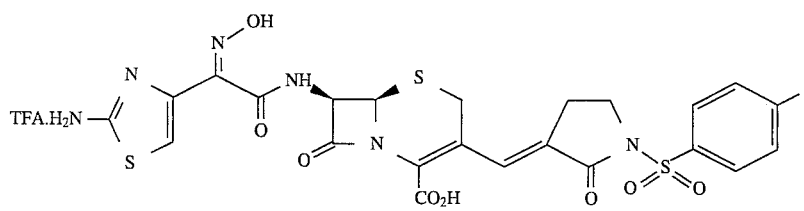

(6R,7R)-7-[(Z)-2-(2-Amino-thiazol-4-yl)-2-hydroxyimi-noacetylamino]-3-[(E)-1-(1,1'-dioxo-tetrahydro-thiophen-3-yl)-2-oxo-pyrrolidin- 3-ylidenemethyl]-8-oxo-5-thia-1-azabicyclo[4.2.0]oct-2 -ene-2-carboxylic acid dimethylformamide (1:1) (1:1 mixture of epimers)
IR(KBr): 1778, 1666, 1531, 1387, 1297 cm$^{-1}$ MS(ISP): 583.3 (M+H)$^{\oplus}$ IR(KBr): 1781, 1691, 1580, 1526 cm$^{-1}$ MS(ISP:) 543.4 (M+H)$^{\oplus}$

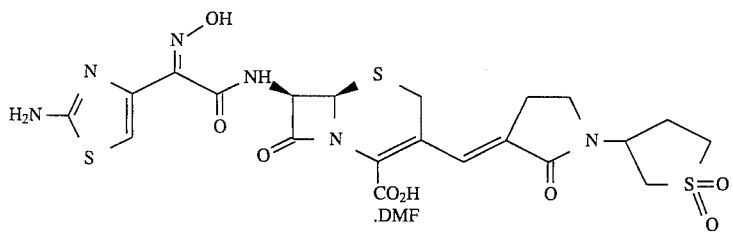

(6R,7R )-7-[(Z)-2-(2-Amino-thiazol-4-yl)-2-hydroxyimi-noacetylamino]-3-[(E)-1-cyclopropylmethyl-2-oxo-pyrroli-din-3-ylidenemethyl]-8-oxo-5-thia-1-azabicyclo[4.2.0]oct-2-ene-2-carboxylic acid trifluoroacetate (1:1)
IR(KBr). 1778, 1673, 1632 MS(ISP): 519.3 (M+H)$^{\oplus}$

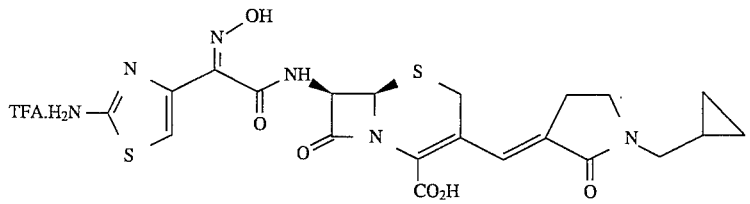

(6R, 7R )-7-[ (Z)-2-(2-Amino-thiazol-4-yl)-2-hydroxy-iminoacetylamino]-8-oxo-3-[(E)-2-oxo-1-prop-2-ynyl-pyr-rolidin-3-ylidenemethyl]-5-thia-1-azabicyclo[4.2.0]oct-2-ene-2-carboxylic acid trifluoroacetate (1:0.6)
IR(KBr): 2120, 1778, 1675, 1633 cm$^{-1}$ MS(ISP): 503.3 (M+H)$^{\oplus}$

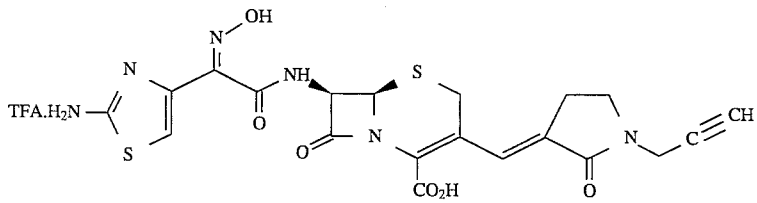

(6R,7R)-7-[(Z)-2-(2-Amino-thiazol-4-yl)-2-hydroxyimi-noacetylamino]-8-oxo-3-[(E)-2-oxo-3-pyrazin-2-yl-pyrroli-din-3-ylidenemethyl]-5-thia-1-azabicyclo[4.2.0]oct-2-ene-2-carboxylic acid

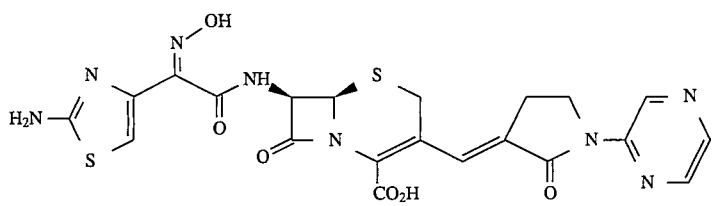

Example 12

(6R,7R)-7-[(Z)-2-(2-Amino-thiazol-4-yl)-2-hydroxyiminoacetylamino]-8-oxo-3-[(E)-2-oxo-1-(2,2,2-trifluoroethyl)-pyrrolidin- 3-ylidenemethyl]-5-thia-1-aza-bicyclo[4.2.0]oct-2-ene-2-carboxylic acid 1.83 g (mMol) (6R,7R)-7-[(Z)-2-(2-Amino-thiazol-4-yl)-2 -hydroxyimino-acetylamino]-8-oxo-3-[(E)-2-oxo-1-(2,2,2-trifluoroethyl)-pyrrolidin- 3-ylidenemethyl]-5-thia-1-aza-bicyclo[4.2.0]oct-2 -ene-2-carboxylic acid trifluoroacetate (1:0.5) were added with stirring portionwise to 18 ml 95% ethanol. After 1.5 hours the solid material was filtered off, washed with ethanol and n-hexane and dried.

yield: 1.33 g beige crystals (83%) IR(KBr): 1770 (C=O) MS(ISP): 547.2 (M+H$^+$) Microanalysis: $C_{19}H_{17}F_3N_6O_6S_2$ Calc. C 41.76 H 3.14 N 15.38 S 11.73 F 10.43 found. C 42.02 H 3.09 N 15.32 S 11.57 F 10.42 was removed in vacuo and the rest chromatographed on reversed phase silica gel (opti-up gel) with water as eluent. The fractions containing the product were collected and lyophilized.

yield: 43 mg (30%) IR(KBr): 1762, 1670, 1630 cm$^{-1}$ MS(ISP): 555.4 (M+H)$^+$

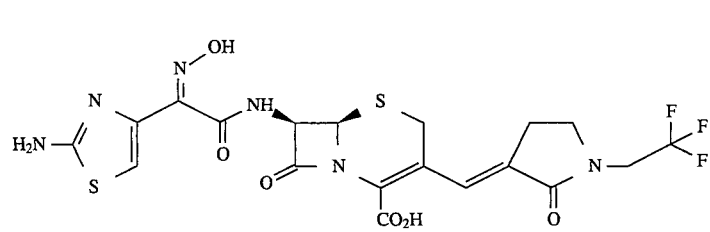

Example 13

(6R, 7R)-7-[(Z)-2-(2- Amino-thiazol-4-yl)-2-hydroxyiminoacetylamino]-8-oxo-3-[(E)-2-oxo-1-phenyl-piperidin-3-ylidenemethyl]-5-thia-1-aza-bicyclo[4.2.0]oct-2-ene-2-carboxylic acid Na salt (1:1)

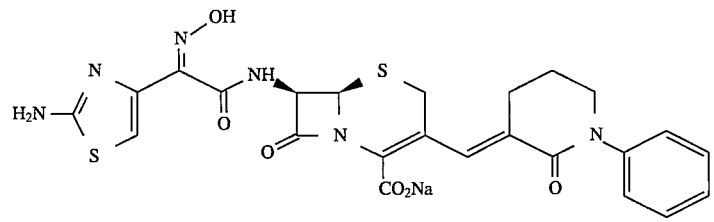

To a solution of 0.1 ml (0.63 mmol) triethylsilane and 1 ml trifluoroacetic acid, 200 mg (0.25 mmol) (6R,7R)-7-[(Z)-2-(2-aminothiazol- 4-yl )-2-trityloxyimino-acetylamino]-8-oxo-3-[(E)-2-oxo-1 -phenyl-piperidin-3-ylidenemethyl]-5-thia-1-azabicyclo[4.2.0]oct-2 -ene-2-carboxylic acid were added portionwise at 0° C. The mixture was stirred for 30 min and then poured on 15 ml diethyl ether. The solid material which separated was collected, washed with diethyl ether and n-hexane and dried. It was suspended in 10 ml water/1 ml acetonitrile and the pH was adjusted to 6.5 by addition of 1N sodium hydroxide solution. The acetonitrile According to the procedure set forth in the preceding example the following additional compounds were prepared:

(6R,7R)-7-[(Z)-2-(2-Amino-thiazol-4-yl)-2-hydroxyiminoacetylamino]-3-[(Z)-1-cyclopropyl-2-oxo-pyrrolidin-3-ylidenemethyl]-8-oxo-5-thia-1-azabicyclo[4.2.0]oct-2-ene-2-carboxylic acid Na salt (1:1)

145

IR(KBr): 1762, 1667 cm$^{-1}$ MS(ISN): 503.2 (M–Na)$^{\oplus}$

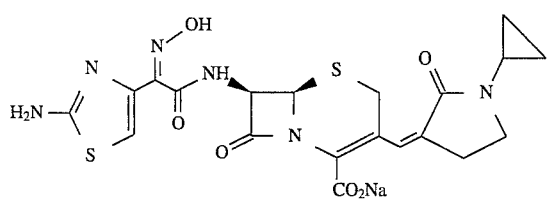

(6R,7R)-7-[(Z)-2-(2-Amino-thiazol-4-yl)-2-hydroxyiminoacetylamino]-3-[(E)-1-(2-cyano-ethyl )-2-oxo-pyrrolidin-2-ylidenemethyl]-8-oxo-5-thia-1-aza-bicyclo[4.2.0]oct-2-ene-2-carboxylic acid Na salt (1:1)

IR(KBr): 2246, 1763, 1667, 1618 MS(ISP): 518.3 (M–Na+2H)$^{\oplus}$

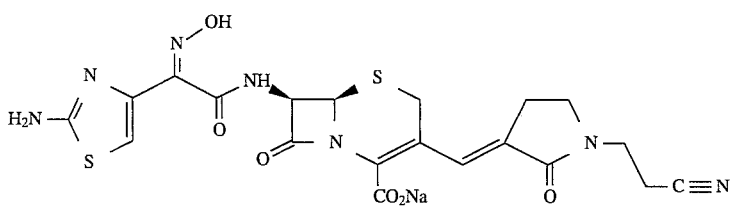

(6R,7R)-7-[(Z)-2-(2-Amino-thiazol-4-yl)-2-hydroxyiminoacetylamino]-8-oxo-3-[(E)-2-oxo-pyridin-4-yl-pyrrolidin-3-ylidenemethyl]-5-thia-1-aza-bicyclo[4.2.0]oct-2-ene-2-carboxylic acid Na salt (1:1)

IR(KBr): 1763, 1675, 1624 cm$^{-1}$ MS(ISN): 557.2 [(M–Na)$^{\oplus}$+NH$_3$]

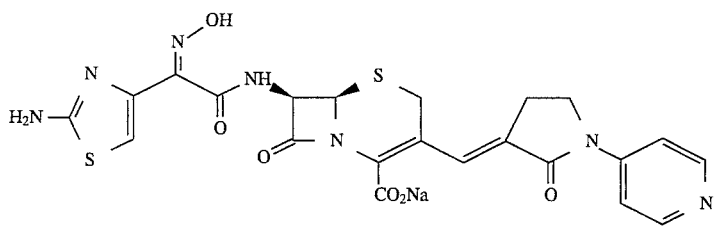

Example 14

[6R-[3(E ), 6α, 7β(Z) ]]-7-[[(2- Amino-4-thiazolyl)(methoxyimino)acetyl]amino]-3-[(1-methoxy-2-oxo-3-pyrrolidinylidene)methyl]-8 -oxo-5-thia-1-azabicyclo[4.2.0]oct-2-ene-2-carboxylic acid (2,2 -dimethyl-1-oxopropoxy)methyl ester.

To [6R-[3-(E),6α,7β(Z)]]-7-[[(2-Amino-4-thiazolyl)-[[2-(methoxyimino)-acetyl]amino]-3-[(1-methoxy-2-oxo-3-pyrrolidinylidene)methyl]-8-oxo-5-thia-1-azabicyclo[4.2.0]oct-2 -ene-2-carboxylic acid monosodium salt 110 mg (0.21 mM), dimethylformamide (2 ml), p-dioxane (2 ml), and sodium bicarbonate 6 mg (71 mM) were combined at 0° C. To this was added pivaloyloxymethyl iodide 107 mg (439 mM) and the reaction mixture was stirred at 0° C. for 15 Hours. Ethyl acetate (50 ml) was added and the reaction extracted with 10% aqueous sodium thiosulfate and brine (2×5 ml each) and dried with anhydrous sodium sulfate. The residue after removal of the drying agent and solvent was purified on silica gel plates to yield the titled compound (46%).

NMR (400 MHz, CDCl$_3$)δ 1.23 (s, 9H), 2.90 (m, 2H), 3.63 (t, 2H), 3.65 (s, 2H), 3.86 (s, 3H), 4.08 (s, 3H), 5.12 (d, 1H), 5.14 (s, 2H), 5.90 (q, 2H), 6.03 (q, 1H), 6.96 (s, 1H), 7.14 (d, 1H), 7.33 (s, 1H).

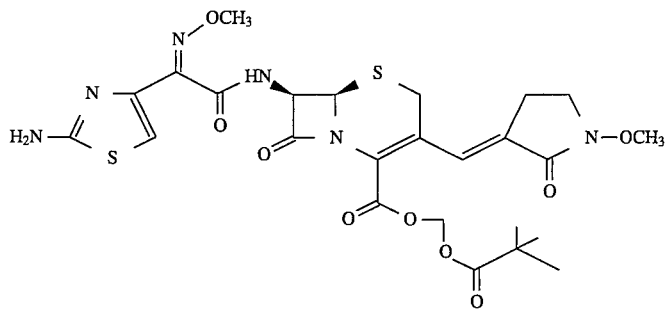

According to the procedure set forth in the preceding example the following additional compounds were prepared:

[6R-[3(E),6α,7β(Z)]]-7-[[(2-Amino-4-thiazolyl)(methoxyimino)acetyl]amino]-3-[(1-methyl-2-oxo-3-pyrrolidinylidene )methyl] -8 -oxo-5-thia-1-azabicyclo[4.2.0] oct-2-ene-2-carboxylic acid (2,2 -dimethyl-1-oxopropoxy)methyl ester NMR (200 MHz, $CDCl_3$) δ 1.23 (s, 9H), 2.88 (s, 2H), 2.96 (s, 3H), 3.43 (t, 2H), 3.70 (q, 2H), 4.07 (s, 3H), 5.10 (d, 1H), 5.93 (m, 3H), 6.90 (s, 1H), 7.32 (s, 1H).

[6R-[3(E), 6α,7β(Z)]]-7-[[(2-Amino-4-thiazolyl)(methoxyimino)acetyl]amino]-3-[(1-methyl-2-oxo-3-pyrrolidinylidene)methyl]-8 -oxo-5-thia-1-azabicyclo[4.2.0] oct-2-ene-2-carboxylic acid 1-[[(1-methylethoxy)carbonyl]oxy]ethyl ester NMR (200 MHz, $CDCl_3$) δ 1.20 (d, 6H), 1.50 (t, 3H), 2.50 (m, 2H), 2.83 (s, 3H), 3.0 (m, 2H), 3.83 (s, 3H), 3.92 (m, 2H), 4.78 (m, 1H), 5.20, 5.85 (m, 2H), 6.71 (s, 1H)6.82 (m, 1H), 7.20 (s, 3H), 9.65 (d, 1H).

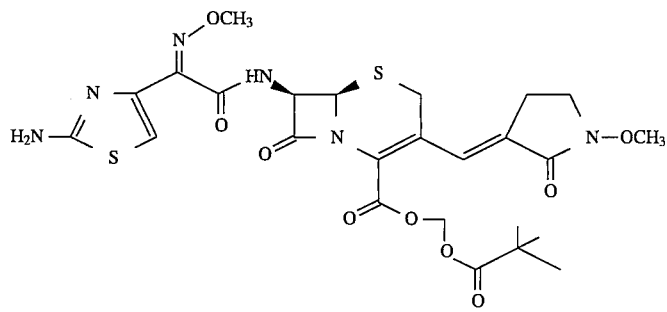

[6R-[2(E ),3(E ),6α,7β(Z)]]-7-[[(2-Amino-4 -thiazolyl)(methoxyimino)-acetyl]amino]-3-[(1-methyl-2-oxo-3-pyrrolidinylidene)methyl]-8-oxo-5-thia-1-azabicyclo[4.2.0] oct-2 -ene-2-carboxylic acid 2-[(2-methylpropoxy)carbonyl]-2-pentenyl ester NMR (200 MHz, $CDCl_3$) δ 0.93 (s, 6H), 1.05 (t, 3H), 1.95 (m, 2H), 2.36 (m, 2H), 2.95 (s, 3H), 3.41 (t, 2H), 3.63 (s, 2H), 3.92 (d,. 2H), 4.06 (s, 3H), 5.03 (s, 2H), 5.10 (d, 1H), 5.36 (s, 2H), 5.96 (q, 1H), 6.95 (s, 1H), 7.07 (t, 1H), 7.25 (s, 1H), 7.46 (d, 1H).

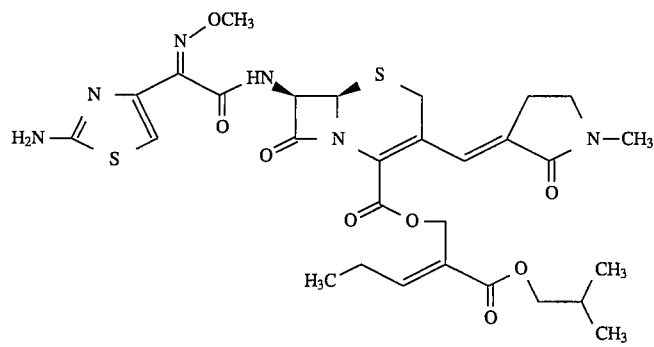

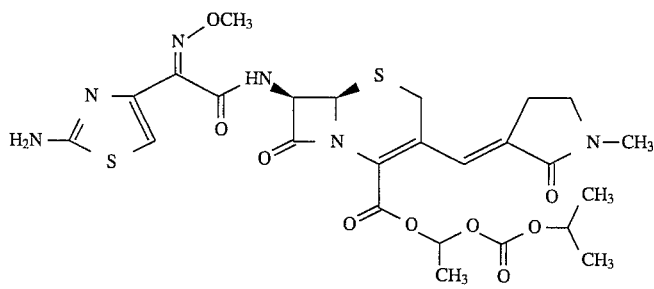

[6R-[3(E), 6α,7β(Z)]]-7-[[(2-Amino-4-thiazolyl-)(methoxyimino)acetyl]amino]-3-[(1-methyl-2-oxo-3-pyrrolidinylidene)methyl]-8-oxo-5-thia-1-azabicyclo[4.2.0]oct-2-ene-2-carboxylic acid 1-(acetyloxy)ethyl ester NMR (200 MHz, CDCl$_3$)δ 1.52 (d, 3H), 2.04 (s, 3H), 2.90, 3.42 (m, 4H), 2.95 (s, 3H), 3.65 (m, 2H), 4.06 (s, 3H), 4.10 (m, 1H), 5.08 (d, 1H), 5.35 (m, 2H), 6.03 (q, 1H), 6.90 (s, 1H) 7.00 (m, 1H), 7.30 (m, 1H), 7.50 (m, 1H).

pentenyl ester IR (KBr) cm$^{-1}$ 2960, 1789, 1689, 690.

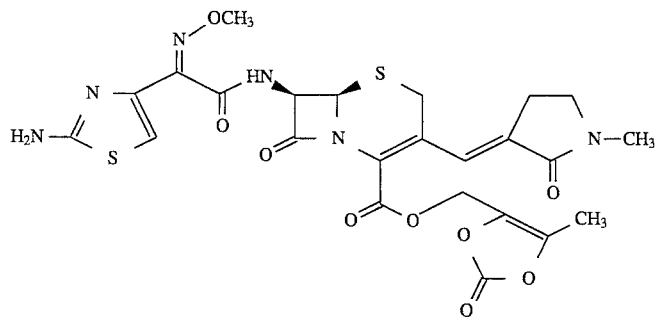

[6R-[3(E), 6α,7β(Z)]]-7-[[(2-Amino-4-thiazolyl-)(methoxyimino)acetyl]amino]-3-[(1-methyl-2-oxo-3-pyrrolidinylidene)methyl]-8-oxo-5-thia-1-azabicyclo[4.2.0]oct-2-ene-2-carboxylic acid (5-methyl-2-oxo-1,3-dioxol-4-yl)methyl ester NMR (200 MHz, CDCl$_3$)δ 2.20 (s, 3H), 2.88 (m, 2H), 2.98 (s, 3H), 3.45 (m, 5H), 3.70 (s, 2H), 4.06 (s, 3H), 5.05 (q, 2H), 5.10 (d, 1H), 5.22 (s, 2H), 6.03 (q, 1H), 6.88 (s, 1H), 7.33 (m, 1H).

[6R-[2(E),3(E),6α,7β(Z)]]-7-[[(2-Amino-4-thiazolyl-)(methoxyimino)acetyl]amino]-8-oxo-3-[(2-oxo-1-phenyl-3-pyrrolidinylidene)methyl]-5-thia-1-azabicyclo[4.2.0]oct-2-ene-2-carboxylic acid 2-[(2-methylpropoxy)carbonyl]-2-

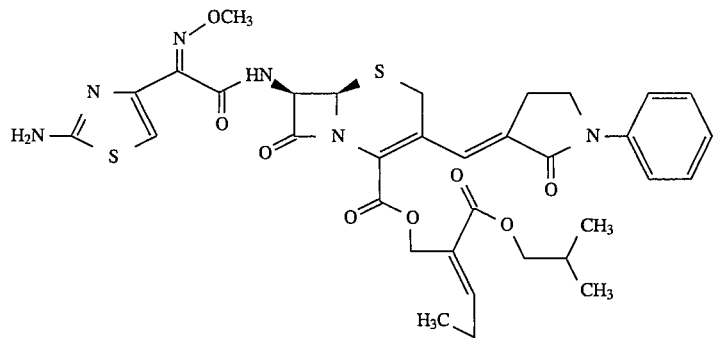

[6R-[3(E ), 6α, 7β(Z)]]-7-[[(2- Amino-4-thiazolyl-)(methoxyimino)acetyl amino]-8-oxo-3-[ (2-oxo-1-phenyl-3-pyrrolidinylidene)methyl]-5-thia-1-azabicyclo[4.2.0]oct-2-ene-2-carboxylic acid 1-[[(cyclohexyloxy)carbonyl]oxy]ethyl ester IR(KBr) cm⁻¹ 2950, 1789, 1760, 1689, 692.

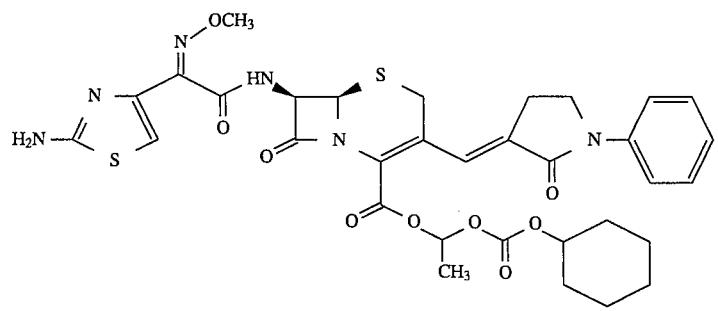

[6R-[3(E),6α,7β(Z)]]-7-[[(2-Amino-4-thiazolyl-)(methoxyimino)acetyl]amino]-8-oxo-3-[(2-oxo-1-phenyl-3-pyrrolidinylidene)methyl]-5-thia-1-azabicyclo[4.2.0]oct-2-ene-2-carboxylic acid 1-(acetyloxy)ethyl ester NMR (200 MHz, CDCl₃) δ 1.56 (d, 3H), 2.08 (d, 3H), 2.95–3.10 (m, 2H), 3.80 (m, 2H), 3.90 (m, 2H), 4.09 (s, 3H), 5.13 (m, 1H), 5.253 (d, 2H), 6.05 (m, 1H), 6.93 (d, 1H), 7.0–7.15 (m, 1H), 7.30 (m, 3H), 7.52 (s, 1H), 7.70 (m, 2H).

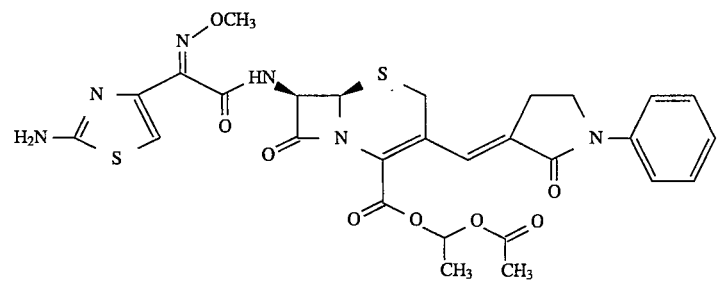

[6R-[3(E), 6α,7β(Z)]]-7-[[(2-Amino-4-thiazolyl-)(methoxyimino)acetyl]amino]-3-[[1-(4-methoxyphenyl)-2-oxo-3-pyrrolidinylidene]methyl]-8-oxo-5-thia-1-azabicyclo

[4.2.0]oct-2-ene-2-carboxylic acid (2,2-dimethyl-1-oxopropoxy)methyl ester

NMR (400 MHz, CDCl₃) δ 1.16 (s, 9H), 3.04, 3.23 (m, 2H), 3.76 (s, 3H), 3.85 (m, 2H), 3.98 (q, 2H), 5.26 (d, 1H), 5.87 (m, 3H), 6.76 (s, 1H), 6.97 (d, 2H), 7.24 (s, 2H), 7.30 (s, 1H), 7.70 (d, 2H).

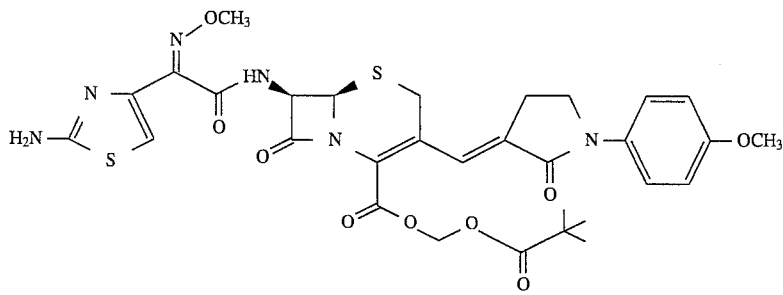

[6R-[3(E),6α,7β(Z)]]-7-[[(2-Amino-4-thiazolyl-)(methoxyimino)acetyl]amino]-3-[[1-(4-methoxyphenyl)-2-oxo-3-pyrrolidinylidene]methyl]-8-oxo-5-thia-1-azabicyclo [4.2.0]oct-2-ene-2-carboxylic acid 2[(2-methylpropoxy)-carbonyl]-2-pentenyl ester hydrochloride NMR (400 MHz, CDCl$_3$) δ 0.86 (d, 6H), 1.02 (t, 3H), 1.90 (m, 1H), 2.34 (m, 2H), 3.00, 3.18 (m, 2H), 3.76 (s, 3H), 3.86 (s, 9H), 5.00 (q, 2H), 5.23 (d, 1H), 5.35 (q, 1H), 6.76 (s, 1H), 7.0 (d, 2H), 7.26 (s, 3H), 7.70 (d, 2H), 9.66 (d, 1H).

bicarbonate 180 mg (1.3 mM) and stirred for 20 minutes. To this was added pivaloyoxymethyl iodide 0.5 g (2.1 mM) which had been stirred with some sodium bicarbonate for five minutes. The reaction was stirred for one hour and added to water:ethyl acetate (200 mL:100 mL). The solid was filtered and purified on silica gel (dichloromethane:methanol 98:2) to afford 0.39 g (64%) of the title compound.

IR (KBr) cm$^{-1}$ 1435, 1789, 1750, 1690, 698.

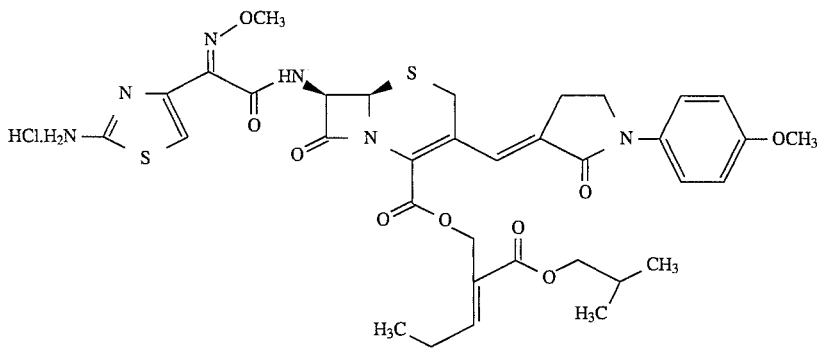

Example 15

[6R-[3(E), 6α,7β(Z)]] -7-[[ (2-Amino-4-thiazolyl)[-[(triphenylmethoxy)imino]acetyl]amino]-3-[(1-methoxy-2-oxo-3-pyrrolidinylidene)methyl]-8-oxo-5-thia-1-azabicyclo [4.2.0]oct-2 -ene-2-carboxylic acid (2,2-dimethyl-1-oxopropoxy)methyl ester To [6R-[3(E),6α,7β(Z)]]-7-[[(2-Amino-4-thiazolyl) [(triphenylmethoxy)imino]acetyl]amino]-3-[(1-methoxy-2-oxo-3-pyrrolidinylidene)methyl]-8-oxo-5-thia-1-azabicyclo [4.2.0]oct-2 -ene-2-carboxylic acid 0.58 g (0.69 mM), 18-crown-6 ether 80 mg 0.34 mM), and dimethylformamide (3.5 mL) cooled in an ice/water bath was added sodium

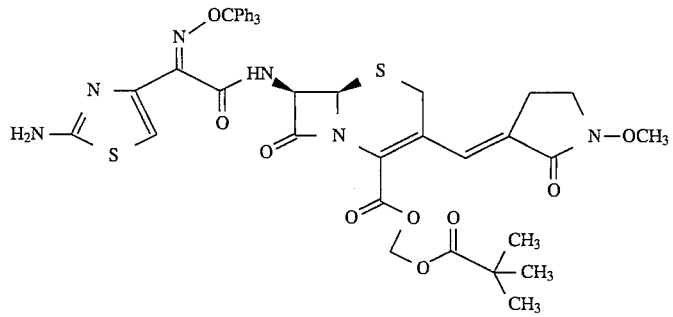

According to the procedure set forth in the preceding example the following additional compounds were prepared:

[6R-[ 2(E ),3(E), 6α,7β(Z)]]-7-[[ (2-Amino-4-thiazolyl)-[(triphenylmethoxy)imino]acetyl]amino] -3-[ (1-methyl-2-oxo-3 -pyrrolidinylidene )methyl ]-8-oxo-5-thia-1-azabicyclo[4.2.0]oct-2 -ene-2-carboxylic acid 2[(2-methylpropoxy)carbonyl]-2-pentenyl ester IR (KBr) cm$^{-1}$ 3441, 1789, 1717, 1685, 701.

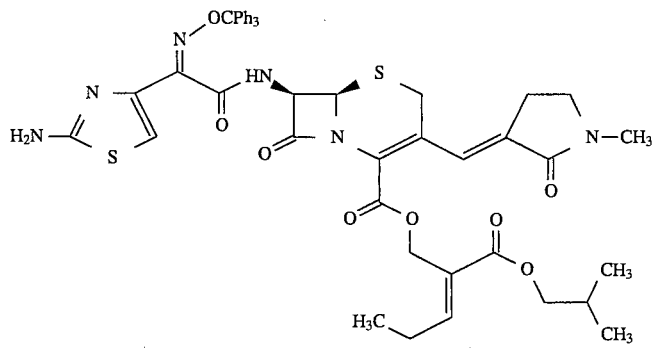

[6R-[2(E),3(E),6α,7β(Z)]]-7-[[ (2-Amino-4-thiazolyl)-[(triphenylmethoxy)imino]acetyl]amino]-8-oxo-3-[(2-oxo-1-phenyl- 3-pyrrolidinylidene)methyl]-5-thia-1-azabicyclo [4.2.0]oct-2-ene-2-carboxylic acid 2-[(2-methylpropoxy)carbonyl]-2-pentenyl ester IR (KBr) cm$^{-1}$ 1 3430, 1789, 1710, 1692, 700.

[4.2.0]oct-2 -ene-2-carboxylic acid 1-[[(cyclohexyloxy)carbonyl]oxy]ethyl ester

IR (KBr) cm$^{-1}$ 3440, 1790, 1758, 1700, 700.

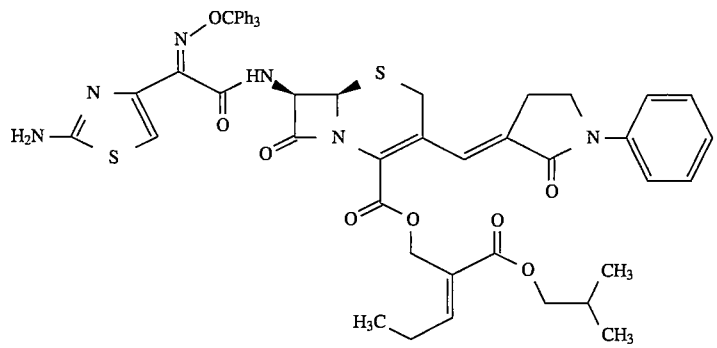

[6R-[2(E),3(E),6α,7β(Z)]]-7-[[(2-Amino-4-thiazolyl)-[(triphenylmethoxy)imino]acetyl]amino]-3-[(1-methoxy-2-oxo-3-pyrrolidinylidene)methyl]-8-oxo-5-thia-1-azabicyclo [4.2.0]oct-2 -ene-2-carboxylic acid 2-[(2-methylpropoxy)carbonyl-2-pentenyl ester IR (KBr) cm$^{-1}$ 1 3440, 1789, 1717, 1685, 700.

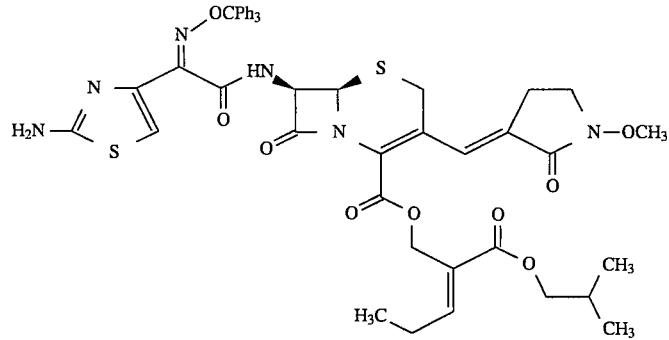

[6R-[3 (E), 6α,7β(Z)]]-7-[[ (2-Amino-4-thiazolyl)-[(triphenylmethoxy)imino]acetyl]amino]-3-[(1-methoxy-2-oxo-3-pyrrolidinylidene)methyl]-8-oxo-5-thia-1-azabicyclo

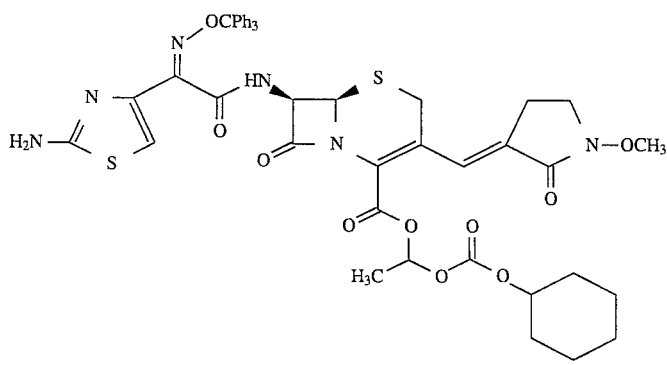

[6R-[3(E), 6α,7β(Z)]]-7-[[(2-Amino-4-thiazolyl )-[(triphenylmethoxy)imino]acetyl]amino]-3-[ (1-methoxy-2-oxo-3-pyrrolidinylidene)methyl]-8-oxo-5-thia-1-azabicyclo[4.2.0]oct-2 -ene-2-carboxylic acid (2,2-dimethyl-1-oxopropoxy)methyl ester    oxy]ethyl ester IR (KBr) cm$^{-1}$ 3435, 1789, 1750, 1690, 698.

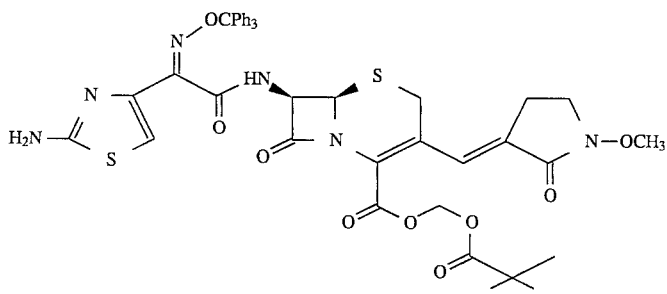

[6R-[3(E),6α,7β(Z)]]-7-[[(2-Amino-4-thiazolyl)-[(triphenylmethoxy)imino]acetyl]amino] -3-[ (1-methyl-2-oxo-3-pyrrolidinylidene)methyl]-8-oxo-5-thia-1-azabicyclo[4.2.0]oct-2 -ene-2-carboxylic acid 3,3-dimethyl-2-oxobutyl ester IR (KBr) cm$^{-1}$ 3439, 1790, 1751, 1604, 700.

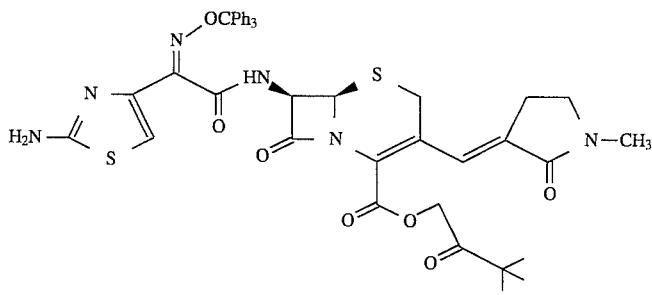

[6R-[3(E ),6α,7β(Z)]]-7-[[ (2-Amino-4-thiazolyl)-[(triphenylmethoxy)imino]acetyl]amino]-3-[(1-methyl-2-oxo-3-pyrrolidinylidene)methyl]-8-oxo-5-thia-1-azabicyclo[4.2.0]oct-2 -ene-2-carboxylic acid 1-[[(cyclohexyloxy)carbonyl]

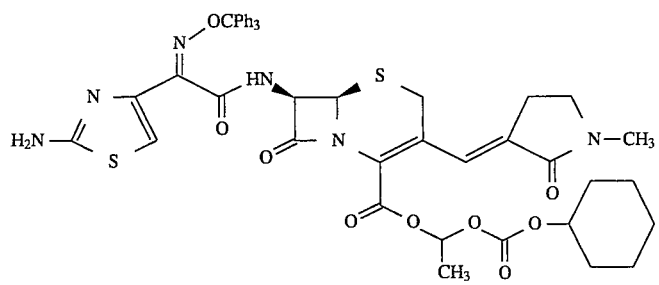

Example 16

(6R,7R)-7-[(Z)-(2-Amino-thiazol-4-yl)-trityloxyiminoacetylamino]-3-[(E)-2-oxo-1-(2-trifluoro-ethyl)-pyrrolidin-3-ylidenemethyl]-8-oxo-5-thia-1-azabicyclo[4.2.0]oct-2-ene-2-carboxylic acid (2,2-dimethyl-1-oxopropoxy)methyl ester 1.893 g (2.4 mmol) (6R,7R)-7-[(Z)-(2-Amino-thiazol-4-yl)-trityloxyimin o-acetylamino]-3-[ (E)-2-oxo-1-(2-trifluoro-ethyl)-pyrrolidin- 3-ylidenemethyl]-8-oxo-5-thia-1-azabicyclo[4.2.0]oct-2 -ene-2-carboxylic acid were dissolved in 25 ml DMF and cooled to 0°–5° C. 263 mg 1,1,3,3-Tetramethylguanidine in 1 ml DMF were added followed by 598 mg (2.4 mmol) pivaloyloxymethyl iodide in 1 ml DMF, and the mixture was stirred for 2 hours before it was poured on 150 ml ethyl acetate. The solution was extracted with 150 ml water, 50 ml 5% sodium thiosulfate solution and 150 ml 15% brine. The organic phase was dried over magnesium sulfate, concentrated in vacuo to a volume of 25 ml and poured on 250 ml n-hexane. The amorphous material was filtered off and dried. The material was purified by chromatography over silica gel with ethyl acetate.

yield: 1.81 g (84%) IR (KBr): 1790, 1754, 1691 cm$^{-1}$ Microanalysis: $C_{44}H_{41}H_6O_8F_3S_2$ calc. C 58.53 H 4.58 N 9.31 S 7.10 found C 58.34 H 4.45 N 9.17 S 7.02 oxo-pyrrolidin-3-ylidenemethyl]-8-oxo-5-thia-1-azabicyclo [4.2.0]oct-2-ene-2-carboxylic acid (2,2-dimethyl-1-oxopropoxy)methyl ester IR(KBr): 1789, 1753, 1685 cm$^{-1}$ Microanalysis: $C_{44}H_{43}H_6O_8FS_2$ calc. C 60.96 H 5.00 N 9.69 found C 61.11 H 5.11 N 9.80

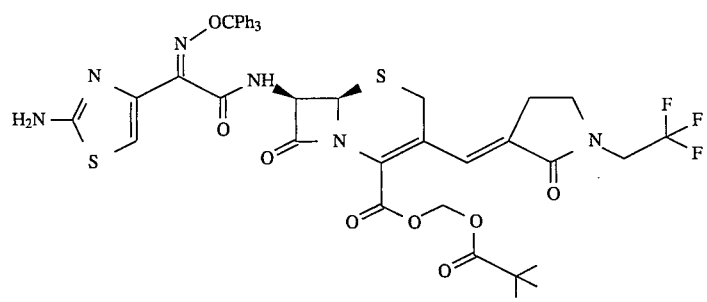

The following additional compounds were prepared in the same manner: (6R, 7R )-7-[ (Z)-(2-Amino-thiazol-4-yl)-trityloxyiminoacetylamino]-3-[(E)-1-(2-fluoro-ethyl)-2-

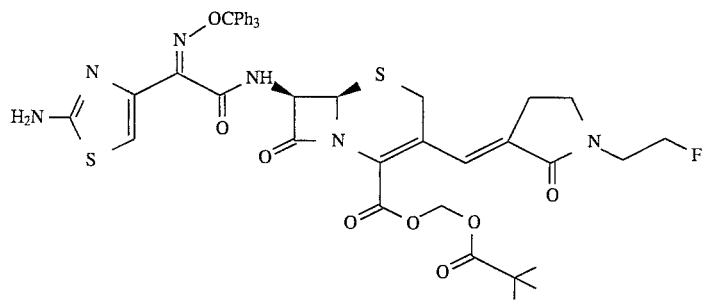

(6R, 7R)-7-[(Z)-(2-Amino-thiazol-4-yl)-trityloxyiminoacetylamino]-3-[(E)-1-cyclopropyl-2-oxo-pyrrolidin-3-ylidenemethyl]-8-oxo-5-thia-1-azabicyclo[4.2.0]oct-2-ene-2-carboxylic acid (2,2-dimethyl-1-oxopropoxy)methyl ester IR(KBr): 1789, 1753, 1684 cm$^{-1}$ Microanalysis: $C_{44}H_{44}H_6O_8S_2$ calc. C 62.78 H 5.15 N 9.76 S 7.45 found C 62.56 H 5.24 N 9.78 S 7.51

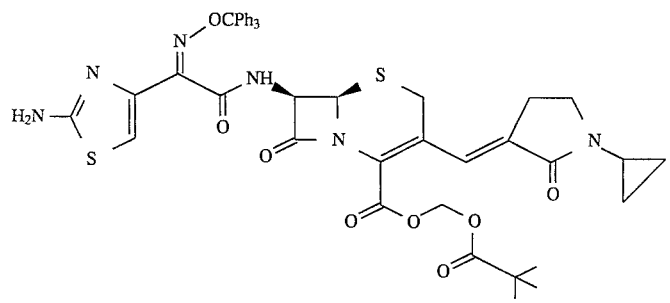

Example 17

[6R-[3(E),6α,7β(Z)]]-7-[[(2-Amino-4-thiazolyl)(hydroxyimino)acetyl]amino]-3-[(1-methoxy-2-oxo-3-pyrrolidinylidene)methyl]-8-oxo-5-thia-1-azabicyclo[4.2.0]oct-2-ene-2-carboxylic acid (2,2-dimethyl-1-oxopropoxy)methyl ester monohydrochloride salt

[6R-[3(E),6α,7β(Z)]]-7-[[(2-Amino-4-thiazolyl)[(triphenylmethoxy)-imino]acetyl]amino]-3-[(1-methoxy-2-oxo-3-pyrrolidinidinylidene)methyl]-8-oxo-5-thia-1-azabicyclo[4.2.0]oct-2-ene-2-carboxylic acid (2,2-dimethyl-1-oxopropoxy)methyl ester 330 mg (0.39 mM) was combined with 90% formic acid (4.0 mL) at room temperature and stirred for two hours. The solvent was removed in vacuum and dissolved in dichloromethane (4 mL) and precipitated with ethyl acetate. The solid was collected, taken up in dichloromethane (3 mL) and cooled in an ice bath. To this was added 1.1N hydrochloric acid, stirred for 30 minutes and a solid was precipitated by the addition of ethyl ether 20 mL. The solid was collected for 0.19 g (86.4%) of the title compound.

IR (KBr) cm$^{-1}$ 1785, 1752, 1680, 1630, 1375.

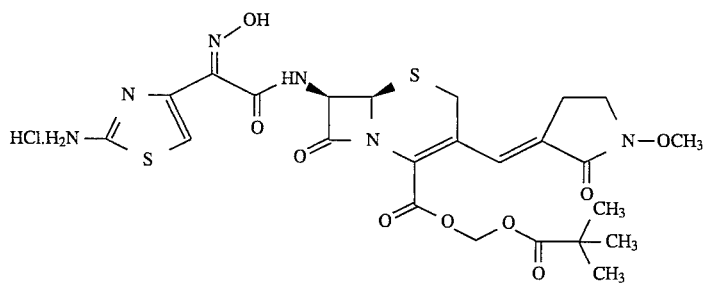

Following the procedure set forth in the preceding example the following additional compounds were prepared:

[6R-[2(E),3(E),6α,7β(Z)]]-7-[[(2-Amino-4-thiazolyl)(hydroxyimino)acetyl]amino]-3-[(1-methyl-2-oxo-3-pyrrolidinylidene)methyl]-8-oxo-5-thia-1-azabicyclo[4.2.0]oct-2-ene-2-carboxylic acid 2-[(2-methylpropoxy)carbonyl]-2-pentenyl ester monohydrochloride salt IR (KBr) cm$^{-1}$ 3261, 1786, 1717, 1683, 1676.

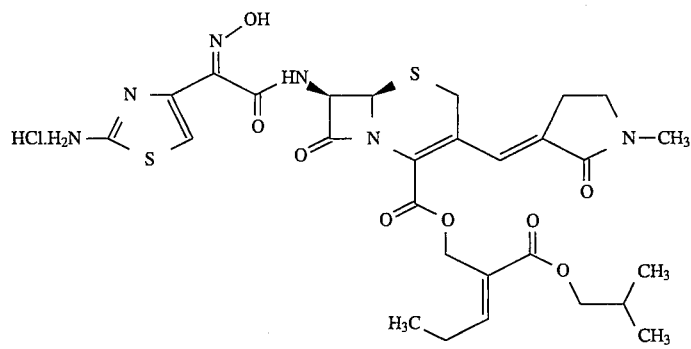

[]6R-[3(E),6α,7β(Z)]]-7-[[(2-Amino-4-thiazolyl)(hydroxyimino)acetyl]amino] -3-[ (1-methyl-2-oxo-3-pyrrolidinylidene )methyl] -8 -oxo-5-thia-1-azabicyclo[4.2.0]oct-2-ene-2-carboxylic acid 1-]](cyclohexyloxy)carbonyl]oxy] ethyl ester monohydrochloride salt -ene-2-carboxylic acid 1-[[(cyclohexyloxy)carbonyl]oxy] ethyl ester monohydrochloride salt IR (KBr) cm$^{-1}$ 1 2950, 1788, 1758, 1680, 1630.

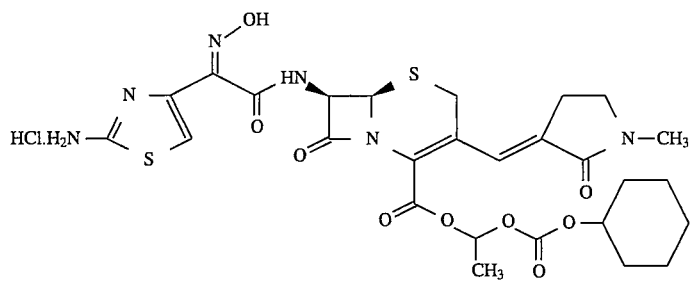

[6R-[3(E),6α,7β(Z)]]-7-[[ (2-Amino-4 -thiazolyl)(hydroxyimino)acetyl]-amino]-3-[(1-methyl-2-oxo-3 -pyrrolidinylidene)methyl] -8-oxo-5-thia-1-azabicyc[4.2.0]oct-2 -ene-2-carboxylic acid (2,2-dimethyl-1-oxopropoxy)methyl ester monohydrochloride salt NMR (200 MHz, CDCl$_3$)δ 2.50 (s, 9H), 2.81 (s, 3H), 2.95 (m, 2H), 3.35 (m, 2H), 3.90 (s, 2H), 5.25 (d, 1H), 5.85 (m, 3H), 6.79 (s, 1H), 7.12 (s, 1H), 8.35 (bs, 2H), 9.70 (d, 1H), 12.00 (bs, 1H).

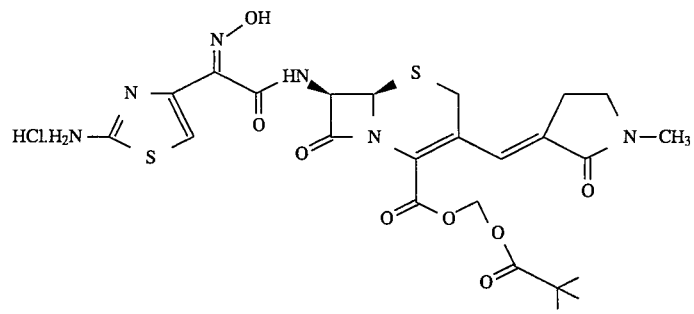

[6R-[3(E ),6α,7β(Z)]]-7-[[(2-Amino-4-thiazolyl)(hydroxyimino)acetyl]-amino]-3-[(1-methoxy-2-oxo-3-pyrrolidinylidene)methyl]-8-oxo-5-thia-1-azabicyclo[4.2.0]oct-2

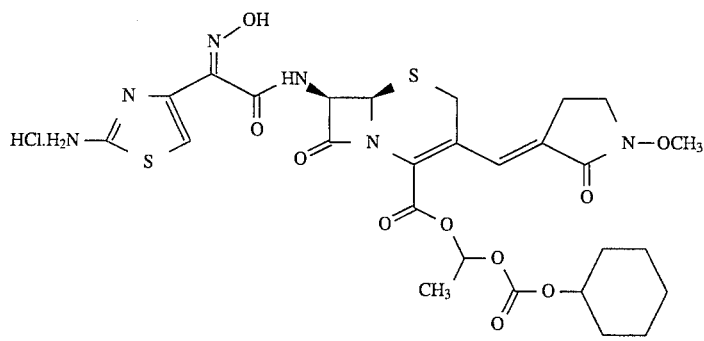

[6R-[2(E ),3 (E),6α, 7β( Z)]]-7-[[ (2-Amino-4-thiazolyl-)(hydroxyimino)acetyl]amino]-3-[(1-methoxy-2-oxo-3-pyrrolidinylidene)methyl]-8-oxo-5-thia-1-azabicyclo[4.2.0]oct-2-ene-2-carboxylic acid 2-[(2-methylpropoxy)carbonyl]-2-pentenyl ester monohydrochloride salt IR (KBr) cm$^{-1}$ 3400, 2950, 1788, 1702, 1692.

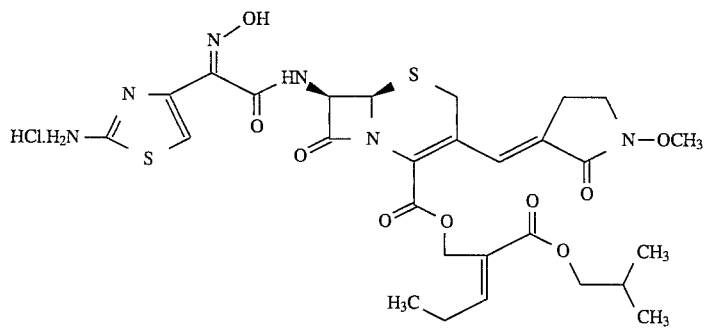

[6R-[2(E ),3(E ),6α,7β(Z)]]-7-[[(2-Amino-4 -thiazolyl-)(hydroxyimino)acetyl]amino]-3-[(2-oxo-1-phenyl-3-pyrrolidinidinylidene)methyl]-5-thia-1-azabicyclo[4.2.0]oct-2-ene-2-carboxylic acid 2-[(2-methylpropoxy)carbonyl]-2-pentenyl ester monohydrochloride salt IR (KBr) cm$^{-1}$ 3300, 3200, 1785, 1712, 1682, 690.

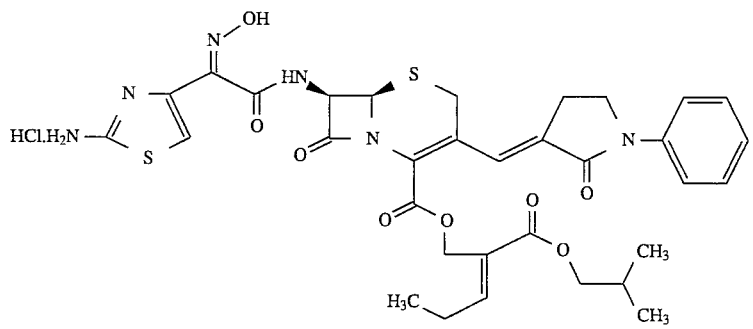

(6R,7R)-7-[(Z)-(2-Amino-thiazol-4-yl)-hydroxyiminoacetylamino]-3-[(E)-1-(2-fluoro-ethyl)-2-oxo-pyrrolidin-3-ylidenemethyl]-8-oxo-5-thia-1-azabicyclo[4.2.0]oct-2-ene-2-carboxylic acid (2,2-dimethyl-1-oxopropoxy)methyl ester hydrochloride (1:1)

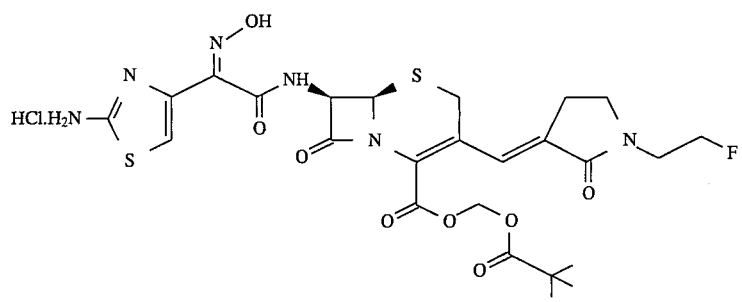

(6R,7R)-7-[(Z)-(2-Amino-thiazol-4-yl)-hydroxyiminoacetylamino]-3-[(E)-1-cyclopropyl-2-oxo-pyrrolidin-3-ylidenemethyl]-8-oxo-5-thia-1-azabicyclo[4.2.0]oct-2-ene-2-carboxylic acid (2,2-dimethyl-1-oxopropoxy)methyl ester hydrochloride (1:1)

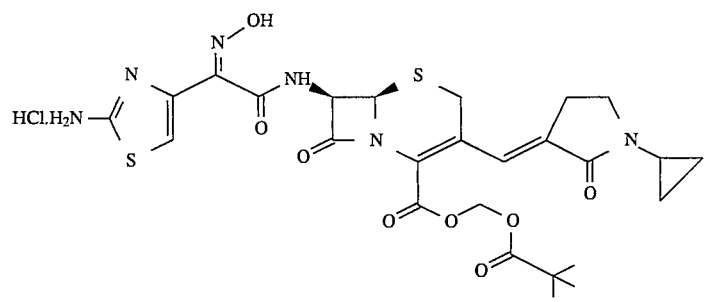

(6R,7R)-7-[(Z)-(2-Amino-thiazol-4-yl)-hydroxyiminoacetylamino]-3-[(E)-1-(2-trifluoro-ethyl)-2-oxo-pyrrolidin-3-ylidenemethyl]-8-oxo-5-thia-1-azabicyclo[4.2.0]oct-2-ene-2-carboxylic acid (2,2-dimethyl-1-oxopropoxy)methyl ester hydrochloride (1:1)

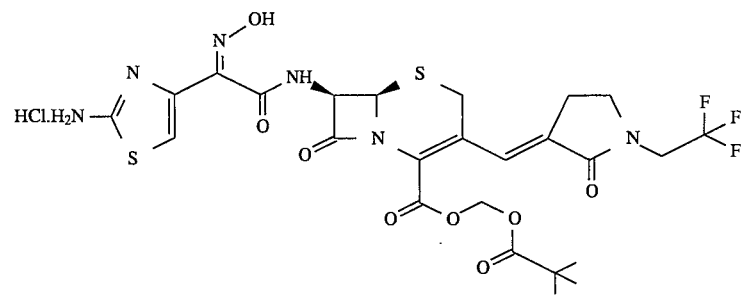

Example 18

[6R-[3(E),6α,7β(Z)]]-7-[[(2-Amino-4-thiazolyl)[(triphenylmethoxy)-imino]acetyl]amino]-3-[[1-cyclopropyl-2-oxo-3-pyrrolidinylidene]methyl]-8-oxo-5-thia-1-azabicyclo[4.2.0]oct-2-ene-2-carboxylic acid To [6R-[3(E),6α,7β(Z)]]-7-Amino-3-[[1-cyclopropyl-2-oxo-3-pyrrolidinylidene]methyl]-8-oxo-5-thia-1-azabicyclo[4.2.0]oct-2-ene-2-carboxylic acid mono-trifluoroacetic acid salt 0.9 g (2.0 mM) at room temperature was added dry dimethylformamide (35 mL) and stirred. To this was added benzotriazol-1-yl-(Z)-2-(2-aminothiazol-4-yl)-2-trityloxyiminoacetate 1.60 g (2.92 mM) and stirred for 15 hours. The reaction was poured into ethyl acetate (200 mL) and the mixture was washed twice with brine (50 mL each) and once with brine (20 mL). The ethyl acetate was dried over anhydrous sodium sulfate, filtered, and the volume reduced to 30 mL. Anhydrous ethyl ether (40 mL) was added and the solid filtered for 1.10 g (73.6% yield) of the title compound.

Microanalysis: $C_{39}H_{34}N_6O_6S_2$ calc. C 62.72 H 4.59 N 11.25 S 8.59 found C 62.40 H 4.62 N 11.32 S 8.38

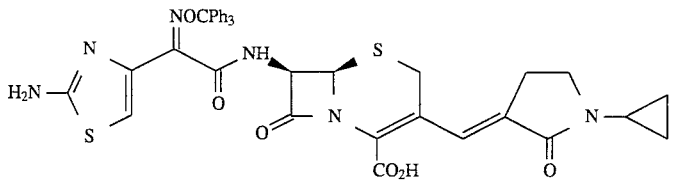

Example 19

[6R-[3(E),6α,7β(Z)]]-7-[[(2-Amino-4-thiazolyl)[(triphenylmethoxy)imino]acetyl]amino]-3-[[ 1-(2 -fluoroethyl)-2-oxo-3-pyrrolidinylidene]methyl]-8-oxo-5-thia-1-azabicyclo[4.2.0]oct-2-ene-2-carboxylic acid To [6R-[3(E),6α,7β(Z)]]-7-Amino-3-[[ 1-(2-fluoroethyl)-2-oxo-3 -pyrrolidinylidene]methyl] -8-oxo-5-thia-1-azabicyclo[4.2.0]oct-2 -ene-2-carboxylic acid mono-trifluoroacetic acid salt 4.50 g (9.88 mM) at room temperature was added dry dimethylformamide (160 mL) and stirred. To this was added benzotriazole-1-yl-(Z)-2-(2 -aminothiazole-4-yl)-2-trityloxyiminoacetate 8.00 g (14.64 mM) and stirred for 18 hours. The reaction was poured into ethyl acetate (1200 mL) and the mixture was washed twice with brine (200 mL each), twice with brine (150 mL each), and once with brine (100 mL). The ethyl acetate was dried over anhydrous sodium sulfate, filtered, and concentrated to the point where solid appeared in the flask. To this was added ethyl acetate (100 mL) and anhydrous ethyl ether (80 mL) and cooled for one hour. The solid was filtered and washed with ethyl acetate:ether (4:1) under nitrogen. This solid was then stirred with ethyl acetate (150 mL) for 30 minutes and filtered for 6.40 g (87.7% yield) of the title compound.

NMR (200 MHz, DMSO-d₆)δ 2.9 (m, 2H), 3.10 (m, 2H), 3.58 (m, 2H), 3.95 (s, 2H), 4.43 (t. 1H), 4.70 (t, 1H), 5.24 (d, 1H), 6.0 (q, 1H), 6.61 (s, 1H), 7.2–7.35 (m, 16H), 9.93 (d, 1H), 13.30 (bd, 1H).

added dry dimethylformamide (150 mL) and stirred. To this was added benzotriazole-1-yl(Z)-2-(2 -aminothiazole-4-yl)-2-trityloxyiminoacetate 5.60 g (10.25 mM) and stirred for 18 hours. The reaction was poured into ethyl acetate (800 mL) and the mixture was washed three times with brine (100 mL each) and twice with brine (80 mL). The ethyl acetate was dried over anhydrous sodium sulfate, filtered, and the volume reduced to 50–70 mL. Anhydrous ethyl ether (200–300 mL) was added for an oily precipitate. The ether was decanted and the oil retreated with fresh ethyl ether. The resulting solid was filtered for 4.6 g. The mother liquors were concentrated and retreated with ether to obtain an additional 0.77 g of solid. The combined solids, 5.37 g (98.7% yield) was confirmed to be the title compound.

[1] H-NMR (DMSO-d₆):δ [ppm] 3.10 (br. m, 2H),; 3.52 (t, 2H), 3.93 (s, 2H), 4.19 (q, 2H), 5.19 (d, 1H), 6.02 (dd, 1H), 6.60 (s, 1H), 7.30 (m, 16H), 9.95 (d, 1H), 13.9 (br., 1H).

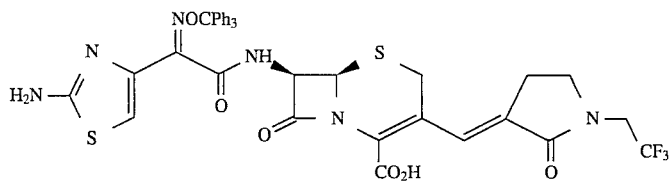

Example 21

[6R-[ 3(E ),6α,7β(Z)]]-7- [[ (2-Amino-4-thiazolyl)(hydroxyimino)acetyl]amino]-3-[[ 1-cyclopropyl-2-oxo-3-pyrrolidinylidene]methyl]- 8-oxo-5-thia-1-azabicyclo[4.2.0]oct-2-ene-2-carboxylic acid mono hydrochloride salt

[6R-[ 3(E),6α,7β(Z)]]-7-[[ 2-Amino-4thiazolyl)[(triphenylmethoxy)imino]acetyl]amino]-3-[(1-cyclopropyl-2-oxo-3-pyrrolidinylidene)methyl]-8-oxo-5-thia-1-azabicyclo[4.2.0]oct-2-ene-2-carboxylic acid 5.70 g (7.63 mM) was treated with 90% formic acid (70 mL) at room temperature. The reaction was stirred for 1.5 hours and the

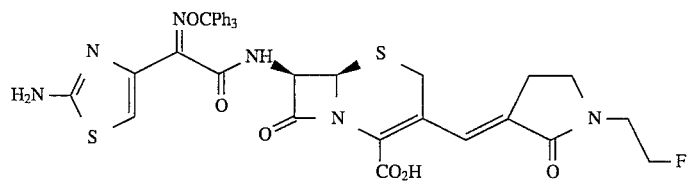

Example 20

[6R-[3(E),6α,7β(Z)]]-7-[[(2- Amino-4-thiazolyl)[(triphenylmethoxy)imino]acetyl]amino]-3-[[ 1-(2,2,2 -trifluoroethyl)-2-oxo-3-pyrrolidinylidene]methyl]-8-oxo-5-thia-1-azabicyclo[4.2.0]oct-2-ene-2-carboxylic acid To [6R-[3(E),6α,7β(Z)]]-7-Amino-3-[(1-2,2,2-trifluoroethyl)-2 -oxo-3-pyrrolidinylidene ]methyl] -8-oxo-5-thia-1-azabicyclo[4.2.0]oct- 2-ene-2-carboxylic acid mono-trifluoroacetic acid salt 3.4 g (6.9 mM) at room temperature was volatile material was removed on the rotary evaporator at water aspirator pressure. The residue was treated with ethyl acetate (60 mL), filtered, and washed with ethyl acetate under nitrogen. The mother liquors were concentrated and treated with ethyl acetate for a second crop. The solids were combined for 3.91 g.

To the above solids in methyl alcohol (80 mL), was added 1N HCl in isopropanol (14 mL), filtered, and concentrated to 60 mL. Acetone (40 mL) was added and the solution concentrated to 60 mL. To this solution was added acetone (80 mL) and followed by the addition of anhydrous ethyl ether (40 mL). The resulting solid was filtered for 2.94 g. Concentration of the mother liquor followed by the addition of ethyl ether, gave an additional 0.53 g of solid. The combined 3.47 g (85.95% yield) was confirmed to be the title compound.

NMR (400 MHz, DMSO-$d_6$) δ 0.70 (m, 4H), 2.80 (m, 1H), 2.88, 3.05 (m, 2H), 3.28 (m, 2H), 3.87 (s, 2H), 5.20 (d, 1H), 5.84 (q, 1H), 6.84 (s, 1H), 7.21 (t, 1H), 8.80 (br.s, 2H), 9.74 (d, 1H), 12.2 (s, 1H).

mM) was treated with 90% formic acid (60 mL) at room temperature. The reaction was stirred for 1.5 hours and the volatile material was removed on the rotary evaporator at water aspirator pressure. To the residue was added ethyl acetate (50 mL) and anhydrous ether (200 mL). The resulting solids were filtered and suspended in acetone (50 mL), methyl alcohol (5 mL), and ethyl acetate (20 mL), and 1N HCl in isopropanol (10 mL) was added. The solution was o filtered and concentrated to 40 mL and anhydrous ethyl ether (100–150 mL) was added. The solid was filtered and washed with acetone:ether (1:2) for 3.18 g. Concentration of the

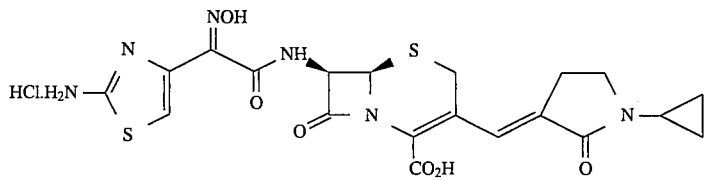

Example 22

[6R-[3(E),6α,7β(Z)]]-7-[[(2-Amino-4-thiazolyl)(hydroxyimino)acetyl]amino]-3-[[ 1-(2-fluoroethyl)-2-oxo-3-pyrrolidinylidene]methyl]-8-oxo-5-thia-1-azabicyclo[4.2.0]oct-2-ene-2-carboxylic acid mono hydrochloride salt

[6R-[3(E),6α,7β(Z)]]-7-[[2-Amino-4-thiazolyl)[(triphenylmethoxy)imino]acetyl]amino]-3-[[ 1-(2 -fluoroethyl)-2-oxo-3-pyrrolidinylidene]methyl]-8-oxo-5-thia-1-azabicyclo[4.2.0]oct-2-ene-2-carboxylic acid 6.30 g (8.37 mM) was treated with 90% formic acid (150 mL) at room temperature. The reaction was stirred for 1.5 hours at room temperature and then removed to dryness. Ethyl acetate was added and the resulting solid filtered for 4.6 g. The solid was suspended in acetone (100 mL) and methanol (60–70 mL) added, followed by the addition of 1N HCl in isopropanol (14 mL) for a solution. The solution was filtered and concentrated to 60 mL. The addition of ethyl acetate (100 mL) produced a precipitate which was filtered for 3.1 g. The mother liquor was concentrated and fresh ethyl acetate added, the suspension was filtered for 0.5 g. The combined material 3.6 g (78.6% yield) was confirmed to be the title compound.

NMR (400MHz, DMSO-$d_6$) δ 2.95, 3.13 (m, 2H), 3.45 (m, 2H), 3.57, 3.64 (m, 2H), 3.91 (s, 2H), 4.51 (t, 1H), 4.65 (t, 1H), 5.10 (d, 1H), 5.84 (q, 1H), 6.77 (s, 1H), 7.24 (s, 1H), 8.10 (br.s, 2H), 9.63 (d, 1H), 11.85 (s, 1H).

mother liquor gave an additional 0.17 g. The combined solids 3.35 g (90.3% yield) was confirmed to be the title compound.

NMR (400 MHz, DMSO-$d_6$) δ 3.11 (m, 2H), 3.68 (m, 2H), 3.92 (s, 2H), 4.12 (q, 2H), 5.28 (d, 1H), 5.88 (q, 1H), 6.85 (s, 1H), 7.34 (s, 1H), 8.10 (br.s, 2H), 9.80 (d, 1H), 12.3 (s, 1H).

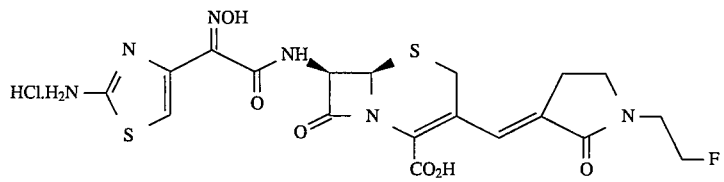

Example 23

6R-[3(E),6α,7β(Z)]]-7-[[(2-Amino-4-thiazolyl)(hydroxyimino)acetyl]-amino]-3-[[ 1-(2,2,2-trifluoroethyl)- 2-oxo-3-pyrrolidinylidene]methyl]-8-oxo-5-thia-1-azabicyclo[4.2.0]oct-2-ene-2-carboxylic acid mono hydrochloride salt

[6R-[3(E),6α,7β(Z)]]-7-[[2-Amino-4-thiazolyl)[(triphenylmethoxy)imino]acetyl]amino]-3-[ 1-(2,2,2-trifluoroethyl)- 2-oxo-3-pyrrolidinylidene)methyl] -8-oxo-5-thia-1-azabicyclo[4.2.0]oct-2-ene-2-carboxylic acid 5.36 g (6.80

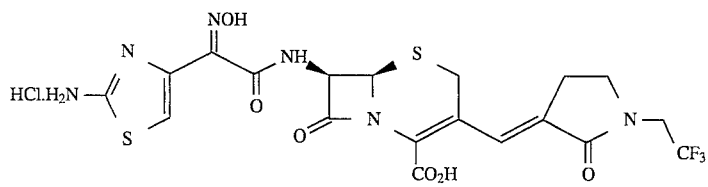

Example 24

(6R,7R)-7-[(Z)-2-(2-Amino-thiazol-4-yl)-2-cyclopentyloxyimino-acetyl-amino]- 3-[(E)-1-(4-methoxy-benzoyl)-2-oxo-pyrrolidin-3-ylidenemethyl]-8-oxo-5-thia-1-azabicyclo[4.2.0]oct-2-ene-2-carboxylic acid 540 mg (1.18 mmol) (E)-(6R,7R)-7-Amino-3-[1-(4-methoxy-benzoyl)-2-oxo-pyrrolidin-3-ylidenemethyl]-8-oxo-5-thia-1-azabicyclo[4.2.0]oct-2-ene-2-carboxylic acid trifluoroacetate (1:0.2) were dissolved in 10 ml DMF and 525 mg (1.3 mmol) (2-aminothiazol-4-yl)-(Z)-2-cyclopentyloxyimino-acetic acid 2-benzothiazolyl thioester were added, and the mixture was stirred at room temperature for 48 hours. The solution was then concentrated at 30° C. in vacuo and the residue digerated with ethyl acetate. The solid material formed was filtered off and again stirred for 1 hour in ethyl acetate, filtered off and dried.

yield: 509 mg (65%) pale yellow powder IR (KBr): 1784, 1727, 1672 cm$^{-1}$ MS (ISP): 667.4 (M+H)$^+$ (6R,7R)-7-[(Z)-2-(2-Amino-thiazol-4-yl)-2-cyclopentyloxyiminolo-acetyl-amino]-8-oxo-3-[(E)-2-oxo-1-phenyl-azetidin-3-ylidenemethyl]-5-thia-1-azabicyclo[4.2.0]oct-2-ene-2-carboxylic acid IR(KBr): 1781, 1745, 1675 cm$^{-1}$ MS(ISP): 595.4 (M+H)$^⊕$

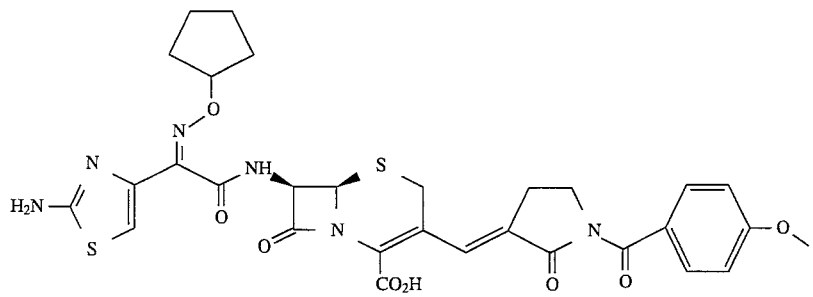

According to the procedure set forth in the preceding exemple the following additional compounds were prepared:

(6R,7R)-7-[(Z)-2-(2-Amino-thiazol-4-yl)-2-cyclopentyloxyimino-acetyl-amino]-8-oxo-3-[(Z)-2-oxo-1-phenyl-azetidin-3-ylidenemethyl]-5-thia-1-azabicyclo[4.2.0]oct-2-ene-2-carboxylic acid IR(KBr): 1765, 1723, 1675, 1527 cm$^{-1}$ MS(ISP): 595.3 (M+H)$^⊕$

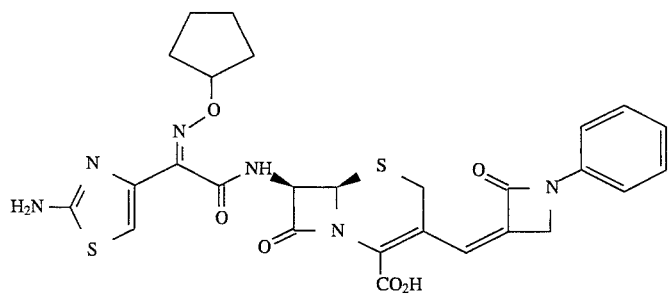

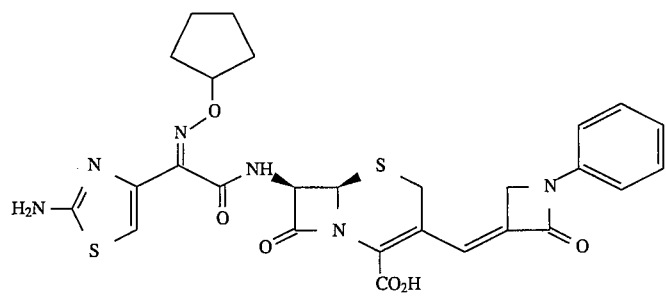

(6R,7R)-7-[(Z)-2-(2-Amino-thiazol-4-yl)-2-cyclopentyloxyimino-acetyl-amino]-8-oxo-3-[ (E)-2-oxo-1-pyridin-2-yl-pyrrolidin-3-ylidenemethyl]-5-thia-1-azabicyclo[4.2.0]oct-2-ene-2-carboxylic acid IR(KBr): 3414, 1782, 1689, 1625, 1529, 1468, 1385 cm$^{-1}$
MS(ISP): 610.4 (M+H)$^{\oplus}$

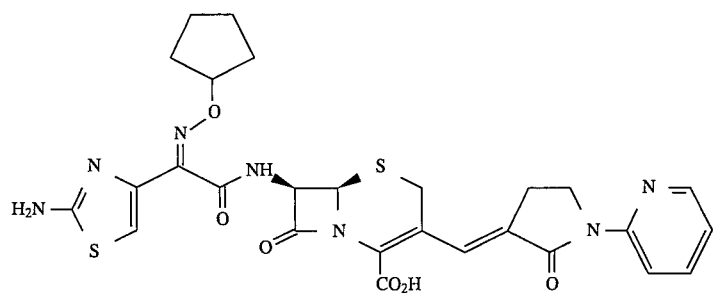

(6R,7R )-7-[ (Z)-2-(2-Amino-thiazol-4-yl )-2-cyclopentyloxyimino-acetyl-amino]-8-oxo-3-[(E)-2-oxo-1-pyridin-3-yl-pyrrolidin-3-ylidenemethyl]-5-thia-1-azabicyclo[4.2.0]oct-2-ene-2-carboxylic acid IR(KBr): 3420, 1767, 1677, 1618, 1386 cm$^{-1}$

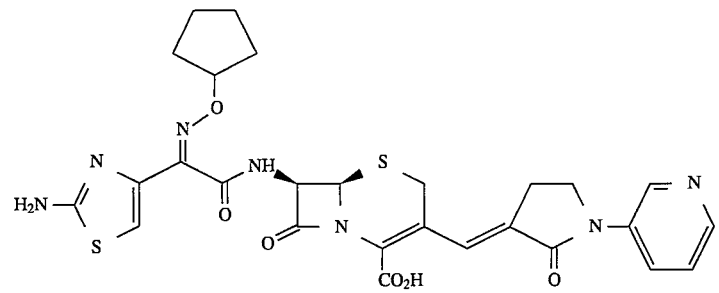

(6R,7R )-4-[ (E)-3-[7-[ (Z)-2-(2-Amino-thiazol-4-yl )-2-cyclopentyloxyimino-acetyl-amino]-2-carboxy-8-oxo-5-thia-1-azabicyclo[4.2.0]oct-2-ene-3-ylmethylene]-2-oxo-pyrrolidin-1-yl]-1 -methyl-pyridinium iodide IR(KBr): 1775, 1705, 1638, 1562, 1519 cm$^{-1}$ MS(ISP): 624.4 (M)$^{\oplus}$

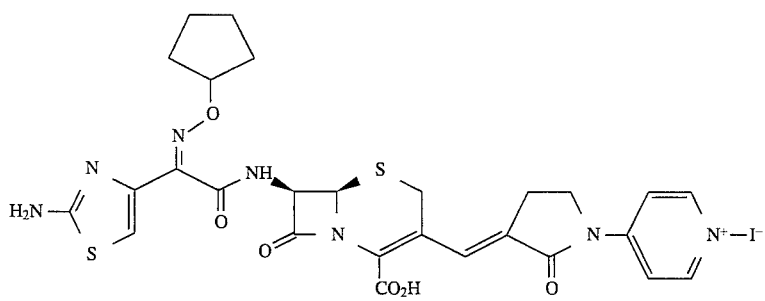

(6R,7R)-7-[(Z)-2-(2-Amino-thiazol-4-yl)-2-cyclopentyloxyimino-acetyl-amino]-3-[(E)-1-(2,2,2-trifluoro-ethyl)-2-oxo-piperidin-3-ylidenemethyl]-8-oxo-5-thia-1-azabicyclo[4.2.0]oct-2-ene-2-carboxylic acid IR(KBr): 1781, 1660, 1625 cm$^{-1}$ MS(ISP): 627.4 (M–H)$^{\oplus}$

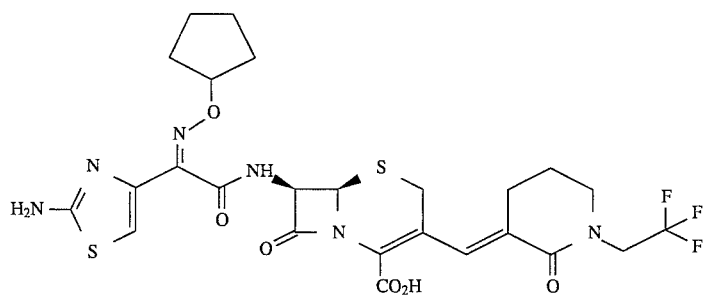

(6R,7R)-7-[(Z)-2-(2-Amino-thiazol-4-yl)-2-cyclopentyloxyimino-acetyl-amino]-3-[(Z)-1-cyclopropyl-2-oxo-pyrrolidin-3-ylidenemethyl]-8-oxo-5-thia-1-azabicyclo[4.2.0]oct-2-ene-2-carboxylic acid trifluoroacetate (1:0.31)

IR(KBr): 1780, 1690, 1676 cm$^{-1}$ MS(ISP): 573.4 (M+H)$^{\oplus}$

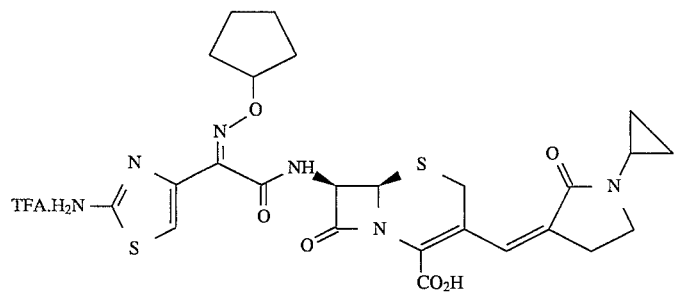

(6R,7R)-7-[(Z)-2-(2-Amino-thiazol-4-yl)-2-cyclopentyloxyimino-acetyl-amino]-8-oxo-3-[(E)-2-oxo-1-phenyl-piperidin-3-ylidenemethyl]-5-thia-1-azabicyclo[4.2.0]oct-2-ene-2-carboxylic acid trifluoroacetate (1:0.17)

IR(KBr): 1783, 1665 cm$^{-1}$ MS(ISP): 523.4 (M+H)$^{\oplus}$

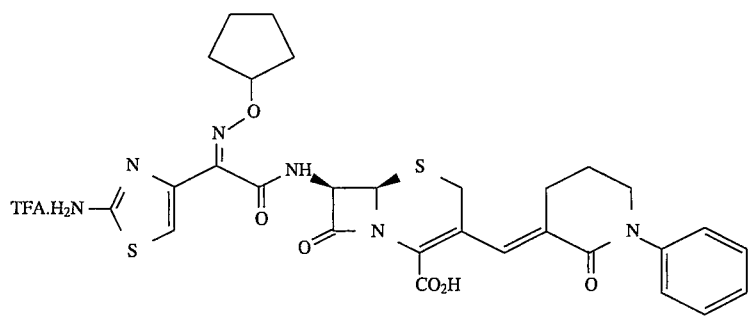

(6R,7R)-7-[(Z)-2-(2-Amino-thiazol-4-yl)-2-cyclopentyloxyimino-acetyl-amino]-3-[(E)-1-cyclopropyl-2-oxo-piperidin-3-ylidenemethyl]-8-oxo-5-thia-1-azabicyclo[4.2.0]oct-2-ene-2-carboxylic acid trifluoroacetate (1:0.35)

IR(KBr): 1778, 1678, 1614 cm$^{-1}$ MS(ISP): 587.4 (M+H)$^{\oplus}$

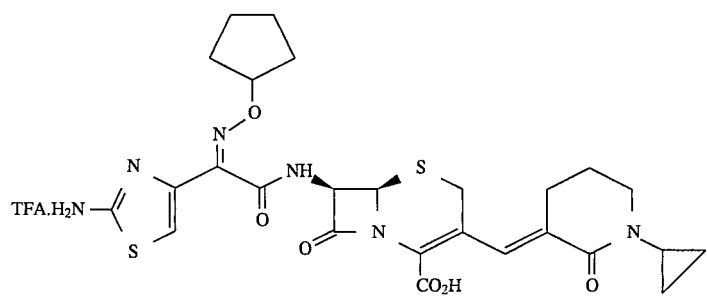

(6R,7R)-7-[(Z)-2-[2-(2-Amino-thiazol-4-yl)-2-cyclopentyloxyimino-acetyl-amino]-8-oxo-3-[(E)-2-oxo-1-(2,2,2-trifluoro-ethyl)-azetidin-3-ylidenemethyl]-5-thia-1-azabicyclo[4.2.0]oct-2-ene-2-carboxylic acid IR(KBr): 1757, 1675, 1531 cm$^{-1}$ MS(ISP): 601.3 (M+H)$^{\oplus}$

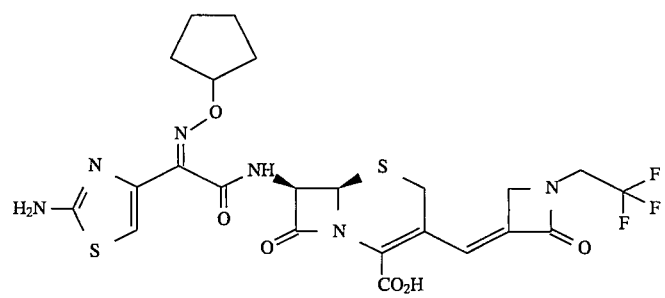

(6R,7R)-7-[(Z)-2-(2-Amino-thiazol-4-yl)-2-cyclopentyloxyimino-acetyl-amino]-8-oxo-3-[(Z)-2-oxo-1-(2,2,2-trifluoro-ethyl)-azetidin-3-ylidenemethyl]-5-thia-1-azabicyclo[4.2.0]oct-2-ene-2-carboxylic acid IR(KBr): 1765, 1738, 1676 cm$^{-1}$ MS(ISP): 601.3 (M+H)$^{\oplus}$

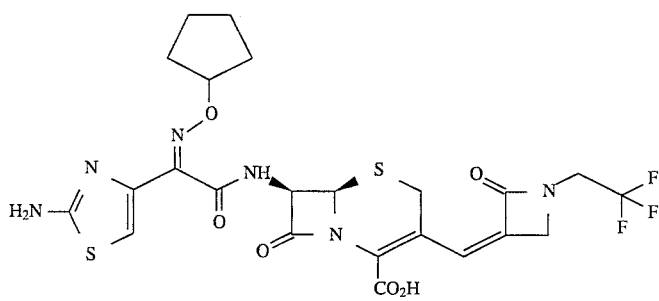

(6R,7R)-7-[(Z)-2-(2-Amino-thiazol-4-yl)-2-cyclopentyloxyimino-acetyl-amino]-8-oxo-3-[(E)-2-oxo-1-pyrazin-2-yl-pyrrolidin-3-ylidenemethyl]-5-thia-1-azabicyclo[4.2.0]oct-2-ene-2-carboxylic acid IR(KBr): 1782, 1687, 1625, 1526 cm$^{-1}$ MS(ISP): 611.4 (M+H)$^{\oplus}$

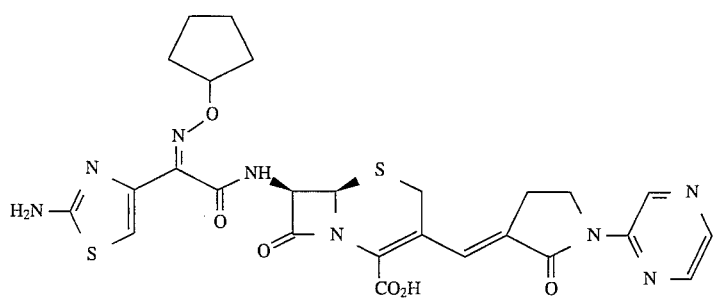

(6R,7R)-7-[(Z)-2-(2-Amino-thiazol-4-yl)-2-cyclopentyloxyimino-acetyl-amino]-3-[(E)-1-(4-methyl-phenylsulfonyl)-2-oxo-pyrrolidin-3-ylidenemethyl]-8-oxo-5-thia-1-azabicyclo[4.2.0]oct-2-ene-2-carboxylic acid IR(KBr): 1784, 1718, 1669 cm$^{-1}$ MS(ISP): 687.5(M+H)$^{\oplus}$

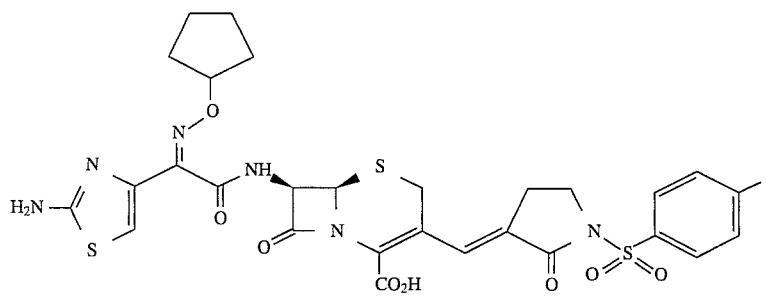

(6R,7R)-7-[(Z)-2-(2-Amino-thiazol-4-yl)-2-cyclopentyloxyimino-acetyl-amino]-3-[(E)-1-cyclopropyl-2-oxo-pyrrolidin-3-ylidenemethyl]-8-oxo-5-thia-1-azabicyclo[4.2.0]oct-2-ene-2-carboxylic acid trifluoroacetate (1:0.22)

IR(KBr): 1782, 1677, 1528 cm$^{-1}$ MS(ISP): 573.4 (M+H)$^{\oplus}$

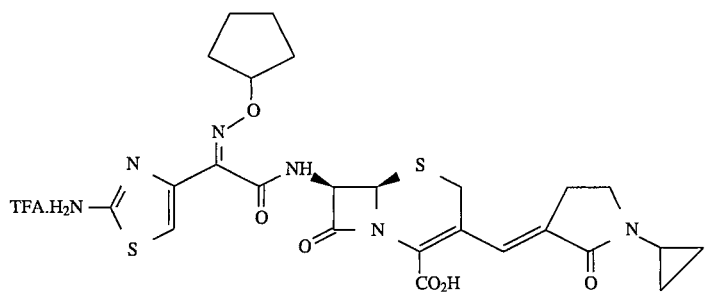

(6R,7R)-7-[(Z)-2-(2-Amino-thiazol-4-yl)-2-cyclopentyloxyimino-acetyl-amino]-3-[(E)-1-cyanomethyl-2-oxo-pyrrolidin-3-ylidenemethyl]-8-oxo-5-thia-1-azabicyclo[4.2.0]oct-2-ene-2-carboxylic acid IR(KBr): 1781, 1681, 1629 cm$^{-1}$ MS(ISP): 572.4 (M+H)$^{\oplus}$

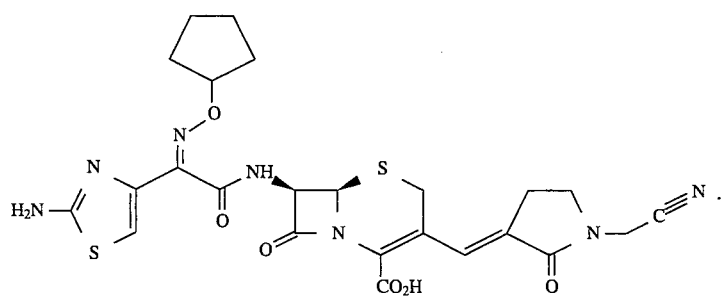

(6R,7R)-7-[(Z)-2-(2-Amino-thiazol-4-yl)-2-cyclopentyloxyimino-acetyl-amino]-3-[(E)-1-cyclopropylmethyl-2-oxo-pyrrolidin-3-ylidenemethyl]-8-oxo-5-thia-1-azabicyclo[4.2.0]oct-2-ene-2-carboxylic acid trifluoroacetate (1:0.2)

IR(KBr): 1782, 1675, 1629 cm$^{-1}$ MS(ISP): 587.4 (M+H)$^{\oplus}$

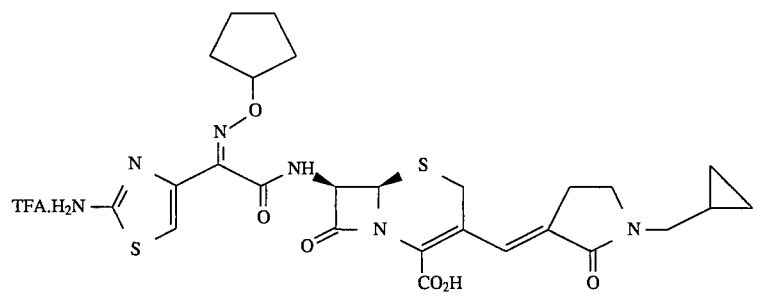

(6R,7R)-7-[(Z)-2-(2-Amino-thiazol-4-yl)-2-cyclopentyloxyimino-acetyl-amino]-8-oxo-3-[(E)-2-oxo-1-prop-2-ynyl-pyrrolidin-3-ylidenemethyl]-5-thia-1-azabicyclo[4.2.0]oct-2-ene-2-carboxylic acid IR(KBr): 2120, 1780, 1679, 1629 cm$^{-1}$ MS(ISP): 571.4 (M+H)$^{\oplus}$

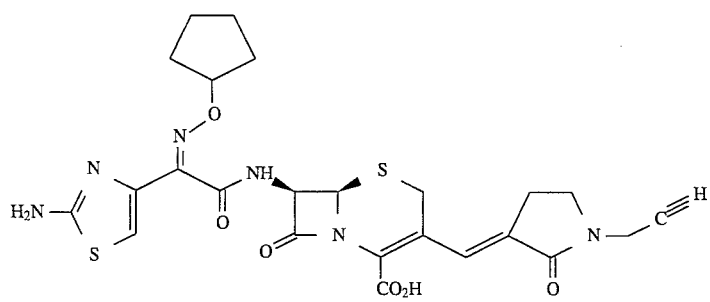

Example 25

(6R,7R )-7-[(Z)-2-(2-Amino-thiazol-4-yl)-2-cyclopentyloxyimino-acetyl-amino]-8-oxo-3-[ (E)-1-(2,2,2-trifluoroethyl)-2-oxo-pyrrolidin- 3-ylidene-methyl]-5-thia-1-azabicyclo[4.2.0]oct-2-ene-2-carboxylic acid Na salt (1:1)

IR(KBr): 1766, 1681, 1529 cm$^{-1}$ MS(ISN): 630.3 [(M+ NH$_3$)–Na]$^\oplus$ 600 mg (1.53 mmol) (E)-(6R,7R)-7-Amino-8-oxo-3-[1-(2,2,2 -trifluoro-ethyl)-2-oxo-pyrrolidin-3-ylidenemethyl]-5-thia-1-azabicyclo[4.2.0]oct-2-ene-2-carboxylic acid trifluoroacetate (1:1) were dissolved in 25 ml DMF and stirred for 1 hour at room temperature before 694 mg (1.71 mmol) (2-aminothiazol-4-yl)-(Z)- 2-cyclopentyloxyimino-acetic acid 2-benzothiazolyl thioester were added. After 4 hours the reaction mixture was concentrated to 10 ml and a solution of 2N sodium 2-ethylcapronate in acetone concentrated to 10 ml and a solution of 2N sodium 2-ethylcapronate in acetone (1.5 ml) were added. The solution was poured on 50 ml diethylether, and the solid material separated was filtered off and dried. It was purified by reversed phase chromatography on opti-up gel with a gradient of water/acetonitrile as eluent. The fractions containing the product were combined and lyophilized.

yield: 430 mg (44%) IR(KBr): 1766, 1681, 1529 cm$^{-1}$ MS(ISN): 630.3 [(M+NH$_3$)–Na]

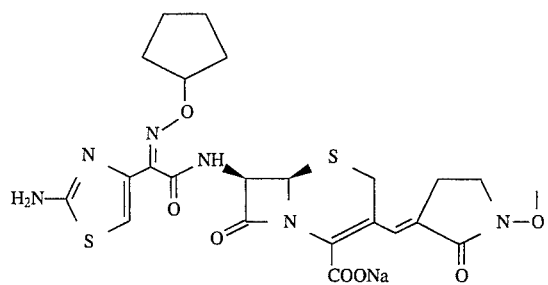

This compound is identical to the penultimate compound described in Example 1a.

(6R,7R)-7-[(Z)-2-(2-Amino-thiazol-4-yl)-2-cyclopentyloxyimino-acetyl-amino]-3-[(E)-1-(5-methyl-isoxazol-3-yl)-2-oxo-pyrrolidin-3-ylidenemethyl]-8-oxo-5-thia-1-azabicyclo[4.2.0]oct-2-ene-2-carboxylic acid Na salt (1:1)

IR(KBr): 3427, 1765, 1689, 1610, 1505 cm$^{-1}$ MS(ISN): 629.5 (M–Na+NH$_3$)$^\oplus$

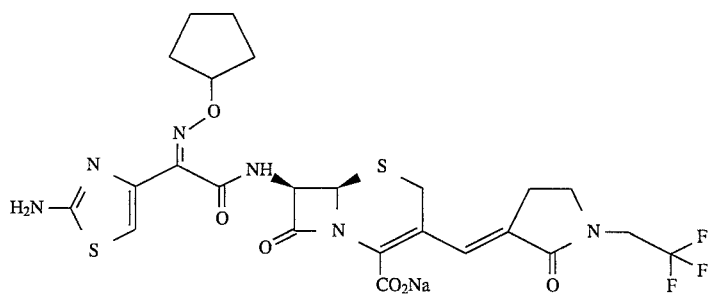

According to the procedure set forth in the preceding example the following additional compounds were prepared:

[6R-[3(E),6α,7β(Z)]]-7-[[(2-Amino-4-thiazolyl)(cyclopentyloxyimino)acetyl]amino]-3-[(1-methoxy-2-oxo-3-pyrrolidinylidene]-8-oxo-5-thia-1-azabicyclo[ 4.2.0 ]oct-2-ene-2-carboxylic acid monosodium salt

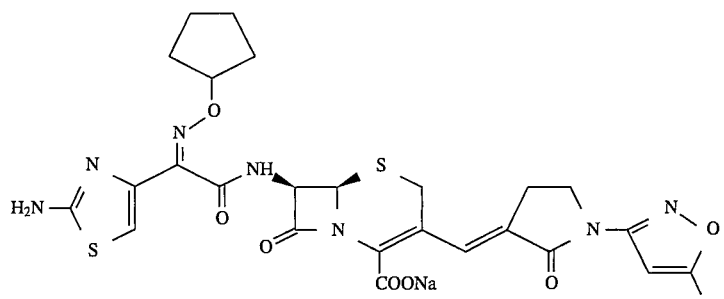

(6R,7R)-7-[(Z)-2-(2-Amino-thiazol-4-yl)-2-cyclopentyloxyimino-acetyl-amino]-8-oxo-3-[(E)-2-oxo-1-thiazol-2-yl-pyrrolidin-3-ylidenemethyl]-5-thia-1-azabicyclo[4.2.0]oct-2-ene-2-carboxylic acid IR(KBr): 3420, 1767, 1681, 1620, 1504 cm$^{-1}$ MS(ISN): 614.3 (M–Na)$^{\oplus}$, 631.1 (M–Na+NH$_3$)$^{\oplus}$

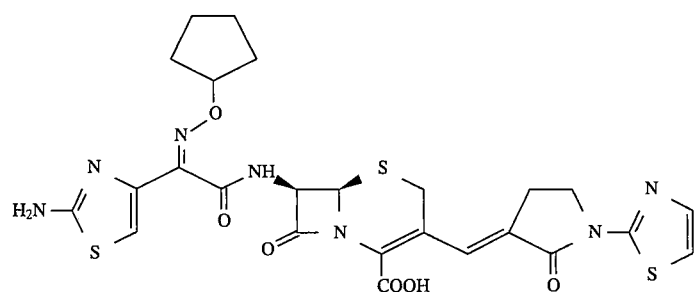

(6R,7R)-7-[(Z)-2-(2-Amino-thiazol-4-yl)-2-cyclopentyloxyimino-acetyl-amino]-3-[ (E)-1-carboxymethyl-2-oxo-pyrrolidin-3-ylidenemethyl ]-8-oxo-5-thia-1-azabicyclo[4.2.0]oct-2-ene-2-carboxylic acid Na salt (1:2)

IR(KBr): 1764, 1665, 1609 cm$^{-1}$ MS(ISP): 591.4 (M+H)$^{\oplus}$

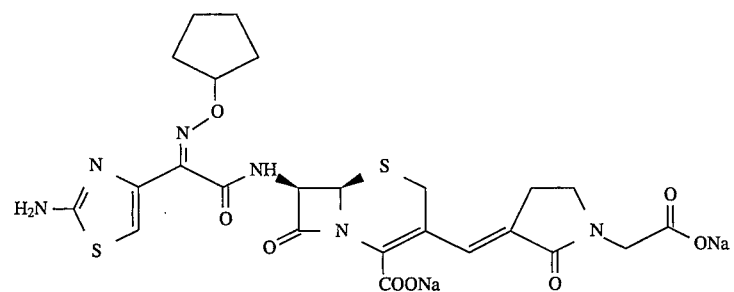

(6R,7R)-3-[(E)-1-Allyl-2-oxo-pyrrolidin-3-ylidenemethyl]-7 -[(Z)-2-(2-amino-thiazol-4-yl )-2-cyclopentyloxyimino-acetyl-amino] -8-oxo-5-thia-1-azabicyclo[4.2.0]oct-2-ene-2-carboxylic acid Na salt (1:1)

IR(KBr): 1764, 1673, 1620 cm$^{-1}$ MS(ISP): 573.4 (M+H)$^{\oplus}$

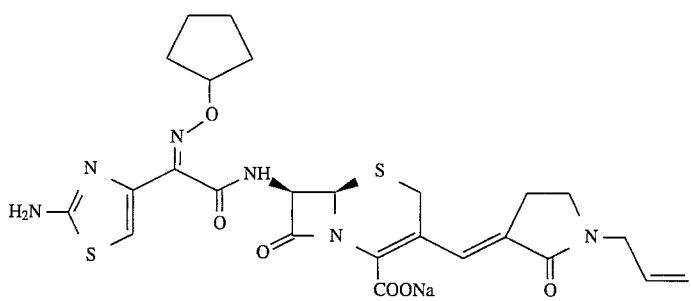

(6R,7R)-7-[(Z)-2-(2-Amino-thiazol-4-yl)-2-cyclopentyloxyimino-acetyl-amino]-3-[(E)-1-(1,1-dioxo-tetrahydro-thiophen-3-yl)-2-oxo-pyrrolidin- 3-ylidenemethyl]-8-oxo-5-thia-1-azabicyclo[4.2.0]oct-2 -ene-2-carboxylic acid Na salt (1:1)

IR(KBr): 1767, 1675, 1620, 1528 cm$^{-1}$ MS(ISN): 649.4 (M–Na)$^⊕$, 666 (M–Na+NH$_3$)$^⊕$ Elem. analysis: Calc. C 46.42 H 4.34 N 12.49 S 14.30

Found C 46.11 H 5.00 N 12.39 S 14.05

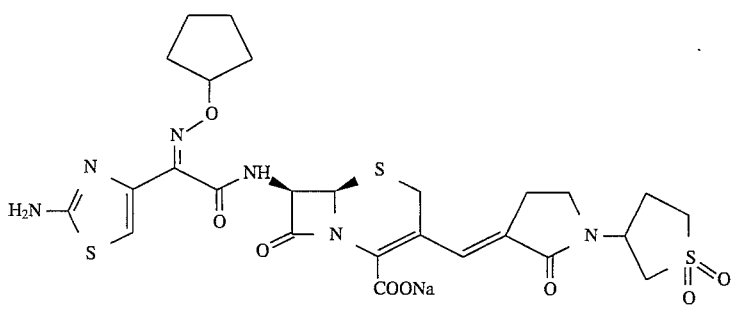

(6R,7R)-7-[(Z)-2-(2-Amino-thiazol-4-yl)-2-cyclopentyloxyimino-acetyl-amino]-8-oxo-3-[(E)-2-oxo-pyridin-4-yl-pyrrolidin-3-ylidenemethyl]-5-thia-1-azabicyclo[4.2.0]oct-2-ene-2-carboxylic acid Na salt (1:1)

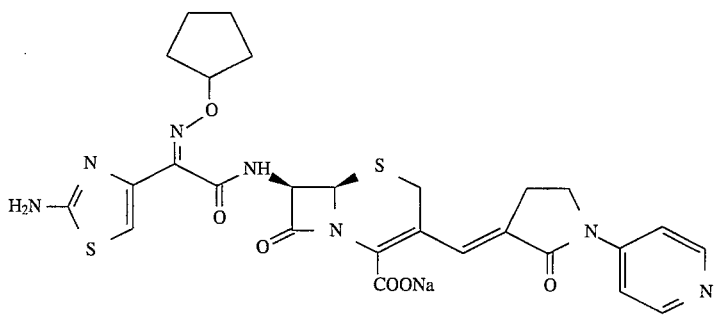

(6R,7R)-7-[(Z)-2-(2-Amino-thiazol-4-yl)-2-cyclopentyloxyimino-acetyl-amino]-8-oxo-3-[(E)-1-[2-oxo-1-(2-oxo-oxazolidin-3-yl)-pyrrolidin- 3-ylidenemethyl]-5-thia-1-azabicyclo[4.2.0]oct-2-ene-2 -carboxylic acid Na salt (1:1)

IR(KBr): 1769, 1679, 1630, 1530, 1392 cm$^{-1}$ MS(ISP): 550.3 (M+H)$^⊕$

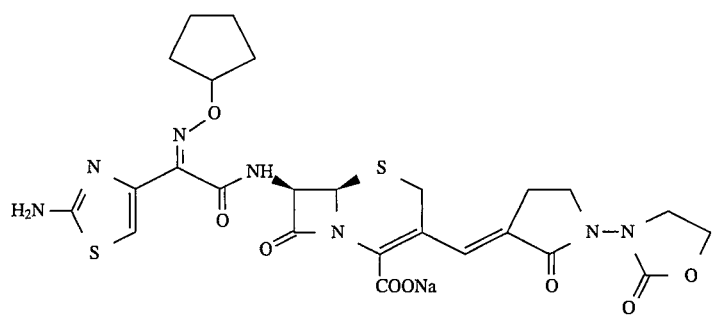

(6R,7R)-7-[(Z)-2-(2-Amino-thiazol-4-yl)-2-cyclopentyloxyimino-acetyl-amino]-3-[ (E)-1-(6-methoxy-pyridin-3-yl )-2-oxo-pyrrolidin- 3-ylidenemethyl]-8-oxo-5-thia-1-azabicyclo[ 4.2.0 ]oct-2-ene-2-carboxylic acid Na salt (1:1)

IR(KBr): 1767, 1677, 1619, 1459 cm$^{-1}$ MS(ISN): 655.2 (M+NH$_3$); 638.3 (M–Na)$^-$ 1.88 g (7.47 mmol)of N-t-butoxycarbonyl-D-α-phenylglycine in 20 ml dioxane were cooled to 10°–15° C. and treated with 1.2 ml (8.3 mmol) triethylamine and 0.79 mmol (8.3 mmol) ethyl chloroformate. After 5 min. the resulting solution was added to a solution of 2.35 g (6 mmol) (E)-(6R,7R)-7-Amino-8-oxo-3-[1-(2,2,2-trifluoro-ethyl)-2

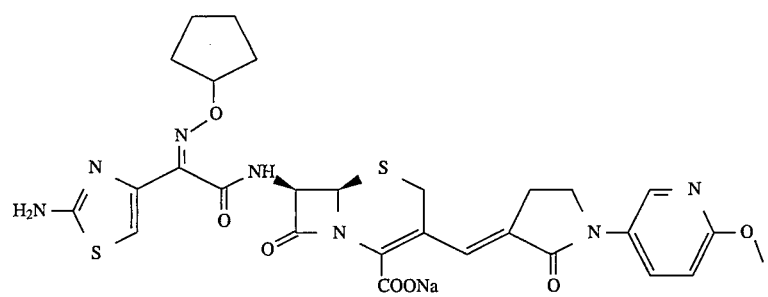

(6R,7R)-7-[(Z)-2-(2-Amino-thiazol-4-yl)-2-cyclopentyloxyimino-acetyl-amino]-3-[ (E)-1-(2-cyano-ethyl )-2-oxopyrrolidin-3 -ylidenemethyl]-8-oxo-5-thia-1-azabicyclo [4.2.0]oct-2-ene-2-carboxylic acid Na salt (1:1)

IR(KBr): 2244, 1765, 1672, 1621 cm$^{-1}$ MS(ISP): 586.4 (M+H)$^\oplus$

-oxo-pyrrolidin-3-ylidenemethyl] -5-thia-1-azabicyclo [4.2.0 ]oct-2 -ene-2-carboxylic acid trifluoroacetate (1:1) dissolved in a mixture of 12 ml water and 3 ml dioxane, which was adjusted to pH 7 by addition of triethylamine. After 30 min. at room temperature the orange solution was poured on 100 ml ethyl acetate and 50 ml water, dried over

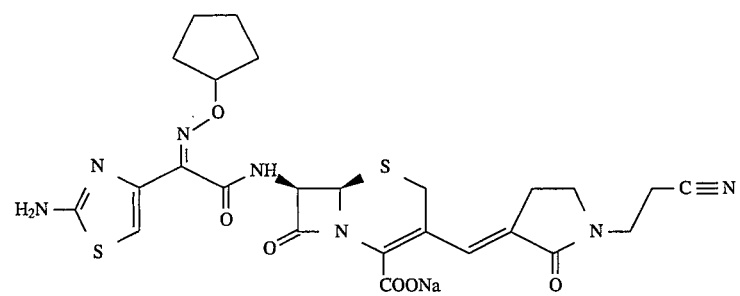

Example 26 a) (6R,7R)-7-[(R)-2-t-butoxycarbonylamino-2-phenylacetylamino]-8-oxo-3-[(E)-2-oxo-1-(2,2,2-trifluoro-ethyl)-pyrrolidin- 4-ylidenemethyl]-5-thia-1-azabicyclo[4.2.0]oct-2-ene-2-carboxylic acid magnesium sulfate and concentrated to 30 ml. 200 ml n-hexane were added and a solid separated, which was filtered off and washed with n-hexane and dried. The solid was stirred in 35 ml diethyl ether for 30 min. and again filtered and washed.

yield: 2.8 g beige powder (77%) IR(KBr): 1784, 1694, 1495 cm$^{-1}$ MS(ISP): 611.2 (M+H)$^+$

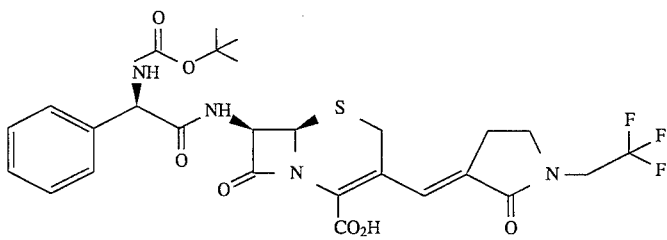

b) (6R,7R)-7-[(R)-2-Amino-2-phenyl-acetylamino]-8-oxo-3-[(E) -5-oxo-1-(2,2,2-trifluoro-ethyl)-pyrrolidin-4-ylidenemethyl]-5-thia- 1-azabicyclo[4.2.0]oct-2-ene-2-carboxylic acid trifluoroacetate 1.0 g (1.64 mmol) (6R,7R)-7-[(R)-2-t-butoxycarbonylamino-2 -phenyl-acetylamino]-8-oxo-3-[(E)-5-oxo-1-(2,2, 2-trifluoro-ethyl)-pyrrolidin- 4-ylidenemethyl]-5-thia-1-azabicyclo[ 4.2.0]oct-2-ene-2-carboxylic acid were dissolved in 5 ml trifluoroacetic acid and stirred for 30 min at 0°–5° C. The solution was then poured on 100 ml diethyl ether and the separated material was filtered off. It was then stirred for 2 hours in 25 ml ethyl acetate; the crystals separated were filtered off and dried.

yield: 750 mg colourless powder (73%) IR(KBr): 1779, 1690, 1521 cm$^{-1}$ MS (ISN): 509.3 (M–H)$^-$

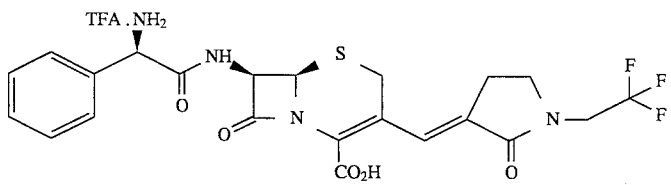

Example 27

(6R,7R)-7-[(Z)-2-(5-Amino-1,2,4-thiadiazol-3-yl)-2 -methoxyimino-acetylamino] -8-oxo-3-[(E)-5-oxo-1-(2,2,2-trifluoroethyl)-pyrrolidin- 4-ylidenemethyl]-5-thia-1-azabicyclo[4.2.0]oct-2 -ene-2-carboxylic acid Na salt (1:1)

393 mg (1 mmol) (E)-(6R,7R)-7-Amino-8-oxo-3-[1-(2, 2,2 -trifluoro-ethyl)-2-oxo-pyrrolidin-3-ylidenemethyl]-5-thia-1-azabicyclo[4.2.0]oct-2-ene-2-carboxylic acid trifluoroacetate (1:1) were suspended in 15 ml DMF and stirred for 1 hour, then 386 mg (1.1 mmol) 2-(5-amino-1,2,4-thiadiazol-3-yl)-(Z)-2-methoxyimino acetic acid-2-benzothiazolyl thioester were added. The mixture was reacted for 20 hours at room temperature and 1 ml (2 mmol) 2N sodium 2-ethylcapronate in acetone were added dropwise. The mixture was then poured on 100 mg diethyl ether and the solid material was filtered off, washed with ether and dried. It was purified by reversed phase chromatography on opti-up gel, using water as eluent. The fractions containing the product were combined and lyophilized.

yield: 380 mg (65%) IR(KBr): 1766, 1678, 1523 cm$^{-1}$ MS (ISN): 560.2 (M–Na)$^-$

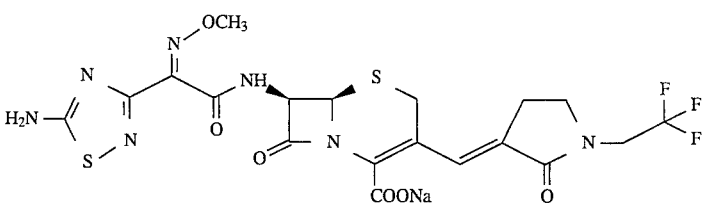

Example 28

(6R,7R )-7-[ (Z)-2-(2-Amino-thiazol-4-yl)-2-(1-carbamoyl-1 -methyl-ethoxyimino)-acetylamino]-8-oxo-3-[(E)-2-oxo-1-(2,2,2 -trifluoroethyl)-pyrrolidin-3-ylidenemethyl]-5-thia-1-azabicyclo[4.2.0]oct-2-ene-2-carboxylic acid 600 mg (1.53 mmol) (E)-(6R,7R)-7-Amino-8-oxo-3-[1-(2,2,2 -trifluoro-ethyl )-2-oxo-pyrrolidin-3-ylidenemethyl]-5-thia-1-azabicyclo[4.2.0]oct-2-ene-2-carboxylic acid trifluoroacetate (1:1) were suspended in 25 ml DMF and stirred for 1 hour at room temperature. Then 774 mg (1.84 mmol) 2-(2-aminothiazol-4-yl)-(Z)- 2-(1-carbamoyl-1-methylethoxyimino)-acetic acid-2-benzothiazolyl thioester were added and the mixture was stirred for 4.5 hours at room temperature. The solvent was evaporated, and the oil was digerated in 100 ml ethyl acetate. The solid formed was filtered off and recrystallized from acetone/ethyl acetate.

yield: 610 mg beige powder (63%) IR(KBr): 1781, 1679, 1531 cm$^{-1}$ Microanalysis: $C_{23}H_{24}F_3M_7O_7S_2$ calc: C 43.74 H 3.83 N 15.52 S 10.15 found: C 43.83 H 3.81 N 15.35 S 10.20

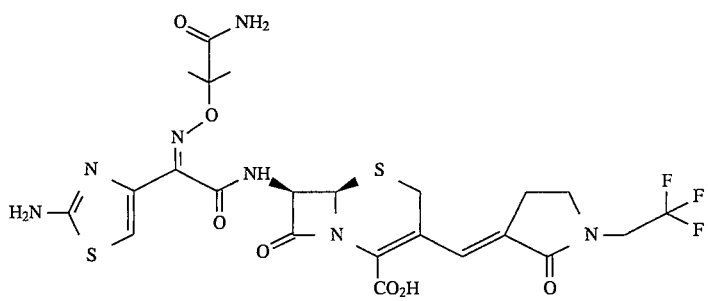

According to the procedure set forth in the preceding example the following additional compound was prepared:

(6R,7R)-7-[(Z)-2-(2-Amino-thiazol-4-yl)-2-(1-carbamoyl-1-methyl-ethoxyimino)-acetylamino]-3-[(E)-1-(5-methyl-isoxazol-3-yl)-2-oxo-pyrrolidin-3-ylidenemethy1]-8-oxo-5-thia-1-azabicyclo[4.2.0]oct-2-ene-2-carboxylic acid MS(ISP): 631.3 (M+H$^+$) IR(KBr): 3431, 1768, 1679, 1610, 1505 cm$^{-1}$

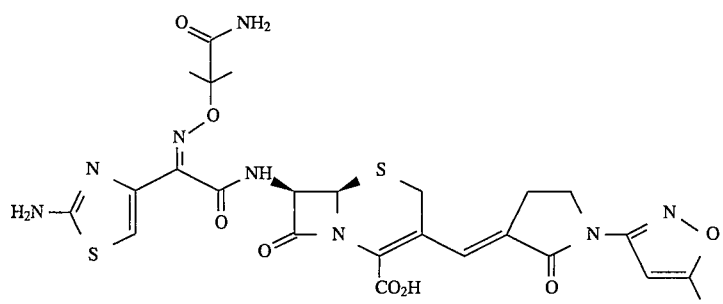

Example 29

Following the procedures set forth in the above examples 14, 15, 16 and 17, the following additional esters, where $R_3$ is hydrogen, methyl, lower alkyl or carboxymethyl, and RP is an easily hydrolyzable ester residue, can be prepared:

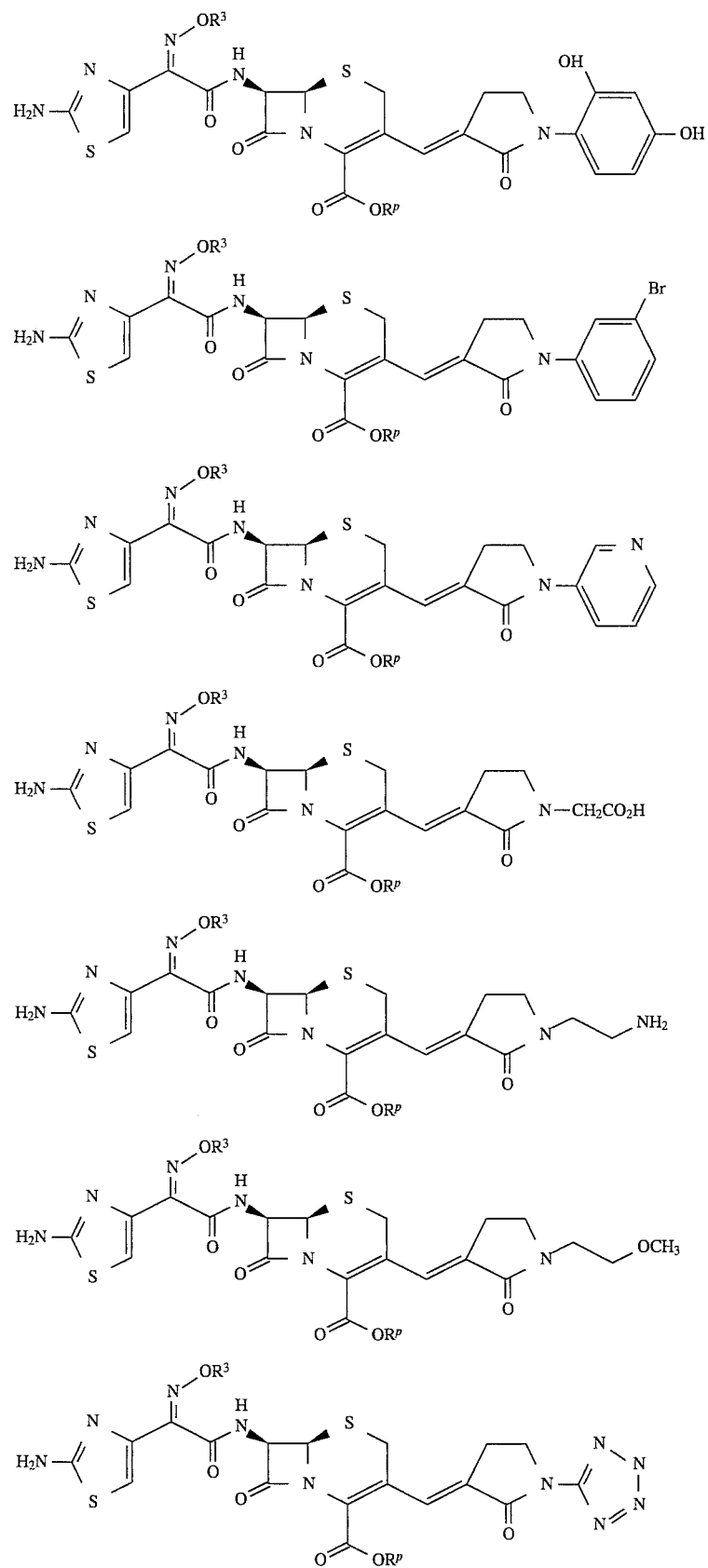

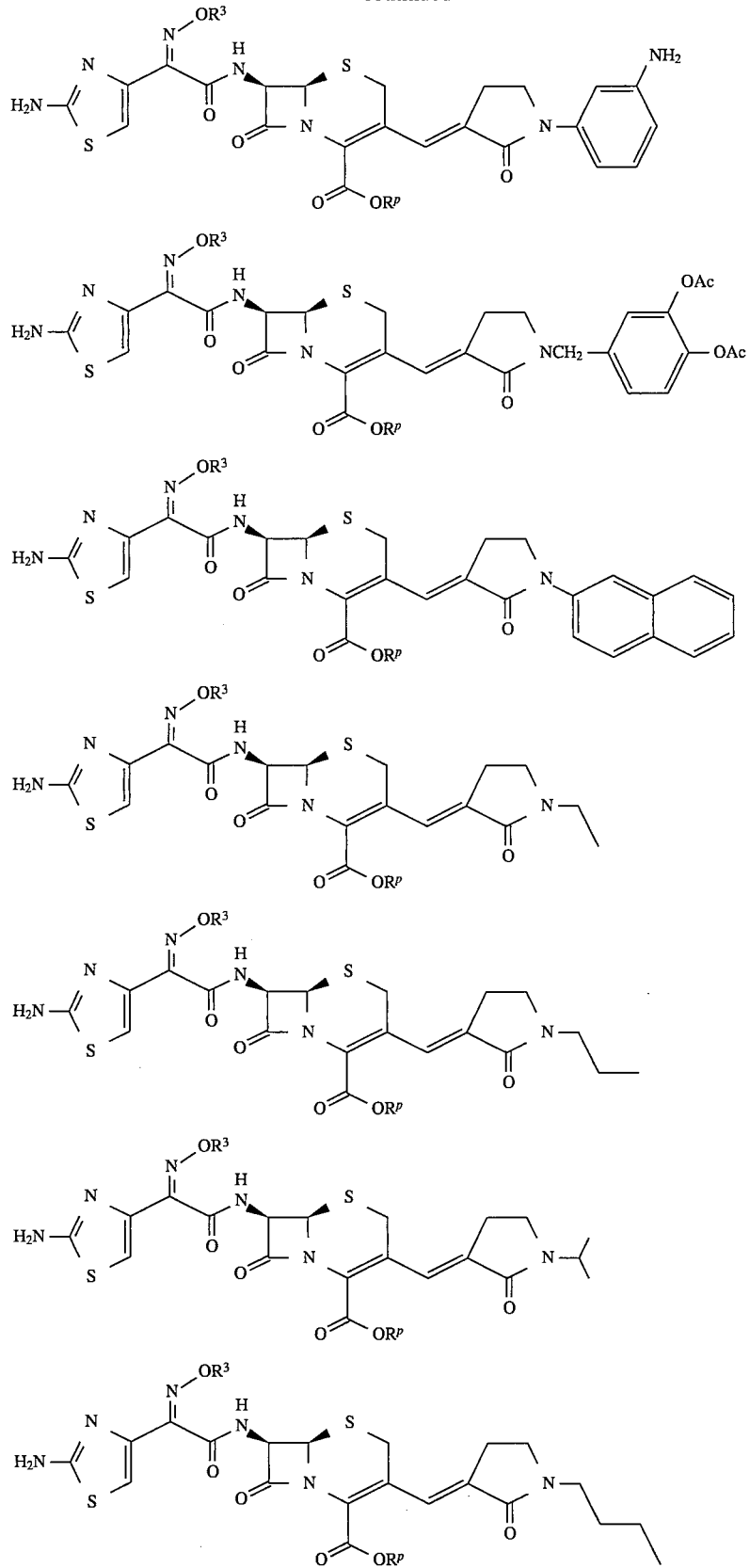

-continued

[Chemical structures shown]

The following example illustrates pharmaceutical preparations containing the compounds provided by the present invention:

EXAMPLE A

Production of dry ampoules for intramuscular administration:

A lyophilisate of 1 g of active ingredient is prepared in the usual manner and filled into an ampoule. The sterile water ampoule contains 10% propylene glycol. Prior to the administration, the lyophilisate is treated with 2.5 ml of a 2% aqueous lidocaine hydrochloride solution.

As active ingredient can be used one of the compounds prepared according to the above Examples.

We claim:

1. A compound of the formula

[Formula I shown with $R^1$—NH, $(O)_m$, S, $(CH_2)_n$, N—$R^2$, COOH]

wherein $R^1$ is an acyl group derived from a carboxylic acid;

$R^2$ is hydrogen, hydroxy, lower alkyl-$Q_p$, cycloalkyl, lower alkoxy, lower alkenyl, cycloalkenyl, lower alkynyl, aralkyl-$Q_p$, aryl-$Q_p$, aryloxy, aralkoxy or an unsaturated or saturated 5-, 6-, or 7-membered heterocyclic ring containing at least one hetero atom selected from the group consisting of oxygen, nitrogen, or sulfur, the lower alkyl, cycloalkyl, lower alkoxy, lower alkenyl, cycloalkenyl, lower alkynyl, aralkyl, aryl, aryloxy, aralkoxy and the heterocyclic ring being unsubstituted or substituted with at least one group selected from carboxy, amino, nitro, oxo, cycloalkyl, cyano, lower alkyl, lower alkoxy, hydroxy, halogen, —CONR$^4$R$^5$, —N(R$^5$)COOR$^9$, R$^5$CO—, R$^5$OCO— or R$^5$COO— where R$^4$ is hydrogen, lower alkyl, or cycloalkyl; R$^5$ is hydrogen or lower alkyl; R$^9$ is lower alkyl, lower alkenyl or a carboxylic acid protecting group;

Q is —CO— or —SO$_2$—;

m is 0 or 1;

n is 0, 1 or 2;

p is 0 or 1;

as well as readily hydrolyzable esters thereof, pharmaceutically acceptable salts of said compounds and hydrates of the compounds of formula I and of their esters and salts.

2. The compound of claim 1 having the formula

[Formula IIA shown]

where $R^a$, $R^b$, $R^2$, X, m and n are as previously defined.

3. The compound of claim 1 having the formula

[Formula IIB shown]

where X, $R^2$, m and n are as previously defined.

4. The compound of claim 1 having the formula

[Formula IIC shown]

where X, $R^2$, $R^3$, m and n are as previously defined.

5. The compound of claim 4, wherein X is an unsaturated or saturated 5-, 6-, or 7-membered heterocyclic ring containing at least one hetero atom selected from the group consisting of oxygen, nitrogen, or sulfur, the heterocyclic ring being unsubstituted or substituted with at least one group selected from carboxy, amino, nitro, cyano, lower alkyl, lower alkoxy, hydroxy and halogen.

6. The compound of claim 5 wherein the heterocyclic ring is substituted with amino.

7. The compound of claim 6 having the formula

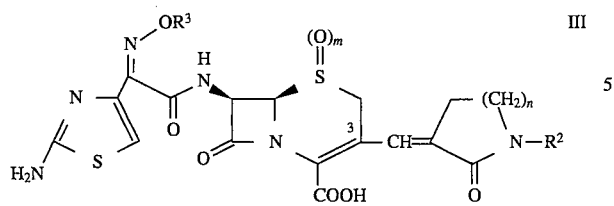

where $R^2$, $R^3$, m, and n are as previously defined.

8. The compound of claim 7, wherein n is 1.

9. The compound of claim 8, wherein $R^3$ is hydrogen, lower alkyl, cycloalkyl or $C(R^7R^8)CO_2R^{9'}$.

10. The compound of claim 9 wherein m is 0.

11. The compound of claim 10, wherein $R^3$ is hydrogen.

12. The compound of claim 11, wherein $R^2$ is hydrogen; cycloalkyl; lower alkyl which is unsubstituted or substituted with halogen, cycloalkyl, or cyano; lower alkoxy; phenyl which is unsubstituted or substituted with at least one of lower alkoxy or halogen; lower alkenyl; lower alkynyl; or a heterocyclic ring.

13. The compound of claim 12 wherein $R_2$ is hydrogen.

14. The compound of claim 12 wherein $R_2$ is cycloalkyl.

15. The compound of claim 12 wherein $R_2$ is lower alkyl which is unsubstituted or substituted with halogen.

16. The compound of claim 12 wherein $R_2$ is lower alkoxy.

17. The compound of claim 12 wherein $R_2$ is phenyl which is unsubstituted or substituted with at least one of lower alkoxy or halogen.

18. The compound of claim 14

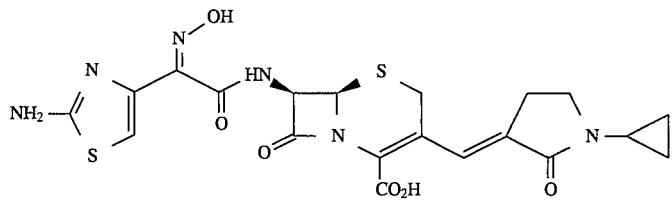

[6R-[3(E),6α,7β(Z)]]-7-[[(2-amino-4-thiazolyl)(hydroxyimino)acetyl]amino]-3-[[1-cyclopropyl-2-oxo-3-pyrrolidinylidene]methyl]-8-oxo-5-thia-1-azabicyclo[4.2.0]oct-2-ene-2-carboxylic acid.

19. The compound of claim 15

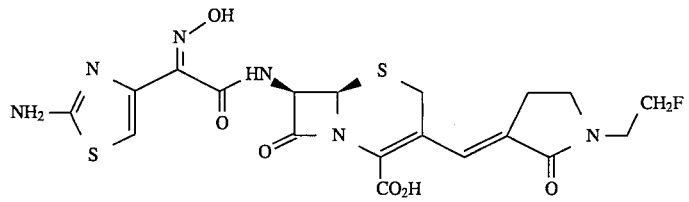

[6R-[3(E),6α,7β(Z)]]-7-[[(2-amino-4-thiazolyl)(hydroxyimino)acetyl]amino]-3-[[1-(2-fluoroethyl)-2-oxo-3-pyrrolidinylidene]methyl]-8-oxo-5-thia-1-azabicyclo[4.2.0]oct-2-ene-2-carboxylic acid.

20. The compound of claim 15

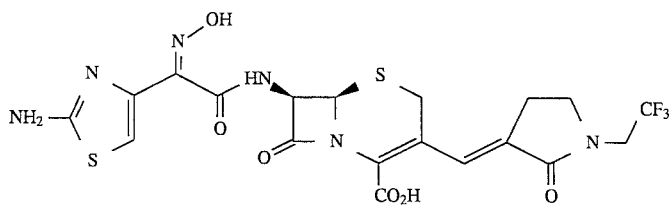

[6R-[3(E),6α,7β(Z) ]]-7-[[(2-amino-4-thiazolyl)(hydroxyimino)acetyl]amino]-3-[[1-(2,2,2-trifluoroethyl)-2-oxo-3-pyrrolidinylidene]methyl]-8 -oxo-5-thia-1-azabicyclo[4.2.0]oct-2-ene-2-carboxylic acid.

21. The compound of claim 16

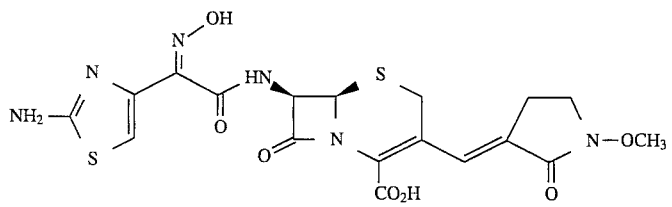

[6R-[3(E),6α,7β(Z)]]-7-[[ (2-Amino-4-thiazolyl)(hydroxyimino)acetyl]amino]-3-[[1-methoxy-2-oxo-3-pyrrolidinylidene]methyl]-8-oxo- 5-thia-1-azabicyclo[4.2.0]oct-2-ene-2-carboxylic acid.

22. The compound of claim 17

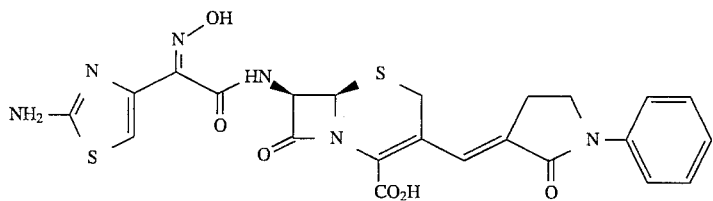

[6R-[3(E),6α,7β(Z) ]]-7-[[ (2-amino-4-thiazolyl)(hydroxyimino)acetyl]amino]-3- [[2-oxo-1-phenyl-3-pyrrolidin ylidene ] methyl ] -8-oxo-5-thia-1 -azabicyclo [4.2.0]oct-2-ene-2-carboxylic acid.

23. The compound of claim 17

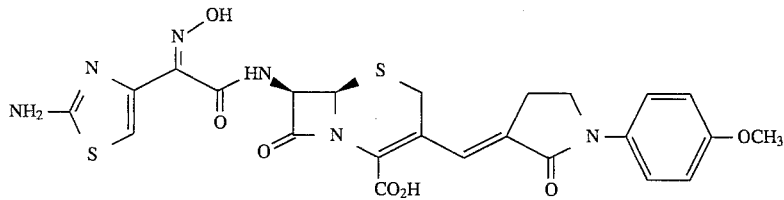

[6R-[3(E),6α,7β(Z)]]-7-[[(2-amino-4-thiazolyl)(hydroxyimino)acetyl]amino]-3-[[1-(4-methoxyphenyl)-2-oxo-3-pyrrolidinylidene]methyl]-8 -oxo-5-thia-1-azabicyclo[4.2.0]oct-2-ene-2-carboxylic acid.

24. The compound of claim 12

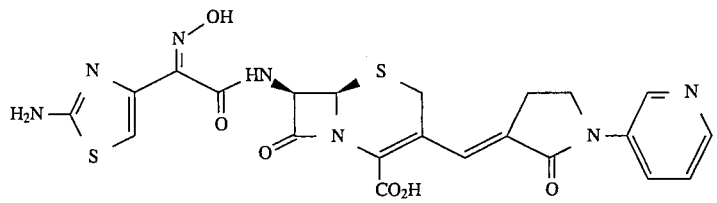

[6R-[3(E),6α,7β(Z)]]-7-[[ (2-amino-4-thiazolyl)(hydroxyimino)acetyl]amino]-8-oxo-3-[[2-oxo-1-(3-pyridinyl)-3-pyrrolidin ylidene]methyl]-5-thia-1-azabicyclo[4.2.0]oct-2-ene-2-carboxylic acid.

25. The compound of claim 12

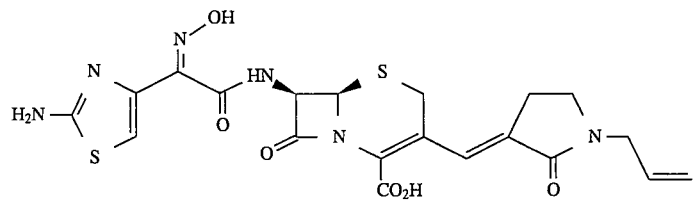

[6R-[3(E),6α,7β(Z)]]-3-[[ 1-allyl-2-oxo-3-pyrrolidinylidene]methyl]-7-[[(2 -amino-4-thiazolyl)(hydroxyimino)acetyl]amino]-8-oxo-5-thia-1-azabicyclo[4.2.0]oct-2-ene-2-carboxylic acid.

26. The compound of claim 12

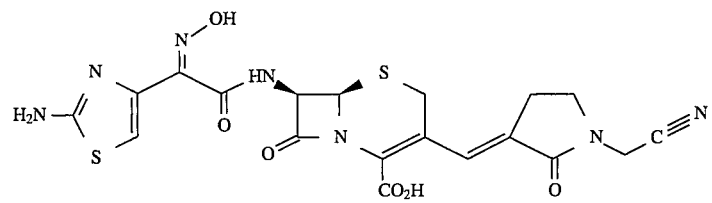

[6R-[3(E),6α,7β(Z)]]-7-[[ (2-amino-4-thiazolyl)(hydroxyimino)acetyl]amino]-3-[[1-cyanomethyl-2-oxo-3-pyrrolidinylidene]methyl]-8-oxo-5 -thia-1-azabicyclo[4.2.0]oct-2-ene-2-carboxylic acid.

27. The compound of claim 12

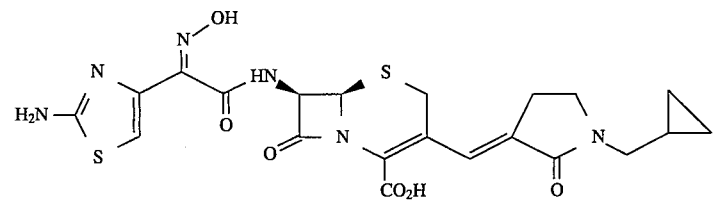

[6R-[3(E),6α,7β(Z)]]-7-[[(2-amino-4-thiazolyl)(hydroxyimino)acetyl]amino]-3-[[ 1-cyclopropylmethyl-2-oxo-3-pyrrolidinylidene]methyl]-8 -oxo-5-thia-1-azabicyclo[4.2.0]oct-2-ene-2-carboxylic acid.

28. The compound of claim 12

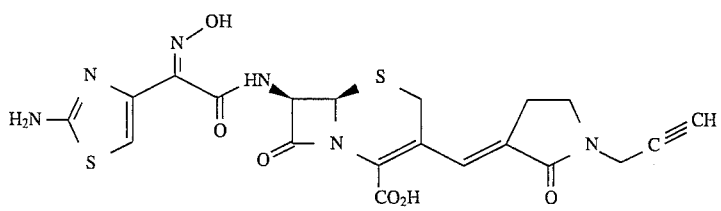

[6R-[3(E),6α,7β(Z)]]-7-[[(2-amino-4-thiazolyl)(hydroxyimino)acetyl]amino]-8-oxo-3-[[2-oxo-1-(2-propynyl)-3-pyrrolidinylidene]methyl]-5-thia-1-azabicyclo[4.2.0]-oct-2-ene-2-carboxylic acid.

29. The compound of claim 12

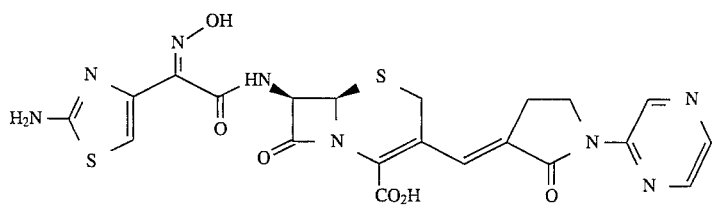

[6R-[3(E),6to,7l3(Z) ]]-7-[[ (2-amino-4-thiazolyl)(hydroxyimino)acetyl]amino]-8-oxo-3-[[2-oxo-1-(2-pyrazinyl)-3-pyrrolidinylidene]methyl]-5 -thia-1-azabicyclo[4.2.0]oct-2-ene-2-carboxylic acid.

30. The compound of claim 15

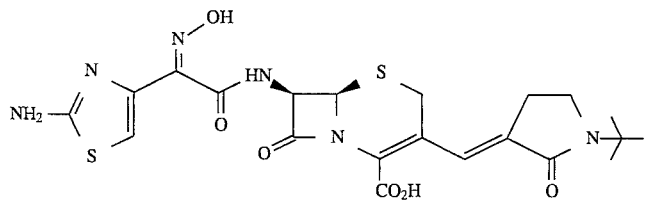

[6R-[3(E),6α,7β(Z)]]-7-[[ (2-Amino-4-thiazolyl)hydroxyimino)acetyl]amino]-3-[[1-(1,1-dimethylethyl)-2-oxo-3-pyrrolidinylidene]methyl]-8-oxo-5-thia-1-azabicyclo[4.2.0]oct-2-ene-2-carboxylic acid.

31. The compound of claim 10 wherein $R_3$ is $C(R_7R_8CO_2R_{9'})$.

32. The compound of claim 31 wherein $R_2$ is hydrogen; cycloalkyl; lower alkyl which is unsubstituted or substituted with halogen, cycloalkyl, or cyano; lower alkoxy; phenyl which is unsubstituted or substituted with at least one of lower alkoxy or halogen; lower alkenyl; lower alkynyl; or a heterocyclic ring which can be unsubstituted or substituted with at least one group selected from carboxy, amino, nitro, oxo, cyano, lower alkyl, lower alkoxy, hydroxy, halogen, —$CONR^4R^5$, —$N(R^5)COOR^9$, $R^5CO$—, $R^5OCO$— or $R^5COO$—.

33. The compound of claim 32 wherein $R_2$ is cycloalkyl.

34. The compound of claim 32 wherein $R_2$ is lower alkyl which is unsubstituted or substituted with halogen.

35. The compound of claim 34

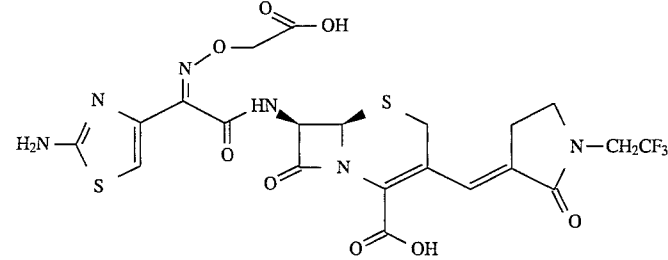

[6R-[3(E),6α,7β(Z)]]-7-[[(2-Amino-4-thiazolyl)[(carboxymethyl)imino]acetyl]amino]-3-[[1-(2,2,2-trifluoroethyl)-2-oxo-3-pyrrolidinylidene]methyl]-8-oxo-5-thia-1-azabicyclo[4.2.0]oct-2-ene-2-carboxylic acid.

36. The compound of claim 34

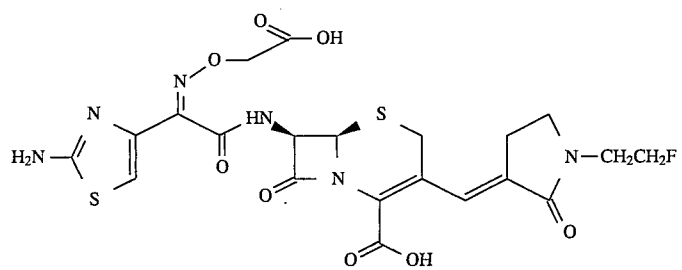

[6R-[3(E),6α,7β(Z)]]-7-[[(2-Amino-4-thiazolyl)[(carboxymethyl)imino]acetyl]amino]-3-[[1-(2-fluoroethyl)-2-oxo-3-pyrrolidinylidene]methyl]-8-oxo-5-thia-1-azabicyclo[4.2.0]oct-2-ene-2-carboxylic acid.

37. The compound of claim 33

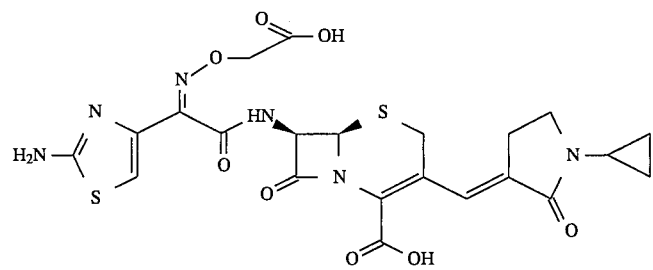

[6R-[3-(E),6α,7β(Z)]]-7-[[(2-Amino-4-thiazolyl)[(carboxymethyl)imino]acetyl]amino]-3-[[1-cyclopropyl-2-oxo-3-pyrrolidinylidene]methyl]-8-oxo-5-thia-1-azabicyclo4.2.0]oct-2-ene-2-carboxylic acid.

38. The compound of claim 1

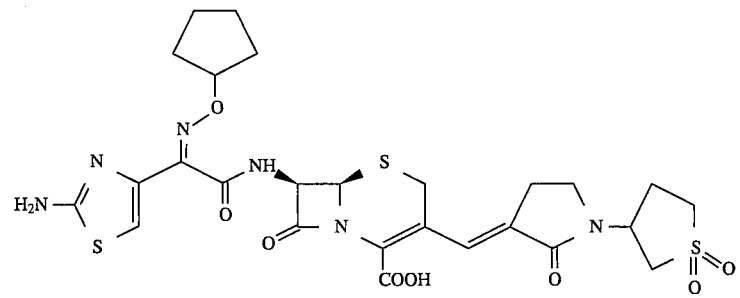

(6R, 7R )-7-[(Z)-2-(2-Amino-thiazol-4-yl )-2-cyclopentyloxyimino-acetyl-amino]-3-[(E)-1-(1,1-dioxo-tetrahydro-thiophen-3-yl)-2-oxo-pyrrolidin-3-ylidenemethyl]-8-oxo-5-thia-1-azabicyclo[4.2.0]oct-2-ene-2-carboxylic acid.

39. The compound of claim 1

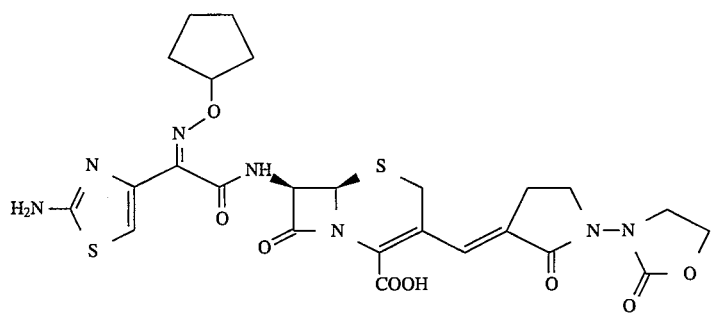

(6R,7R)-7-[(Z)-2-(2-Amino-thiazol-4-yl)-2-cyclopentyloxyimino-acetylamino]-8-oxo-3-[(E)-1-[2-oxo-1-(2-oxo-oxazolidin-3-yl)-pyrrolidin-3-ylidenemethyl]-5-thia-1-azabicyclo[4.2.0]oct-2-ene-2-carboxylic acid.

40. The compound of claim 1

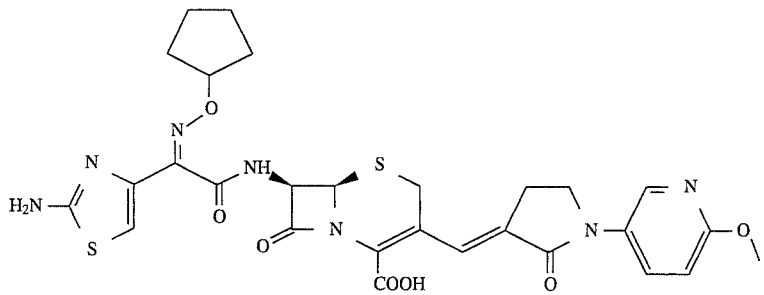

(6R,7R)-7-[(Z)-2-(2-Amino-thiazol-4-yl)-2-cyclopentyloxyimino-acetylamino]-3-[(E)-1-(6-methoxy-pyridin-3-yl)-2-oxo-pyrrolidin-3-ylidenemethyl]-8-oxo-5-thia-1-azabicyclo[4.2.0]oct-2-ene-2-carboxylic acid.

41. The compound of claim 1

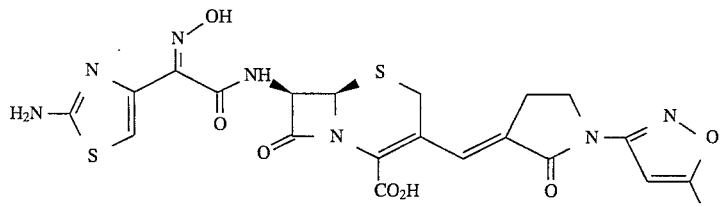

(6R,7R)-7-[(Z)-2-(2-Amino-thiazol-4-yl)-2-hydroxyiminoacetylamino]-3-[(E)-1-(5-methyl-isoxazol-3-yl)-2-oxo-pyrrolidin-3-ylidenemethyl]-8-oxo-5-thia-1-azabicyclo[4.2.0]oct-2-ene-2-carboxylic acid,

42. The compound according to claim 1 in the E-form, viz. having the formula

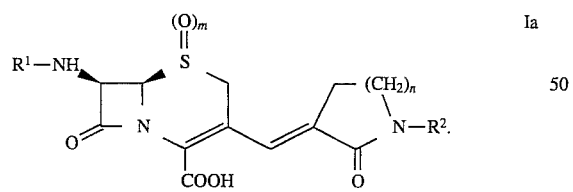

Ia

43. The compound according to claim 1 in the Z-form, viz. having the formula

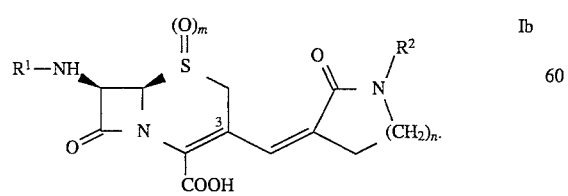

Ib

44. A pharmaceutical composition comprising a therapeutically effective amount of a compound of the formula

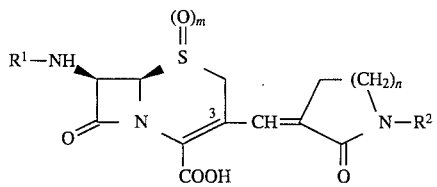

I wherein $R^1$ is an acyl group derived from a carboxylic acid;

$R^2$ is hydrogen, hydroxy, lower alkyl-$Q_p$, cycloalkyl, lower alkoxy, lower alkenyl, cycloalkenyl, lower alkynyl, aralkyl-$Q_p$, aryl-$Q_p$, aryloxy, aralkoxy or an unsaturated or saturated 5-, 6-, or 7-membered heterocyclic ring containing at least one hetero atom selected from the group consisting of oxygen, nitrogen, or sulfur, the lower alkyl, cycloalkyl, lower alkoxy, lower alkenyl, cycloalkenyl, lower alkynyl, aralkyl, aryl, aryloxy, aralkoxy and the heterocyclic ring being unsubstituted or substituted with at least one group selected from carboxy, amino, nitro, oxo, cycloalkyl, cyano, lower alkyl, lower alkoxy, hydroxy, halogen, —$CONR^4R^5$, —$N(R^5)COOR^9$, $R^5CO$—, $R^5OCO$— or $R^5COO$— where $R^4$ is hydrogen, lower alkyl, or cycloalkyl; $R^5$ is hydrogen or lower alkyl; $R^9$ is lower alkyl, lower alkenyl or a carboxylic acid protecting group;

Q is —CO— or —$SO_2$—;

m is 0 or 1;

n is 0, 1 or 2;

p is 0 or 1;

as well as readily hydrolyzable esters thereof, pharmaceutically acceptable salts of said compounds and hydrates of the compounds of formula I and of their esters and salts, and a pharmaceutically acceptable carrier.

45. The composition of claim 44, wherein the compound of formula II, Z is —C(X)=N—OR$_3$ [IIC].
46. The composition of claim 45 wherein R$_3$ is hydrogen.
47. The composition of claim 46, wherein the compound is selected from the group consisting of

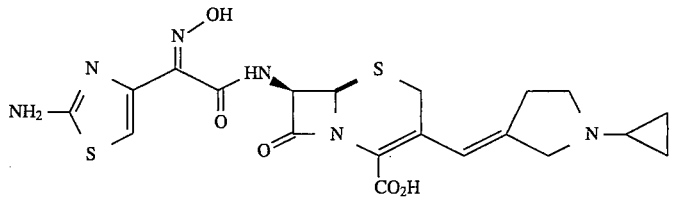

[6R-[3(E),6α,7β(Z)]]-7-[[ (2-Amino-4-thiazolyl)(hydroxyimino)acetyl]amino]-3-[[1-cyclopropyl-2-oxo-3-pyrrolidinylidene]methyl]-8 -oxo-5-thia-1-azabicyclo [4.2.0]oct-2-ene-2-carboxylic acid;

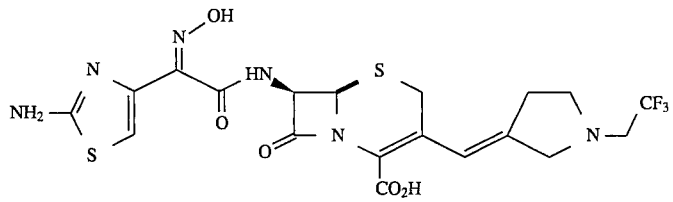

[6R-[3(E), 6α,7β(Z)]]-7-[ [ (2-Amino-4-thiazoyl)hydroxyimino)acetyl]amino]-3-[[1-(2,2,2-trifluoroethyl)-2-oxo-3-pyrrolidinylidene]methyl]-8-oxo-5-thia-1-azabicyclo[4.2.0]oct-2-ene-2-carboxylic acid;

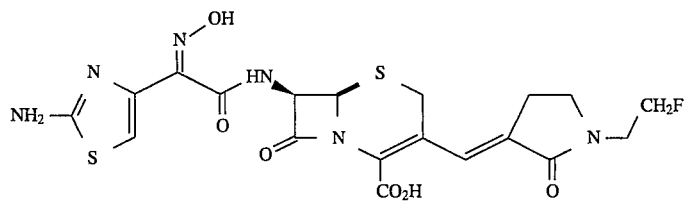

[6R-[3-(E),6α,7β(Z)]]-7-[[ (2- Amino-4-thiazolyl)hydroxyimino)acetyl]amino]-3-[[1-(2-fluoroethyl)-2-oxo-3-pyrrolidinylidene]methyl] -8-oxo-5-thia-1-azabicyclo[4.2.0]oct-2-ene-2-carboxylic acid;

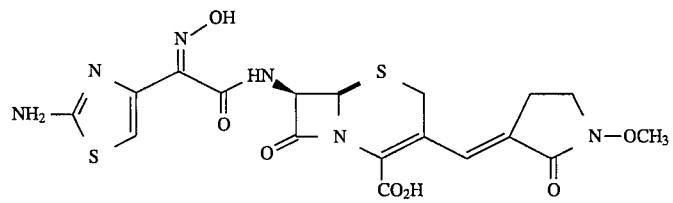

[6R-[3(E),6α,7β(Z)]] -7-[[ (2-Amino-4-thiazolyl)hydroxyimino)acetyl]amino]-3-[[ 1-methoxy-2-oxo-3-pyrrolidinylidene]methyl]-8 -oxo-5-thia-1-azabicyclo [4.2.0]oct-2-ene-2-carboxylic acid;

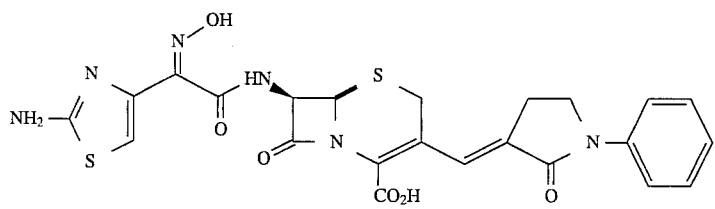

[6R-[3(E),6α,7β(Z)]]-7-[[ (2-Amino-4-thiazolyl)hydroxyimino)acetyl]amino]-3-[[1-phenyl-2-oxo-3-pyrrolidinylidene]methyl]-8-oxo-5 -thia-1-azabicyclo[4.2.0]oct-2-ene-2-carboxylic acid;

[6R-[3(E),6α,7β(Z)]]-3-[[ 1-allyl-2-oxo-3-pyrrolidinylidene]methyl]-7 -[[(2 -amino-4-thiazolyl)(hydroxyimino)acetyl]amino]-8-oxo-5-thia-1-azabicyclo[4.2.0]oct-2-ene-2-carboxylic acid;

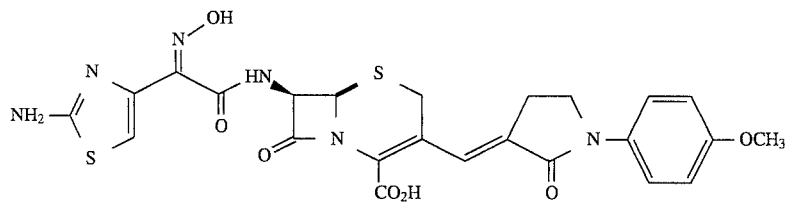

[6R-3(E),6α,7β(Z)]]-7-[[(2-Amino-4-thiazolyl)(hydroxyimino)acetyl]amino]-3-[[ 1-(4-methoxyphenyl)-2-oxo-3-pyrrolidinylidene]methyl]-8-oxo-5-thia-1-azabicyclo[4.2.0]oct-2-ene-2 -carboxylic acid;

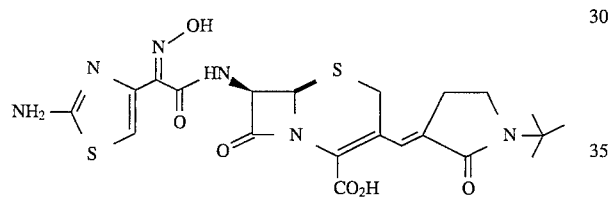

[6R-[3(E),6α,7β(Z)]] -7-[[ (2- Amino-4-thiazolyl)(hydroxyimino)acetyl]amino]-3-[[ 1-(1,1-dimethylethyl)-2-oxo-3-pyrrolidinylidene]methyl]-8-oxo-5-thia-1-azabicyclo[4.2.0]oct-2-ene-2-carboxylic acid;

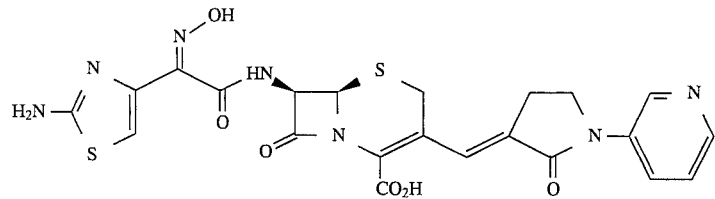

[6R-[3(E),6α,7β(Z)]]-7-[[ (2-amino-4-thiazolyl)(hydroxyimino)acetyl]amino]-8-oxo-3-[[2-oxo-1-(3-pyridinyl)-3-pyrrolidinylidene]methyl]-5 -thia-1-azabicyclo[4.2.0]oct-2-ene-2-carboxylic acid;

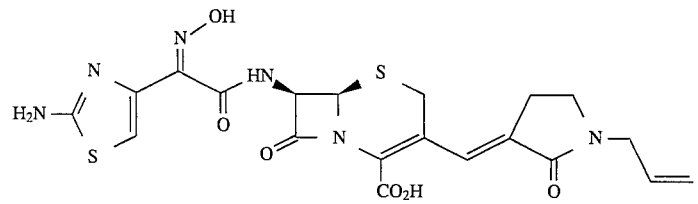

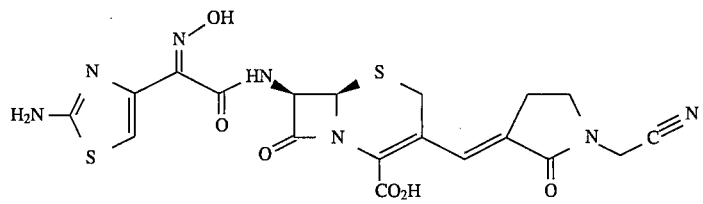

[6R-[3(E),6α,7β(Z)]]-7-[[(2-amino-4-thiazolyl)(hydroxyimino)acetyl]amino]-3-[[1-cyanomethyl-2-oxo-3-pyrrolidinylidene]methyl]-8-oxo-5 -thia-1-azabicyclo[4.2.0]oct-2-ene-2-carboxylic acid;

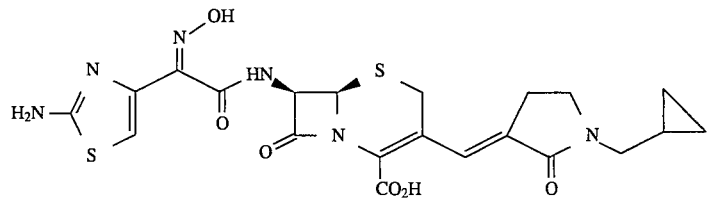

[6R-[3(E),6α,7β(Z)]]-7-[[ (2-amino-4-thiazolyl)(hydroxyimino)acetyl]amino]-3-[[1-cyclopropylmethyl-2-oxo-3-pyrrolidinylidene]methyl]-8 -oxo-5-thia-1-azabicyclo[4.2.0]oct-2-ene-2-carboxylic acid;

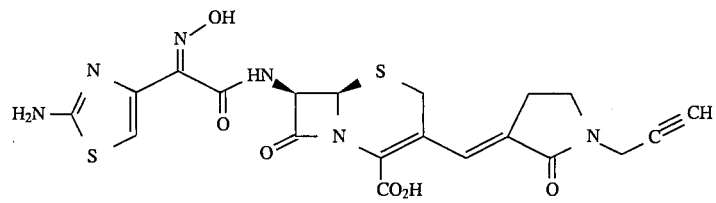

[6R-[3(E),6α,7β(Z)]]-7-[[(2-amino-4-thiazolyl)(hydroxyimino)acetyl]amino] -8-oxo-3-[ [ 2-oxo-1-(2-propynyl)-3-pyrrolidinylidene]methyl]-5-thia-1-azabicyclo[4.2.0]-oct-2-ene-2-carboxylic acid; and

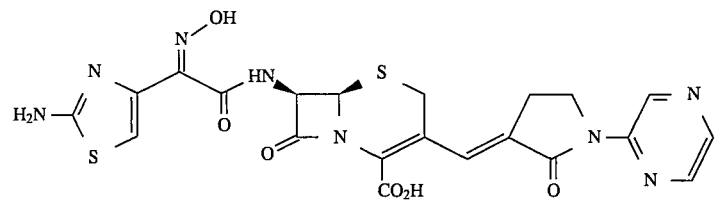

[6R-[3(E),6α,7β(Z)]]-7-[[ (2-amino-4-thiazolyl)(hydroxyimino)acetyl]amino]-8-oxo-3-[[2-oxo-1-(2-pyrazinyl)-3-pyrrolidinylidene]methyl]-5 -thia-1-azabicyclo[4.2.0]oct-2-ene-2-carboxylic acid.

48. The composition of claim 45, wherein $R_3$ is —$C(R^7R^8CO^2R^{9'})$.

49. The composition of claim 48, wherein the compound is selected from the group consisting of

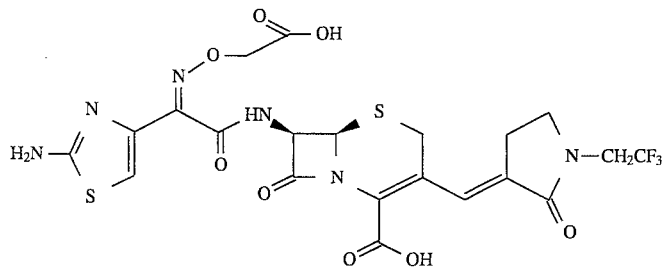

[6R-[3(E),6α,7β(Z)]]-7-[[(2-Amino-4-thiazolyl)[(carboxymethyl)imino]acetyl]amino]-3-[[ 1-(2,2,2-trifluoroethyl)-2-oxo-3-pyrrolidinylidene]methyl]-8-oxo-5-thia-1-azabicyclo[4.2.0]oct-2-ene-2-carboxylic acid;

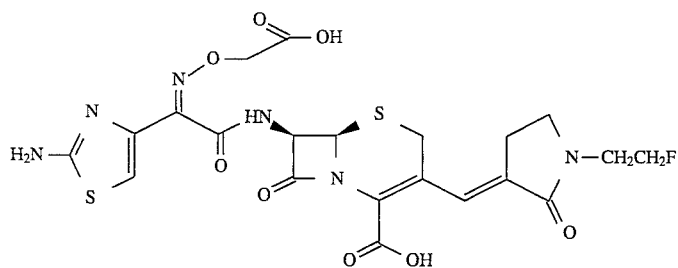

6R-[3(E),6α,7β(Z)]]-7-[[(2-Amino-4-thiazolyl)[(carboxymethyl)imino]acetyl]amino]-3-[[ 1-(2-fluoroethyl)-2-oxo-3-pyrrolidinylidene]methyl]-8-oxo-5-thia-1-azabicyclo[4.2.0]oct-2-ene-2-carboxylic acid; and

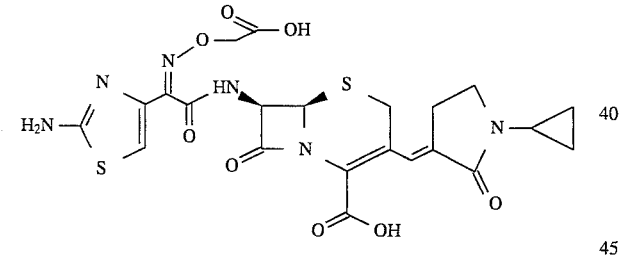

[6R-[3(E),6α,7β(Z)]]-7-[[(2-Amino-4-thiazolyl)[(carboxymethyl)imino]acetyl]amino]-3-[[1-cyclopropyl-2-oxo-3-pyrrolidinylidene]methyl]-8-oxo-5-thia-1-azabicyclo[4.2.0]oct-2-ene-2-carboxylic acid.

50. The composition of claim 44 wherein the amount of said compound is from about 10 mg to about 4000 mg.

51. The composition of claim 50 wherein the amount of said compound is from about 50 mg to about 3000 mg.

52. The composition of claim 44 which is in unit dosage form.

53. The composition of claim 52 wherein said unit dosage form is selected from the group consisting of tablets, coated tablets, dragees, soft gelatine capsules, hard gelatine capsules, solutions, syrups, and suppositories.

54. A method for treating bacterial infections in a mammal comprising administering to said mammal a compound of the formula

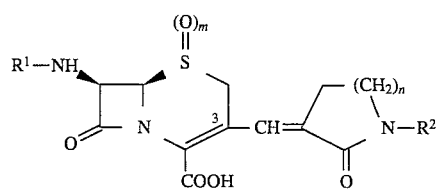

wherein $R^1$ is an acyl group derived from a carboxylic acid;

$R^2$ is hydrogen, hydroxy, lower alkyl-$Q_p$, cycloalkyl, lower alkoxy, lower alkenyl, cycloalkenyl, lower alkynyl, aralkyl-$Q_p$, aryl-$Q_p$, aryloxy, aralkoxy or an unsaturated or saturated 5-, 6-, or 7-membered heterocyclic ring containing at least one hetero atom selected from the group consisting of oxygen, nitrogen, or sulfur, the lower alkyl, cycloalkyl, lower alkoxy, lower alkenyl, cycloalkenyl, lower alkynyl, aralkyl, aryl, aryloxy, aralkoxy and the heterocyclic ring being unsubstituted or substituted with at least one group selected from carboxy, amino, nitro, oxo, cycloalkyl, cyano, lower alkyl, lower alkoxy, hydroxy, halogen, —$CONR^4R^5$, —$N(R^5)COOR^9$, $R^5CO$—, $R^5OCO$— or $R^5COO$— where $R^4$ is hydrogen, lower alkyl, or cycloalkyl; $R^5$ is hydrogen or lower alkyl; $R^9$ is lower alkyl, lower alkenyl or a carboxylic acid protecting group;

Q is —CO— or —$SO_2$—;

m is 0 or 1;

n is 0, 1 or 2;

p is 0 or 1;

as well as readily hydrolyzable esters thereof, pharmaceutically acceptable salts of said compounds and hydrates of the compounds of formula I and of their esters and salts, and a therapeutically acceptable carrier in an amount which is effective in treating bacterial infections.

55. The method of claim 54, wherein the compound of formula II, Z is —C(X)=N—OR₃[IIC].

56. The method of claim 55, wherein R₃ is hydrogen.

57. The method of claim 56, wherein the compound is selected from the group consisting of

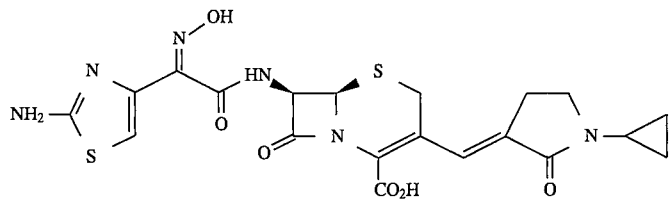

[6R-[3(E),6α,7β(Z)]]-7-[[(2-amino-4-thiazolyl)(hydroxyimino)acetyl]amino]-3-[[1-cyclopropyl-2-oxo-3-pyrrolidinylidene]methyl]-8-oxo-5 -thia-1-azabicyclo[4.2.0]oct-2-ene-2-carboxylic acid;

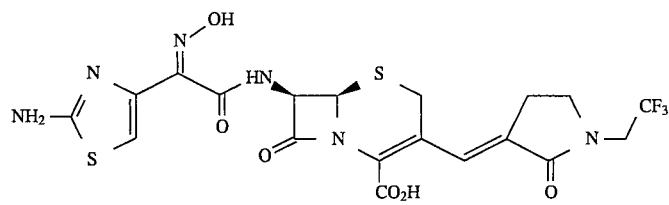

[6R-[3(E),6α,7β(Z)]]-7-[[(2-amino-4-thiazolyl)(hydroxyimino)acetyl]amino]-3-[[ 1-(2,2,2-trifluoroethyl)-2-oxo-3-pyrrolidinylidene]methyl]-8 -oxo-5-thia-1-azabicyclo[4.2.0]oct-2-ene-2-carboxylic acid;

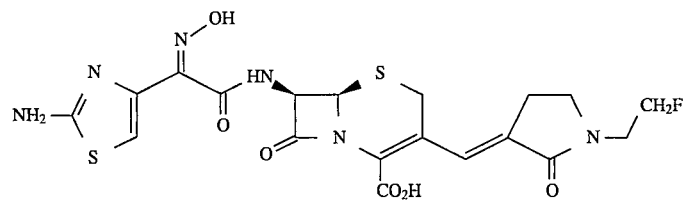

[6R-[3(E),6α,7β(Z)]]-7-[[ (2-amino-4-thiazolyl)(hydroxyimino)acetyl] -aminol-3-[[ 1-(2-fluoroethyl)-2-oxo-3-pyrrolidinylidene]methyl]-8-oxo- 5-thia-1-azabicyclo[4.2.0]oct-2-ene-2-carboxylic acid;

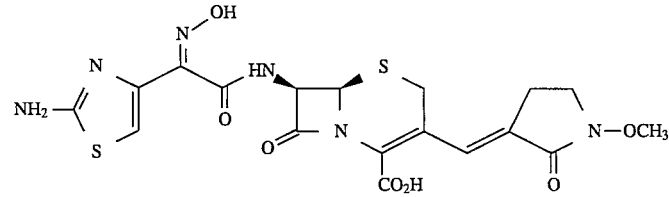

[6R-[3(E),6α,7β(Z)]]-7-[[ (2-Amino-4-thiazolyl)(hydroxyimino)acetyl]amino]-3-[[ 1-methoxy-2-oxo-3-pyrrolidinylidene]methyl]-8-oxo- 5-thia-1-azabicyclo[4.2.0]oct-2-ene-2-carboxylic acid;

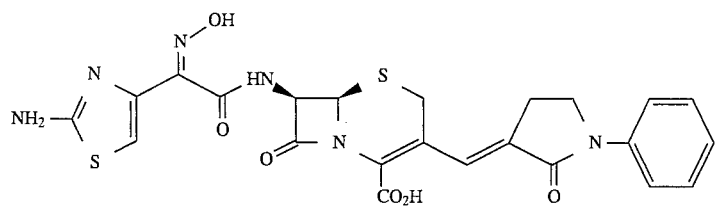

6R-[3(E),6α,7β(Z)]]-7-[[(2-amino-4-thiazolyl)(hydroxyimino)acetyl]amino]-3-[[2-oxo-1-phenyl-3-pyrrolidinylidene]methyl]-8-oxo-5-thia-1-azabicyclo[4.2.0]oct-2-ene-2-carboxylic acid;

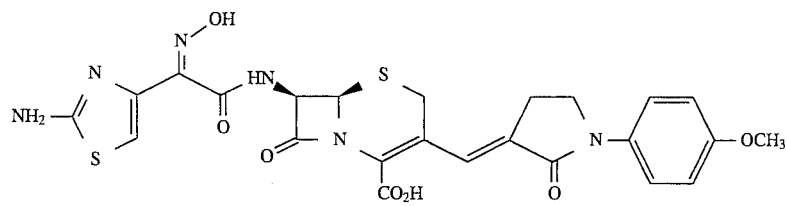

[6R-[3(E),6α,7β(Z)]]-7-[[(2-amino-4-thiazolyl)(hydroxyimino)acetyl]amino]-3-[[1-(4-methoxyphenyl)-2-oxo-3-pyrrolidinylidene]methyl]-8-oxo-5-thia-1-azabicyclo[4.2.0]oct-2-ene-2-carboxylic acid;

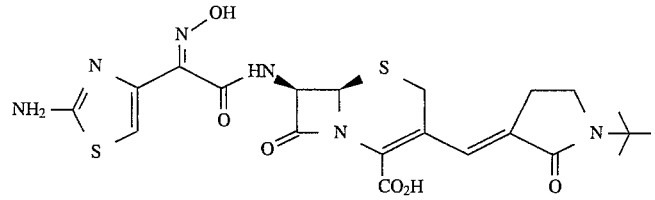

[6R-[3(E),6α,7β(Z)]]-7-[[(2-Amino-4-thiazolyl)hydroxyimino)acetyl]amino]-3-[[1-(1,1-dimethylethyl)-2-oxo-3-pyrrolidinylidene]methyl]-8-oxo-5-thia-1-azabicyclo[4.2.0]oct-2-ene-2-carboxylic acid;

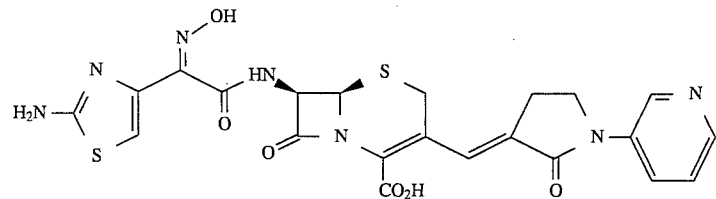

[6R-[3(E),6α,7β(Z)]]-7-[[(2-amino-4-thiazolyl)(hydroxyimino)acetyl]amino]-8-oxo-3-[[2-oxo-1-(3-pyridinyl)-3-pyrrolidinylidene]methyl]-5-thia-1-azabicyclo[4.2.0]oct-2-ene-2-carboxylic acid;

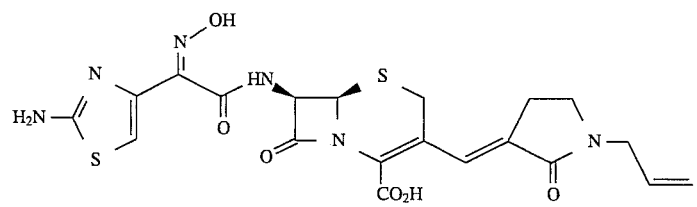

[6R-[3(E),6α,7β(Z)]]-3-[[ 1-allyl-2-oxo-3-pyrrolidinylidene]methyl]-7-[[(2-amino-4-thiazolyl)(hydroxyimino)acetyl]amino]-8-oxo-5-thia-1-azabicyclo[4.2.0]oct-2-ene-2-carboxylic acid;

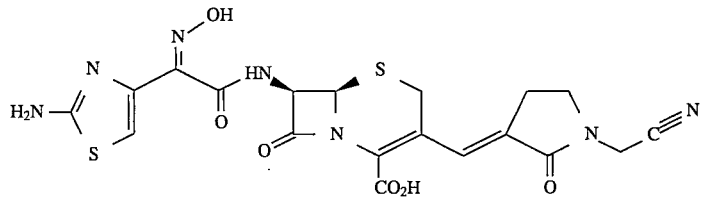

[6R-[3(E),6α,7β(Z)]]-7-[[(2-amino-4-thiazolyl)(hydroxyimino)acetyl]amino]-3-[[ 1-cyanomethyl-2-oxo-3-pyrrolidinylidene]methyl]-8-oxo-5-thia-1-azabicyclo[4.2.0]oct-2-ene-2-carboxylic acid;

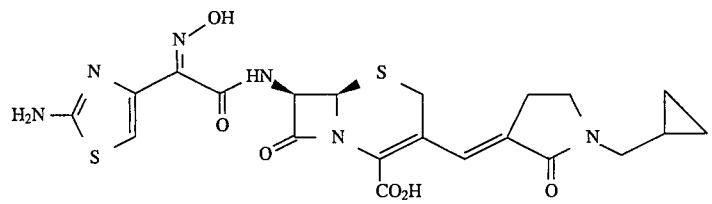

[6R-[3(E),6α,7β(Z)]]-7-[[ (2-amino-4-thiazolyl)(hydroxyimino)acetyl]amino]-3-[[ 1-cyclopropylmethyl-2-oxo-3-pyrrolidinylidene]methyl]-8-oxo-5-thia-1-azabicyclo[4.2.0]oct-2-ene-2-carboxylic acid;

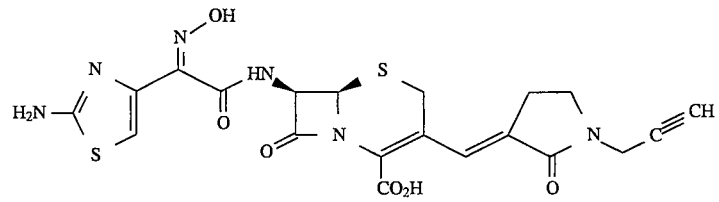

[6R-[3(E),6α,7β(Z)]]-7-[[(2-amino-4-thiazolyl)(hydroxyimino)acetyl]amino]-8-oxo-3-[[2-oxo-1-(2-propynyl)-3-pyrrolidinylidene]methyl]-5-thia-1-azabicyclo[4.2.0]-oct-2-ene-2-carboxylic acid; and

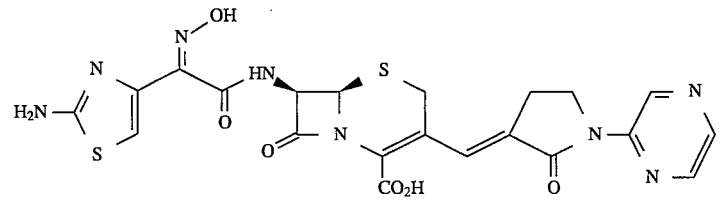

[6R-[3(E),6α,7β(Z)]]-7-[[(2-amino-4-thiazolyl)(hydroxyimino)acetyl]amino]-8-oxo-3-[[2-oxo-1-(2-pyrazinyl)-3-pyrrolidinylidene]methyl]-5-thia-1-azabicyclo[4.2.0]oct-2-ene-2-carboxylic acid.

58. The method of claim 55, wherein $R_3$ is $-C(R^7R^8CO^2R^9)$.

59. The method of claim 58, wherein the compound is selected from the group consisting of

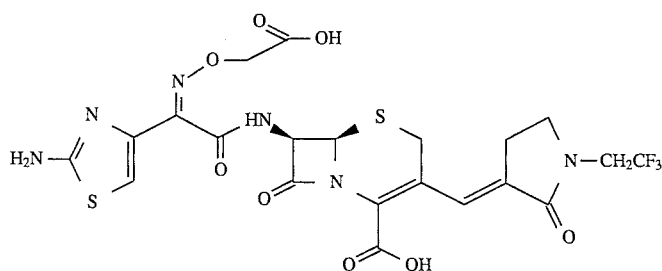

[6R-[3(E),6α,7β(Z)]]-7-[[(2-Amino-4-thiazolyl)[(carboxymethyl)imino]acetyl]amino]-3-[[ 1-(2,2,2-trifluoroethyl)-2-oxo-3-pyrrolidinylidene]methyl] -8-oxo-5-thia-1-azabicyclo[4.2.0 ]oct-2-ene-2carboxylic acid;

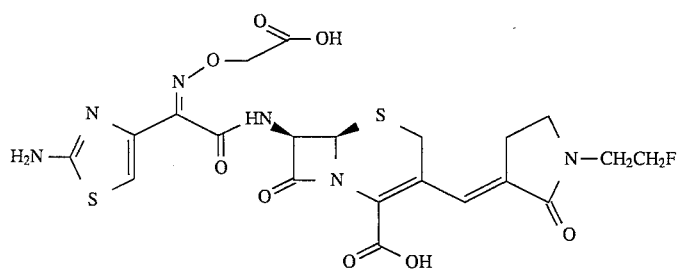

[6R-[3(E),6α,7β(Z)]]-7-[[(2-Amino-4-thiazolyl)[(carboxymethyl)imino]acetyl]amino]-3-[[ 1-(2-fluoroethyl)-2-oxo-3-pyrrolidinylidene]methyl]-8-oxo-5-thia-1-azabicyclo[4.2.0]oct-2-ene-2-carboxylic acid; and

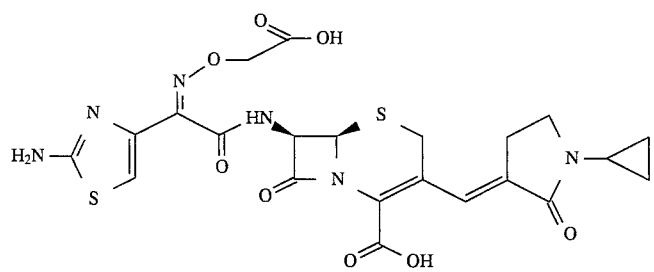

[6R-[3(E),6α,7β(Z)]]-7-[[(2-Amino-4-thiazolyl)[(carboxymethyl)imino]acetyl]amino]-3-[[1-cyclopropyl-2-oxo-3-pyrrolidinylidene]methyl]-8-oxo-5-thia-1-azabicyclo[4.2.0]oct-2-ene-2-carboxylic acid.

60. The compound of claim 1 having the formula

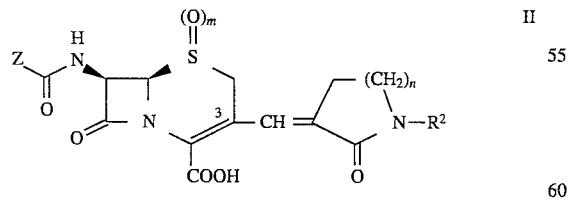

where Z is —C(X)=CR$^a$R$^b$ [IIA], —CH(X)NH$_2$ [IIB] or —C(X)=N—OR$^3$ [IIC], R$^a$ is hydrogen, lower alkyl or CH$_2$CO$_2$R$^4$, the lower alkyl being unsubstituted or substituted with at least one group selected from carboxy, amino, nitro, cyano, lower alkyl, lower alkoxy, hydroxy, halogen, —CONR$^4$R$^5$, —N(R$^5$)COOR$^9$, R$^5$CO—, R$^5$OCO— or R$^5$COO—; R$^b$ is hydrogen or lower alkyl; X is aryl, cyclohexyl, 1,4-cyclohexadienyl, an unsaturated or saturated 5-, 6-, or 7-membered heterocyclic ring containing at least one heteratom selected from the group consisting of oxygen, nitrogen, sulfur, or an unsaturated or saturated 5-, 6-, or 7-membered heterocyclic ring containing at least one hetero atom selected from the group consisting of oxygen, nitrogen, or sulfur which is fused together with a benzene ring, the aryl, cyclohexyl, 1,4-cyclohexadienyl and heterocyclic ring being unsubstituted or substituted with at least one group selected from the carboxy, amino, nitro, cyano, lower alkyl, lower alkoxy, hydroxy, halogen, —CONR$^4$R$^5$, —N(R$^5$)COOR$^9$, R$^5$CO—, R$^5$OCO— or R$^5$COO—; R$^3$ is hydrogen, lower alkyl, aralkyl, cycloalkyl, R$^5$CO— or —C(R$^7$R$^8$)CO$_2$R$^{9'}$; where R$^7$ and R$^8$ are each independently hydrogen or lower alkyl, or R$^7$ and R$^8$ taken together form a cycloalkyl group; R$^{9'}$ is hydrogen or R$^9$, and R$^2$, R$^4$, R$^5$, R$^9$, m and n are as previously defined.

61. The composition of claim 44 wherein the compound is of the formula

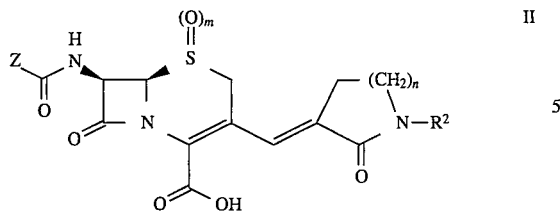

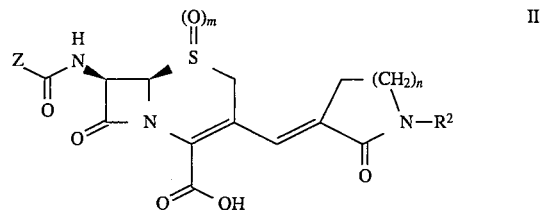

where Z is —C(X)=CR$^a$R$^b$ [IIA], —CH(X)NH$_2$ [IIB] or —C(X)=N—OR$^3$ [IIC], R$^a$ is hydrogen, lower alkyl or CH$_2$CO$_2$R$^4$, the lower alkyl being unsubstituted or substituted with at least one group selected from carboxy, amino, nitro, cyano, lower alkyl, lower alkoxy, hydroxy, halogen, —CONR$^4$R$^5$, —N(R$^5$)COOR$^9$, R$^5$CO—, R$^5$OCO— or R$^5$COO—; R$^b$ is hydrogen or lower alkyl; X is aryl, cyclohexyl, 1,4-cyclohexadienyl, an unsaturated or saturated 5-, 6-, or 7-membered heterocyclic ring containing at least one heteroatom selected from the group consisting of oxygen, nitrogen, sulfur, or an unsaturated or saturated 5-, 6-, or 7-membered heterocyclic ring containing at least one hetero atom selected from the group consisting of oxygen, nitrogen, or sulfur which is fused together with a benzene ring, the aryl, cyclohexyl, 1,4-cyclohexadienyl and heterocyclic ring being unsubstituted or substituted with at least one group selected from the carboxy, amino, nitro, cyano, lower alkyl, lower alkoxy, hydroxy, halogen, —CONR$^4$R$^5$, —N(R$^5$)COOR$^9$, R$^5$CO—, R$^5$OCO— or R$^5$COO—; R$^3$ is hydrogen, lower alkyl, aralkyl, cycloalkyl, R$^5$CO— or —C(R$^7$R$^8$)CO$_2$R$^{9'}$; where R$^7$ and R$^8$ are each independently hydrogen or lower alkyl, or R$^7$ and R$^8$ taken together form a cycloalkyl group; R$^{9'}$ is hydrogen or R$^9$, and R$^2$, R$^4$, R$^5$, R$^9$, m, and n are as previously defined.

62. The method of claim 54 wherein the compound is of the formula where Z is —C(X)=CR$^a$R$^b$ [IIA], —CH(X)NH$_2$ [IIB] or —C(X)=N—OR$^3$, R$^a$ is hydrogen, lower alkyl or CH$_2$CO$_2$R$^4$, the lower alkyl being unsubstituted or substituted with at least one group selected from carboxy, amino, nitro, cyano, lower alkyl, lower alkoxy, hydroxy, halogen, —CONR$^4$R$^5$, —N(R$^5$)COOR$^9$, R$^5$CO—, R$^5$OCO— or R$^5$COO—; R$^b$ is hydrogen or lower alkyl; X is aryl, cyclohexyl, 1,4-cyclohexadienyl, an unsaturated or saturated 5-, 6-, or 7-membered heterocyclic ring containing at least one heteroatom selected from the group consisting of oxygen, nitrogen, sulfur, or an unsaturated or saturated 5-, 6-, or 7-membered heterocyclic ring containing at least one hetero atom selected from the group consisting of oxygen, nitrogen, or sulfur which is fused together with a benzene ring, the aryl, cyclohexyl, 1,4-cyclohexadienyl and heterocyclic ring being unsubstituted or substituted with at least one group selected from the carboxy, amino, nitro, cyano, lower alkyl, lower alkoxy, hydroxy, halogen, —CONR$^4$R$^5$, —N(R$^5$)COOR$^9$, R$^5$CO—, R$^5$OCO— or R$^5$COO—; R$^3$ is hydrogen, lower alkyl, aralkyl, cycloalkyl, R$^5$CO— or —C(R$^7$R$^8$)CO$_2$R$^{9'}$; where R$^7$ and R$^8$ are each independently hydrogen or lower alkyl, or R$^7$ and R$^8$ taken together form a cycloalkyl group; R$^{9'}$ is hydrogen or R$^9$, and R$^2$, R$^4$, R$^5$, R$^9$, m, and n are as previously defined.

* * * * *

UNITED STATES PATENT AND TRADEMARK OFFICE
CERTIFICATE OF CORRECTION

PATENT NO. : 5,523,400
DATED : June 4, 1996
INVENTOR(S) : Chung-Chen Wei and Peter Angehrn It is certified that error appears in the above-indentified patent and that said Letters Patent is hereby corrected as shown below:

In claim 29, column 209, line 21, delete "[6R-[3(E),6to,713(Z)]]" and insert therefor -- [6R-[3(E),6α,7β(Z)]] --.

In claim 37, column 211, line 27, delete "cyclo4.2.0]" and insert therefor -- cyclo[4.2.0] --.

*In claim 41, column 213, line 43, delete "acid," and insert therefor -- acid. --.

In claim 57, column 225, line 40, delete "[6R-[3(E),6α,7β(Z)]]-7-[[2-Amino-4-thiazolyl)" and insert therefor -- [6R-[3(E),6α,7β(Z)]]-7-[[2-Amino-4-thiazolyl) --.

In claim 59, column 229, line 17, delete "2carboxylic" and insert therefor -- 2-carboxylic --.

In claim 62, column 232, line 11, delete "-C(X)=N-OR$^3$," and insert therefor -- -C(X)=N-OR$^3$ [IIC], --.

Signed and Sealed this

Seventeenth Day of September, 1996

*Attest:*

BRUCE LEHMAN

*Attesting Officer*     Commissioner of Patents and Trademarks